US007846938B2

(12) United States Patent
Cai et al.

(10) Patent No.: US 7,846,938 B2
(45) Date of Patent: *Dec. 7, 2010

(54) TARTRATE SALTS OF QUINAZOLINE BASED EGFR INHIBITORS CONTAINING A ZINC BINDING MOIETY

(75) Inventors: Xiong Cai, Belmont, MA (US); Changgeng Qian, Wayland, MA (US); Haixiao Zhai, Bedford, MA (US)

(73) Assignee: Curis, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/207,833

(22) Filed: Sep. 10, 2008

(65) Prior Publication Data

US 2009/0076022 A1 Mar. 19, 2009

Related U.S. Application Data

(60) Provisional application No. 60/971,056, filed on Sep. 10, 2007.

(51) Int. Cl.
*A61K 31/517* (2006.01)

(52) U.S. Cl. .................... 514/266.4; 544/293

(58) Field of Classification Search .................. 544/293
See application file for complete search history.

(56) References Cited

U.S. PATENT DOCUMENTS

| | | | |
|---|---|---|---|
| 5,457,105 A | 10/1995 | Barker | |
| 5,556,860 A | 9/1996 | Muraoka et al. | |
| 5,616,582 A | 4/1997 | Barker et al. | |
| 5,747,498 A | 5/1998 | Schnur et al. | |
| 5,942,514 A | 8/1999 | Barker et al. | |
| 6,087,367 A | 7/2000 | Breslow et al. | |
| 6,184,225 B1 | 2/2001 | Thomas et al. | |
| 6,537,988 B2 | 3/2003 | Lee | |
| 6,777,217 B1 | 8/2004 | Schreiber et al. | |
| 6,900,221 B1 | 5/2005 | Norris et al. | |
| 7,250,514 B1 | 7/2007 | Xiao | |
| 7,230,000 B1 | 12/2007 | Finer et al. | |
| 2006/0025430 A1 | 2/2006 | Mishani et al. | |
| 2006/0111375 A1 | 5/2006 | Shimizu et al. | |
| 2006/0287295 A1 | 12/2006 | Balaram et al. | |
| 2008/0125448 A1 | 5/2008 | Qian et al. | |
| 2008/0139590 A1 | 6/2008 | Qian et al. | |
| 2008/0194578 A1 | 8/2008 | Qian et al. | |
| 2008/0221132 A1 | 9/2008 | Cai et al. | |

FOREIGN PATENT DOCUMENTS

| | | |
|---|---|---|
| WO | 9633980 | 10/1996 |
| WO | 00/47212 | 8/2000 |
| WO | 0268396 A1 | 6/2002 |
| WO | 2004069791 | 8/2004 |
| WO | 2005097137 A2 | 10/2005 |
| WO | 2006082428 A2 | 8/2006 |
| WO | 2006/113498 A2 | 10/2006 |
| WO | 2006110811 | 10/2006 |
| WO | 2006111570 A2 | 10/2006 |
| WO | 2007131364 A1 | 11/2007 |
| WO | WO2008/033747 | * 3/2008 |
| WO | 2008055068 A2 | 8/2008 |

OTHER PUBLICATIONS

Berge et al. Pharmaceutical Salts, 1977, Journal of Pharmaceutical Sciences, 66, 1-19.*
Wood, Edgar R. et. al., "A Unique Structure for Epidermal Growth Factor Receptor Bound to GW572016 (Lapatinib): Relationships among Protein Conformation, Inhibitor Off-Rate, and Receptor Activity in Tumor Cells," Cancer Research, 64: 6652-6659 (2004).
Matsuno, Kenji, et. al, "Potent and Selective Inhibitors of Platelet-Derived Growth Factor Receptor Phosphorylation. 3. Replacement of Quinazoline Moiety and Improvement of Metabolic Polymorphism of 4-[4-(N-Substituted (thio)carbamoyl)-1-piperazinyl]-6,7-dimethoxyquinazoline Derivatives," Journal of Medicinal Chemistry, 46: 4910-4925 (2003).
Ple, Patrick A., et. al., Discovery of a New Class of Anilinoquinazoline Inhibitors with High Affinity and Specificity for the Tyrosine Kinase Domain of c-Src, Journal of Medicinal Chemistry, 47: 871-887 (2004).
Banker, G.S. et al, "Modern Pharmaceutics, 3ed.", Marcel Dekker, New York, 1996, pp. 451 and 596.
Wolff, Manfred E., "Burger's Medicinal Chemistry, 5ed, Part I", John Wiley & Sons, 1995, pp. 975-977.
West, Anthony R., Solid State Chemistry and its Applications, Wiley, New York, 1988, pp. 358 and 365.

(Continued)

*Primary Examiner*—James O Wilson
*Assistant Examiner*—Brian McDowell
(74) *Attorney, Agent, or Firm*—Elmore Patent Law Group, P.C.; Edgar W. Harlan; Carolyn S. Elmore

(57) ABSTRACT

The present invention relates to tartrate salts of quinazoline containing zinc-binding moiety based derivatives of Formula II, below.

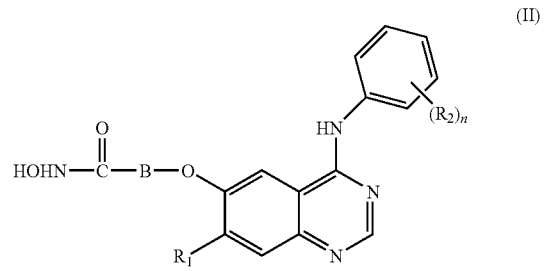

These compounds are inhibitors of epidermal growth factor receptor tyrosine kinase (EGFR-TK) and may further act as HDAC inhibitors. The invention further relates to the use of these tartrate salts in the treatment of EGFR-TK related diseases and disorders such as cancer.

25 Claims, 20 Drawing Sheets

OTHER PUBLICATIONS

Hennequin, et al., "Design and Structure-Activity Relationship of a New Class of Potent VEGF Receptor Tyrosine Kinase Inhibitors," J. Med. Chem., 30: 5369-5389 (1999).

Butler, Lisa M., et al., "Suberoylanilide Hydroxamic Acid, an Inhibitor of Histone Deacetylase, Suppresse the Growth of Prostate Cancer Cells in Vitro and in Vivo," Cancer Research, 60: 5165-5170 (2000).

* cited by examiner (a)

(b)

(a)

(b)

(c)

(a)

(b)

(c)

(d)

(a)

(b)

| | | #1 | #2 | #3 | Mean | SD |
|---|---|---|---|---|---|---|
| K10 | 1/hr | 9.05 | 6.78 | 6.93 | 7.59 | 1.27 |
| K10_HL | hr | 0.08 | 0.10 | 0.10 | 0.09 | 0.01 |
| Alpha_HL | hr | 0.03 | 0.07 | 0.05 | 0.05 | 0.02 |
| Beta_HL | hr | 0.27 | 0.77 | 0.47 | 0.50 | 0.25 |
| Cmax | ng/ml | 15769.20 | 11199.46 | 18425.33 | 15131.33 | 3654.92 |
| | µM | 36.29 | 25.78 | 42.41 | 34.82 | 8.41 |
| AUC | hr*ng/ml | 1742.41 | 1651.94 | 2658.31 | 2017.55 | 556.75 |
| | hr*µM | 4.01 | 3.80 | 6.12 | 4.64 | 1.28 |
| CL | L/hr/kg | 14.35 | 15.13 | 9.40 | 12.96 | 3.11 |
| Vd | L/kg | 5.53 | 16.76 | 6.33 | 9.54 | 6.27 |
| AUMC | hr*hr*ng/ml | 457.53 | 667.55 | 1030.27 | 718.45 | 289.74 |
| MRT | hr | 0.26 | 0.40 | 0.39 | 0.35 | 0.08 |
| Vss | L/kg | 3.77 | 6.12 | 3.64 | 4.51 | 1.39 |

TARTRATE SALTS OF QUINAZOLINE BASED EGFR INHIBITORS CONTAINING A ZINC BINDING MOIETY

RELATED APPLICATIONS

This application claims the benefit of U.S. Provisional Application No. 60/971,056, filed on Sep. 10, 2007. The entire teachings of the above application are incorporated herein by reference.

BACKGROUND OF THE INVENTION

The epidermal growth factor receptor (EGFR, Erb-B1) belongs to a family of proteins, involved in the proliferation of normal and malignant cells (Artega, C. L., *J. Clin Oncol* 19, 2001, 32-40). Overexpression of Epidermal Growth Factor Receptor (EGFR) is present in at least 70% of human cancers (Seymour, L. K., *Curr Drug Targets* 2, 2001, 117-133) such as, non-small cell lung carcinomas (NSCLC), breast cancers, gliomas, squamous cell carcinoma of the head and neck, and prostate cancer (Raymond et al., *Drugs* 60 *Suppl* 1, 2000, discussion 41-2; Salomon et al., *Crit. Rev Oncol Hematol* 19, 1995, 183-232; Voldborg et al., *Ann Oncol* 8, 1997, 1197-1206). The EGFR-TK is therefore widely recognized as an attractive target for the design and development of compounds that can specifically bind and inhibit the tyrosine kinase activity and its signal transduction pathway in cancer cells, and thus can serve as either diagnostic or therapeutic agents. For example, the EGFR tyrosine kinase (EGFR-TK) reversible inhibitor, Tarceva®, was recently approved by the FDA for treatment of NSCLC and advanced pancreatic cancer. Other anti-EGFR targeted molecules have also been approved such as Iressa®.

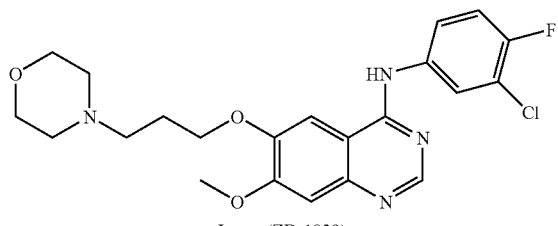

Iressa (ZD-1839)

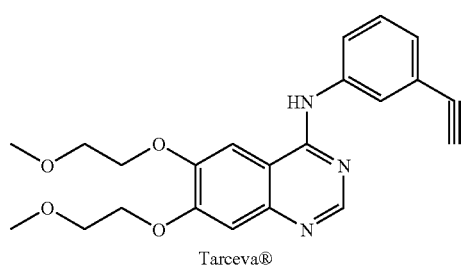

Tarceva®

Despite the early success of Tarceva, it has become clear that selectively targeting individual kinases can lead to the development of drug resistant tumors. Cells that have developed mutations within the drug/kinase binding pocket display a growth advantage in the presence of drug eventually leading to disease progression. Current clinical strategies aimed at combining these molecularly targeted drugs with standard chemotherapeutics, radiation, or other targeted agents will lead to novel strategies to improve overall response rate and increase the number of complete remissions.

Furthermore, elucidation of the complex and multifactorial nature of various diseases that involve multiple pathogenic pathways and numerous molecular components suggests that multi-targeted therapies may be advantageous over monotherapies. For example, the use of EGFR inhibitors in combination with histone deacetylases (HDAC) has been shown to produce synergistic effects. Histone acetylation is a reversible modification, with deacetylation being catalyzed by a family of enzymes termed HDAC's. HDACs are represented by X genes in humans and are divided into four distinct classes (*J Mol Biol*, 2004, 338:1, 17-31). In mammalians class I HDAC's (HDAC1-3, and HDAC8) are related to yeast RPD3 HDAC, class 2 (HDAC4-7, HDAC9 and HDAC10) related to yeast HDA1, class 4 (HDAC11), and class 3 (a distinct class encompassing the sirtuins which are related to yeast Sir2).

Recent advances suggest that EGFR-TK inhibitors in combination with HDAC inhibitors may provide advantageous results in the treatment of cancer. U.S. Provisional Application No. 60/843,644, filed on Sep. 11, 2006 and U.S. Provisional Application No. 60/895,873, filed on Mar. 20, 2007, and U.S. Ser. No. 11/852,604 filed Sep. 10, 2007, and U.S. Ser. No. 11/852,585 filed on Sep. 10, 2007, the contents of which are hereby incorporated by reference describe quinazoline containing zinc-binding moiety based derivatives that have enhanced and unexpected properties as inhibitors of epidermal growth factor receptor tyrosine kinase (EGFR-TK), HDAC and HER2. It was surprisingly found that the compounds have enhanced activity when compared to the activities of separate molecules individually having the EGFR-TK and HDAC activities and combinations thereof. In other words, the combination of pharmacophores into a single molecule may provide a synergistic effect as compared to the individual pharmacophores.

The quinazoline compounds described above have been demonstrated as effective in decreasing tumor size in various animal models. It would be advantageous to prepare pharmaceutically acceptable salts of these quinazoline compounds.

SUMMARY OF THE INVENTION

The present application is directed to tartrate salts or complexes of the quinazoline compounds of formulae I-IV below. As shown below in Example 53, tartrate salts or complexes of the quinazoline compounds have greater solubility and stability than the corresponding sodium, hydrochloride and citric acid salts. Furthermore, the tartrate salt or complex of a compound encompassed by Formula I has been shown to permit delivery of a higher daily dose of the active compound than sodium, hydrochloride or citrate salts.

In one embodiment, the present invention provides tartaric acid-containing formulations, a tartrate salt of or complex with a compound having the general Formula I:

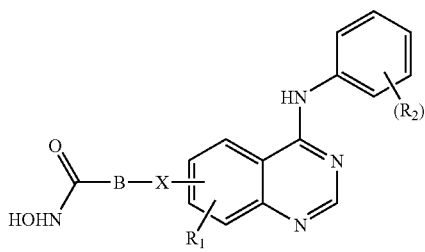

or its geometric isomers, enantiomers, diastereomers or racemates thereof, wherein B is a $C_3$ to $C_9$ alkylene, preferably a straight chain $C_5$ to $C_7$ alkylene, most preferably a straight chain $C_6$ alkylene;

$R_1$ is independently selected from hydrogen; $C_1$ to $C_4$ alkoxy, preferably methoxy; or substituted $C_1$ to $C_4$ alkoxy, preferably $C_1$ to $C_4$ alkoxy substituted $C_1$ to $C_4$ alkoxy, such as most preferably methoxyethoxy; and $R_2$ is each independently selected from halogen (preferably Br, Cl and F), $C_1$ to $C_4$ alkyl, $C_2$ to $C_4$ alkenyl, and $C_2$ to $C_4$ alkynyl (preferably ethynyl);

n is 1, 2 or 3, preferably 1 or 2.

"Complex" is meant to include an association between the active compound and tartaric acid or a tartrate salt (including but not limited to, ionic bonding) that imparts a modification to at least one physical or chemical property of the active agent (e.g., solubility or stability).

In yet another embodiment, the tartrate described above is the L-tartrate.

In an additional embodiment, the tartrate is the D-tartrate.

In a further embodiment, the tartrate is the meso-tartrate.

In yet another embodiment, the tartrate is the D,L-tartrate.

In a further embodiment, the invention is a pharmaceutical composition comprising a tartrate salt or complex of a compound encompassed by Formula I. In one embodiment, the pharmaceutical composition further comprises a cyclodextrin. In another embodiment, the cyclodextrin is selected from the group consisting of an α-cyclodextrin or a derivative thereof, a β-cyclodextrin or a derivative thereof and a γ-cyclodextrin or a derivative thereof. In one embodiment, the cyclodextrin is a β-cyclodextrin or a derivative thereof. In yet another embodiment, the β-cyclodextrin is a 2-hydroxypropyl-β-cyclodextrin or a sulfobutyl derivatized-β-cyclodextrin. In another embodiment, the cyclodextrin is a sulfobutyl derivatized-β-cyclodextrin. In a further embodiment, the cyclodextrin is sulfobutylether(7)-sulfobutyl derivatized-β-cyclodextrin-cyclodextrin.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
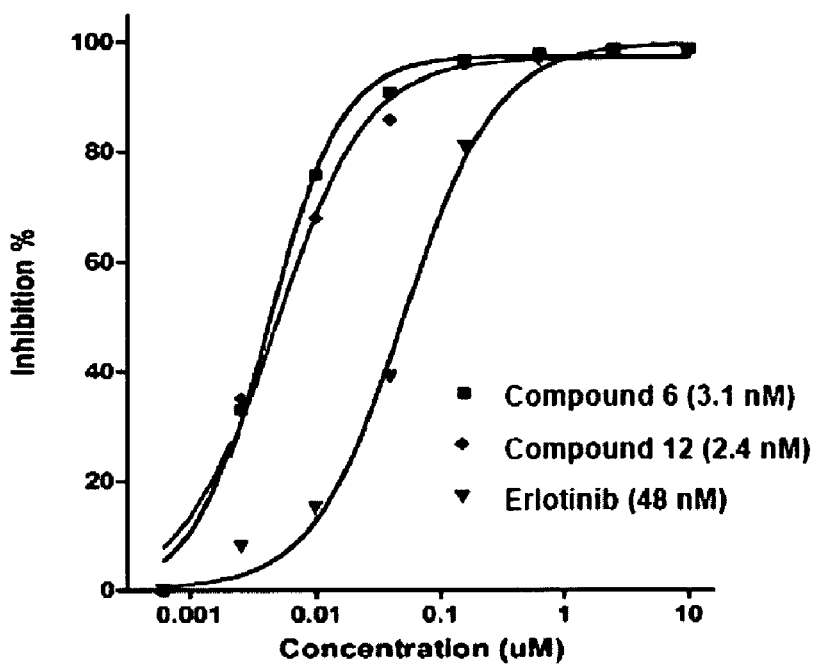
FIG. 1 (a) depicts a graph of EGFR enzyme assay results, (b) depicts a graph of HDAC enzyme assay results.
Figure 1:
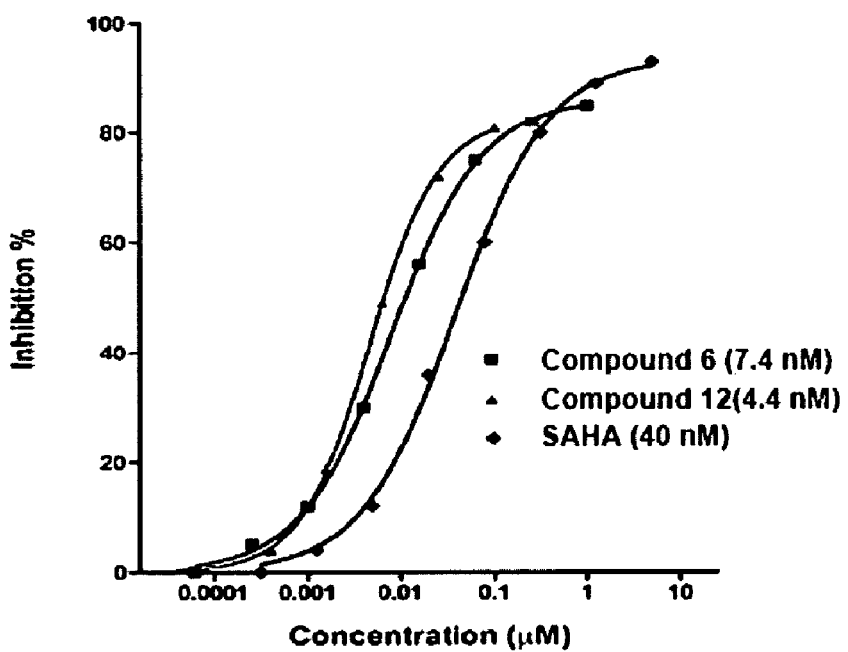

In a first embodiment, the inventive compound is a tartrate salt or complex of a compound represented by formula (I) as illustrated above, or geometric isomers, enantiomers, diastereomers or racemates thereof.

In a second embodiment, the compound is represented by formula (II), or geometric isomers, enantiomers, diastereomers or racemates, thereof:

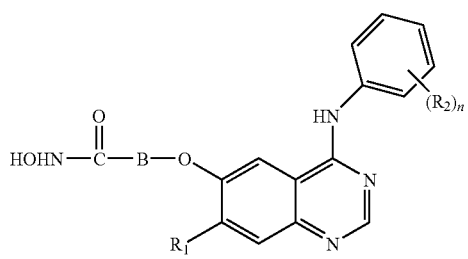

wherein B, R$_1$, R$_2$, and n are as previously defined.

In a third embodiment, the compound is represented by formula (III) or geometric isomers, enantiomers, diastereomers or racemates, thereof:

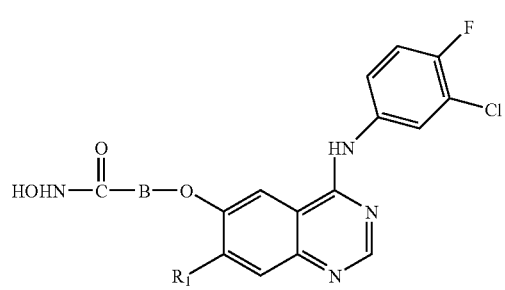

wherein B and R$_1$ are as previously defined.

In a fourth embodiment, the compound is represented by formula (IV), or its geometric isomers, enantiomers, diastereomers or racemates thereof:

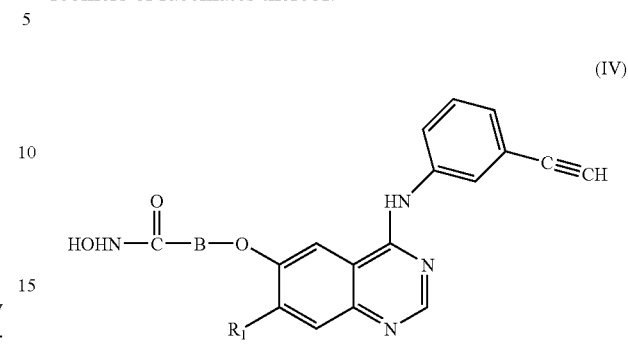

wherein B and R$_1$ are as previously defined.

In each of the above embodiments, R$_1$ is preferably hydrogen or methoxy and, independently or collectively, B is preferably a straight chain C$_5$ to C$_7$ alkylene, most preferably a straight chain C$_6$ alkylene.

In one embodiment, the present invention is directed to a tartrate salt of or complex with a compound U.S. Provisional Application No. 60/843,644, filed on Sep. 11, 2006 and U.S. Provisional Application No. 60/895,873, filed on Mar. 20, 2007, and U.S. Ser. No. 11/852,604 filed on Sep. 10, 2007, and U.S. Ser. No. 11/852,585 filed on Sep. 10, 2007, or selected from the Table A below or geometric isomers, enantiomers, diastereomers or racemates thereof:

TABLE A

| Compound # | Structure |
|---|---|
| 1 | 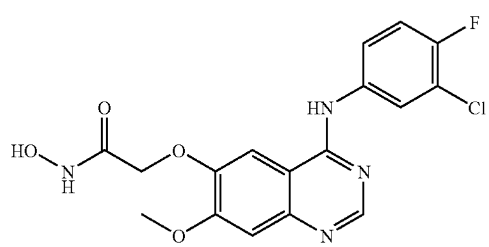 |
| 2 | 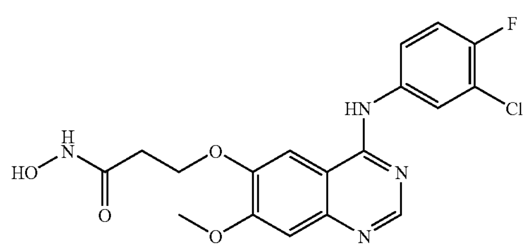 |

TABLE A-continued
| Compound # | Structure |
|---|---|
| 3 | 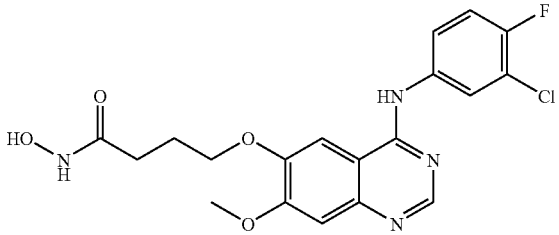 |
| 4 | 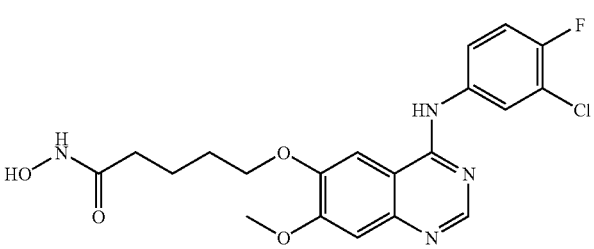 |
| 5 | 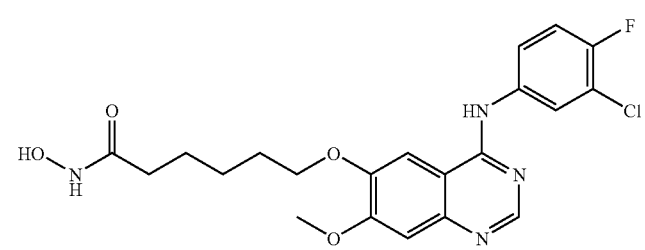 |
| 6 | 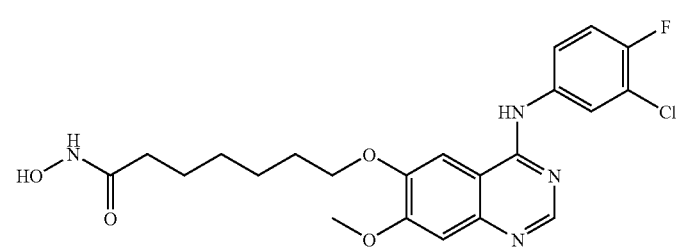 |
| 7 | 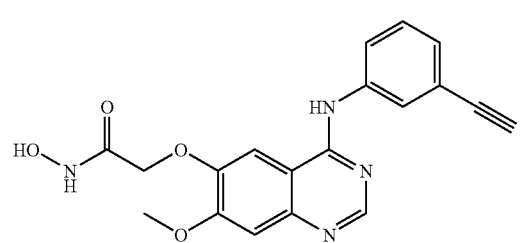 |
| 8 | 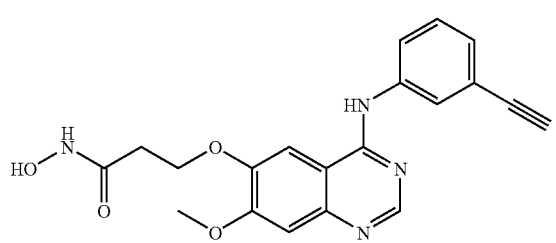 |

TABLE A-continued

| Compound # | Structure |
|---|---|
| 9 | (structure: N-hydroxy-4-[(7-methoxy-4-((3-ethynylphenyl)amino)quinazolin-6-yl)oxy]butanamide) |
| 10 | (structure: N-hydroxy-5-[(7-methoxy-4-((3-ethynylphenyl)amino)quinazolin-6-yl)oxy]pentanamide) |
| 11 | (structure: N-hydroxy-6-[(7-methoxy-4-((3-ethynylphenyl)amino)quinazolin-6-yl)oxy]hexanamide) |
| 12 | (structure: N-hydroxy-7-[(7-methoxy-4-((3-ethynylphenyl)amino)quinazolin-6-yl)oxy]heptanamide) |
| 13 | (structure: N-hydroxy-2-[(4-((3-chloro-4-fluorophenyl)amino)quinazolin-6-yl)oxy]acetamide) |
| 14 | (structure: N-hydroxy-3-[(4-((3-chloro-4-fluorophenyl)amino)quinazolin-6-yl)oxy]propanamide) |

TABLE A-continued

| Compound # | Structure |
|---|---|
| 15 | 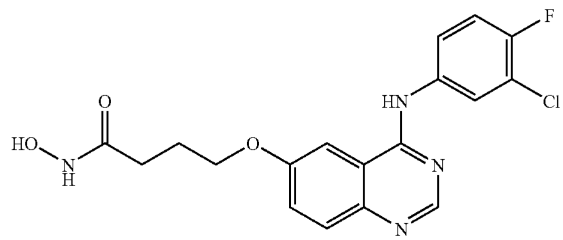 |
| 16 | 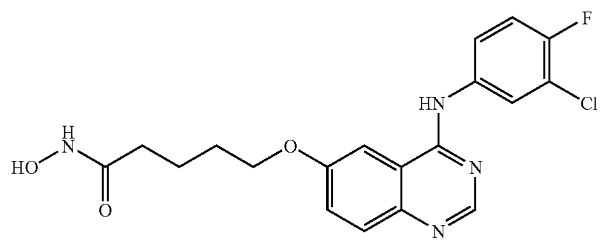 |
| 17 | 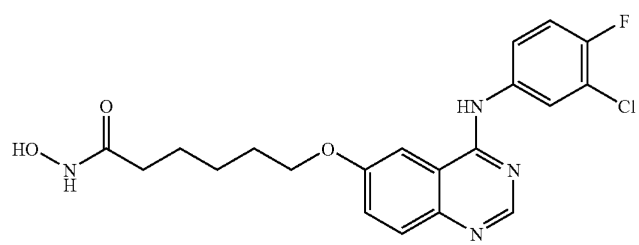 |
| 18 | 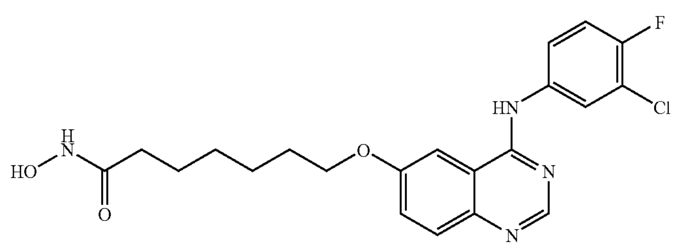 |
| 19 | 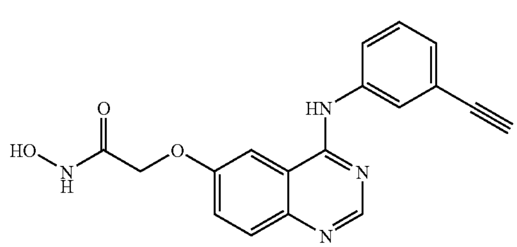 |
| 20 | 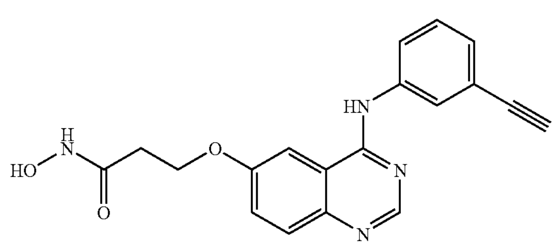 |

TABLE A-continued
| Compound # | Structure |
|---|---|
| 21 | 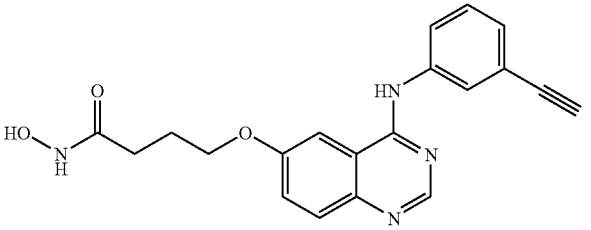 |
| 22 | 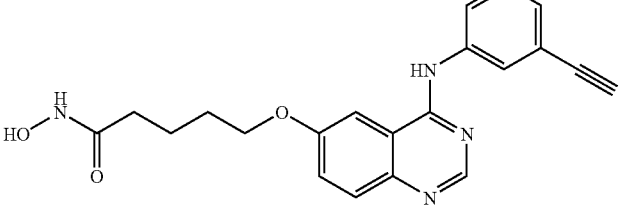 |
| 23 | 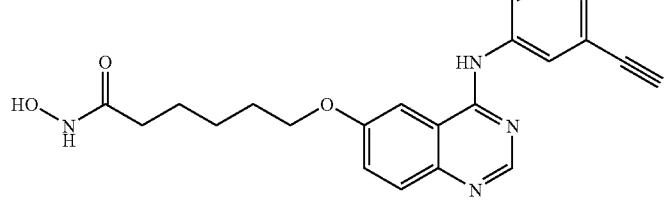 |
| 24 | 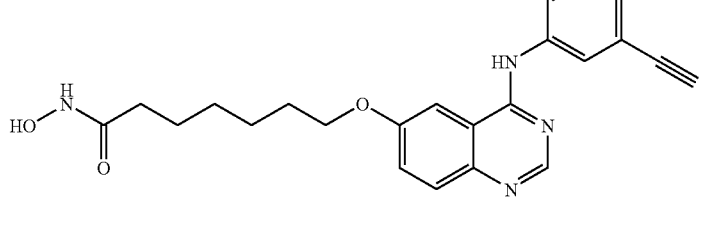 |
| 25 | 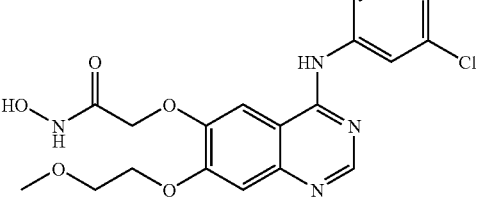 |
| 26 | 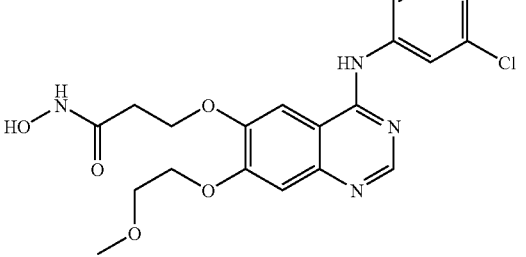 |

TABLE A-continued

| Compound # | Structure |
|---|---|
| 27 | 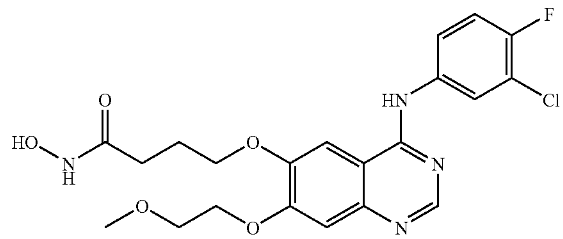 |
| 28 | 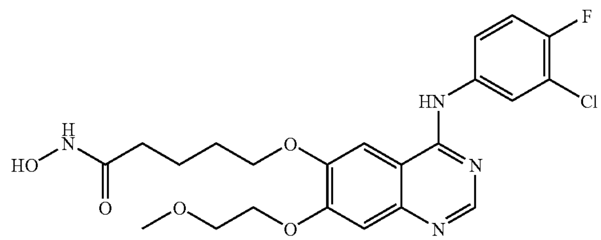 |
| 29 | 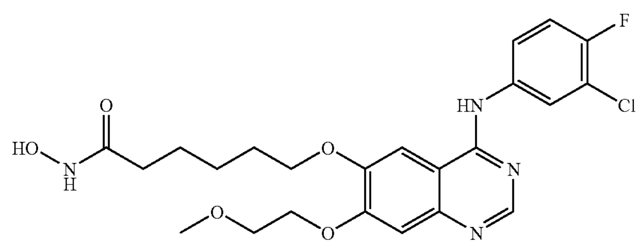 |
| 30 | 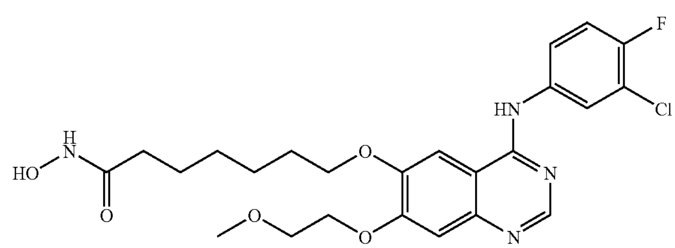 |
| 31 | 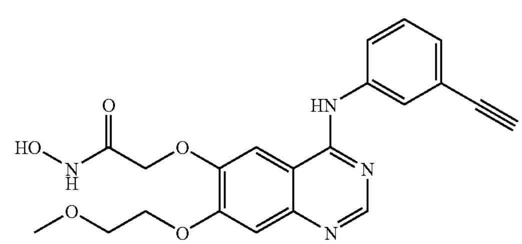 |
| 32 | 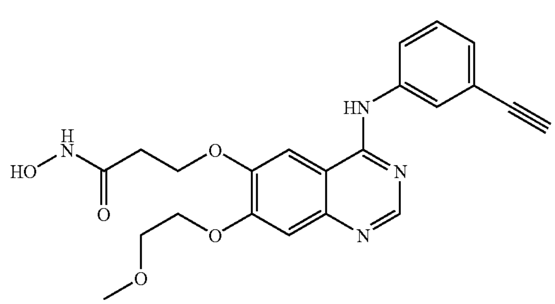 |

TABLE A-continued

| Compound # | Structure |
|---|---|
| 33 | 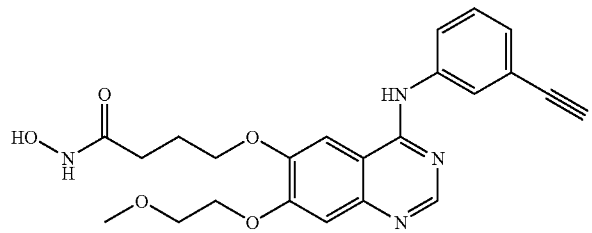 |
| 34 | 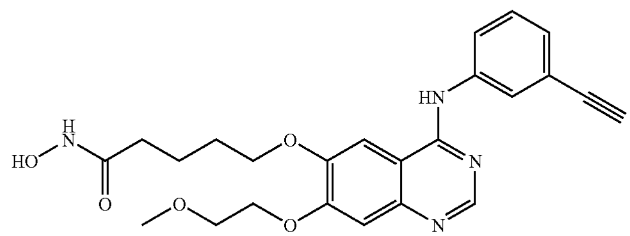 |
| 35 | 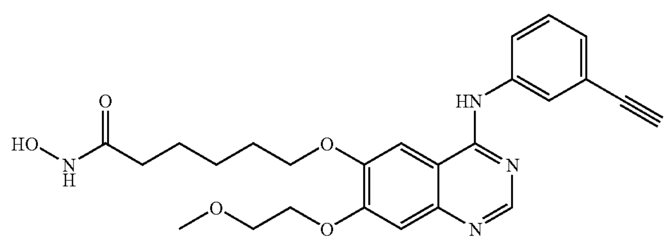 |
| 36 | 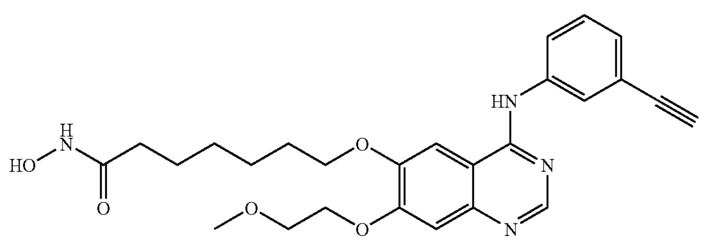 |
| 37 | 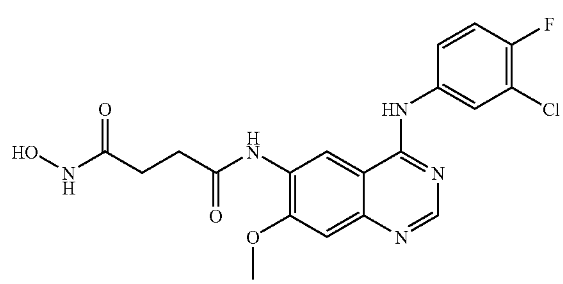 |
| 38 | 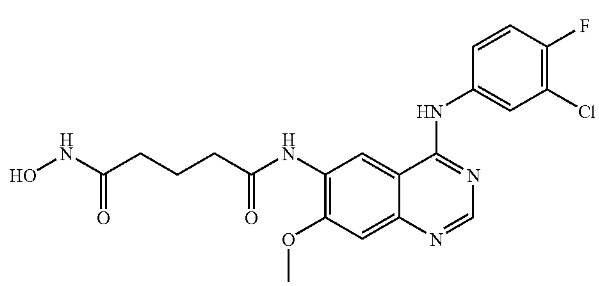 |

TABLE A-continued
| Compound # | Structure |
|---|---|
| 39 | 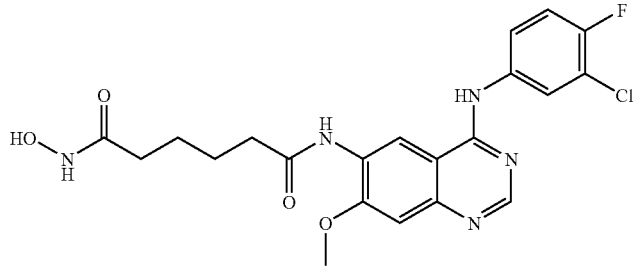 |
| 40 | 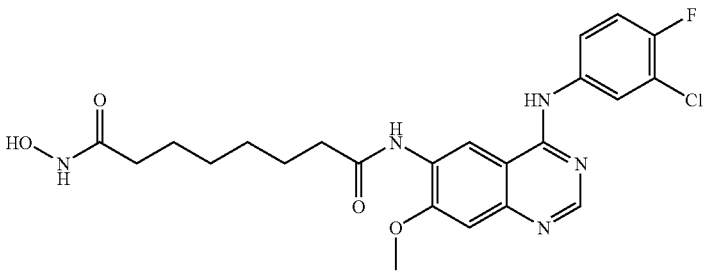 |
| 41 | 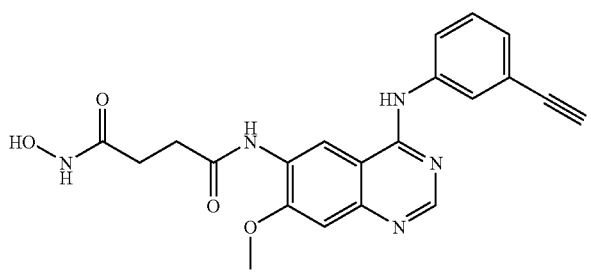 |
| 42 | 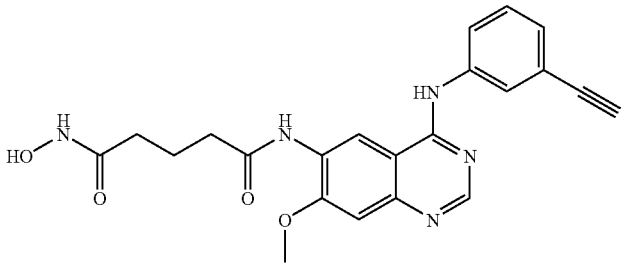 |
| 43 | 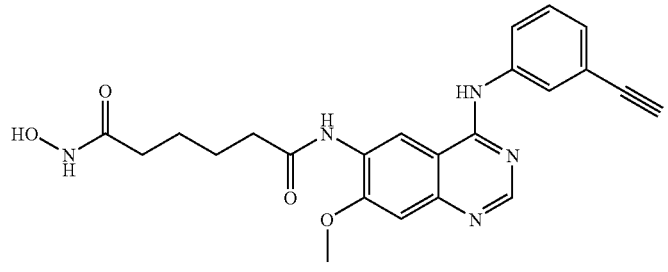 |

TABLE A-continued

| Compound # | Structure |
| --- | --- |
| 44 | 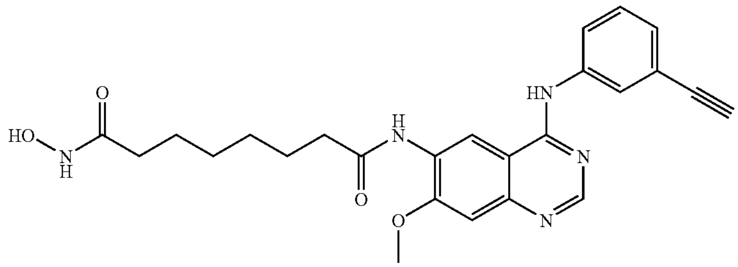 |
| 45 | 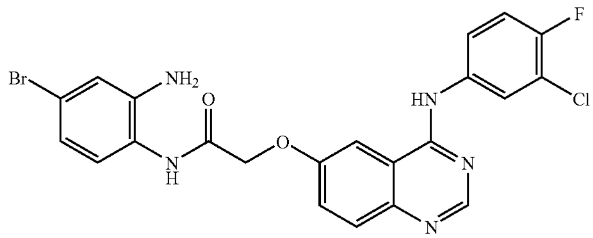 |
| 46 | 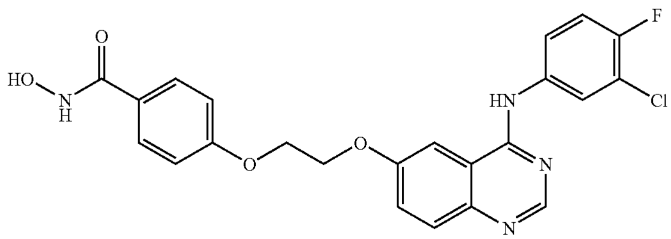 |
| 47 | 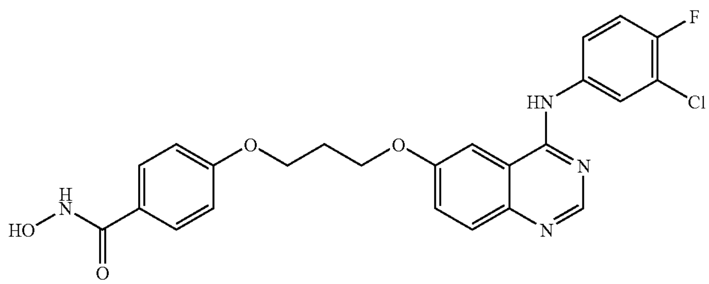 |
| 48 | 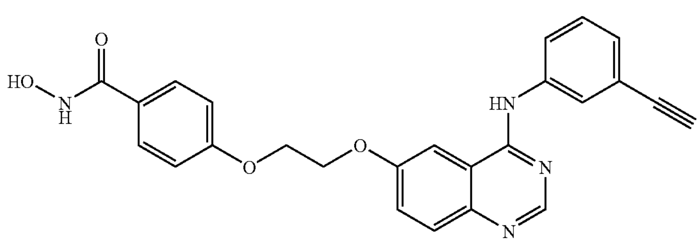 |
| 49 | 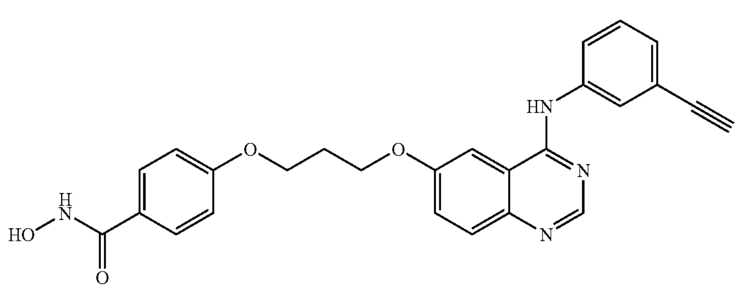 |

TABLE A-continued

| Compound # | Structure |
|---|---|
| 50 | 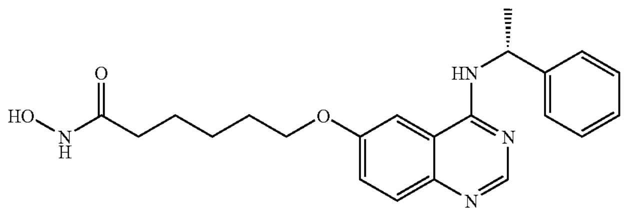 |
| 51 | 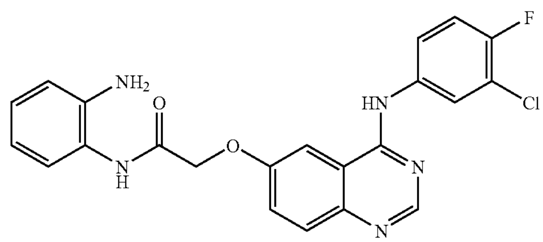 |
| 52 | 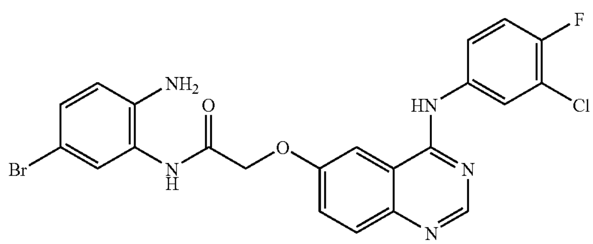 |
| 53 | 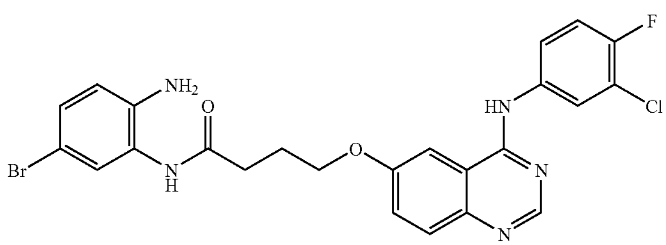 |
| 54 | 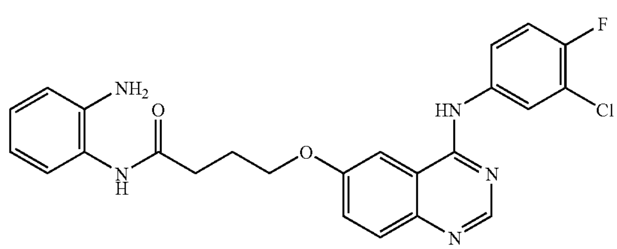 |
| 55 | 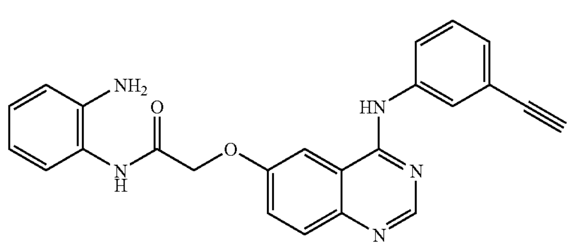 |

TABLE A-continued

| Compound # | Structure |
|---|---|
| 56 | 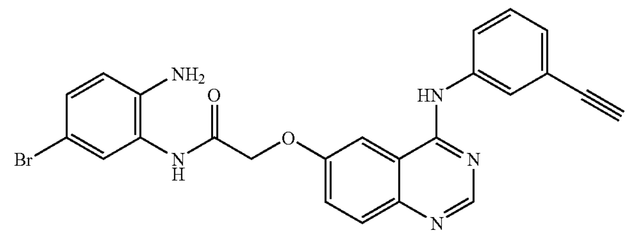 |
| 57 | 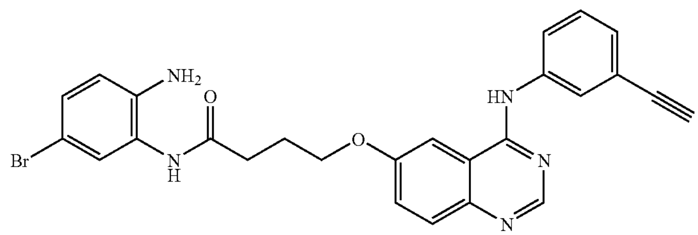 |
| 58 | 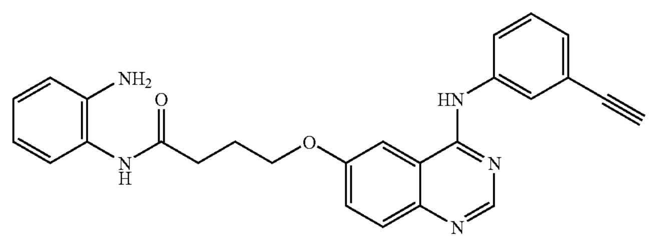 |
| 59 | 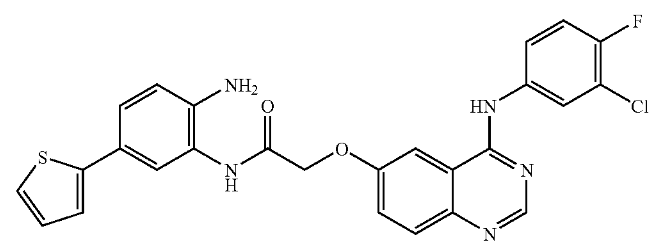 |
| 60 | 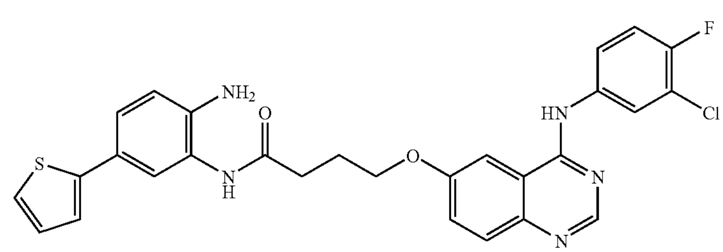 |
| 61 | 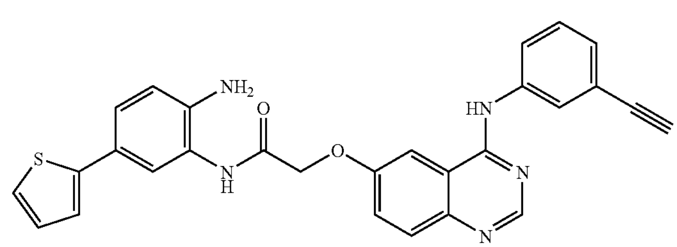 |

TABLE A-continued
| Compound # | Structure |
|---|---|
| 62 | 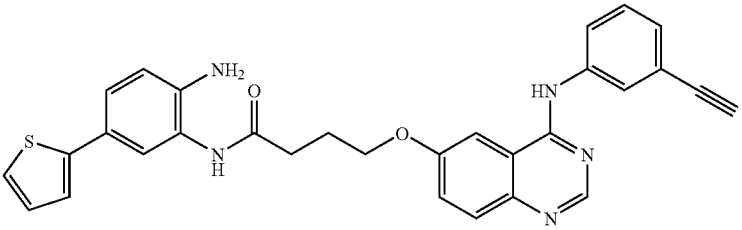 |
| 63 | 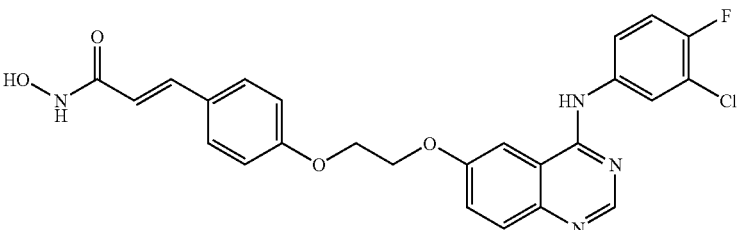 |
| 64 | 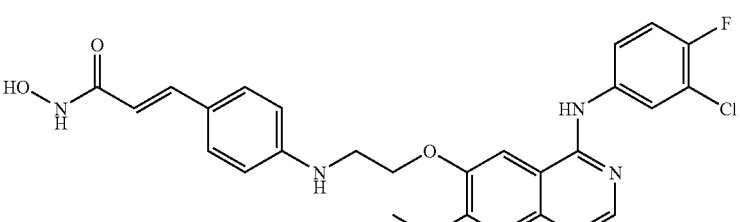 |
| 65 | 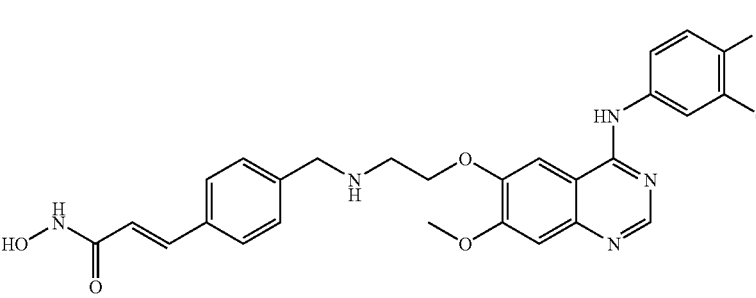 |
| 66 | 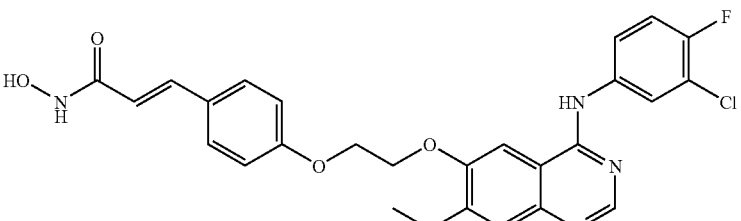 |
| 67 | 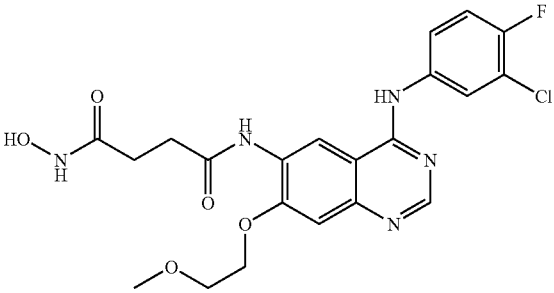 |

TABLE A-continued

| Compound # | Structure |
| --- | --- |
| 68 | 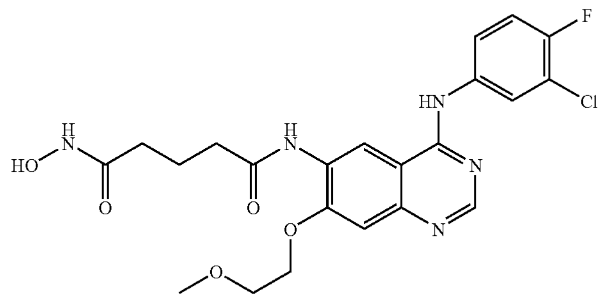 |
| 69 | 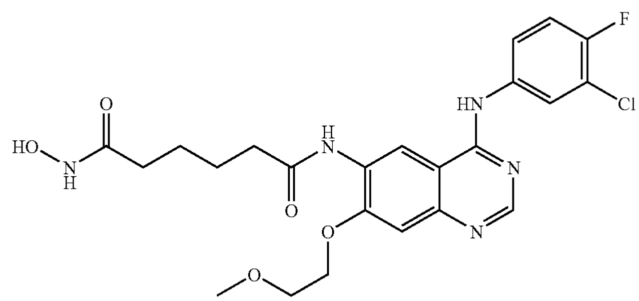 |
| 70 | 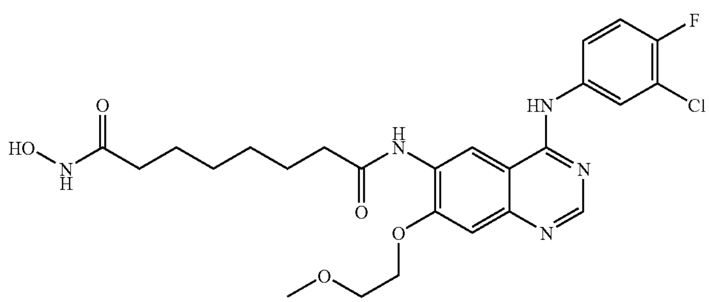 |
| 71 | 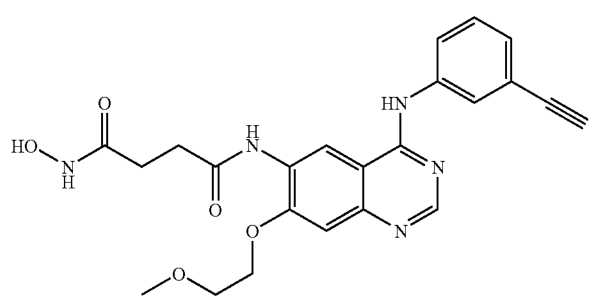 |
| 72 | 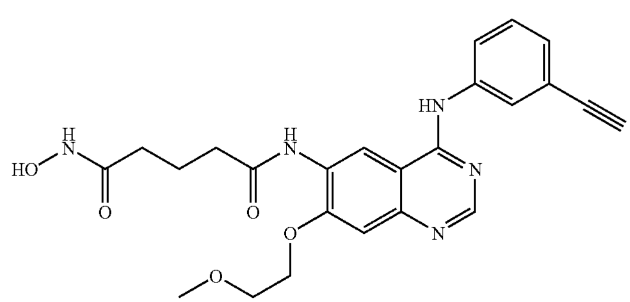 |

TABLE A-continued
| Compound # | Structure |
|---|---|
| 73 | 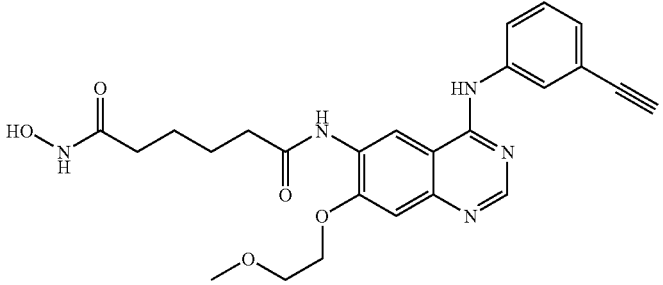 |
| 74 | 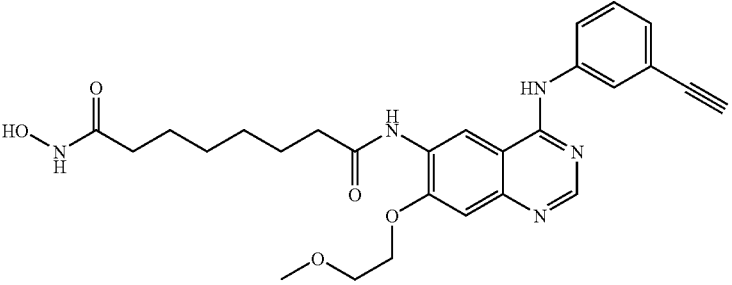 |
| 75 | 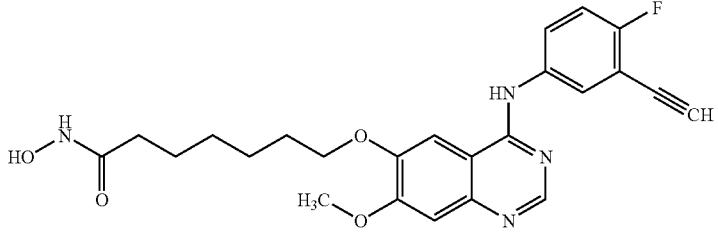 |
| 76 | 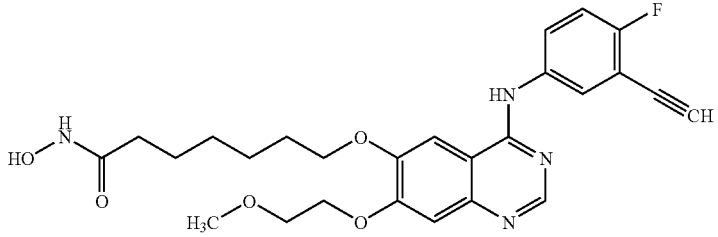 |
| 77 | 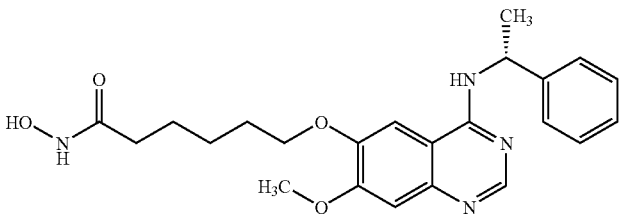 |
| 78 | 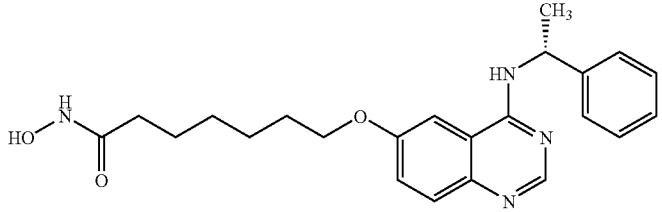 |

TABLE A-continued

| Compound # | Structure |
|---|---|
| 79 | 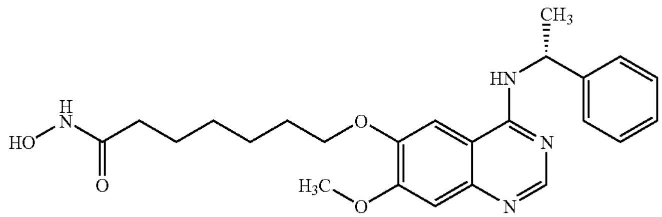 |
| 80 | 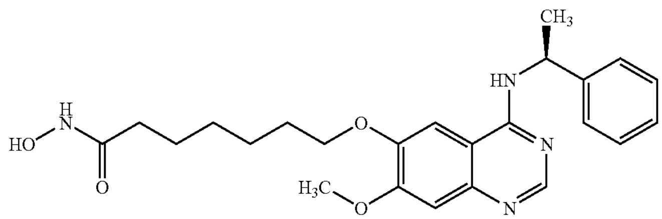 |
| 81 | 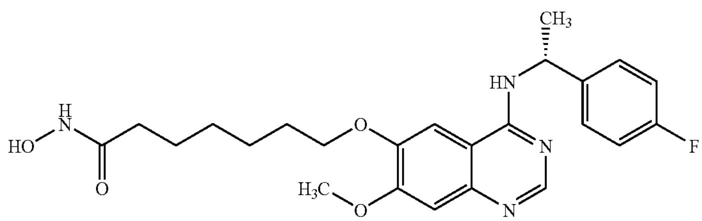 |
| 82 | 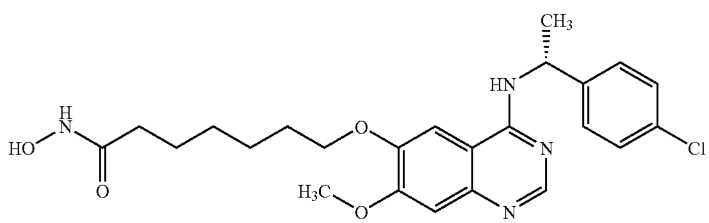 |
| 83 | 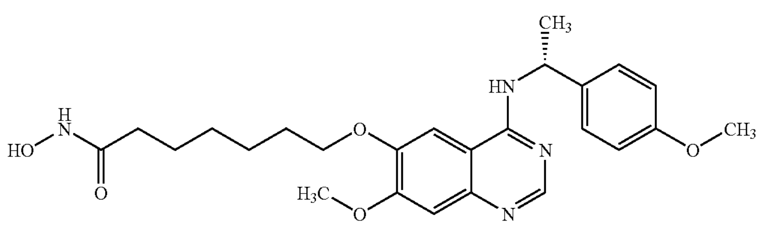 |
| 84 | 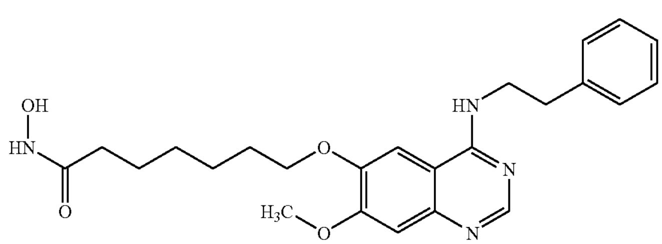 |
| 85 | 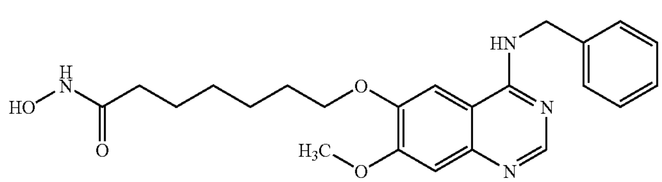 |

TABLE A-continued
| Compound # | Structure |
|---|---|
| 86 | 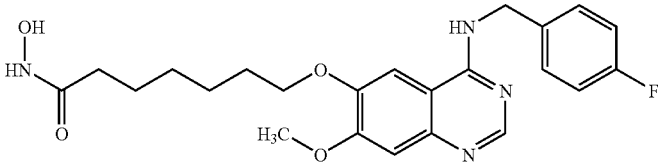 |
| 87 | 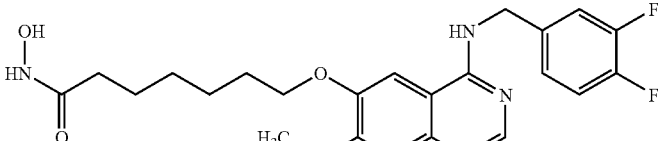 |
| 88 | 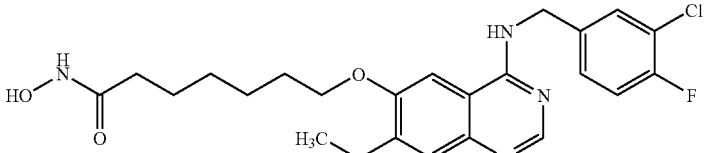 |
| 89 | 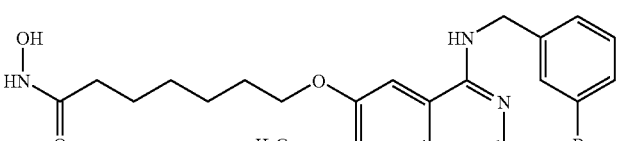 |
| 90 | 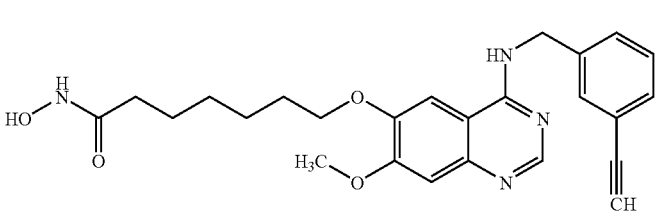 |
| 91 | 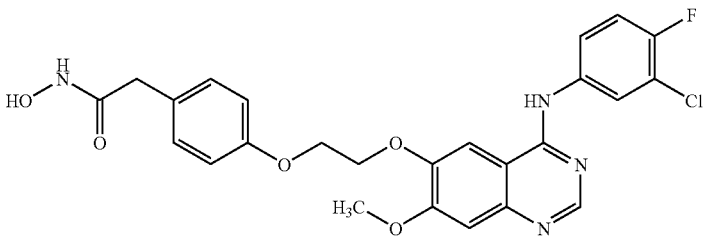 |
| 92 | 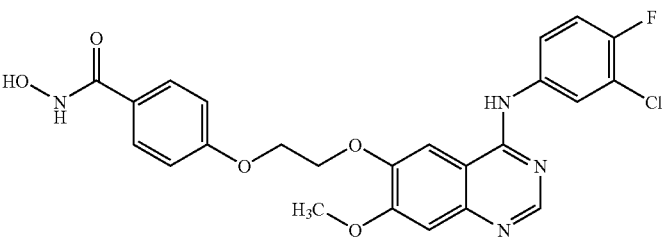 |

TABLE A-continued

| Compound # | Structure |
|---|---|
| 93 | 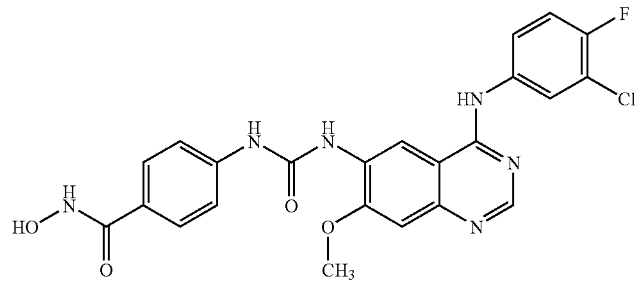 |
| 94 | 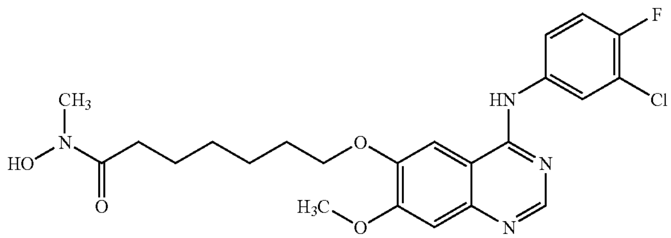 |
| 95 | 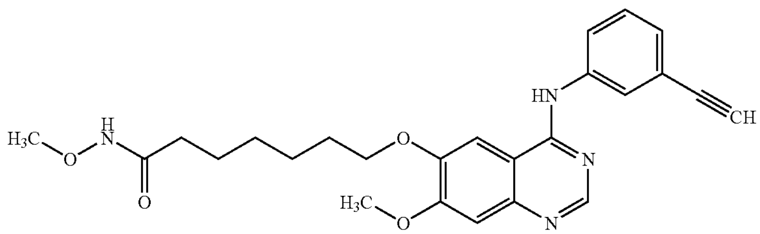 |
| 96 | 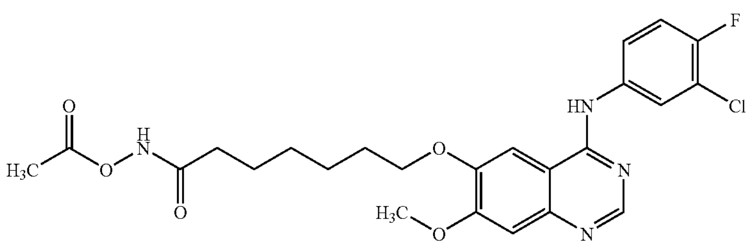 |
| 97 | 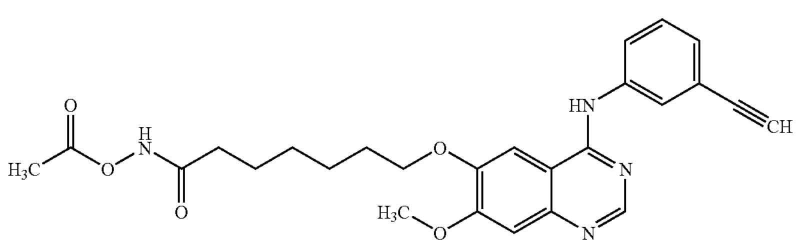 |
| 98 | 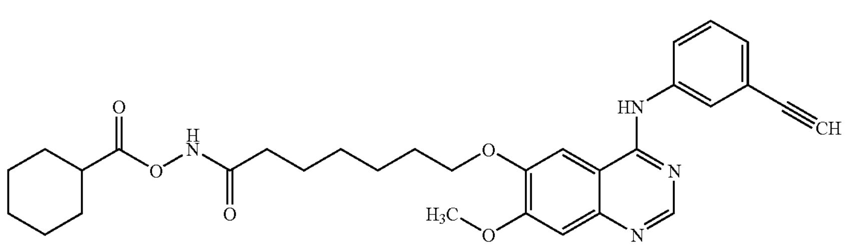 |

TABLE A-continued
| Compound # | Structure |
| --- | --- |
| 99 | 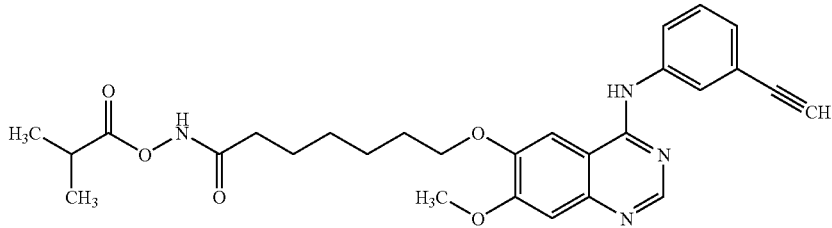 |
| 100 | 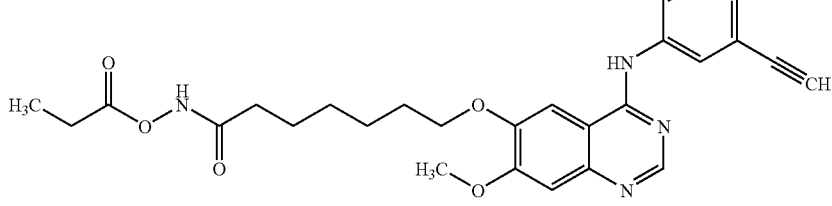 |
| 101 | 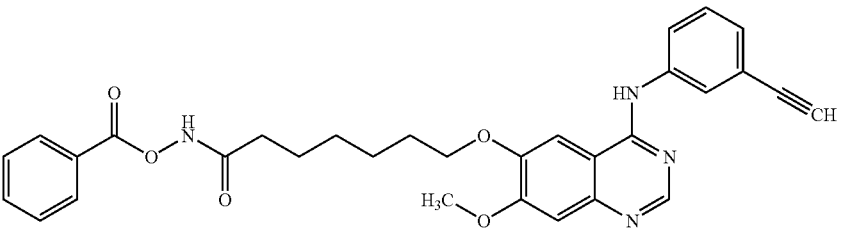 |
| 102 | 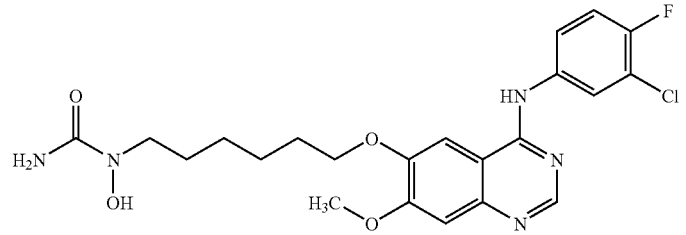 |
| 103 | 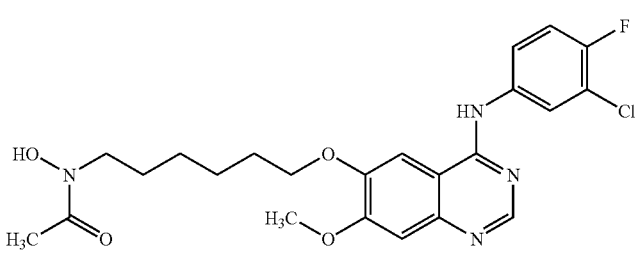 |
| 104 | 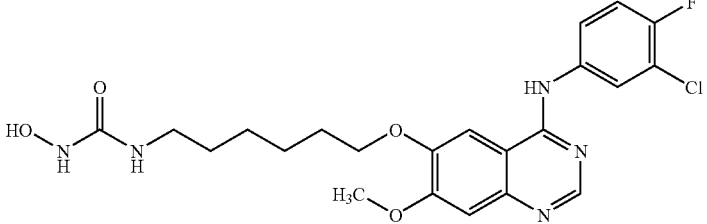 |

TABLE A-continued

| Compound # | Structure |
|---|---|
| 105 | 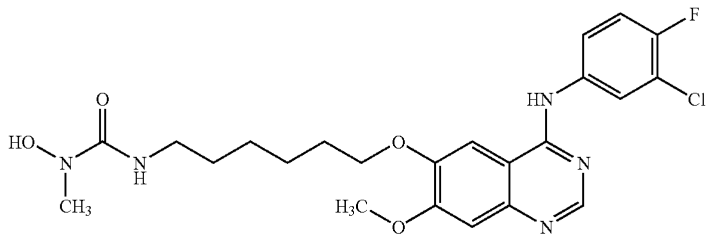 |
| 106 | 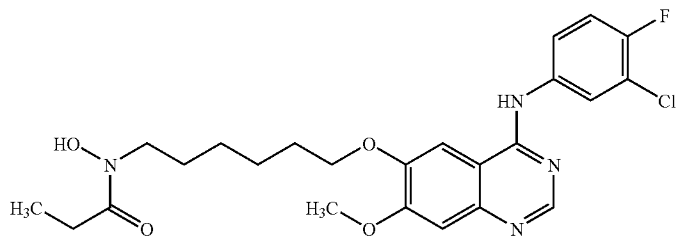 |
| 107 | 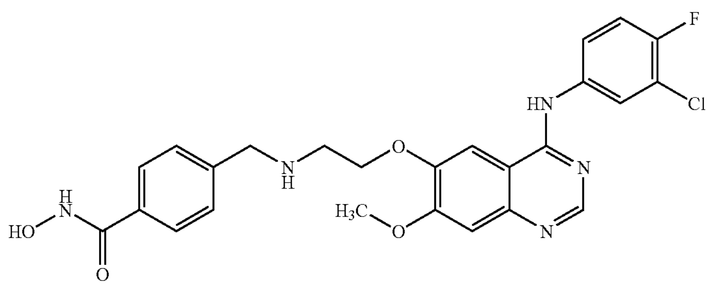 |
| 108 | 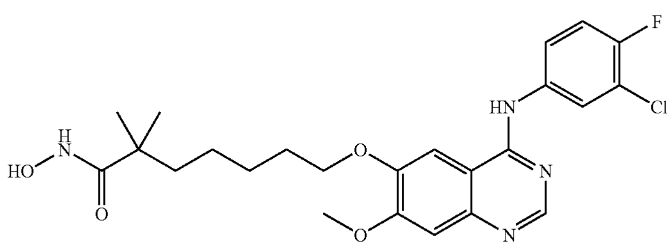 |
| 109 | 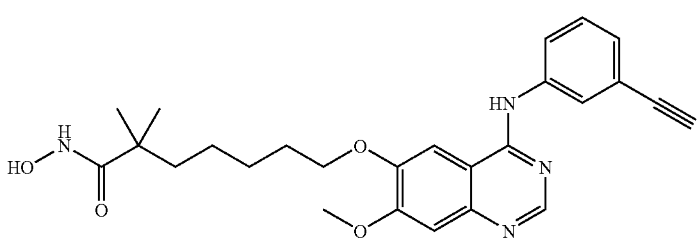 |
| 110 | 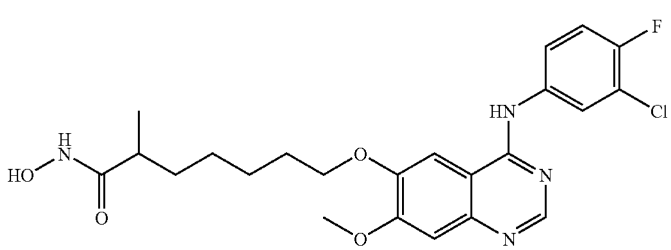 |

TABLE A-continued

| Compound # | Structure |
|---|---|
| 111 | 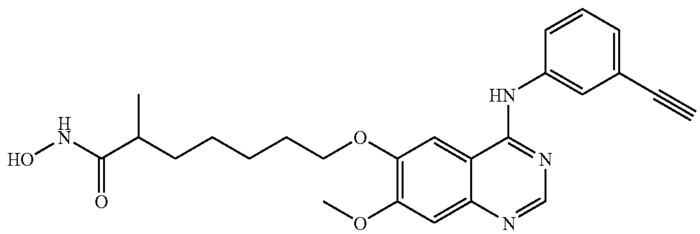 |
| 112 | 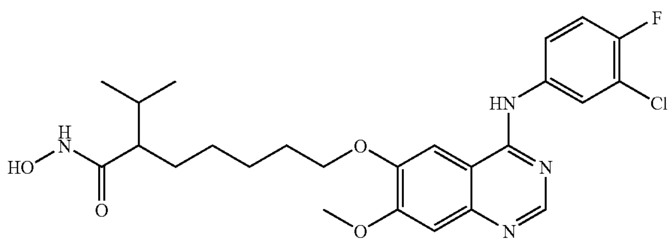 |
| 113 | 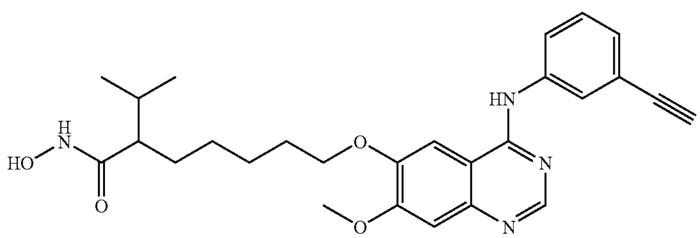 |
| 114 | 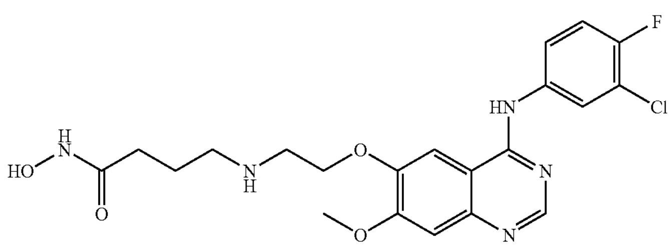 |
| 115 | 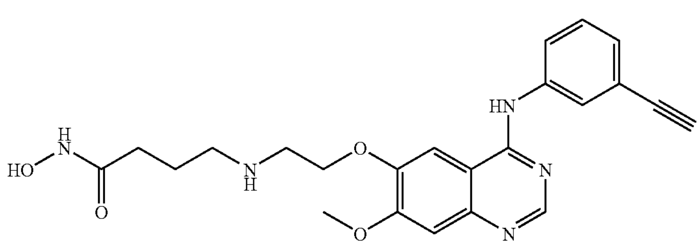 |
| 116 | 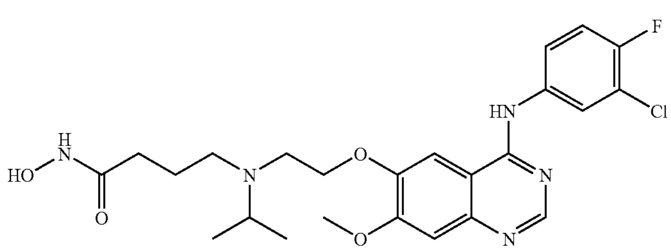 |

TABLE A-continued

| Compound # | Structure |
| --- | --- |
| 117 | 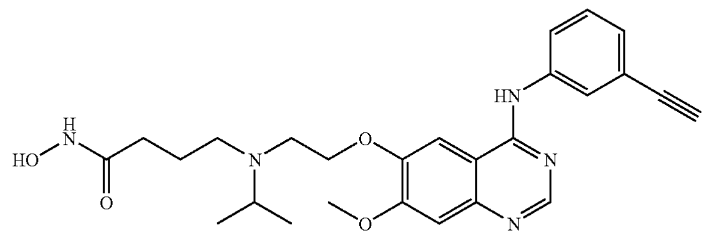 |
| 118 | 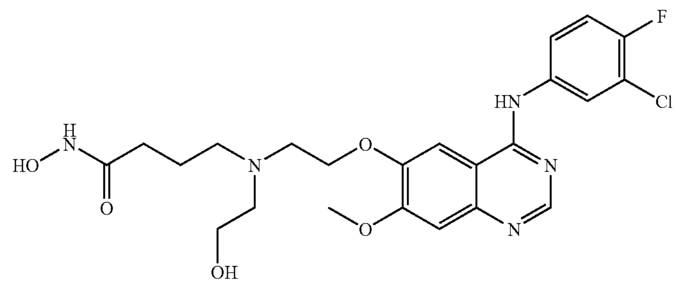 |
| 119 | 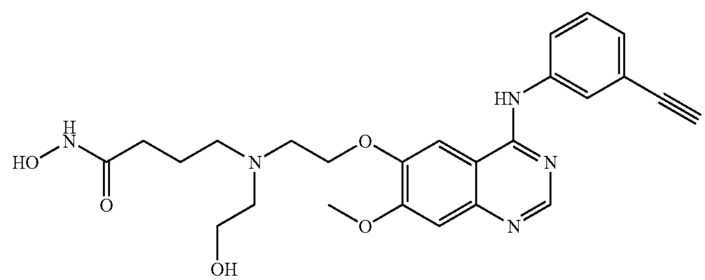 |
| 120 | 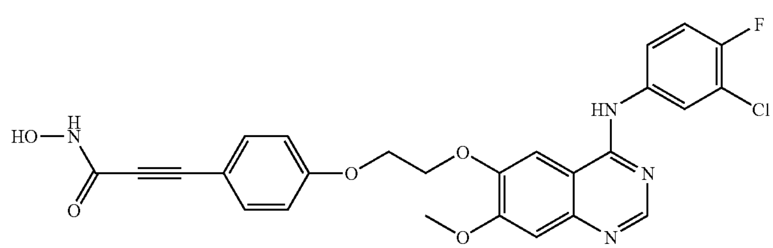 |
| 121 | 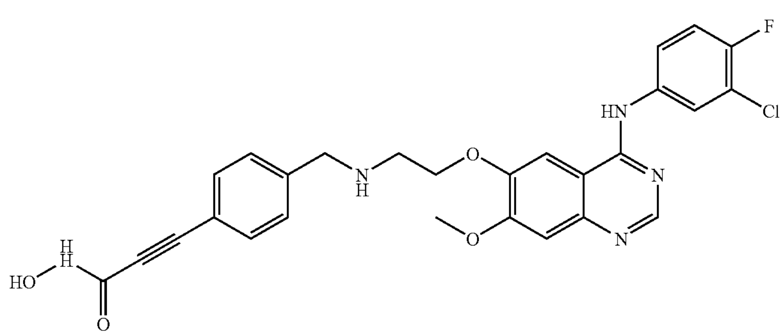 |

TABLE A-continued
| Compound # | Structure |
|---|---|
| 122 | 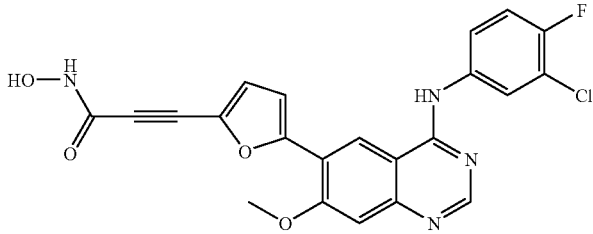 |
| 123 | 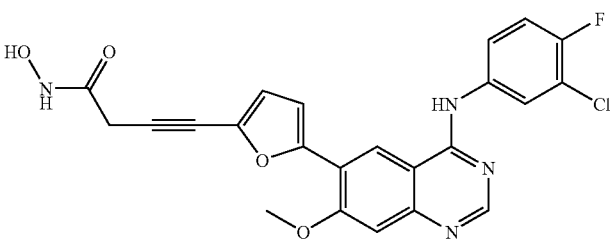 |
| 124 | 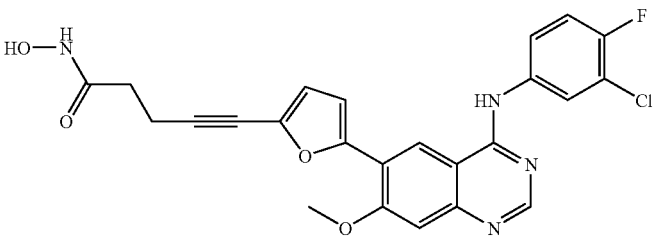 |
| 125 | 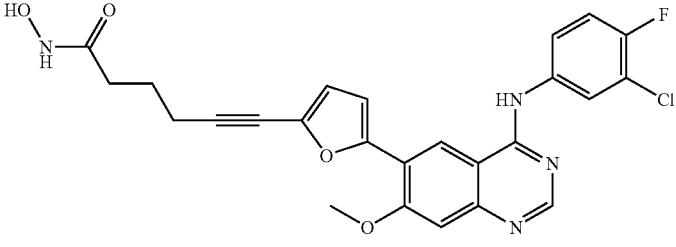 |
| 126 | 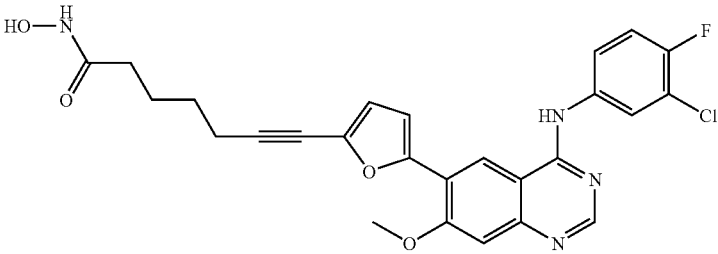 |
| 127 | 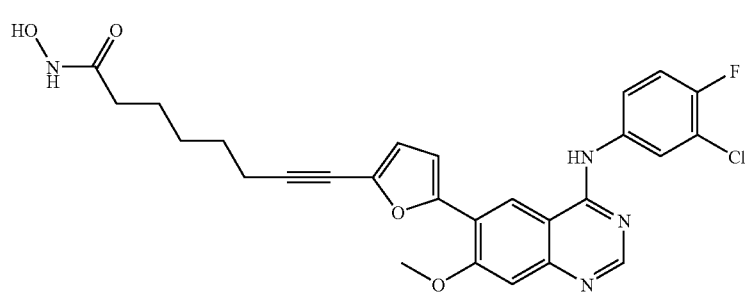 |

TABLE A-continued
| Compound # | Structure |
|---|---|
| 128 | 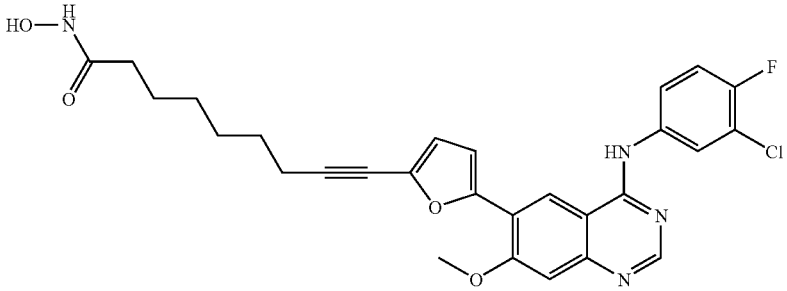 |
| 129 | 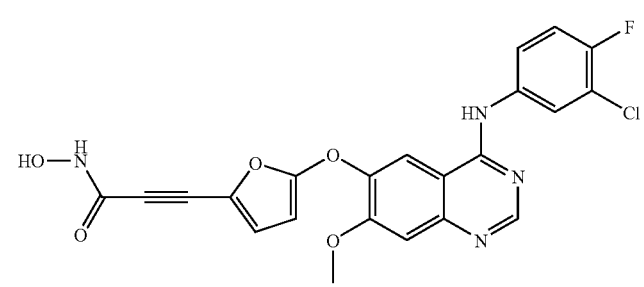 |
| 130 | 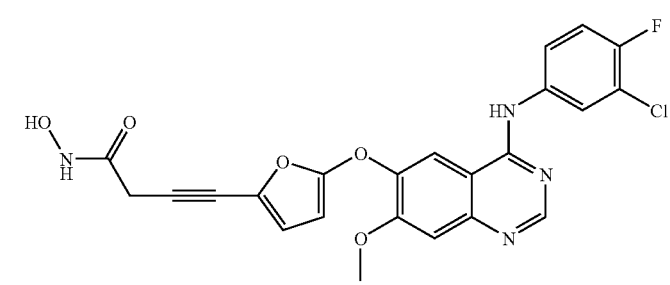 |
| 131 | 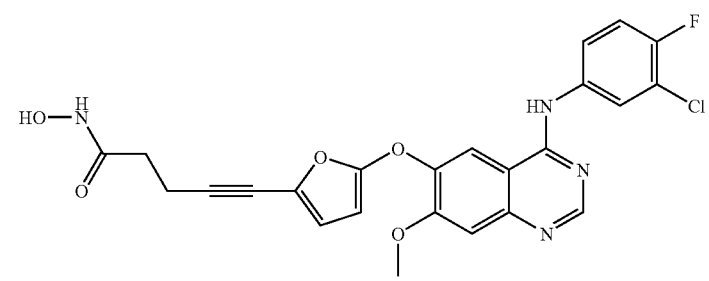 |
| 132 | 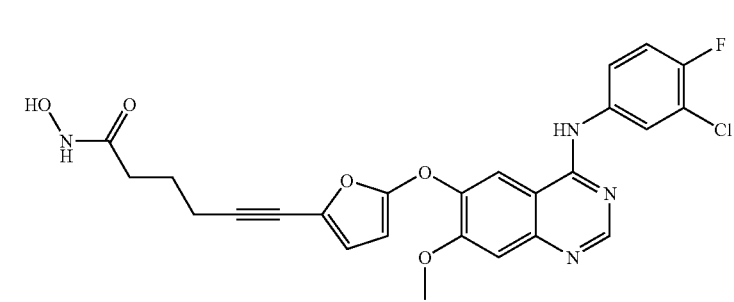 |

TABLE A-continued
| Compound # | Structure |
|---|---|
| 133 | 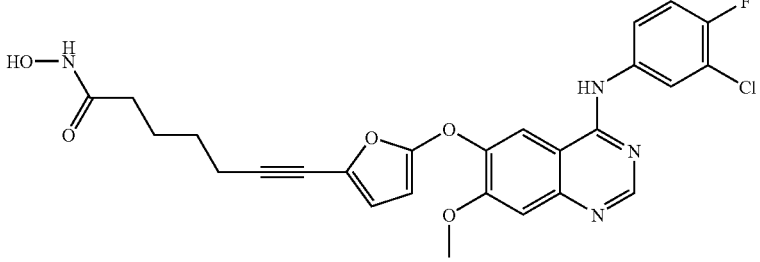 |
| 134 | 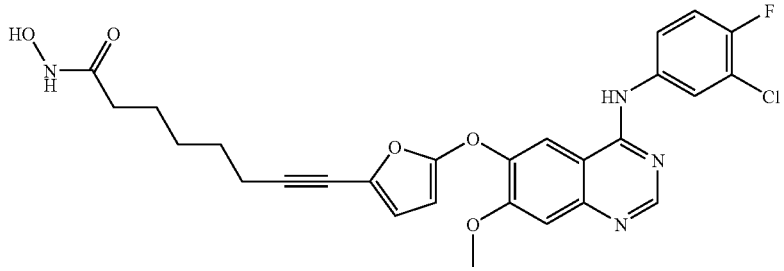 |
| 135 | 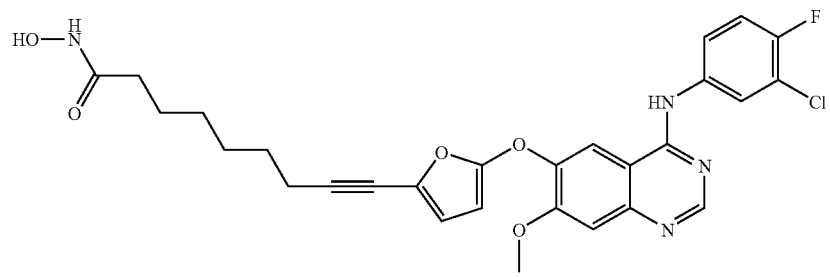 |
| 136 | 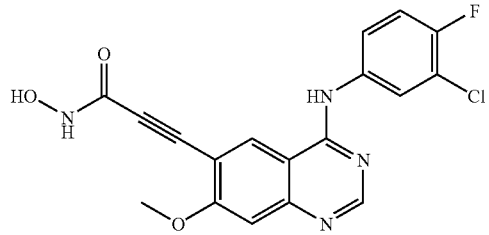 |
| 137 | 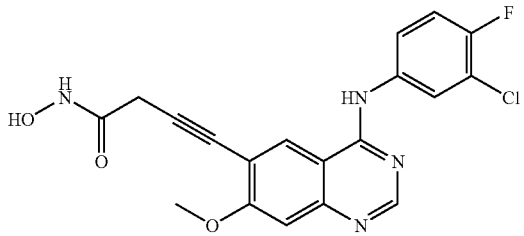 |
| 138 | 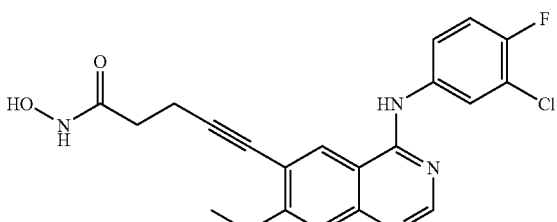 |

TABLE A-continued
| Compound # | Structure |
|---|---|
| 139 | 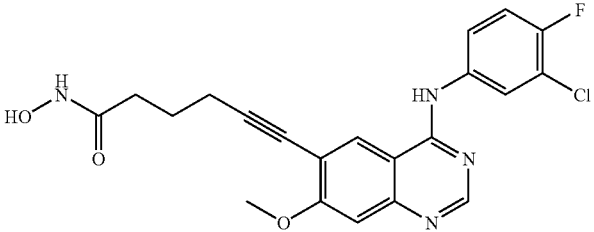 |
| 140 | 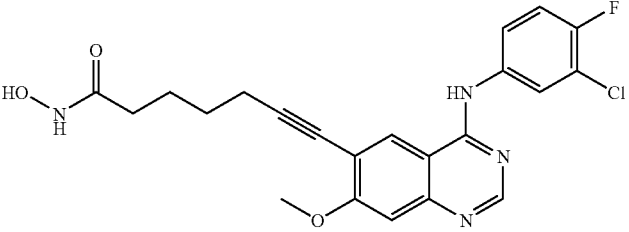 |
| 141 | 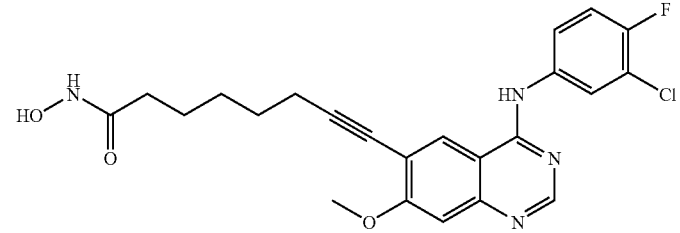 |
| 142 | 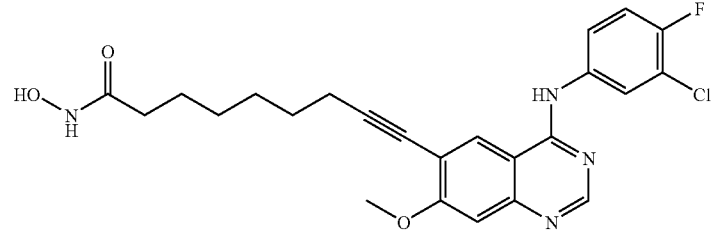 |
| 143 | 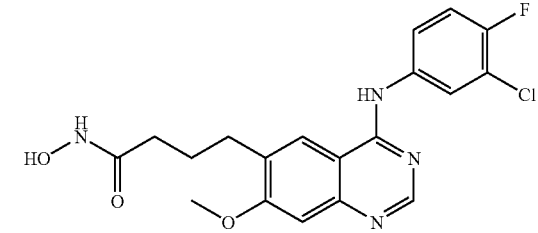 |
| 144 | 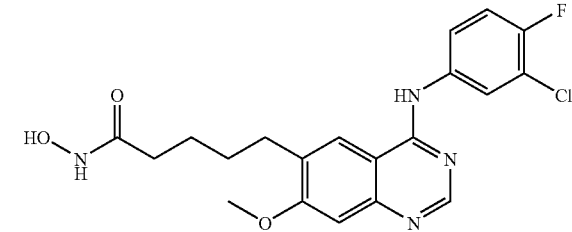 |

TABLE A-continued

| Compound # | Structure |
|---|---|
| 145 | *structure: 4-(3-chloro-4-fluoroanilino)-7-methoxyquinazoline with 6-(5-(hydroxycarbamoyl)pentyl) substituent* |
| 146 | *structure: 4-(3-chloro-4-fluoroanilino)-7-methoxyquinazoline with 6-(6-(hydroxycarbamoyl)hexyl) substituent* |
| 147 | *structure: 4-(3-chloro-4-fluoroanilino)-7-methoxyquinazoline with 6-(7-(hydroxycarbamoyl)heptyl) substituent* |
| 148 | *structure: 4-(3-chloro-4-fluoroanilino)-7-methoxyquinazoline with 6-(8-(hydroxycarbamoyl)octyl) substituent* |
| 149 | *structure: 4-(3-chloro-4-fluoroanilino)-7-methoxyquinazoline with 6-(S-linked 3-(hydroxycarbamoyl)propyl thio) substituent* |
| 150 | *structure: 4-(3-chloro-4-fluoroanilino)-7-methoxyquinazoline with 6-(SO₂-linked 3-(hydroxycarbamoyl)propyl sulfonyl) substituent* |

TABLE A-continued

| Compound # | Structure |
|---|---|
| 151 | 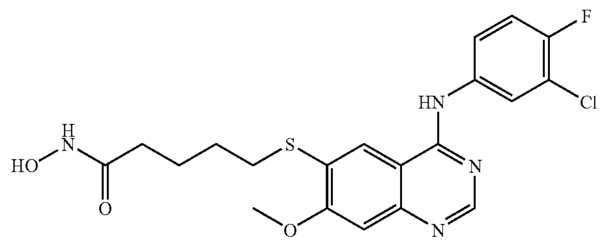 |
| 152 | 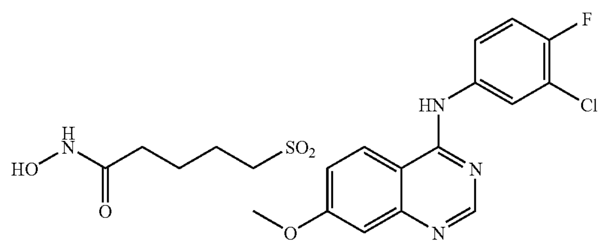 |
| 153 | 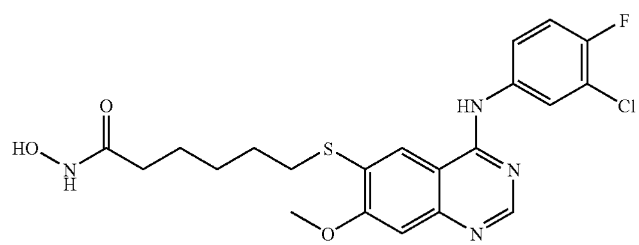 |
| 154 | 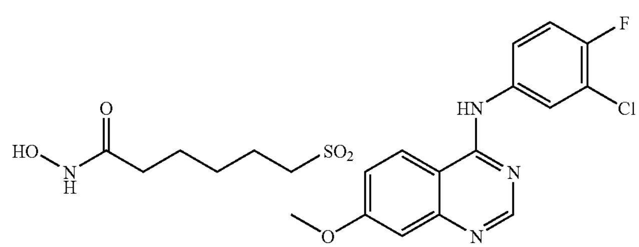 |
| 155 | 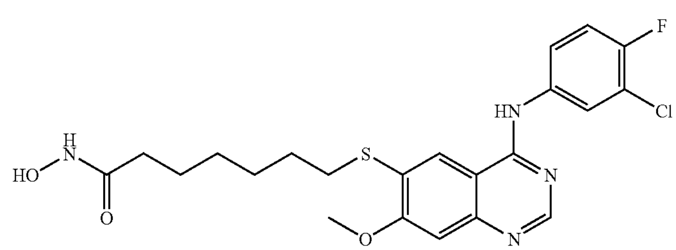 |
| 156 | 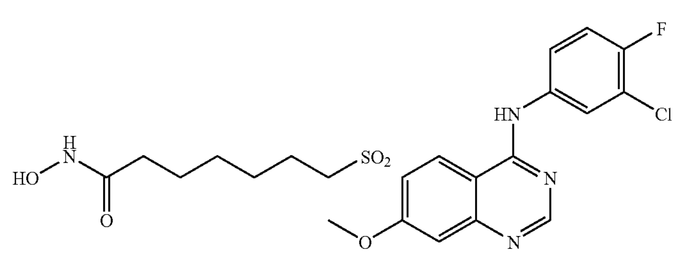 |

TABLE A-continued
| Compound # | Structure |
|---|---|
| 157 | 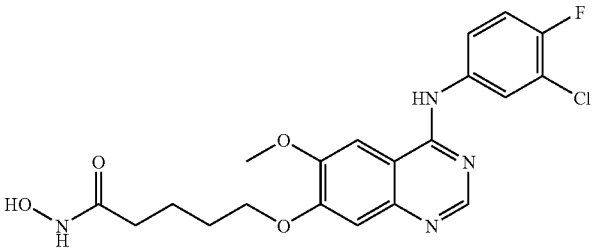 |
| 158 | 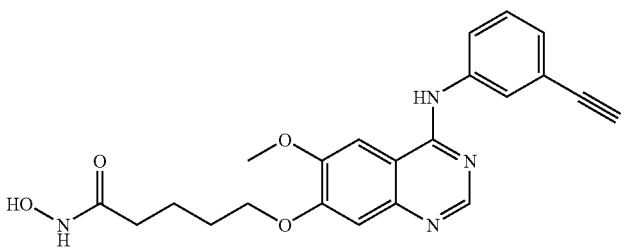 |
| 159 | 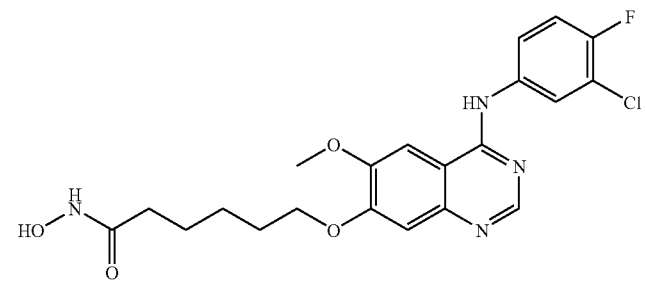 |
| 160 | 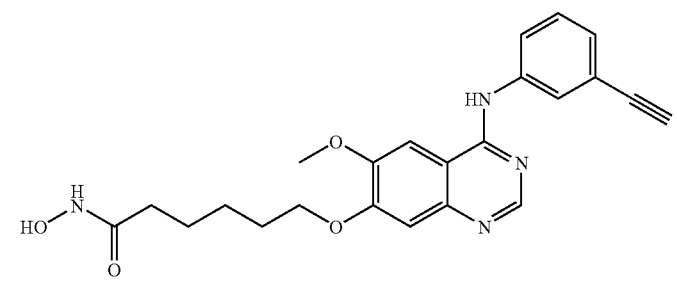 |
| 161 | 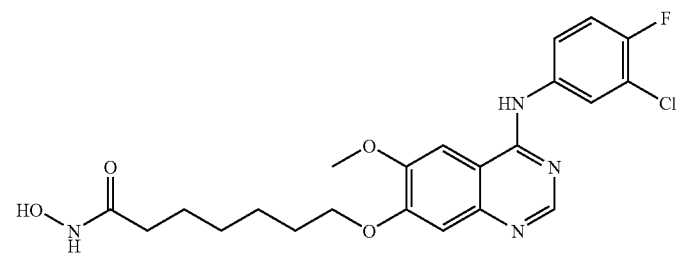 |
| 162 | 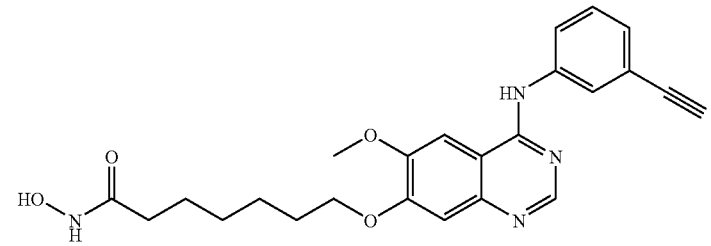 |

TABLE A-continued

| Compound # | Structure |
|---|---|
| 163 | 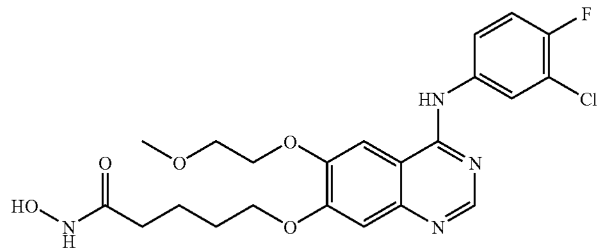 |
| 164 | 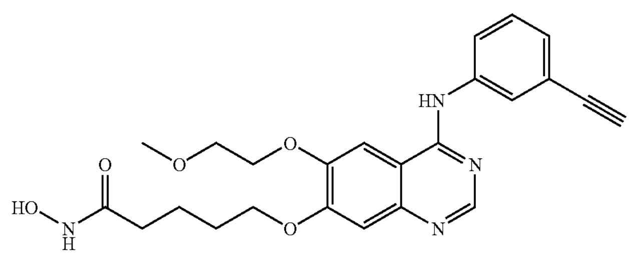 |
| 165 | 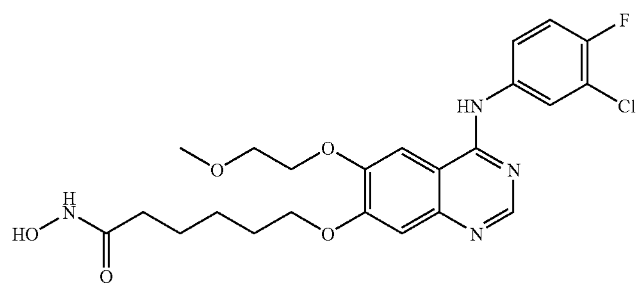 |
| 166 | 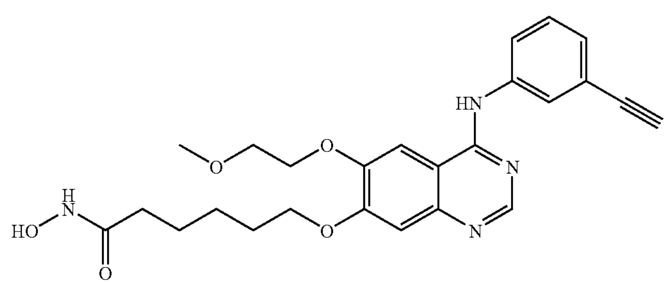 |
| 167 | 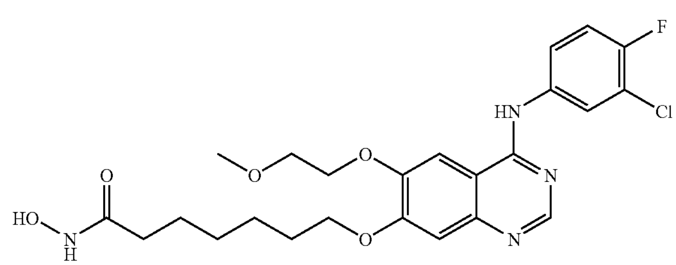 |

TABLE A-continued
| Compound # | Structure |
|---|---|
| 168 | 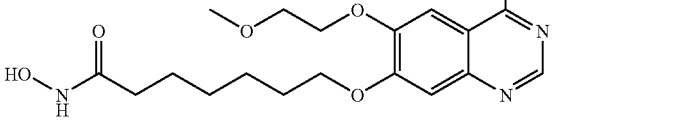 |
| 169 | 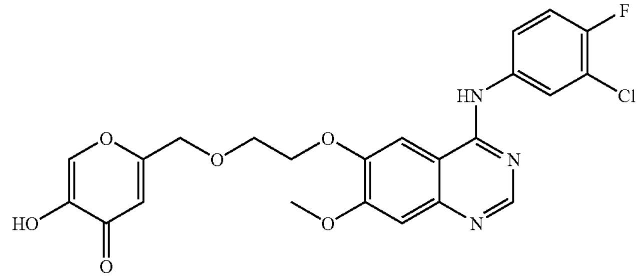 |
| 170 | 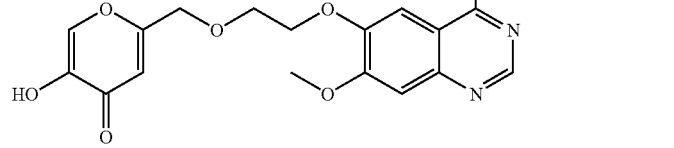 |
| 171 | 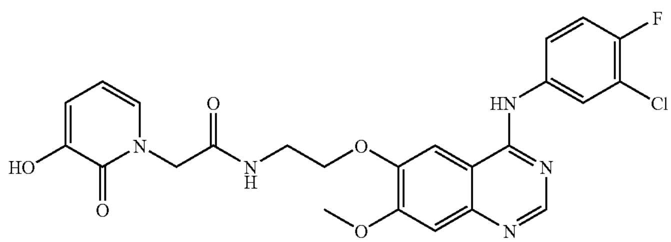 |
| 172 | 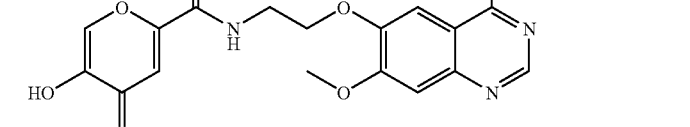 |
| 173 | 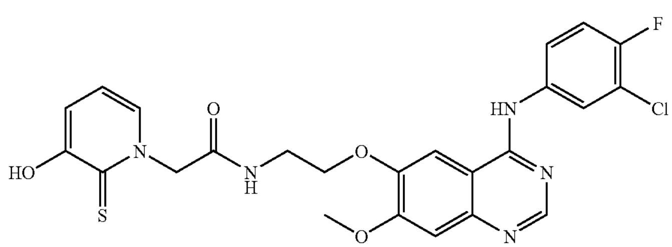 |

TABLE A-continued
| Compound # | Structure |
|---|---|
| 174 | 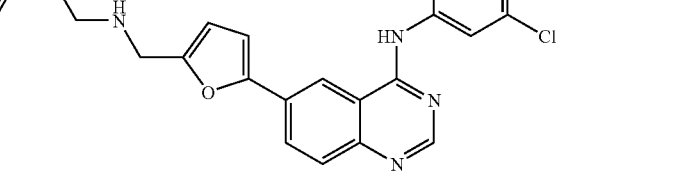 |
| 175 | 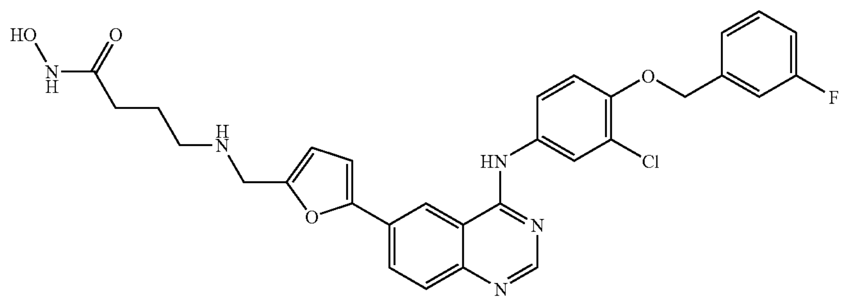 |
| 176 | 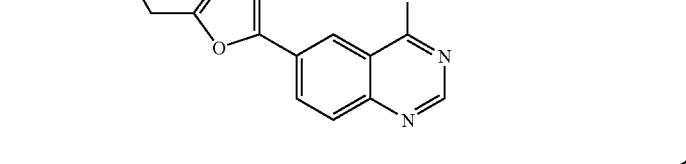 |
| 177 | 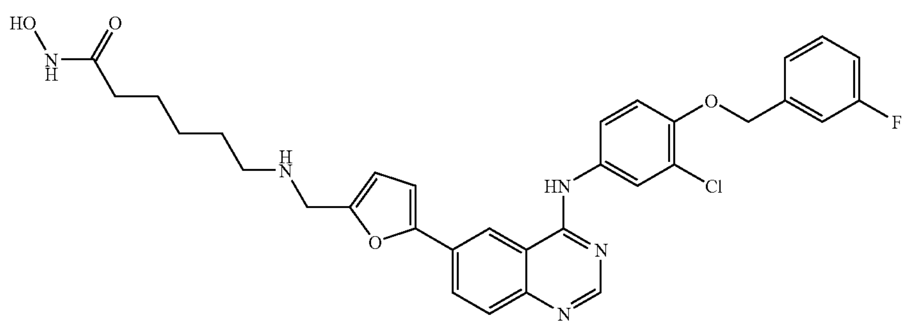 |
| 178 | 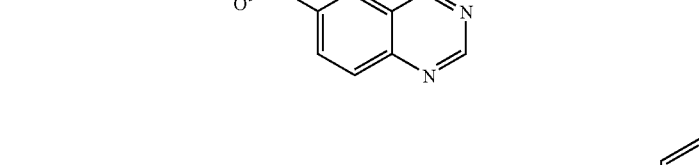 |

TABLE A-continued

| Compound # | Structure |
|---|---|
| 179 | 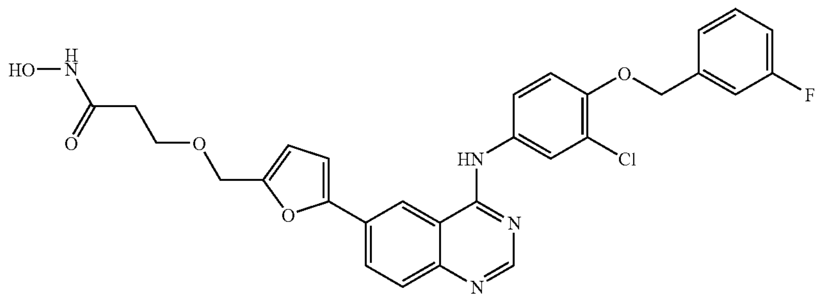 |
| 180 | 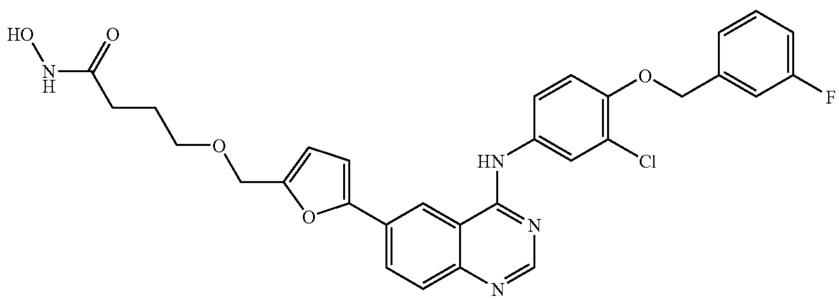 |
| 181 | 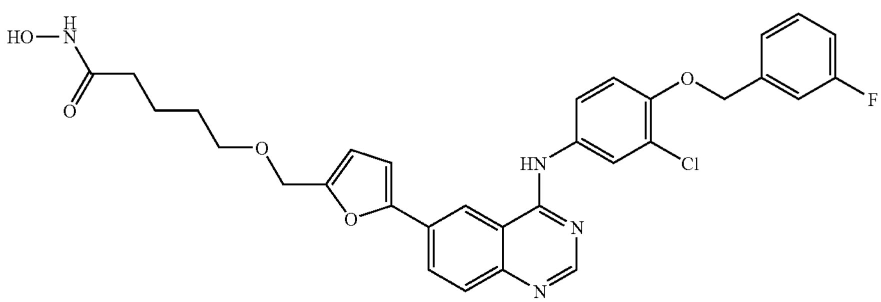 |
| 182 | 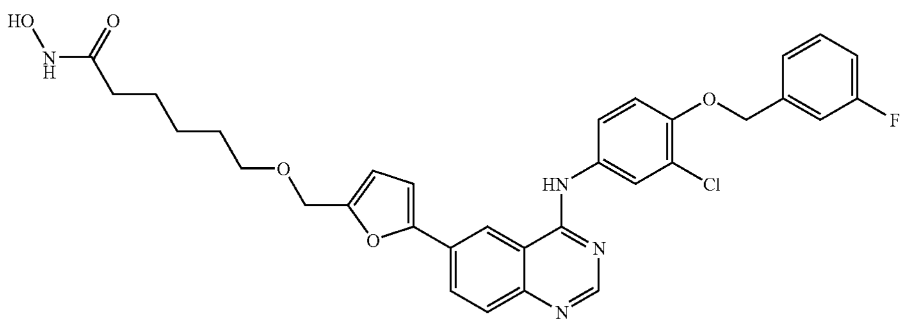 |
| 183 | 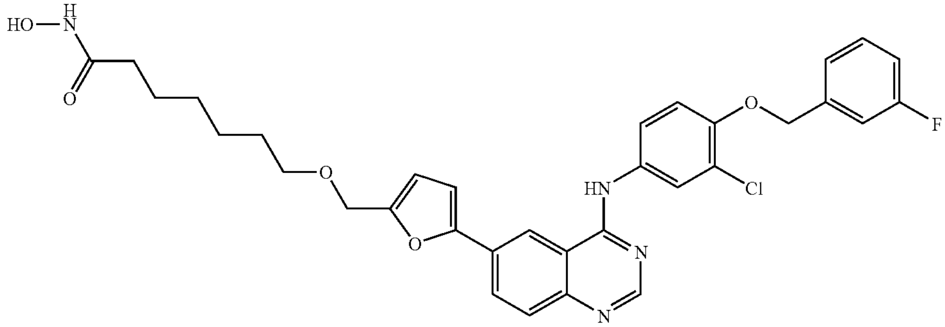 |

TABLE A-continued

| Compound # | Structure |
|---|---|
| 184 | 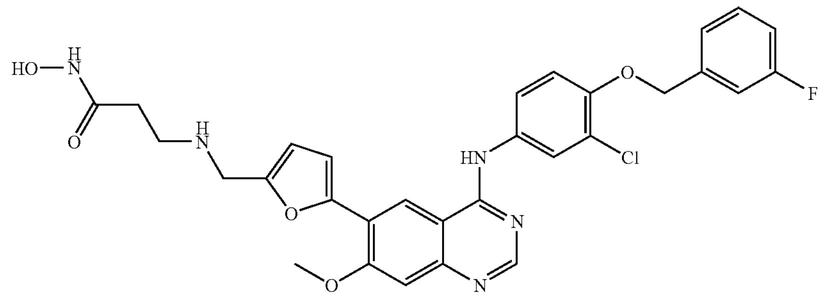 |
| 185 | 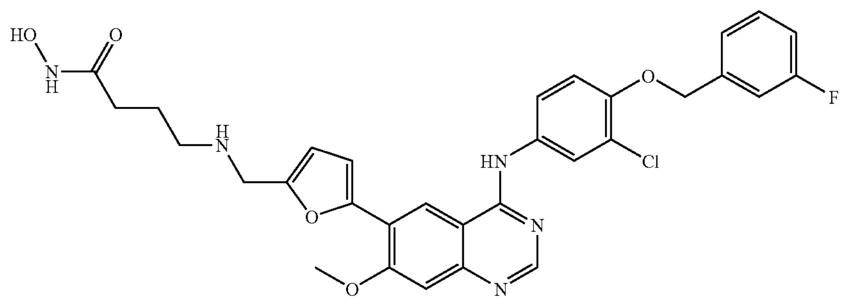 |
| 186 | 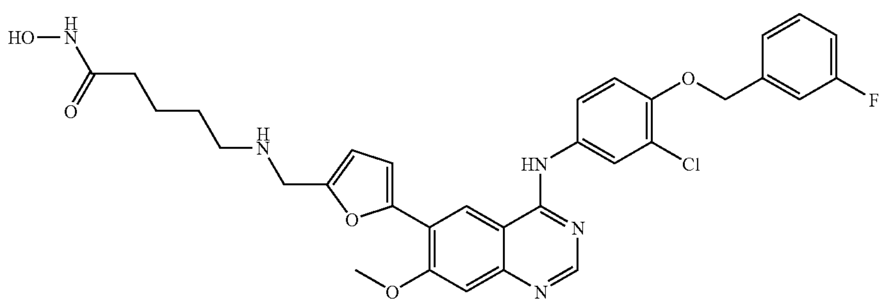 |
| 187 | 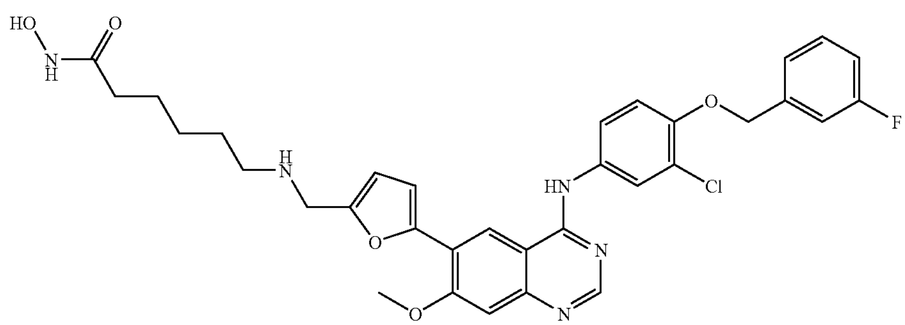 |
| 188 | 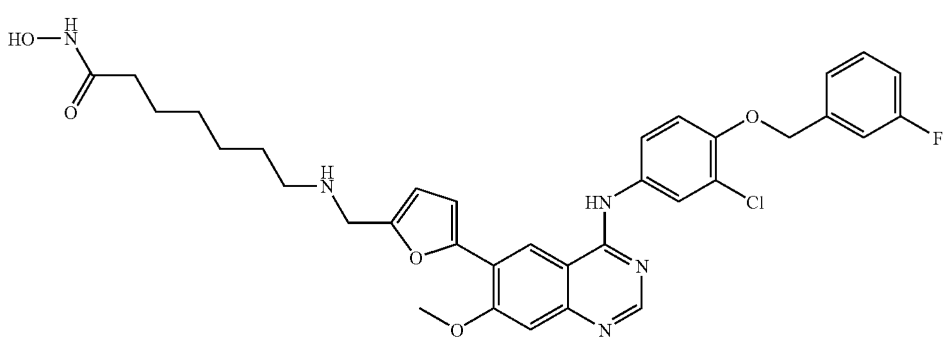 |

TABLE A-continued

| Compound # | Structure |
|---|---|
| 189 | 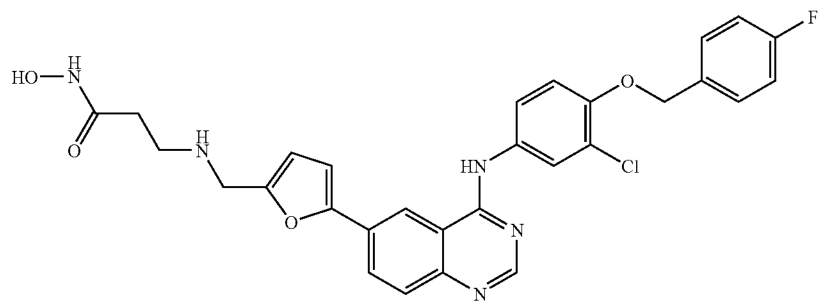 |
| 190 | 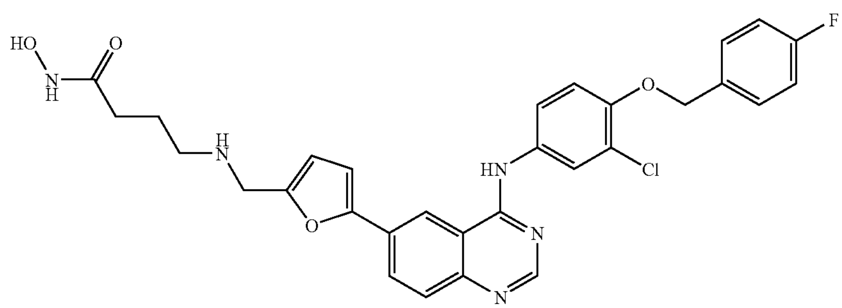 |
| 191 | 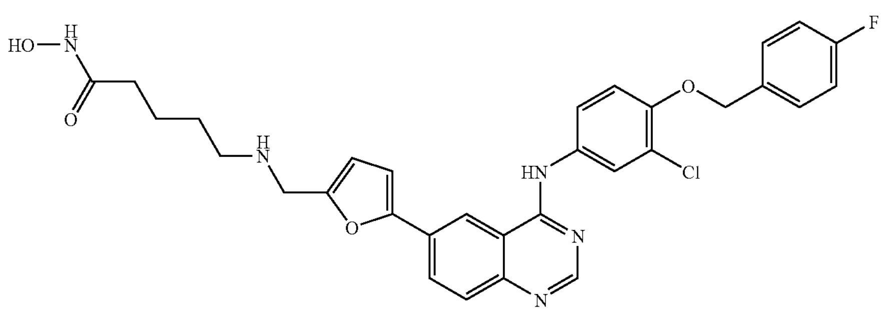 |
| 192 | 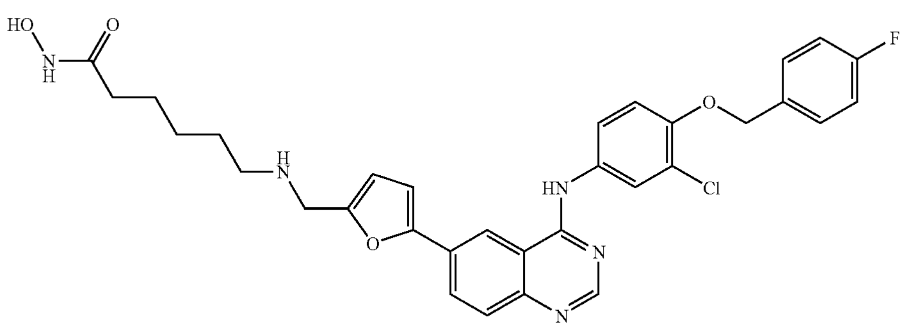 |
| 193 | 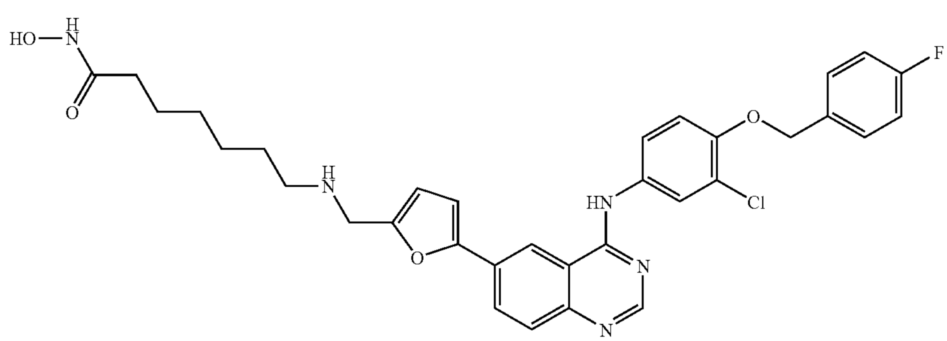 |

TABLE A-continued
| Compound # | Structure |
|---|---|
| 194 | 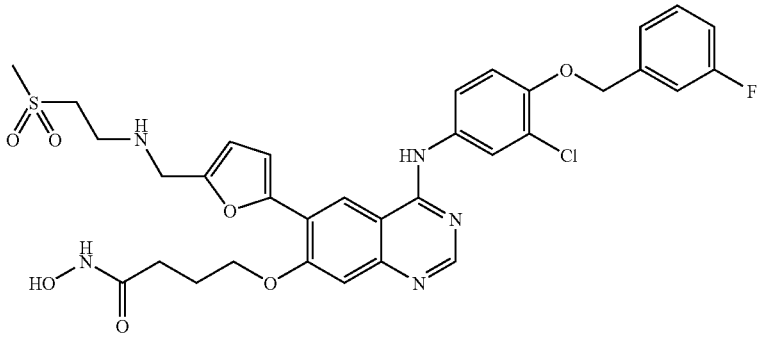 |
| 195 | 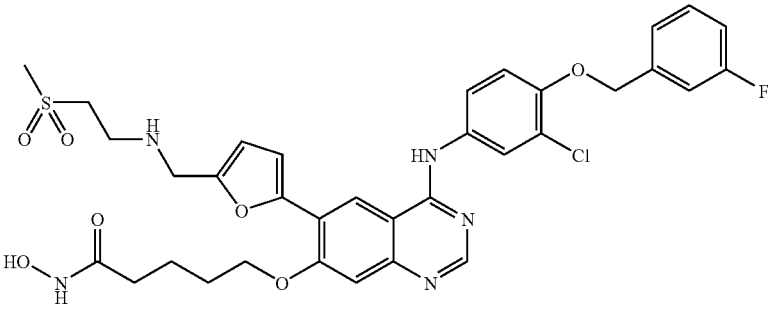 |
| 196 | 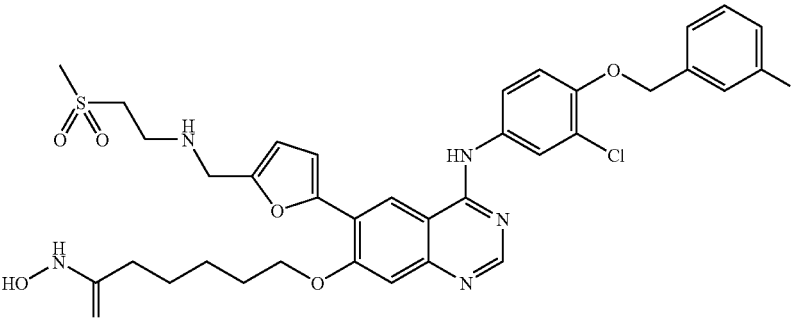 |
| 197 | 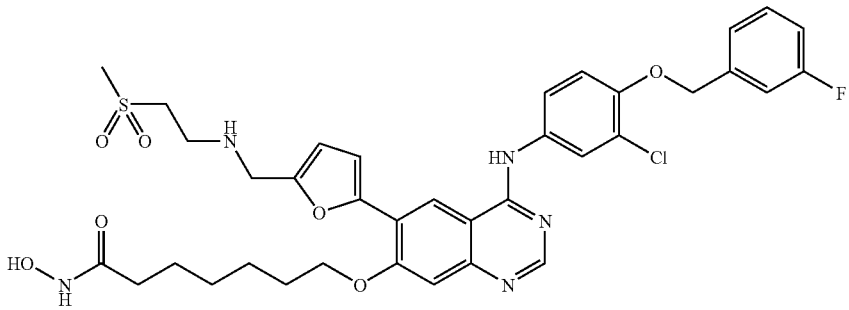 |

TABLE A-continued
| Compound # | Structure |
|---|---|
| 198 | 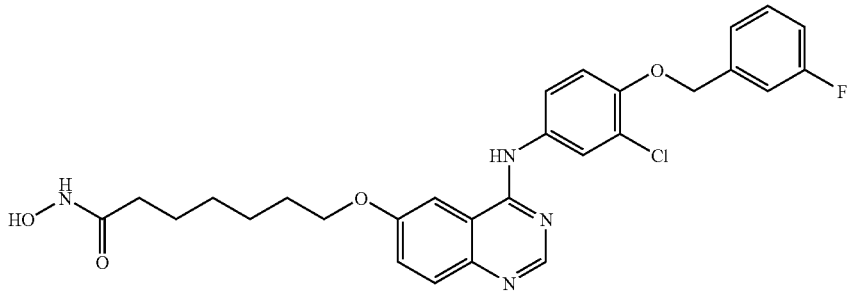 |
| 199 | 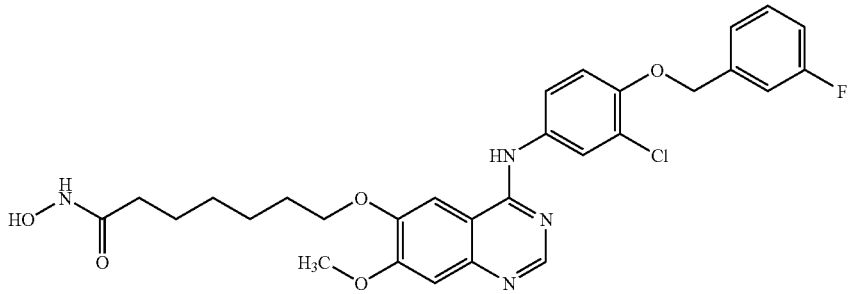 |
| 200 | 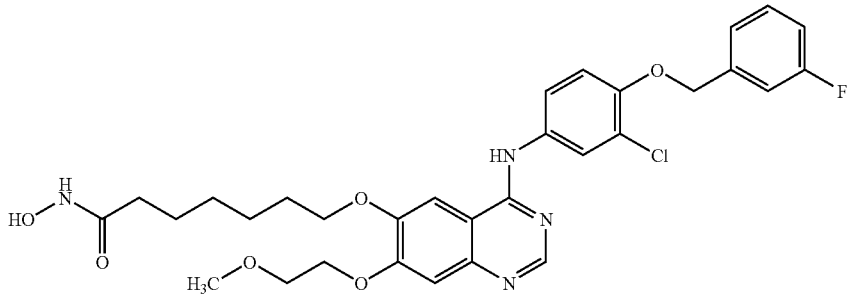 |
| 201 | 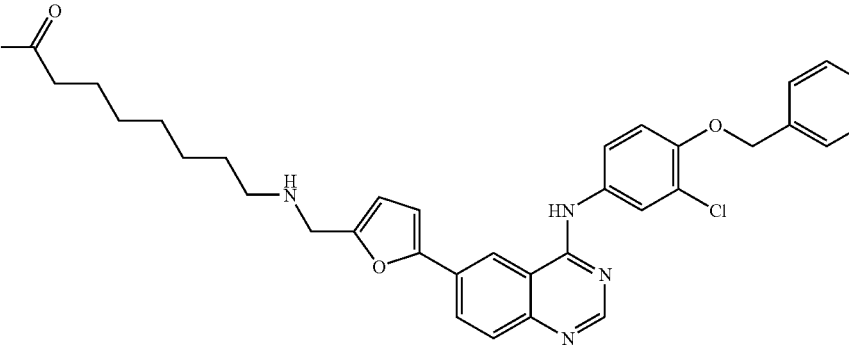 |
| 202 | 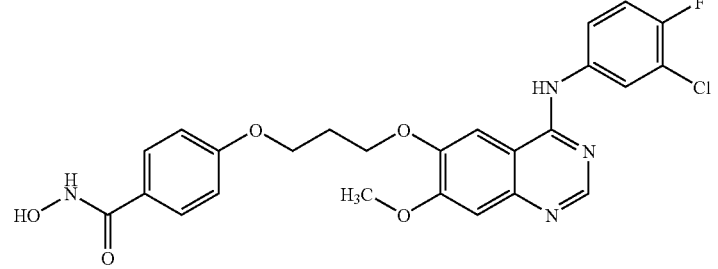 |

TABLE A-continued
| Compound # | Structure |
|---|---|
| 203 | 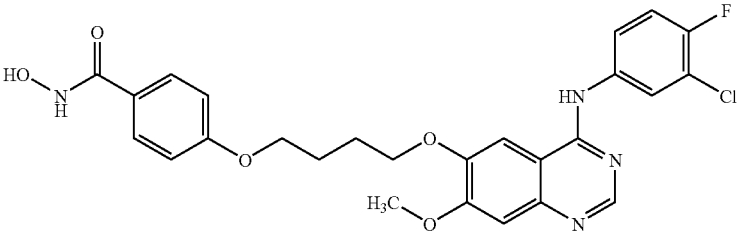 |
| 204 | 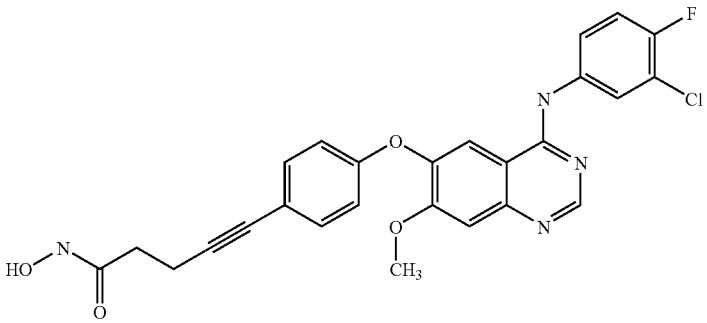 |
| 205 | 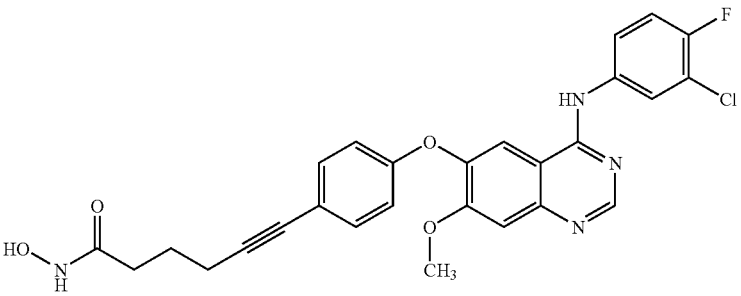 |
| 206 | 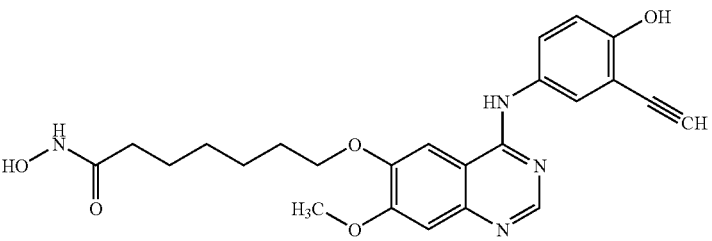 |
| 207 | 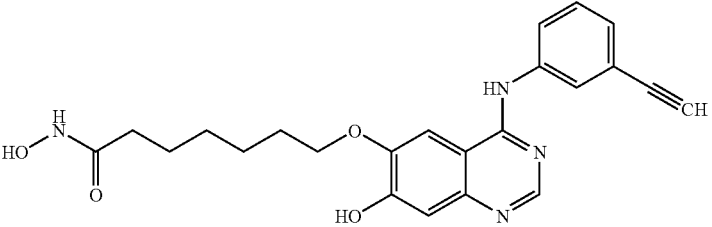 |

TABLE A-continued

| Compound # | Structure |
|---|---|
| 208 | 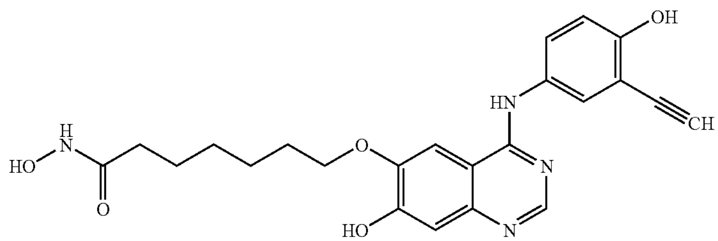 |
| 209 | 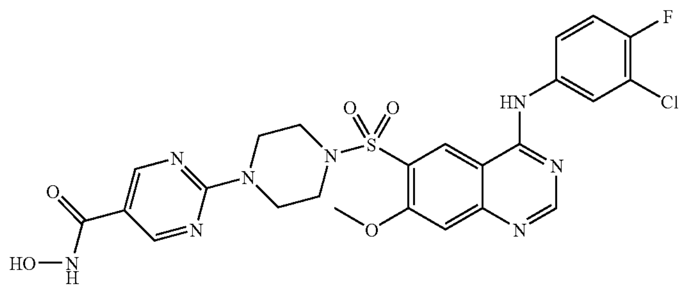 |
| 210 | 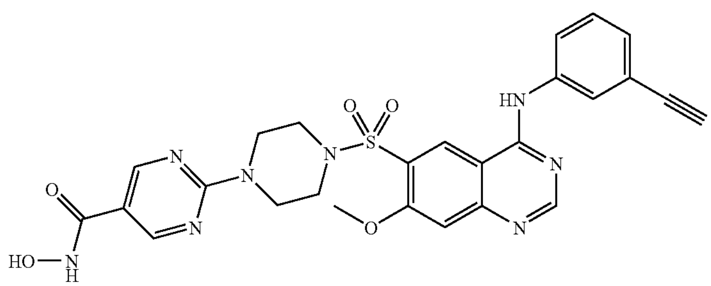 |
| 211 | 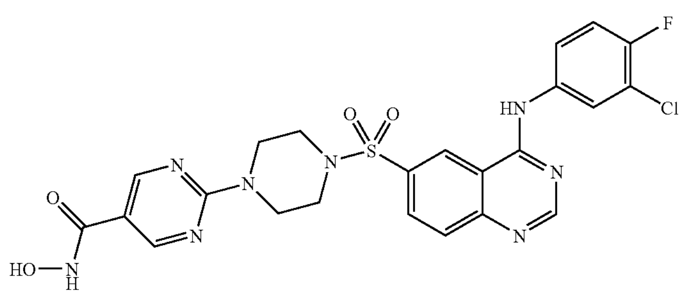 |
| 212 | 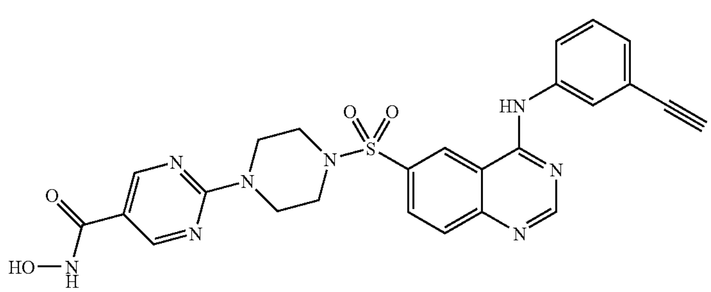 |

In a particularly preferred embodiment, the invention relates to a tartrate salt or complex of compound 12 or 18 shown in Table A above. In yet another embodiment, the invention relates to a tartrate salt of or complexes with compound 12. In an additional embodiment, the invention is an L-tartrate salt of or complexes with compound 12.

The tartrate salts of the invention include the L-tartrate (L-(R,R)-(+)-tartrate), D-tartrate (D-((S,S)-(−)-tartrate), D,L-tartrate and meso-tartrate (2R,3S-tartrate) salts. In another embodiment, the tartrate salt is an anhydrous salt. In a further embodiment, the tartrate salt is a hydrate salt. The term "hydrate" includes but is not limited to hemihydrate, monohydrate, dihydrate, trihydrate and the like.

In a further embodiment, the invention pertains to an L-tartrate salt of or complexes with a compound represented by Formulae I, II, III or IV. In yet another embodiment, the invention is an L-tartrate salt of or complexes with a compound selected from the compounds 1-197 shown in Table A above. In an additional embodiment, the invention is an L-tartrate salt of or complexes with a compound selected from the group consisting of compound 12 and compound 18. In a further embodiment, the invention is an L-tartrate salt of or complexes with compound 12.

In an additional embodiment, the invention pertains to a D-tartrate salt of or complexes with a compound represented by Formulae I, II, III or IV. In yet another embodiment, the invention is a D-tartrate salt of or complexes with a compound selected from the compounds 1-197 shown in Table A above. In an additional embodiment, the invention is a D-tartrate salt of or complexes with a compound selected from the group consisting of compound 12 and compound 18. In a further embodiment, the invention is a D-tartrate salt of or complexes with compound 12.

In a further embodiment, the invention pertains to a D,L-tartrate salt of or complexes with a compound represented by Formulae I, II, III or IV. In yet another embodiment, the invention is a D,L-tartrate salt of or complexes with a compound selected from the compounds 1-197 shown in Table A above. In an additional embodiment, the invention is a D,L-tartrate salt of or complexes with a compound selected from the group consisting of compound 12 and compound 18. In a further embodiment, the invention is a D,L-tartrate salt of or complexes with compound 12.

In yet another embodiment, the invention is a meso-tartrate salt of or complexes with a compound represented by Formulae I, II, III or IV. In yet another embodiment, the invention is a meso-tartrate salt of or complexes with a compound selected from the compounds 1-197 shown in Table A above. In an additional embodiment, the invention is a meso-tartrate salt of or complexes with a compound selected from the group consisting of compound 12 and compound 18. In a further embodiment, the invention is a meso-tartrate salt of or complexes with compound 12.

In one embodiment, the invention pertains to a pharmaceutical composition comprising a tartrate salt of or complexes with the invention at a therapeutically effective amount and a pharmaceutically acceptable carrier. In another embodiment, the pharmaceutical composition is a liquid formulation. In yet another embodiment, the pharmaceutical composition is an aqueous formulation. In yet another embodiment, the liquid formulation is a parenteral formulation. In yet another embodiment, the formulation is an intravenous formulation.

In a further embodiment, the composition is a dried formulation. Such formulations can be prepared by known methods including, for example, lyophilization, spray-drying and/or super-critical fluid extraction. These solid concentrates can then be re-suspended at the time of or shortly before administration to a patient.

In another embodiment of the invention, the composition comprises a solubilizing agent. In one embodiment, the solubilizing agent is a cyclodextrin. Cyclodextrins are cyclic oligomers of dextrose with a truncated cone structure consisting of a hydrophilic exterior and a hydrophobic interior cavity. A cyclodextrin can form an inclusion complex with a guest molecule by complexing with all or a portion of a hydrophobic guest molecule within its cavity (for example, as described in, U.S. Pat. No. 4,727,064, the contents of which are herein incorporated by reference). The size of the cavity is determined by the number of glucopyranose units in the cyclodextrin. Alpha- ($\alpha$), beta- ($\beta$) and gamma- ($\gamma$) cyclodextrins are the most common cyclodextrins and possess six, seven and eight glucopyranose units, respectively. Because natural cyclodextrins have relatively low aqueous solubility and are associated with toxicity, chemically modified cyclodextrin derivatives have been developed to overcome these limitations. Such cyclodextrin derivatives typically possess a chemical modification at one or more of the 2, 3, or 6 position hydroxyl groups. Cyclodextrin derivatives have, for example, been described in U.S. Pat. Nos. 5,134,127, 5,376,645, 5,571,534, 5,874,418, 6,046,177 and 6,133,248, the contents of which are herein incorporated by reference and made a part hereof. As used herein, the terms "cyclodextrin," "$\alpha$-cyclodextrin," "$\beta$-cyclodextrin" and "$\gamma$-cyclodextrin" are intended to encompass unmodified cyclodextrins as well as chemically modified derivatives thereof.

In one embodiment, the cyclodextrin is selected from the group consisting of $\alpha$-cyclodextrin or a derivative thereof, $\beta$-cyclodextrin or a derivative thereof and a $\gamma$-cyclodextrin or a derivative thereof. In yet another embodiment, the cyclodextrin is a $\beta$-cyclodextrin or a derivative or a $\gamma$-cyclodextrin or a derivative thereof. In an additional embodiment, the cyclodextrin is a $\beta$-cyclodextrin or a derivative thereof. In a further embodiment, the cyclodextrin is selected from the group consisting of a 2-hydroxypropyl-$\beta$-cyclodextrin (Pitha et al, J Pharm Sci, 84 (8), 927-32 (1995)) and sulfobutyl derivatized-$\beta$-cyclodextrin (described, for example, in U.S. Pat. Nos. 5,134,127; 5,376,645; 5,874,418; 6,046,177; and 6,133,248). In another embodiment, the cyclodextrin is a sulfobutyl derivatized-$\beta$-cyclodextrin. One such sulfobutyl derivatized-$\beta$-cyclodextrin is sulfobutylether-7-$\beta$-cyclodextrin and is sold by CyDex, Inc. under the tradename CAPTISOL®. In yet another embodiment of the invention, the cyclodextrin is sulfobutylether-7-$\beta$-cyclodextrin.

The cyclodextrin may be included in an amount that increases the solubility of the active compound in the composition. In one embodiment, the amount of cyclodextrin included within the composition is the minimal amount needed to solubilize the drug in the composition. In yet another embodiment, the amount of cyclodextrin included within the composition is within about 5% of the minimal amount needed to solubilize the drug. In a further embodiment, the composition is a parenteral formulation and the amount of cyclodextrin included within the formulation is the minimal amount of cyclodextrin needed to solubilize the drug. In order to determine the minimum amount of cyclodextrin needed to solubilize a compound encompassed by Formulae I-IV, a plot of the compound's solubility versus cyclodextrin concentration can be carried out. By interpolating or extrapolating from the plot, a composition can be prepared that contains the minimum amount of cyclodextrin needed to dissolve the desired concentration of the active compound.

In one embodiment, the composition comprises at least about 0.5 or 1% (weight/volume) of a cyclodextrin. In another embodiment, the composition comprises at least about 5% of a cyclodextrin. In yet another embodiment, the composition comprises at least about 15% of a cyclodextrin. In a further embodiment, the composition comprises from about 0.5 to about 50% of a cyclodextrin. In yet another embodiment, the composition comprises from about 0.5% to about 40% of a cyclodextrin. In another embodiment, the composition comprises about 0.5% to about 35% of a cyclodextrin. In yet another embodiment, the composition comprises about 30% of a cyclodextrin.

In another embodiment, the composition comprises at least about 0.5 or 1% (weight/volume) of a sulfobutyl derivatized-β-cyclodextrin. In another embodiment, the composition comprises at least about 5% of a sulfobutyl derivatized-β-cyclodextrin. In yet another embodiment, the composition comprises at least about 15% of a sulfobutyl derivatized-β-cyclodextrin. In a further embodiment, the composition comprises from about 0.5 to about 50% of a sulfobutyl derivatized-β-cyclodextrin. In yet another embodiment, the composition comprises from about 0.5% to about 40% of a sulfobutyl derivatized-β-cyclodextrin. In another embodiment, the composition comprises about 0.5% to about 35% of a sulfobutyl derivatized-β-cyclodextrin. In yet another embodiment, the composition comprises about 30% of a sulfobutyl derivatized-3-cyclodextrin.

In one embodiment, the composition comprises at least about 0.5 or 1% (weight/volume) CAPTISOL®. In another embodiment, the composition comprises at least about 5% CAPTISOL®. In yet another embodiment, the composition comprises at least about 15% CAPTISOL®. In a further embodiment, the composition comprises from about 0.5 to about 50% CAPTISOL®. In yet another embodiment, the composition comprises from about 0.5% to about 40% CAPTISOL®. In another embodiment, the composition comprises about 0.5% to about 35% CAPTISOL®. In yet another embodiment, the composition comprises about 30% CAPTISOL®.

In a further embodiment, the composition further comprises one or more acids or bases. In one embodiment, the acid or base is added in an amount of 0.5 to 1.5 mol equivalents, preferably 1 to 1.3 mol equivalents to formulate the compound. Acids that may be included in the composition include inorganic acids such as hydrochloric acid, sulfuric acid and phosphoric acid preferably hydrochloric acid, and organic acids such as citric acid, L(−)-malic acid and L(+)-tartaric acid preferably L(+)-tartaric acid. Examples of bases that may be included in the composition include sodium hydroxide and potassium hydroxide, preferably sodium hydroxide.

In a further embodiment, the composition comprises dextran. In yet another embodiment, the composition comprises dextran in an amount from about 1% to about 5% weight/volume dextran. In a further embodiment, the composition comprises from about 2 to about 4% weight/volume dextran.

The invention further provides methods for the prevention or treatment of diseases or conditions involving aberrant proliferation, differentiation or survival of cells. In one embodiment, the invention provides for the use of one or more salts of the invention in the manufacture of a medicament for halting or decreasing diseases involving aberrant proliferation, differentiation, or survival of cells. In preferred embodiments, the disease is cancer. In one embodiment, the invention relates to a method of treating cancer in a subject in need of treatment comprising administering to said subject a therapeutically effective amount of a tartrate salt of or complex with the invention.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute nonlymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the salts described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer, medullary and papillary thyroid carcinoma, renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the invention, the present invention provides for the use of one or more compounds of the invention in the manufacture of a medicament for the treatment of cancer.

In one embodiment, the present invention includes the use of one or more salts of the invention in the manufacture of a medicament that prevents further aberrant proliferation, differentiation, or survival of cells. For example, salts of the invention may be useful in preventing tumors from increasing in size or from reaching a metastatic state. The subject salts may be administered to halt the progression or advancement of cancer or to induce tumor apoptosis or to inhibit tumor angiogenesis. In addition, the instant invention includes use of the subject compounds to prevent a recurrence of cancer.

This invention further embraces the treatment or prevention of cell proliferative disorders such as hyperplasias, dysplasias and pre-cancerous lesions. Dysplasia is the earliest form of pre-cancerous lesion recognizable in a biopsy by a pathologist. The subject salts may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intra-epithelial tissue.

"Combination therapy" includes the administration of the subject salts in further combination with other biologically active ingredients (such as, but not limited to, a second and different antineoplastic agent) and non-drug therapies (such as, but not limited to, surgery or radiation treatment). For instance, the salts of the invention can be used in combination with other pharmaceutically active compounds, preferably compounds that are able to enhance the effect of the compounds of the invention. The salts of the invention can be administered simultaneously (as a single preparation or separate preparation) or sequentially to the other drug therapy. In general, a combination therapy envisions administration of two or more drugs during a single cycle or course of therapy.

In one aspect of the invention, the subject salts may be administered in combination with one or more separate agents that modulate protein kinases involved in various disease states. Examples of such kinases may include, but are not limited to: serine/threonine specific kinases, receptor tyrosine specific kinases and non-receptor tyrosine specific kinases. Serine/threonine kinases include mitogen activated protein kinases (MAPK), meiosis specific kinase (MEK), RAF and aurora kinase. Examples of receptor kinase families include epidermal growth factor receptor (EGFR) (e.g. HER2/neu, HER3, HER4, ErbB, ErbB2, ErbB3, ErbB4, Xmrk, DER, Let23); fibroblast growth factor (FGF) receptor (e.g. FGF-R1, GFF-R2/BEK/CEK3, FGF-R3/CEK2, FGF-R4/TKF, KGF-R); hepatocyte growth/scatter factor receptor (HGFR) (e.g, MET, RON, SEA, SEX); insulin receptor (e.g. IGFI-R); Eph (e.g. CEK5, CEK8, EBK, ECK, EEK, EHK-1, EHK-2, ELK, EPH, ERK, HEK, MDK2, MDK5, SEK); Axl (e.g. Mer/Nyk, Rse); RET; and platelet-derived growth factor receptor (PDGFR) (e.g. PDGFα-R, PDGFβ-R, CSF1-R/FMS, SCF-R/C-KIT, VEGF-R/FLT, NEK/FLK1, FLT3/FLK2/STK-1). Non-receptor tyrosine kinase families include, but are not limited to, BCR-ABL (e.g. p43$^{ab1}$, ARG); BTK (e.g. ITK/EMT, TEC); CSK, FAK, FPS, JAK, SRC, BMX, FER, CDK and SYK.

In another aspect of the invention, the subject salts may be administered in combination with one or more separate agents that modulate non-kinase biological targets or processes. Such targets include histone deacetylases (HDAC), DNA methyltransferase (DNMT), heat shock proteins (e.g. HSP90), and proteosomes.

In a preferred embodiment, subject salts may be combined with antineoplastic agents (e.g. small molecules, monoclonal antibodies, antisense RNA, and fusion proteins) that inhibit one or more biological targets such as Zolinza, Tarceva, Iressa, Tykerb, Gleevec, Sutent, Sprycel, Nexavar, Sorafinib, CNF2024, RG108, BMS387032, Affinitak, Avastin, Herceptin, Erbitux, AG24322, PD325901, ZD6474, PD184322, Obatodax, ABT737 and AEE788. Such combinations may enhance therapeutic efficacy over efficacy achieved by any of the agents alone and may prevent or delay the appearance of resistant mutational variants.

In certain preferred embodiments, the salts of the invention are administered in combination with a chemotherapeutic agent. Chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as mustard gas derivatives (Mechlorethamine, cylophosphamide, chlorambucil, melphalan, ifosfamide), ethylenimines (thiotepa, hexamethylmelanine), Alkylsulfonates (Busulfan), Hydrazines and Triazines (Altretamine, Procarbazine, Dacarbazine and Temozolomide), Nitrosoureas (Carmustine, Lomustine and Streptozocin), Ifosfamide and metal salts (Carboplatin, Cisplatin, and Oxaliplatin); plant alkaloids such as Podophyllotoxins (Etoposide and Tenisopide), Taxanes (Paclitaxel and Docetaxel), Vinca alkaloids (Vincristine, Vinblastine, Vindesine and Vinorelbine), and Camptothecan analogs (Irinotecan and Topotecan); anti-tumor antibiotics such as Chromomycins (Dactinomycin and Plicamycin), Anthracyclines (Doxorubicin, Daunorubicin, Epirubicin, Mitoxantrone, Valrubicin and Idarubicin), and miscellaneous antibiotics such as Mitomycin, Actinomycin and Bleomycin; anti-metabolites such as folic acid antagonists (Methotrexate, Pemetrexed, Raltitrexed, Aminopterin), pyrimidine antagonists (5-Fluorouracil, Floxuridine, Cytarabine, Capecitabine, and Gemcitabine), purine antagonists (6-Mercaptopurine and 6-Thioguanine) and adenosine deaminase inhibitors (Cladribine, Fludarabine, Mercaptopurine, Clofarabine, Thioguanine, Nelarabine and Pentostatin); topoisomerase inhibitors such as topoisomerase I inhibitors (Ironotecan, topotecan) and topoisomerase II inhibitors (Amsacrine, etoposide, etoposide phosphate, teniposide); monoclonal antibodies (Alemtuzumab, Gemtuzumab ozogamicin, Rituximab, Trastuzumab, Ibritumomab Tioxetan, Cetuximab, Panitumumab, Tositumomab, Bevacizumab); and miscellaneous anti-neoplastics such as ribonucleotide reductase inhibitors (Hydroxyurea); adrenocortical steroid inhibitor (Mitotane); enzymes (Asparaginase and Pegaspargase); anti-microtubule agents (Estramustine); and retinoids (Bexarotene, Isotretinoin, Tretinoin (ATRA).

In certain preferred embodiments, the compounds of the invention are administered in combination with a chemoprotective agent. Chemoprotective agents act to protect the body or minimize the side effects of chemotherapy. Examples of such agents include, but are not limited to, amfostine, mesna, and dexrazoxane.

In one aspect of the invention, the subject salts are administered in combination with radiation therapy. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

It will be appreciated that salts of the invention can be used in combination with an immunotherapeutic agent. One form of immunotherapy is the generation of an active systemic tumor-specific immune response of host origin by administering a vaccine composition at a site distant from the tumor.

Various types of vaccines have been proposed, including isolated tumor-antigen vaccines and anti-idiotype vaccines. Another approach is to use tumor cells from the subject to be treated, or a derivative of such cells (reviewed by Schirrmacher et al. (1995) J. Cancer Res. Clin. Oncol. 121:487). In U.S. Pat. No. 5,484,596, Hanna Jr. et al. claims a method for treating a resectable carcinoma to prevent recurrence or metastases, comprising surgically removing the tumor, dispersing the cells with collagenase, irradiating the cells, and vaccinating the patient with at least three consecutive doses of about $10^7$ cells.

It will be appreciated that the salts of the invention may advantageously be used in conjunction with one or more adjunctive therapeutic agents. Examples of suitable agents for adjunctive therapy include a $5HT_1$ agonist, such as a triptan (e.g. sumatriptan or naratriptan); an adenosine A1 agonist; an EP ligand; an NMDA modulator, such as a glycine antagonist; a sodium channel blocker (e.g. lamotrigine); a substance P antagonist (e.g. an $NK_1$ antagonist); a cannabinoid; acetaminophen or phenacetin; a 5-lipoxygenase inhibitor (e.g., zileuton); a leukotriene receptor antagonist (e.g., montelukast or zafirlukast); a DMARD (e.g. methotrexate); gabapentin and related compounds; a tricyclic antidepressant (e.g. amitryptilline); a neurone stabilising antiepileptic drug; a mono-aminergic uptake inhibitor (e.g. venlafaxine); a matrix metalloproteinase inhibitor; a nitric oxide synthase (NOS) inhibitor, such as an iNOS or an nNOS inhibitor; an inhibitor of the release, or action, of tumour necrosis factor .alpha.; an antibody therapy, such as a monoclonal antibody therapy; an antiviral agent, such as a nucleoside inhibitor (e.g. lamivudine) or an immune system modulator (e.g. interferon); an opioid analgesic; a local anaesthetic; a stimulant, including caffeine; an $H_2$-antagonist (e.g. ranitidine); a proton pump inhibitor (e.g. omeprazole); an antacid (e.g. aluminium or magnesium hydroxide); an antiflatulent (e.g. simethicone); a decongestant (e.g. phenylephrine, phenylpropanolamine, pseudoephedrine, oxymetazoline, epinephrine, naphazoline, xylometazoline, propylhexedrine, or levo-desoxyephedrine); an antitussive (e.g. codeine, hydrocodone, carmiphen, carbetapentane, or dextramethorphan); a diuretic; or a sedating or non-sedating antihistamine.

Matrix metalloproteinases (MMPs) are a family of zinc-dependent neutral endopeptidases collectively capable of degrading essentially all matrix components. Over 20 MMP modulating agents are in pharmaceutical development, almost half of which are indicated for cancer. The University of Toronto researchers have reported that HDACs regulate MMP expression and activity in 3T3 cells. In particular, inhibition of HDAC by trichostatin A (TSA), which has been shown to prevent tumorigenesis and metastasis, decreases mRNA as well as zymographic activity of gelatinase A (MMP2; Type IV collagenase), a matrix metalloproteinase, which is itself, implicated in tumorigenesis and metastasis (Ailenberg M., Silverman M., *Biochem Biophys Res Commun.* 2002, 298:110-115). Another recent article that discusses the relationship of HDAC and MMPs can be found in Young D. A., et al., *Arthritis Research & Therapy*, 2005, 7: 503. Furthermore, the commonality between HDAC and MMPs inhibitors is their zinc-binding functionality. Therefore, in one aspect of the invention, salts of the invention can be used as MMP inhibitors and may be of use in the treatment of disorders relating to or associated with dysregulation of MMP. The overexpression and activation of MMPs are known to induce tissue destruction and are also associated with a number of specific diseases including rheumatoid arthritis, periodontal disease, cancer and atherosclerosis.

The salts may also be used in the treatment of a disorder involving, relating to or, associated with dysregulation of histone deacetylase (HDAC). There are a number of disorders that have been implicated by or known to be mediated at least in part by HDAC activity, where HDAC activity is known to play a role in triggering disease onset, or whose symptoms are known or have been shown to be alleviated by HDAC inhibitors. Disorders of this type that would be expected to be amenable to treatment with the compounds of the invention include the following, but are not limited to: Anti-proliferative disorders (e.g. cancers); Neurodegenerative diseases including Huntington's disease, polyglutamine disease, Parkinson's disease, Alzheimer's disease, seizures, striatonigral degeneration, Progressive supranuclear palsy, Torsion dystonia, Spasmodic torticollis and dyskinesis, Familial tremor, Gilles de la Tourette syndrome, Diffuse Lewy body disease, Progressive supranuclear palsy, Pick's disease, intracerebral hemorrhage, Primary lateral sclerosis, Spinal muscular atrophy, Amyotrophic lateral sclerosis, Hypertrophic interstitial polyneuropathy, Retinitis pigmentosa, Hereditary optic atrophy, Hereditary spastic paraplegia, Progressive ataxia and Shy-Drager syndrome; Metabolic diseases including Type 2 diabetes; Degenerative diseases of the Eye including Glaucoma, Age-related macular degeneration, Rubeotic glaucoma; Inflammatory diseases and/or Immune system disorders including rheumatoid arthritis (RA), inflammatory osteoarthritis, juvenile chronic arthritis, Graft versus Host disease, psoriasis, asthma, spondyloarthropathy, Crohn's disease, inflammatory bowel disease, colitis ulcerosa, alcoholic hepatitis, pancreatitis, Type 2 diabetes, Sjoegrens's syndrome, multiple sclerosis, ankylosing spondylitis, membranous glomerulopathy, discogenic pain and systemic lupus erythematosus; Disease involving angiogenesis including cancer, psoriasis, rheumatoid arthritis; Psychological disorders including bipolar disease, schizophrenia, mania, depression and dementia; Cardiovascular diseases including heart failure, restenosis and arteriosclerosis; Fibrotic diseases including liver fibrosis, cystic fibrosis and angiofibroma; Infectious diseases including Fungal infections, such as *Candida Albicans*, bacterial infections, viral infections, such as Herpes Simplex, protozoal infections, such as malaria, *Leishmania* infection, *Trypanosoma brucei* infection, toxoplasmosis and coccidlosis and haematopoietic disorders including thalassemia, anemia and sickle cell anemia.

In one embodiment, salts of the invention can be used to induce or inhibit apoptosis, a physiological cell death process critical for normal development and homeostasis. Alterations of apoptotic pathways contribute to the pathogenesis of a variety of human diseases. Salts of the invention, as modulators of apoptosis, will be useful in the treatment of a variety of human diseases with abberations in apoptosis including cancer (particularly, but not limited to, follicular lymphomas, carcinomas with p53 mutations, hormone dependent tumors of the breast, prostate and ovary, and precancerous lesions such as familial adenomatous polyposis), viral infections (including, but not limited to, herpesvirus, poxvirus, Epstein-Barr virus, Sindbis virus and adenovirus), autoimmune diseases (including, but not limited to, systemic lupus, erythematosus, immune mediated glomerulonephritis, rheumatoid arthritis, psoriasis, inflammatory bowel diseases, and autoimmune diabetes mellitus), neurodegenerative disorders (including, but not limited to, Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including, but not limited to, chronic anemia and aplastic anemia), degenerative diseases of the musculoskeletal system (including, but not limited to, osteoporosis and arthritis), aspirin-sensitive rhinosinusitis, cystic fibrosis, multiple sclerosis, kidney diseases, and cancer pain.

In one aspect, the invention provides the use of salts of the invention for the treatment and/or prevention of immune response or immune-mediated responses and diseases, such as the prevention or treatment of rejection following transplantation of synthetic or organic grafting materials, cells, organs or tissue to replace all or part of the function of tissues, such as heart, kidney, liver, bone marrow, skin, cornea, vessels, lung, pancreas, intestine, limb, muscle, nerve tissue, duodenum, small-bowel, pancreatic-islet-cell, including xeno-transplants, etc.; to treat or prevent graft-versus-host disease, autoimmune diseases, such as rheumatoid arthritis, systemic lupus erythematosus, thyroiditis, Hashimoto's thyroiditis, multiple sclerosis, myasthenia gravis, type I diabetes uveitis, juvenile-onset or recent-onset diabetes mellitus, uveitis, Graves disease, psoriasis, atopic dermatitis, Crohn's disease, ulcerative colitis, vasculitis, auto-antibody mediated diseases, aplastic anemia, Evan's syndrome, autoimmune hemolytic anemia, and the like; and further to treat infectious diseases causing aberrant immune response and/or activation, such as traumatic or pathogen induced immune disregulation, including for example, that which are caused by hepatitis B and C infections, HIV, *staphylococcus aureus* infection, viral encephalitis, sepsis, parasitic diseases wherein damage is induced by an inflammatory response (e.g., leprosy); and to prevent or treat circulatory diseases, such as arteriosclerosis, atherosclerosis, vasculitis, polyarteritis nodosa and myocarditis. In addition, the present invention may be used to prevent/suppress an immune response associated with a gene therapy treatment, such as the introduction of foreign genes into autologous cells and expression of the encoded product. Thus in one embodiment, the invention relates to a method of treating an immune response disease or disorder or an immune-mediated response or disorder in a subject in need of treatment comprising administering to said subject a therapeutically effective amount of a compound of the invention.

In one aspect, the invention provides the use of salts of the invention in the treatment of a variety of neurodegenerative diseases, a non-exhaustive list of which includes: I. Disorders characterized by progressive dementia in the absence of other prominent neurologic signs, such as Alzheimer's disease; Senile dementia of the Alzheimer type; and Pick's disease (lobar atrophy); II. Syndromes combining progressive dementia with other prominent neurologic abnormalities such as A) syndromes appearing mainly in adults (e.g., Huntington's disease, Multiple system atrophy combining dementia with ataxia and/or manifestations of Parkinson's disease, Progressive supranuclear palsy (Steel-Richardson-Olszewski), diffuse Lewy body disease, and corticodentatonigral degeneration); and B) syndromes appearing mainly in children or young adults (e.g., Hallervorden-Spatz disease and progressive familial myoclonic epilepsy); III. Syndromes of gradually developing abnormalities of posture and movement such as paralysis agitans (Parkinson's disease), striatonigral degeneration, progressive supranuclear palsy, torsion dystonia (torsion spasm; dystonia musculorum deformans), spasmodic torticollis and other dyskinesis, familial tremor, and Gilles de la Tourette syndrome; IV. Syndromes of progressive ataxia such as cerebellar degenerations (e.g., cerebellar cortical degeneration and olivopontocerebellar atrophy (OPCA)); and spinocerebellar degeneration (Friedreich's ataxia and related disorders); V. Syndrome of central autonomic nervous system failure (Shy-Drager syndrome); VI. Syndromes of muscular weakness and wasting without sensory changes (motorneuron disease such as amyotrophic lateral sclerosis, spinal muscular atrophy (e.g., infantile spinal muscular atrophy (Werdnig-Hoffman), juvenile spinal muscular atrophy (Wohlfart-Kugelberg-Welander) and other forms of familial spinal muscular atrophy), primary lateral sclerosis, and hereditary spastic paraplegia; VII. Syndromes combining muscular weakness and wasting with sensory changes (progressive neural muscular atrophy; chronic familial polyneuropathies) such as peroneal muscular atrophy (Charcot-Marie-Tooth), hypertrophic interstitial polyneuropathy (Dejerine-Sottas), and miscellaneous forms of chronic progressive neuropathy; VIII. Syndromes of progressive visual loss such as pigmentary degeneration of the retina (retinitis pigmentosa), and hereditary optic atrophy (Leber's disease). Furthermore, salts of the invention can be implicated in chromatin remodeling.

The invention encompasses pharmaceutical compositions comprising a therapeutically effective amount of a tartrate salt of or complex with the invention as described above and a pharmaceutically acceptable excipient or carrier. In one embodiment, a therapeutically effective amount when treating cancer is an amount effective to selectively induce terminal differentiation of suitable neoplastic cells and less than an amount which causes toxicity in a patient. The invention also encompasses pharmaceutical compositions comprising solvates or hydrates of the salts of the invention.

Salts of the invention may be administered by any suitable means, including, without limitation, parenteral, intravenous, intramuscular, subcutaneous, implantation, oral, sublingual, buccal, nasal, pulmonary, transdermal, topical, vaginal, rectal, and transmucosal administrations or the like. Topical administration can also involve the use of transdermal administration such as transdermal patches or iontophoresis devices. Pharmaceutical preparations include a solid, semi-solid or liquid preparation (tablet, pellet, troche, capsule, suppository, cream, ointment, aerosol, powder, liquid, emulsion, suspension, syrup, injection etc.) containing a compound of the invention as an active ingredient, which is suitable for selected mode of administration. In one embodiment, the pharmaceutical compositions are administered orally, and are thus formulated in a form suitable for oral administration, i.e., as a solid or a liquid preparation. Suitable solid oral formulations include tablets, capsules, pills, granules, pellets, sachets and effervescent, powders, and the like. Suitable liquid oral formulations include solutions, suspensions, dispersions, emulsions, oils and the like. In one embodiment of the present invention, the composition is formulated in a capsule. In accordance with this embodiment, the compositions of the present invention comprise in addition to the active compound and the inert carrier or diluent, a hard gelatin capsule. In another embodiment, the inventive salt or pharmaceutical composition is administered parenterally. In a further embodiment, the inventive compound or pharmaceutical composition is administered intravenously.

Any inert excipient that is commonly used as a carrier or diluent may be used in the formulations of the present invention, such as for example, a gum, a starch, a sugar, a cellulosic material, an acrylate, or mixtures thereof. A preferred diluent is microcrystalline cellulose. The compositions may further comprise a disintegrating agent (e.g., croscarmellose sodium) and a lubricant (e.g., magnesium stearate), and may additionally comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCI., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol, cyclodextrins), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Daily administration may be repeated continuously for a period of several days to several years. Oral treatment may continue for between one week and the life of the patient. Preferably the administration may take place for five consecutive days after which time the patient can be evaluated to determine if further administration is required. The administration can be continuous or intermittent, e.g., treatment for a number of consecutive days followed by a rest period. The salts of the present invention may be administered intravenously on the first day of treatment, with oral administration on the second day and all consecutive days thereafter.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the salt administered to the patient is less than an amount that would cause toxicity in the patient. In certain embodiments, the amount of the salt that is administered to the patient is less than the amount that causes a concentration of the compound in the patient's plasma to equal or exceed the toxic level of the compound. Preferably, the concentration of the salt in the patient's plasma is maintained at about 10 nM. In one embodiment, the concentration of the salt in the patient's plasma is maintained at about 25 nM. In one embodiment, the concentration of the salt in the patient's plasma is maintained at about 50 nM. In one embodiment, the concentration of the salt in the patient's plasma is maintained at about 100 nM. In one embodiment, the concentration of the salt in the patient's plasma is maintained at about 500 nM. In one embodiment, the concentration of the salt in the patient's plasma is maintained at about 1000 nM. In one embodiment, the concentration of the salt in the patient's plasma is maintained at about 2500 nM. In one embodiment, the concentration of the salt in the patient's plasma is maintained at about 5000 nM. The optimal amount of the salt that should be administered to the patient in the practice of the present invention will depend on the particular compound used and the type of cancer being treated.

DEFINITIONS

Listed below are definitions of various terms used to describe this invention. These definitions apply to the terms as they are used throughout this specification and claims, unless otherwise limited in specific instances, either individually or as part of a larger group.

The term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about eight carbon atoms. Examples of such radicals include methyl, ethyl, n-propyl, isopropyl, n-butyl, isobutyl, sec-butyl, tert-butyl, pentyl, iso-amyl, hexyl and the like.

The term "alkenyl" embraces linear or branched radicals having at least one carbon-carbon double bond of two to about twenty carbon atoms or, preferably, two to about twelve carbon atoms. More preferred alkenyl radicals are "lower alkenyl" radicals having two to about ten and more preferably about two to about eight carbon atoms. Examples of alkenyl radicals include ethenyl, allyl, propenyl, butenyl and 4-methylbutenyl. The terms "alkenyl", and "lower alkenyl", embrace radicals having "cis" and "trans" orientations, or alternatively, "E" and "Z" orientations.

The term "alkynyl" embraces linear or branched radicals having at least one carbon-carbon triple bond of two to about twenty carbon atoms or, preferably, two to about twelve carbon atoms. More preferred alkynyl radicals are "lower alkynyl" radicals having two to about ten and more preferably two to about eight carbon atoms. Examples of alkynyl radicals include propargyl, 1-propynyl, 2-propynyl, 1-butyne, 2-butynyl and 1-pentynyl.

The term "alkoxy" embraces linear or branched oxy-containing radicals each having alkyl portions of one to about twenty carbon atoms or, preferably, one to about twelve carbon atoms. More preferred alkoxy radicals are "lower alkoxy" radicals having one to about ten and more preferably having one to about eight carbon atoms. Examples of such radicals include methoxy, ethoxy, propoxy, butoxy and tert-butoxy.

The term "alkoxyalkoxy" embraces alkoxy radicals having one or more alkoxy radicals attached to the alkyl radical, that is, to form monoalkoxyalkyl and dialkoxyalkyl radicals.

The term "compound" is defined herein to include pharmaceutically acceptable salts, solvates, hydrates, polymorphs, enantiomers, diastereoisomers, racemates and the like of the compounds encompassed by formulae I, II, III or IV as set forth herein.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent can be further substituted.

The terms "halogen" or "halo" as used herein, refers to an atom selected from fluorine, chlorine, bromine and iodine.

As used herein, the term "aberrant proliferation" refers to abnormal cell growth.

The phrase "adjunctive therapy" encompasses treatment of a subject with agents that reduce or avoid side effects associated with the combination therapy of the present invention, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The term "angiogenesis," as used herein, refers to the formation of blood vessels. Specifically, angiogenesis is a multi-step process in which endothelial cells focally degrade and invade through their own basement membrane, migrate through interstitial stroma toward an angiogenic stimulus, proliferate proximal to the migrating tip, organize into blood vessels, and reattach to newly synthesized basement membrane (see Folkman et al., Adv. Cancer Res., Vol. 43, pp. 175-203 (1985)). Anti-angiogenic agents interfere with this process. Examples of agents that interfere with several of these steps include thrombospondin-1, angiostatin, endostatin, interferon alpha and compounds such as matrix metalloproteinase (MMP) inhibitors that block the actions of enzymes that clear and create paths for newly forming blood vessels to follow; compounds, such as .alpha.v.beta.3 inhibitors, that interfere with molecules that blood vessel cells use to bridge between a parent blood vessel and a tumor; agents, such as specific COX-2 inhibitors, that prevent the growth of cells that form new blood vessels; and protein-based compounds that simultaneously interfere with several of these targets.

The term "apoptosis" as used herein refers to programmed cell death as signaled by the nuclei in normally functioning human and animal cells when age or state of cell health and condition dictates. An "apoptosis inducing agent" triggers the process of programmed cell death.

The term "cancer" as used herein denotes a class of diseases or disorders characterized by uncontrolled division of cells and the ability of these cells to invade other tissues, either by direct growth into adjacent tissue through invasion or by implantation into distant sites by metastasis.

The term "compound" is defined herein to include pharmaceutically acceptable salts, solvates, hydrates, polymorphs, enantiomers, diastereoisomers, racemates and the like of the compounds having a formula as set forth herein.

The term "devices" refers to any appliance, usually mechanical or electrical, designed to perform a particular function.

As used herein, the term "dysplasia" refers to abnormal cell growth and typically refers to the earliest form of pre-cancerous lesion recognizable in a biopsy by a pathologist.

As used herein, the term "effective amount of the subject compounds," with respect to the subject method of treatment, refers to an amount of the subject compound which, when delivered as part of desired dose regimen, brings about, e.g. a change in the rate of cell proliferation and/or state of differentiation and/or rate of survival of a cell to clinically acceptable standards. This amount may further relieve to some extent one or more of the symptoms of a neoplasia disorder, including, but is not limited to: 1) reduction in the number of cancer cells; 2) reduction in tumor size; 3) inhibition (i.e., slowing to some extent, preferably stopping) of cancer cell infiltration into peripheral organs; 4) inhibition (i.e., slowing to some extent, preferably stopping) of tumor metastasis; 5) inhibition, to some extent, of tumor growth; 6) relieving or reducing to some extent one or more of the symptoms associated with the disorder; and/or 7) relieving or reducing the side effects associated with the administration of anticancer agents.

The term "hyperplasia," as used herein, refers to excessive cell division or growth.

The phrase an "immunotherapeutic agent" refers to agents used to transfer the immunity of an immune donor, e.g., another person or an animal, to a host by inoculation. The term embraces the use of serum or gamma globulin containing performed antibodies produced by another individual or an animal; nonspecific systemic stimulation; adjuvants; active specific immunotherapy; and adoptive immunotherapy. Adoptive immunotherapy refers to the treatment of a disease by therapy or agents that include host inoculation of sensitized lymphocytes, transfer factor, immune RNA, or antibodies in serum or gamma globulin.

The term "inhibition," in the context of neoplasia, tumor growth or tumor cell growth, may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention or chemoprevention.

The term "metastasis," as used herein, refers to the migration of cancer cells from the original tumor site through the blood and lymph vessels to produce cancers in other tissues. Metastasis also is the term used for a secondary cancer growing at a distant site.

The term "neoplasm," as used herein, refers to an abnormal mass of tissue that results from excessive cell division. Neoplasms may be benign (not cancerous), or malignant (cancerous) and may also be called a tumor. The term "neoplasia" is the pathological process that results in tumor formation.

As used herein, the term "pre-cancerous" refers to a condition that is not malignant, but is likely to become malignant if left untreated.

The term "proliferation" refers to cells undergoing mitosis.

The phrase "EGFR-TK related disease or disorder" refers to a disease or disorder characterized by inappropriate EGFR-TK activity or over-activity of the EGFR-TK. Inappropriate activity refers to either; (i) EGFR-TK expression in cells which normally do not express EGFR-TKs; (ii) increased EGFR-TK expression leading to unwanted cell proliferation, differentiation and/or growth; or, (iii) decreased EGFR-TK expression leading to unwanted reductions in cell proliferation, differentiation and/or growth. Over-activity of EGFR-TKs refers to either amplification of the gene encoding a particular EGFR-TK or production of a level of EGFR-TK activity which can correlate with a cell proliferation, differentiation and/or growth disorder (that is, as the level of the EGFR-TK increases, the severity of one or more of the symptoms of the cellular disorder increases). Over activity can also be the result of ligand independent or constitutive activation as a result of mutations such as deletions of a fragment of an EGFR-TK responsible for ligand binding.

The phrase a "radiotherapeutic agent" refers to the use of electromagnetic or particulate radiation in the treatment of neoplasia.

The term "recurrence" as used herein refers to the return of cancer after a period of remission. This may be due to incomplete removal of cells from the initial cancer and may occur locally (the same site of initial cancer), regionally (in vicinity of initial cancer, possibly in the lymph nodes or tissue), and/or distally as a result of metastasis.

The term "treatment" refers to any process, action, application, therapy, or the like, wherein a mammal, including a human being, is subject to medical aid with the object of improving the mammal's condition, directly or indirectly.

The term "vaccine" includes agents that induce the patient's immune system to mount an immune response against the tumor by attacking cells that express tumor associated antigens (TAAs).

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences*, 66: 1-19 (1977). The salts can be prepared in situ during the final isolation and purification of the compounds of the invention, or separately by reacting the free base function with a suitable organic acid or inorganic acid.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development", Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As used herein, the term "pre-cancerous" refers to a condition that is not malignant, but is likely to become malignant if left untreated.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The salts of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The synthesized compounds or tartrate salts thereof can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds described herein may contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers and/or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

In some embodiments, the inventive compound is a crystalline or an amorphous form of a compound of the invention. In another embodiment, the inventive compound is a mixture of two or more crystalline forms of the compound. In a further embodiment, the invention is a crystalline form or a mixture of two or more crystalline forms of compound 12. A crystalline form of compound 12 can be prepared substantially as described in Example 8 (Method 2) below.

Different crystalline forms of chemical compounds (or polymorphs) each exhibit different physical, chemical, spectroscopic and/or crystallographic properties. In one embodiment, the crystalline form of the invention has an X-ray powder diffraction (XRPD) pattern with at least three, four, five, six, seven or eight major peaks in common with the X-ray powder diffraction pattern of the crystal prepared according to working Example 8 (Method 2). A major peak is an XRPD peak with a relative intensity greater than about 25%; relative intensity is calculated as a ratio of the peak intensity of the peak of interest versus the peak intensity of the largest peak. As used herein, a peak for the crystalline form is in common with the XRPD pattern of the crystal prepared according to Example 8 (Method 2) if it is within 0.5° 2θ of a peak location for the crystal prepared according to Example 8 (Method 2). In another embodiment, the crystalline form of compound 12 has an endothermic transition within about 1.0° C. as the crystalline form prepared according to Example 8 (Method 2). In yet another embodiment, the crystalline form of compound 12 has an endothermic transition (as observed by differential scanning calorimetry) within about 0.5° C. of as the crystal formed according to Example 8 (Method 2) and at least three, four, five, six, seven or eight major peaks in common with the XRPD pattern of the compound prepared according to Example 8 (Method 2). In a further embodiment, the crystalline form of compound 12 exhibits a differential scanning calorimetry pattern that is substantially the same as the differential scanning calorimetry pattern of the compound produced according the Example 8 (Method 2).

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; cyclodextrins such as alpha- (α), beta- (β) and gamma- (γ) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as solubilizing agents, coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The salts of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of salt or pharmaceutical composition comprising the salt to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active salt (w/w). Alternatively, such preparations may contain from about 20% to about 80% active salt.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a salt, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Synthetic Methods

A quinazoline derivative of any of the formulae I-IV, or a pharmaceutically-acceptable salt thereof, may be prepared by any process known to be applicable to the preparation of chemically-related compounds. Suitable processes for making certain intermediates include, for example, those illustrated in European Patent Applications Nos. 0520722, 0566226, 0602851, 0635498, 0635507, U.S. Pat. Nos. 5,457, 105, 5,770,599, US publication No. 2003/0158408 and reference such as, *J. Med Chem.* 2004, 47, 871-887. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of a chemist.

The compounds and processes of the present invention will be better understood in connection with the following representative synthetic schemes that illustrate the methods by which the compounds of the invention may be prepared, which are intended as an illustration only and not limiting of the scope of the invention.

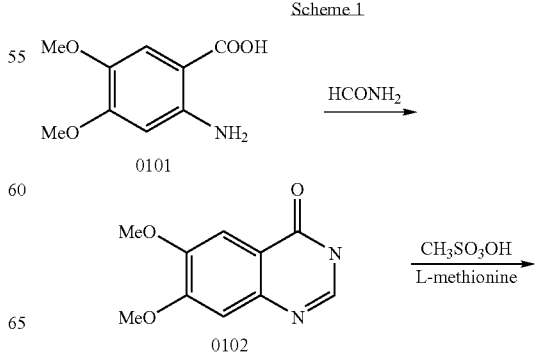

Scheme 1

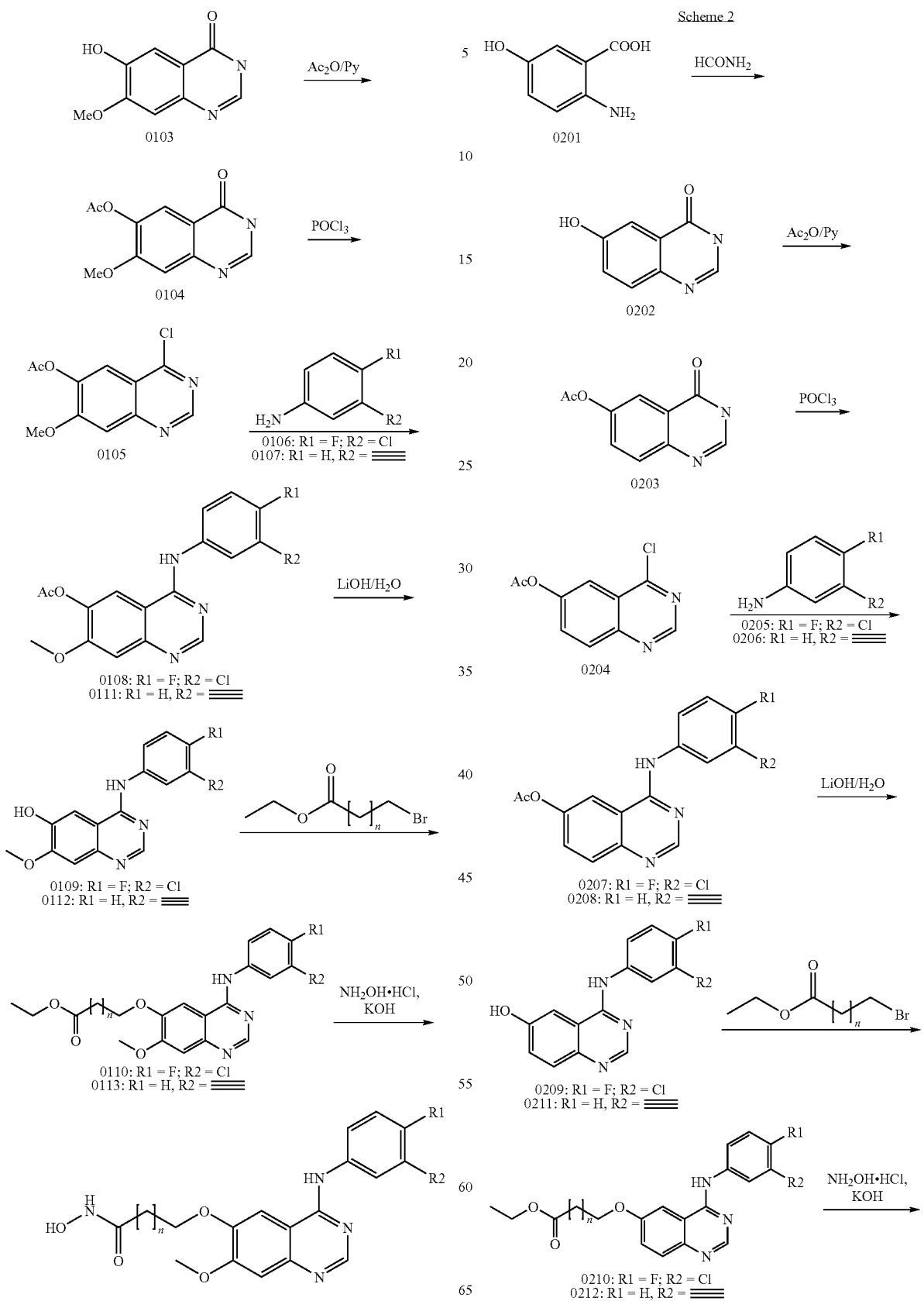

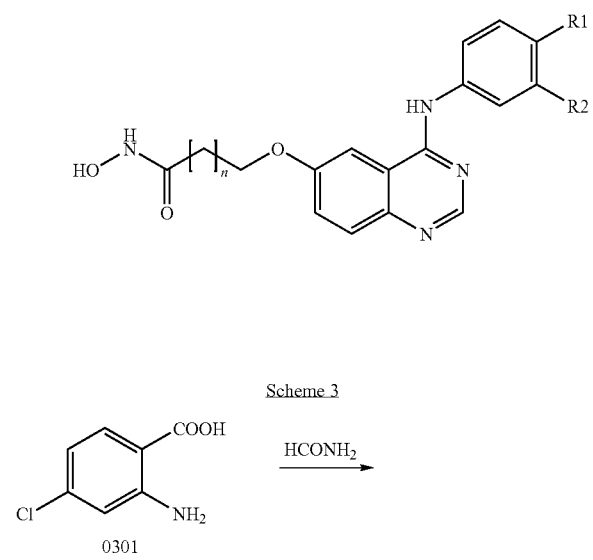
Scheme 3
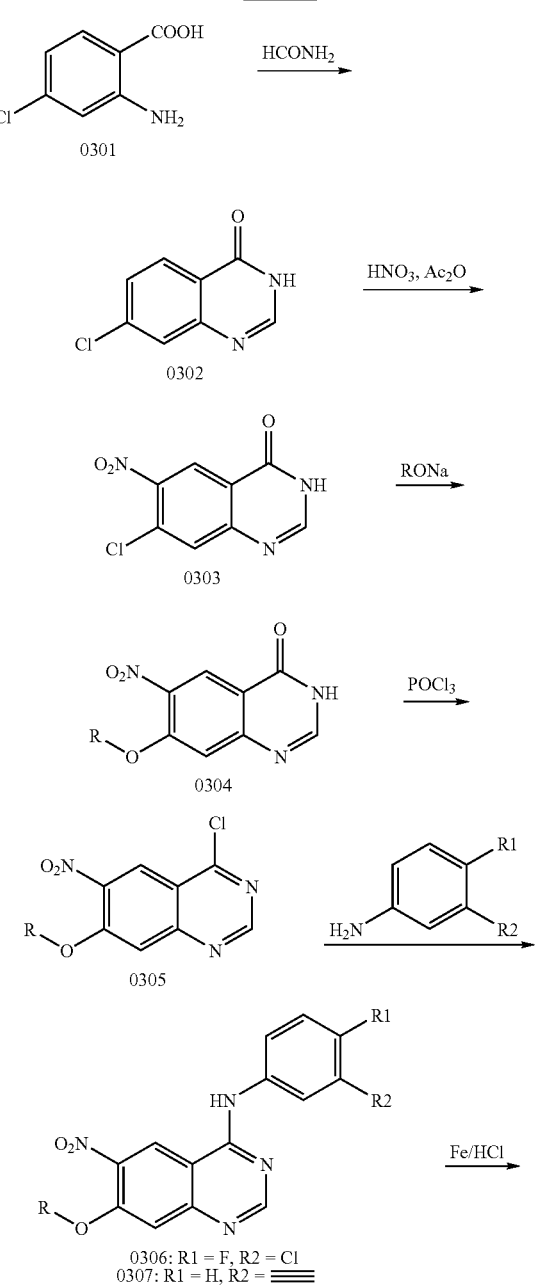
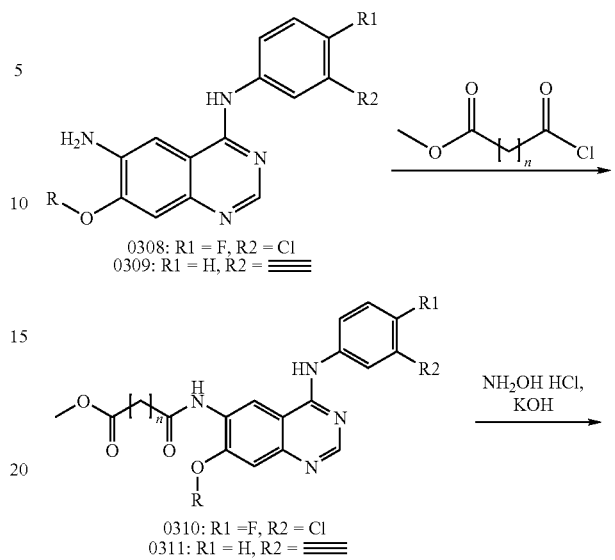
Scheme 4

-continued
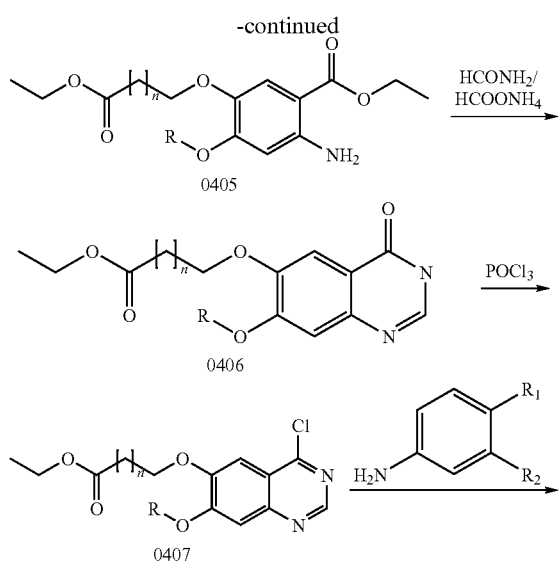
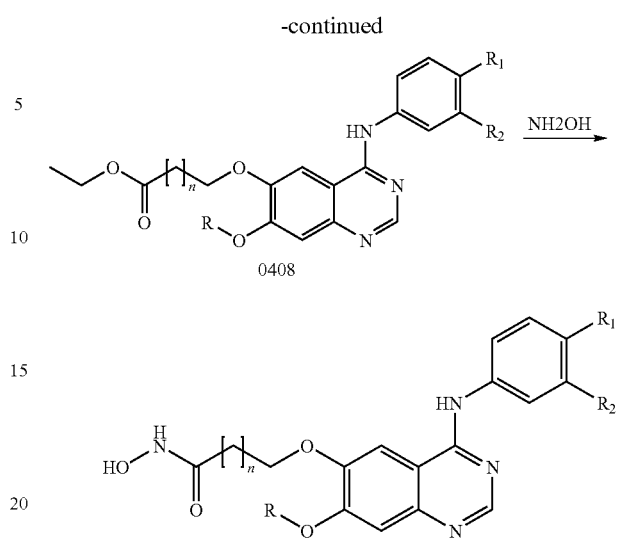
Scheme 5
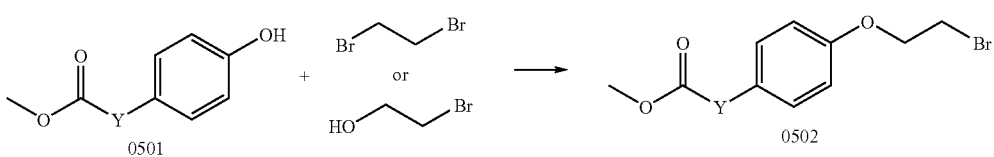
wherein Y is absent, $C_1$-$C_6$ alkyl,
$C_2$-$C_6$ akenyl, $C_2$-$C_6$ alkynyl
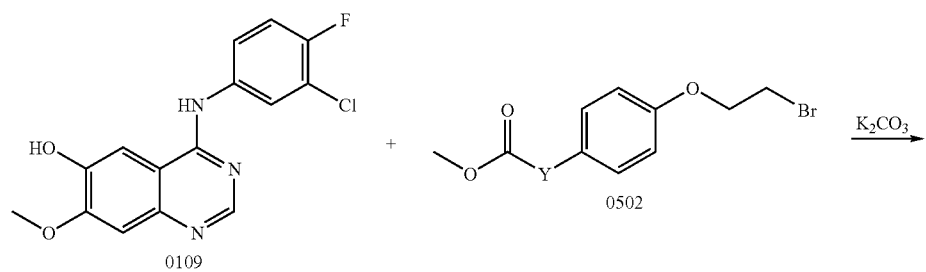
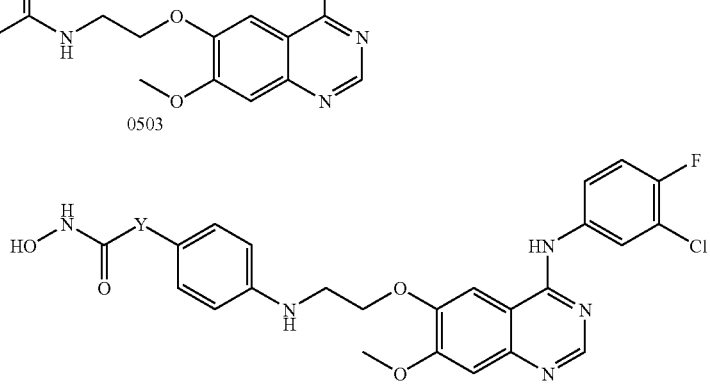

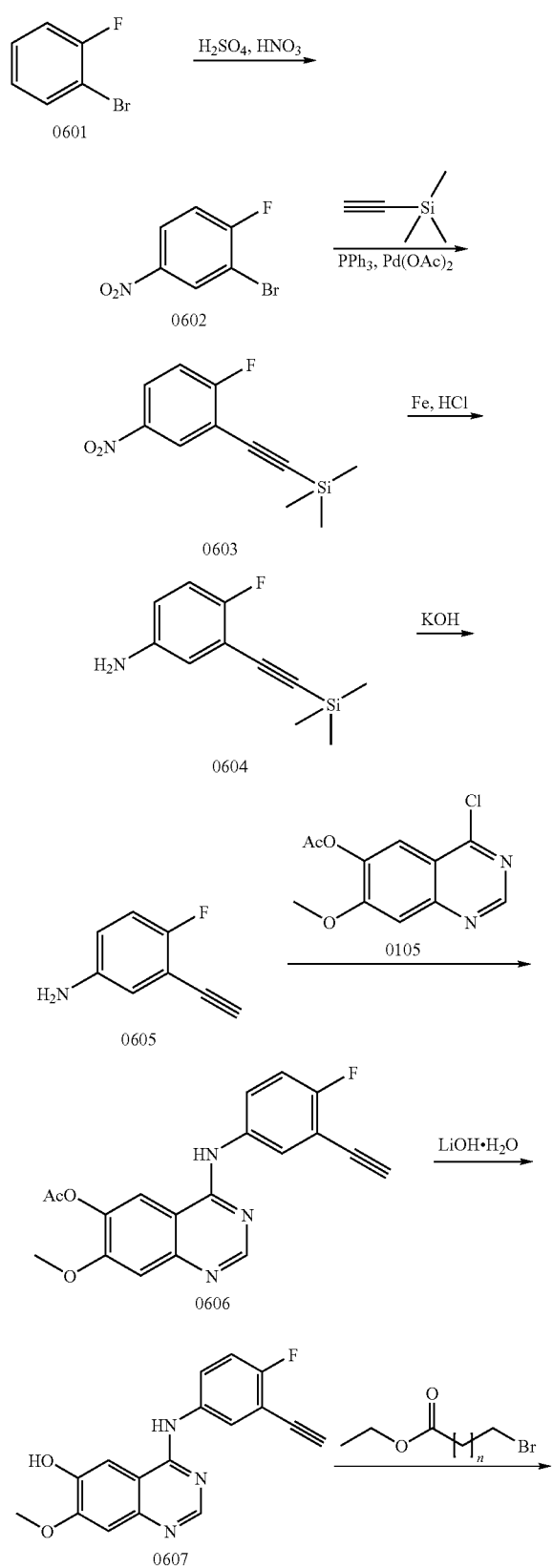
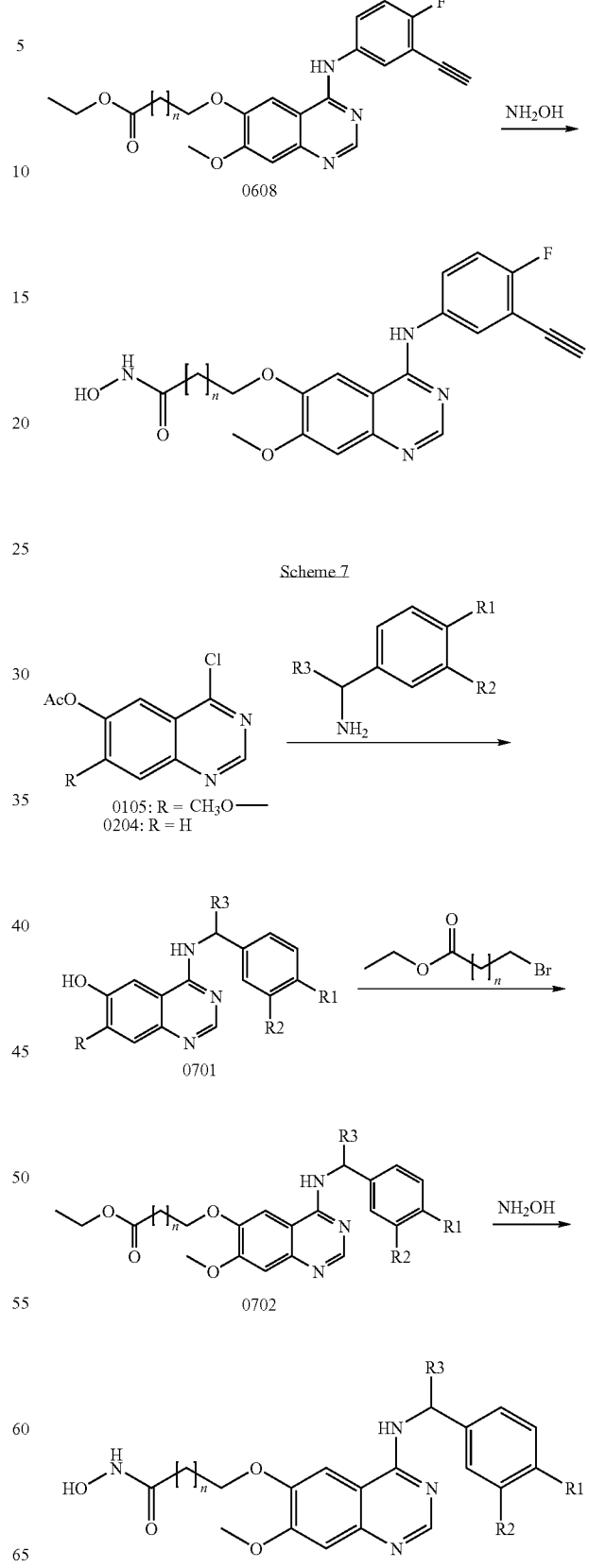

Scheme 8
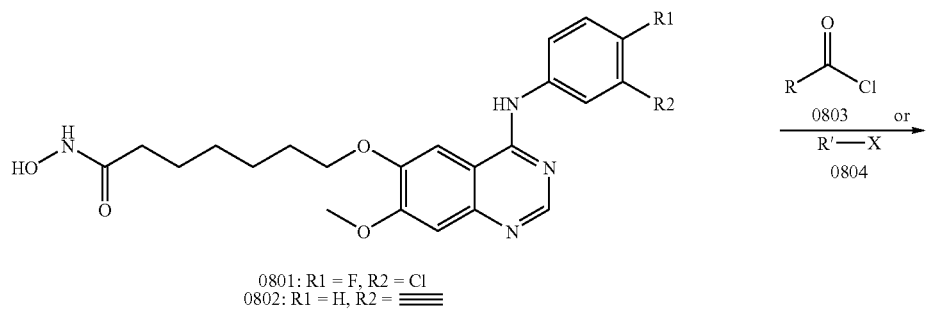
0801: R1 = F, R2 = Cl
0802: R1 = H, R2 = ≡
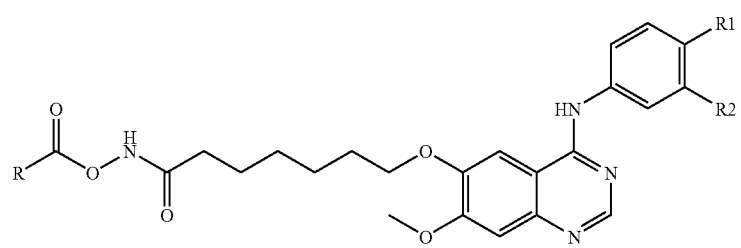
Scheme 9
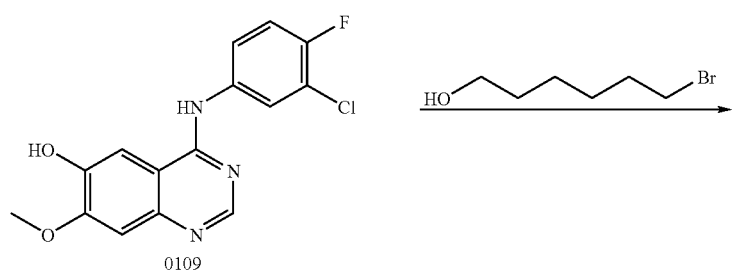
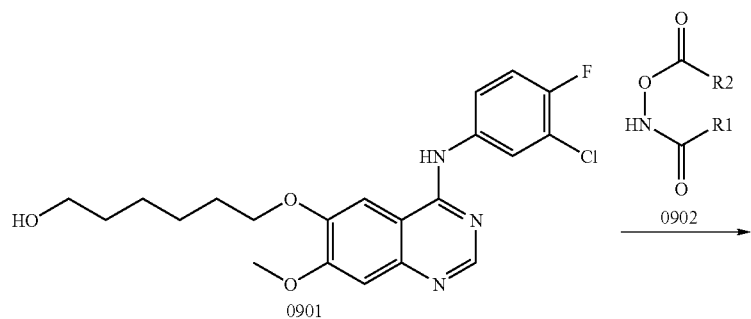

-continued
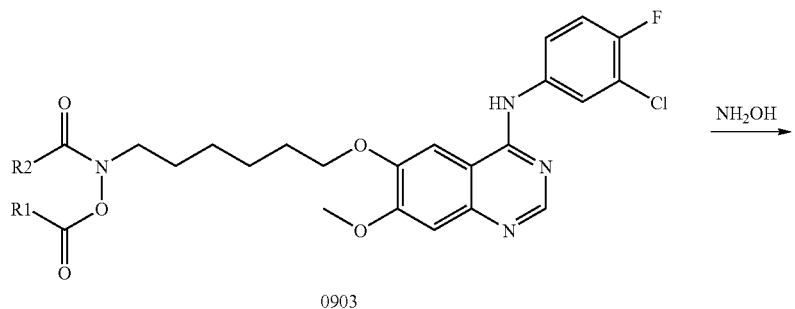
0903
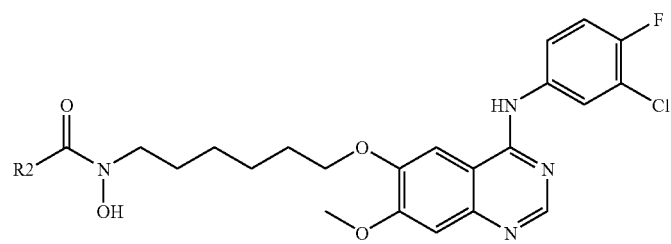
Scheme 10
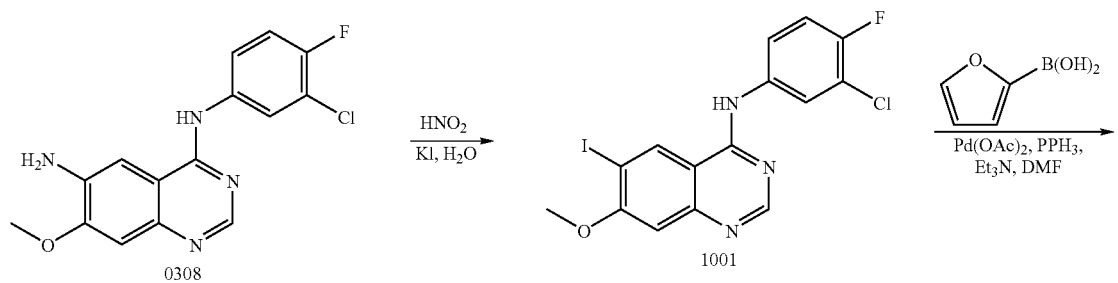
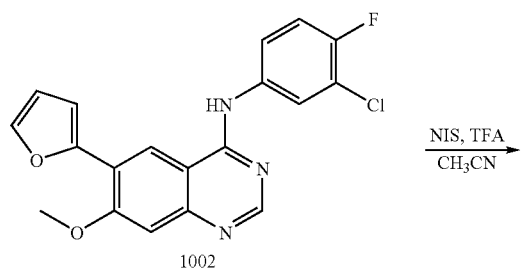
1002
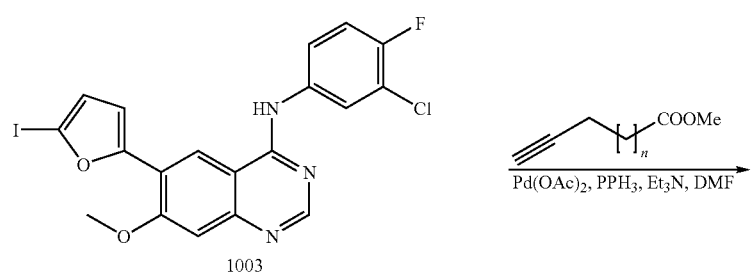

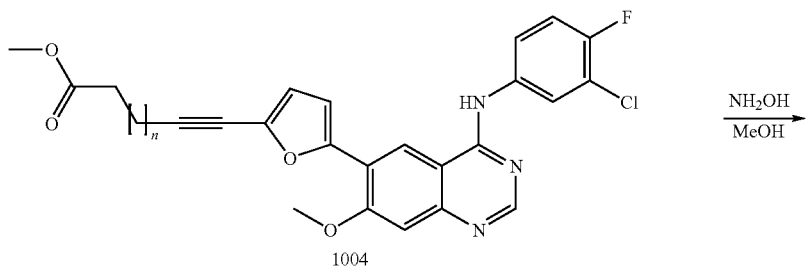
1004
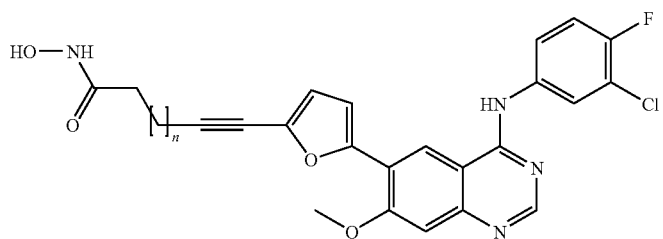
Scheme 11
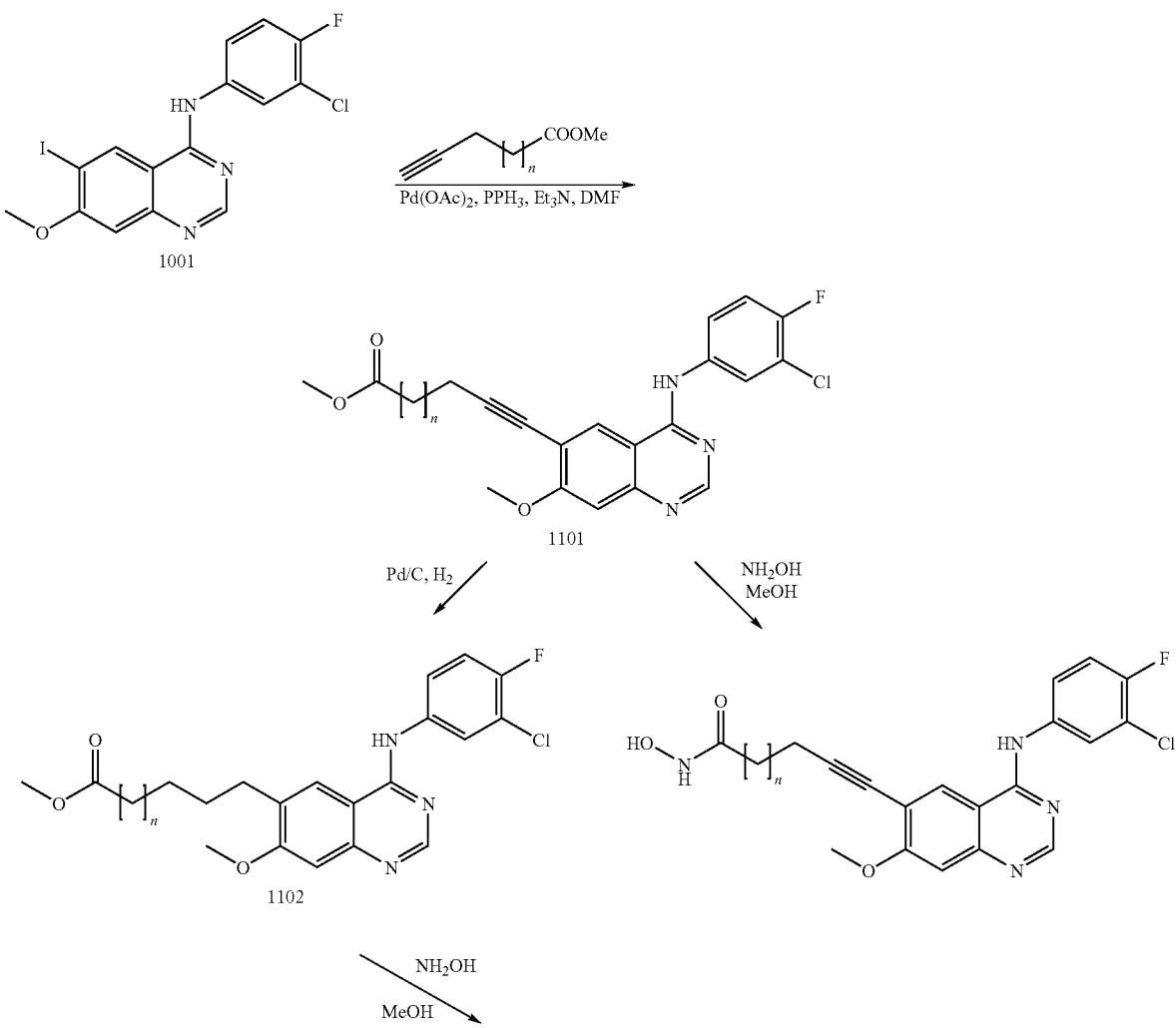

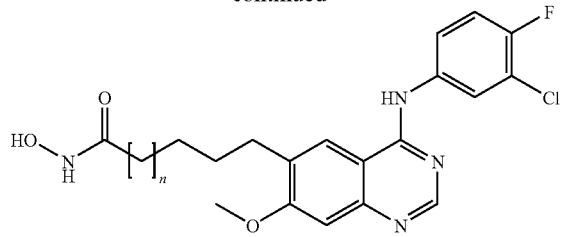
Scheme 12
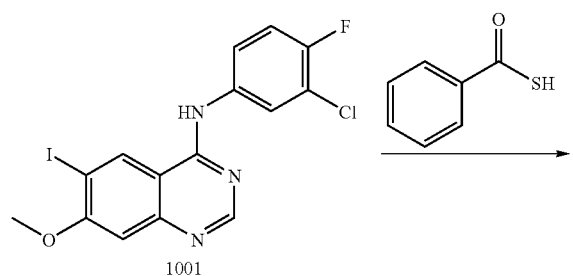
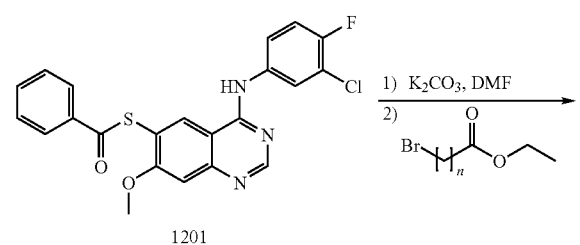
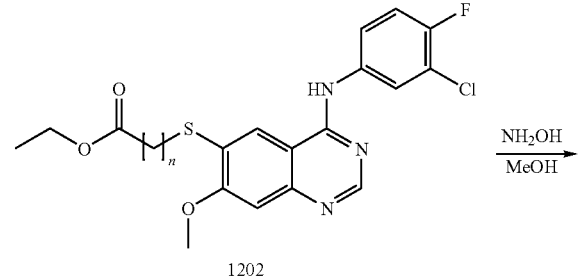
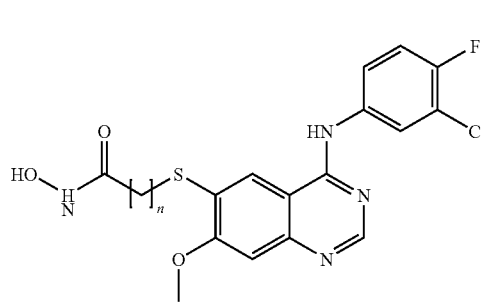
Scheme 13
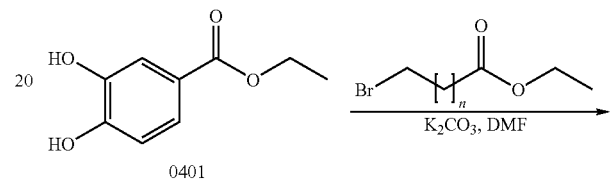
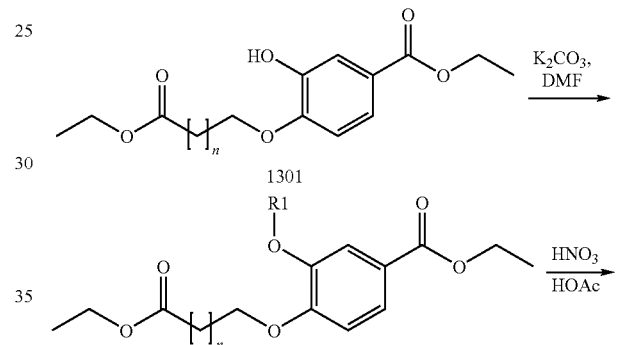
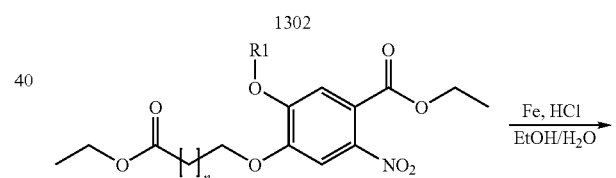
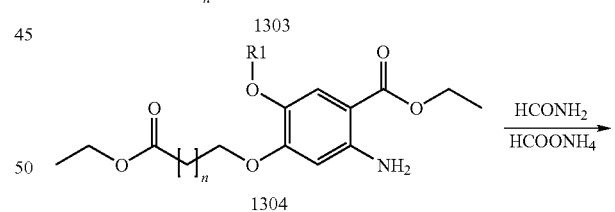
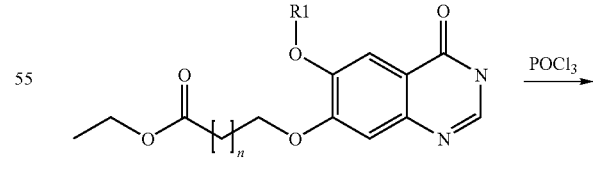
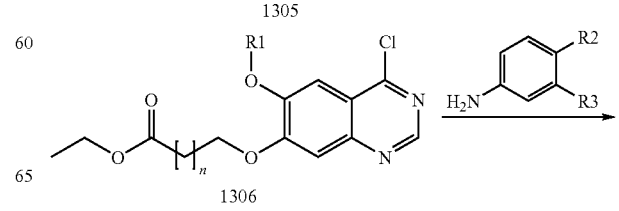

-continued
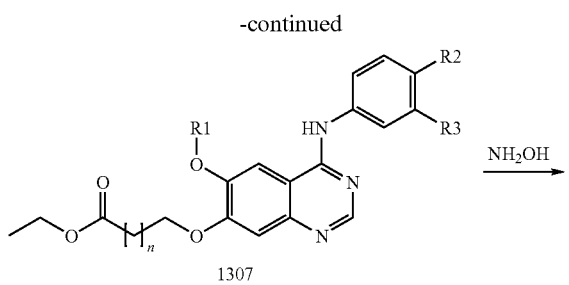 →NH₂OH→ 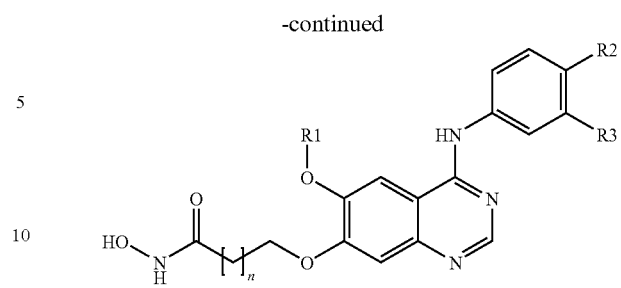
Scheme 14
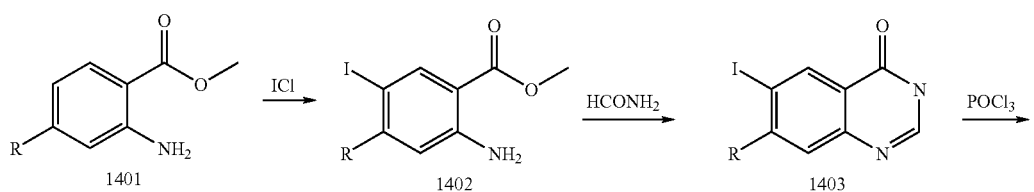
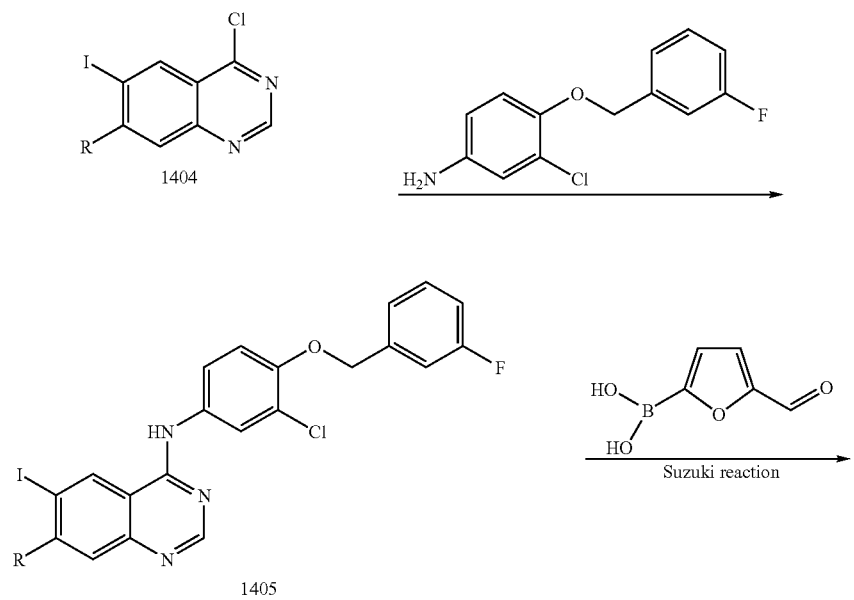
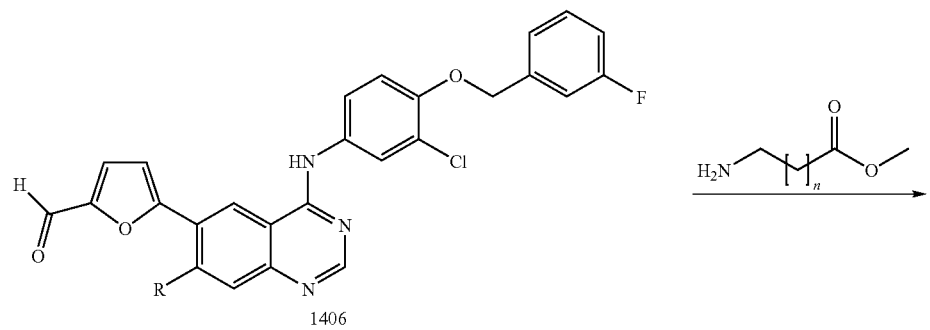

-continued
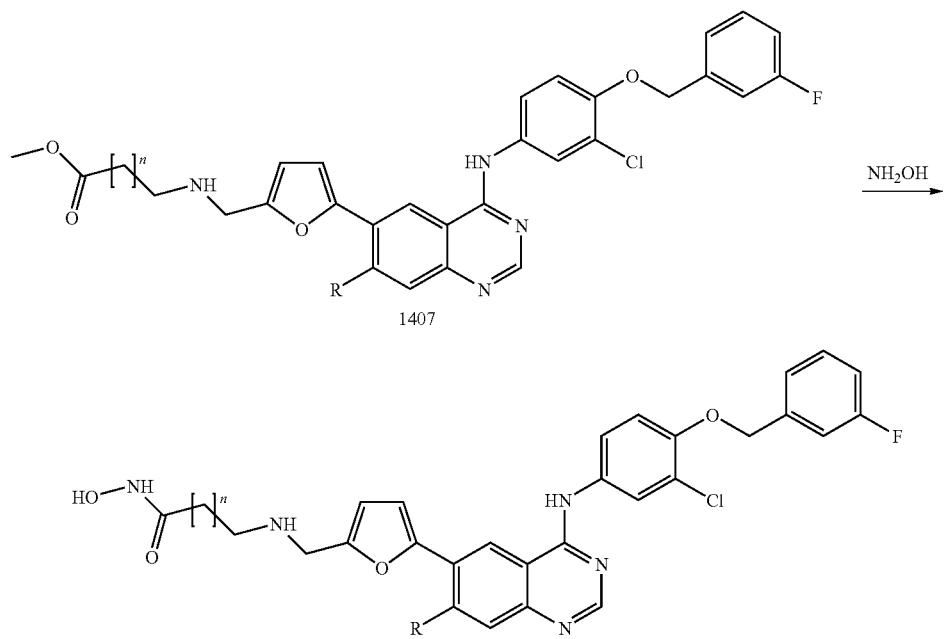
Scheme 15
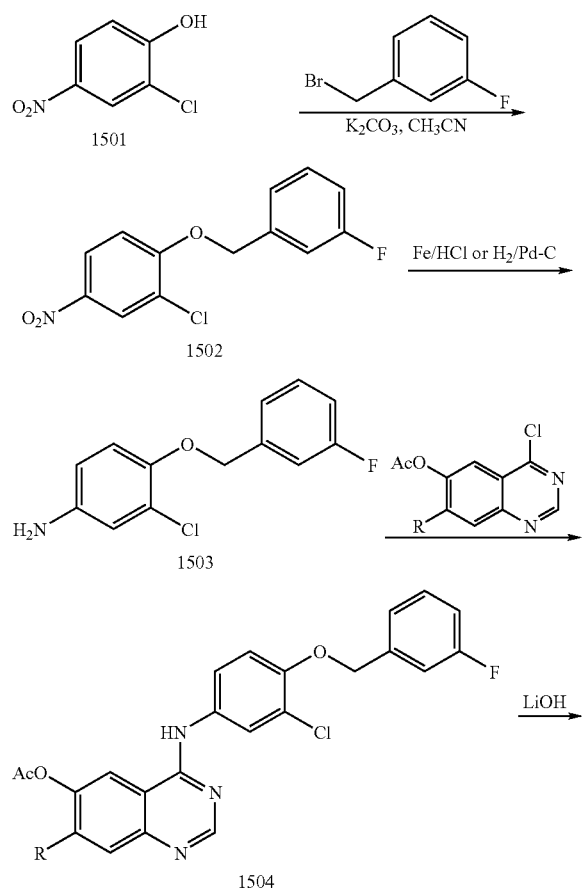

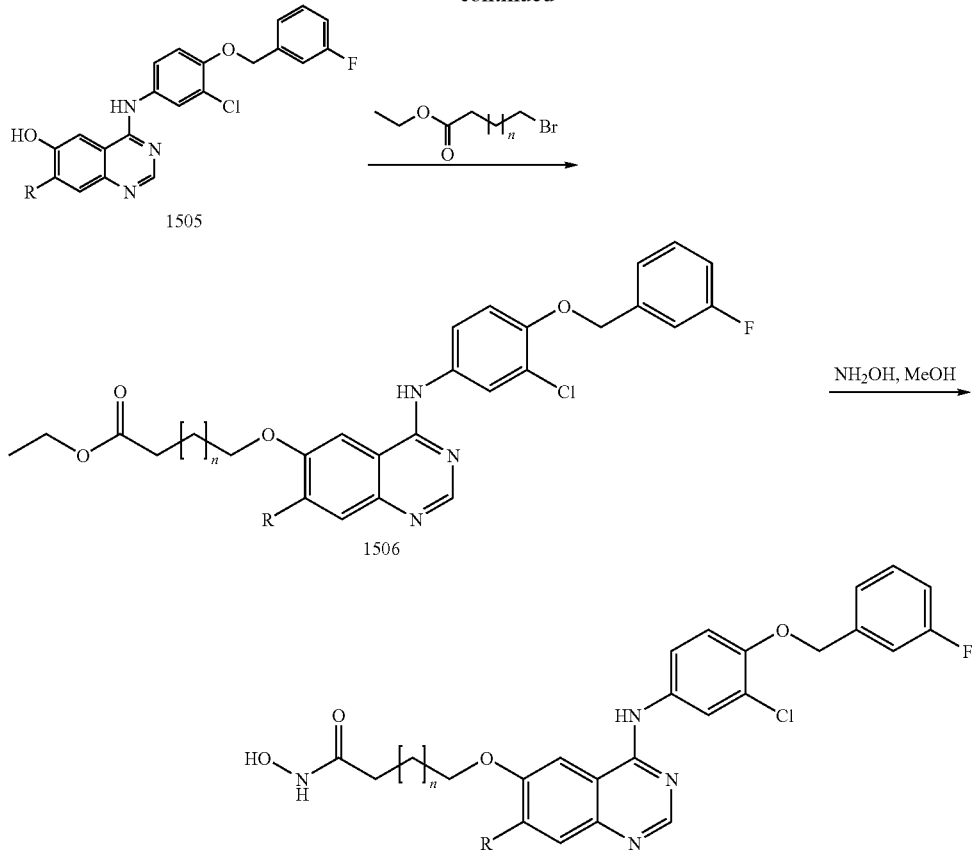

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Preparation of 2-(4-(3-Chloro-4-fluorophenylamino)-7-methoxyquinazolin-6-yloxy)-N-hydroxyacetamide (Compound 1)

Step 1a. 6,7-Dimethoxyquinazolin-4(3H)-one (Compound 0102)

A mixture of methyl 2-amino-4,5-dimethoxybenzoic acid 0101 (2.1 g, 10 mmol), ammonium formate (0.63 g, 10 mmol) and formamide (7 ml) was stirred and heated to 190~200° C. for 2 hours. Then the mixture was cooled to room temperature. The precipitate was isolated, washed with water and dried to provide the title compound 0102 as a brown solid (1.8 g, 84.7%): LCMS: m/z 207 [M+1]$^+$; $^1$H NMR (DMSO) δ 3.87 (s, 3H), 3.89 (s, 3H), 7.12 (s, 1H), 7.43 (s, 1H), 7.97 (s, 1H), 12.08 (bs, 1H).

Step 1b. 6-Hydroxy-7-methoxyquinazolin-4(3H)-one (Compound 0103)

6,7-Dimethoxyquinazolin-4(3H)-one (0102) (10.3 g, 50 mmol) was added portionwise to stirred methanesulphonic acid (68 ml). L-Methionone (8.6 g, 57.5 mmol) was then added and resultant mixture was heated to 150~160° C. for 5 hours. The mixture was cooled to room temperature and poured onto a mixture (250 ml) of ice and water. The mixture was neutralized by the addition of aqueous sodium hydroxide solution (40%). The precipitate was isolated, washed with water and dried to yield title compound 0103 as a grey solid (10 g, crude): LCMS: m/z 193 [M+1]$^+$.

Step 1c. 3,4-Dihydro-7-methoxy-4-oxoquinazolin-6-yl acetate (Compound 0104)

A mixture of 6-hydroxy-7-methoxyquinazolin-4(3H)-one (0103) (10 g crude), acetic anhydride (100 ml) and pyridine (8 ml) was stirred and heated to reflux for 3 hours. The mixture was cooled to room temperature and poured into a mixture (250 ml) of ice and water. The precipitate was isolated and dried to yield the title product 0104 as a grey solid (5.8 g, 50% two step overall yield): LCMS: m/z 235 [M+1]$^+$; $^1$H NMR (CDCl$_3$) δ 2.27 (s, 3H), 3.89 (s, 3H), 7.28 (s, 1H), 7.72 (s, 1H), 8.08 (d, 1H), 12.20 (bs, 1H).

Step 1d. 4-Chloro-7-methoxyquinazolin-6-yl acetate (Compound 0105)

A mixture of 3,4-dihydro-7-methoxy-4-oxoquinazolin-6-yl acetate (0104) (2.0 g, 8.5 mmol) and phosphoryl trichloride (20 ml) was stirred and heated to reflux for 3 hours. When a clear solution was obtained, the excessive phosphoryl trichloride was removed under reduced pressure. The residue was dissolved in dichloromethane (50 ml) and the organic layer was washed with aqueous $NaHCO_3$ solution (20 ml×2) and brine (20 ml×1) and dried over $MgSO_4$, filtered and evaporated to give the title product 0105 as a yellow solid (1.4 g, 65%): LCMS: m/z 249 [M+1]$^+$; $^1$H NMR (CDCl$_3$) δ 2.40 (s, 3H), 4.03 (s, 3H), 7.44 (s, 1H), 7.90 (s, 1H), 8.95 (bs, 1H).

Step 1e. 4-(3-Chloro-4-fluorophenylamino)-7-methoxyquinazolin-6-yl acetate hydrochloride (Compound 0108)

A mixture of 4-chloro-7-methoxyquinazolin-6-yl acetate (0105) (1.3 g, 5.1 mmol) and 3-chloro-4-fluorobenzenamine 0106 (1.5 g, 10.2 mmol) in isopropanol (45 ml) was stirred and heated to reflux for 3 hours. The mixture was cooled to room temperature and resulting precipitate was isolated. The solid was then dried to give the title compound 0108 as a light yellow solid (1.6 g, 79%): LCMS: m/z 362 [M+1]$^+$; $^1$H NMR (DMSO) δ 2.36 (s, 3H), 3.98 (s, 3H), 7.49 (s, 1H), 7.52 (d, 1H), 7.72 (m, 1H), 8.02 (dd, 1H), 8.71 (s, 1H), 8.91 (s, 1H), 11.4 (bs, 1H).

Step 1f. 4-(3-Chloro-4-fluorophenylamino)-7-methoxyquinazolin-6-ol (Compound 0109)

A mixture of compound (0107) (1.41 g, 3.5 mmol), LiOH H$_2$O (0.5 g, 11.7 mmol) in methanol (100 ml) and H$_2$O (100 ml) was stirred at room temperature for 0.5 hour. The mixture was neutralized by addition of dilution acetic acid. The precipitate was isolated and dried to give the title compound 0109 as a grey solid (1.06 g, 94%): LCMS: m/z 320 [M+1]$^+$; $^1$H NMR (DMSO) δ 3.99 (s, 3H), 7.20 (s, 1H), 7.38 (t, 1H), 7.75 (s, 1H), 7.81 (m, 1H), 8.20 (m, 1H), 8.46 (s, 1H), 9.46 (s, 1H), 9.68 (s, 1H).

Step 1g. Ethyl 2-(4-(3-chloro-4-fluorophenylamino)-7-methoxyquinazolin-6-yloxy)acetate (Compound 0110-1)

A mixture of compound 0109 (300 mg, 0.94 mmol) and Ethyl 2-bromoacetate (163 mg, 0.98 mmol) and potassium carbonate (323 mg, 2.35 mmol) in N,N-dimethylformamide (6 ml) was stirred and heated to 400 for 30 minutes. The reaction process was monitored by TLC. The mixture was filtrated. The filtration was concentrated under reduce pressure. The residues was wash with diethyl ether and dried to give the title compound 0110-1 as a yellow solid (280 mg, 74%): LCMS: m/z 406 [M+1]$^+$; $^1$H NMR (DMSO) δ 1.23 (t, 3H), 3.96 (s, 3H), 4.20 (q, 2H), 4.95 (s, 2H), 7.24 (s, 1H), 7.44 (t, 1H), 7.75 (m, 1H), 7.82 (s, 1H), 8.10 (dd, 1H), 8.51 (s, 1H), 9.54 (s, 1H).

Step 1h. 2-(4-(3-Chloro-4-fluorophenylamino)-7-methoxyquinazolin-6-yloxy)-N-hydroxyacetamide (Compound 1)

To a stirred solution of hydroxyamine hydrochloride (4.67 g, 67 mmol) in methanol (24 ml) at 0° C. was added a solution of potassium hydroxide (5.61 g, 100 mmol) in methanol (14 ml). After addition, the mixture was stirred for 30 minutes at 0° C., and was allowed to stand at low temperature. The resulting precipitate was isolated, and the solution was prepared to give free hydroxyamine.

The above freshly prepared hydroxyamine solution (1.4 ml, 2.4 mmol) was placed in 5 ml flask. Compound 0110-1 (250 mg, 0.6 mmol) was added to this solution and stirred at 0° C. for 10 minutes, and raise to room temperature. The reaction process was monitored by TLC. The mixture was neutralized with acetic acid. The mixture was concentrated under reduce pressure. The residue was purified by preparation HPLC. To give the title compound 1 as a grey solid (50 mg, 21%): LCMS: m/z 393 [M+1]$^+$; $^1$H NMR (DMSO) δ 3.96 (s, 3H), 4.62 (s, 2H), 7.24 (s, 1H), 7.45 (t, 1H), 7.78 (m, 1H), 7.86 (s, 1H), 8.10 (dd, 1H), 8.52 (s, 1H), 9.07 (s, 1H), 9.57 (s, 1H), 10.80 (s, 1H).

Example 2

Preparation of 4-(4-(3-Chloro-4-fluorophenylamino)-7-methoxyquinazolin-6-yloxy)-N-hydroxybutanamide (Compound 3)

Step 2a. Ethyl 4-(4-(3-chloro-4-fluorophenylamino)-7-methoxyquinazolin-6-yloxy)butanoate (Compound 0110-3)

The title compound 0110-3 was prepared as a yellow solid (220 mg, 80.5%) from compound 0109 from step 1f (200 mg, 0.63 mmol) and ethyl 4-bromobutyrate (135 mg, 0.69 mmol) using a procedure similar to that described for compound 0110-1 (example 1): LCMS: m/z 434 [M+1]$^+$; $^1$H NMR (CDCl$_3$) δ 1.36 (t, 3H), 2.23 (m, 2H), 2.57 (t, 2H), 4.03 (s, 3H), 4.32 (m, 4H), 7.15 (t, 1H), 7.25 (m, 1H), 7.87 (s, 1H), 8.00 (m, 2H), 8.15 (bs, 1H), 8.57 (s, 1H).

Step 2b. 4-(4-(3-Chloro-4-fluorophenylamino)-7-methoxyquinazolin-6-yloxy)-N-hydroxybutanamide (Compound 3)

The title compound 3 was prepare as a grey solid (25 mg, 12%) from compound 0110-3 (200 mg, 0.23 mmol) using a procedure similar to that described for compound 1 (Example 1): LCMS: m/z 421 [M+1]$^+$; $^1$H NMR (DMSO): δ 2.06 (m, 2H), 2.22 (t, 2H), 3.95 (s, 3H), 4.15 (t, 2H), 7.21 (s, 1H), 7.43 (t, 1H), 7.83 (s, 2H), 8.14 (dd, 1H), 8.51 (s, 1H), 8.75 (s, 1H), 9.56 (s, 1H), 10.50 (s, 1H).

Example 3

Preparation of 7-(4-(3-Chloro-4-fluorophenylamino)-7-methoxyquinazolin-6-yloxy)-N-hydroxyhexanamide (Compound 5)

Step 3a. Ethyl 6-(4-(3-chloro-4-fluorophenylamino)-7-methoxyquinazolin-6-yloxy)hexanoate (Compound 0110-5)

The title compound 0110-5 was prepared as a yellow solid (510 mg, 68%) from compound 0109 from step 1f (510 mg, 1.6 mmol) and ethyl 6-bromohexanoate (430 mg, 1.9 mmol) using a procedure similar to that described for compound 0110-1 (Example 1): LCMS: m/z 462 [M+1]$^+$; $^1$H NMR (CDCl$_3$): δ 1.24 (t, 3H), 1.55 (m, 2H), 1.74 (m, 2H), 1.91 (m, 2H), 2.38 (m, 2H), 3.97 (s, 3H), 4.13 (m, 4H), 7.15 (t, 1H), 7.25 (m, 2H), 7.60 (m, 1H), 7.86 (m, 1H), 7.91 (dd, 1H), 8.61 (s, 1H).

Step 3b. 7-(4-(3-Chloro-4-fluorophenylamino)-7-methoxyquinazolin-6-yloxy)-N-hydroxyhexanamide (Compound 5)

The title compound 5 was prepared as a grey solid (100 mg, 34%) form compound 0110-5 (305 mg, 0.66 mmol) using a procedure similar to that described for compound 1 (Example 1): m.p. 206.6~207.1° C. (dec); LCMS: m/z 449 [M+1]$^+$; $^1$H NMR (DMSO) δ 1.44 (m, 2H), 1.64 (m, 2H), 1.82 (m, 2H), 1.99 (t, 2H), 3.93 (s, 3H), 4.12 (t, 2H), 7.19 (s, 1H), 7.43 (t, 1H), 7.79 (m, 2H), 8.12 (dd, 1H), 8.49 (s, 1H), 8.68 (s, 1H), 9.53 (s, 1H), 10.37 (s, 1H).

Example 4

Preparation of 7-(4-(3-Chloro-4-fluorophenylamino)-7-methoxyquinazolin-6-yloxy)-N-hydroxyheptanamide (Compound 6)

Step 4a. Ethyl 7-(4-(3-chloro-4-fluorophenylamino)-7-methoxyquinazolin-6-yloxy)heptanoate (compound 0110-6)

The title compound 0110-6 was prepared as a yellow solid (390 mg, 53%) from compound 0109 from step 1f (512 mg, 1.6 mmol) and ethyl 7-bromoheptanoate (438 mg, 1.8 mmol) using a procedure similar to that described for compound 0110-1 (Example 1): LCMS: m/z 476 [M+1]$^+$; $^1$H NMR (CDCl$_3$) δ 1.24 (t, 3H), 1.43 (m, 4H), 1.66 (m, 2H), 1.88 (m, 2H), 2.32 (t, 2H), 3.97 (s, 3H), 4.07 (t, 2H), 4.12 (q, 2H), 7.15 (t, 1H), 7.23 (t, 2H), 7.66 (m, 1H), 7.75 (m, 1H), 7.87 (dd, 1H), 8.65 (s, 1H).

Step 4b. 7-(4-(3-Chloro-4-fluorophenylamino)-7-methoxyquinazolin-6-yloxy)-N-hydroxyheptanamide (compound 6)

The title compound 6 was prepared as a grey solid (80 mg, 25%) from compound 0110-6 (323 mg, 0.68 mmol) using a procedure similar to that described for compound 1 (Example 1): m.p. 180.8~182.3° C. (dec); LCMS: m/z 463 [M+1]$^+$; $^1$H NMR (DMSO) δ 1.34 (m, 2H), 1.50 (m, 4H), 1.81 (m, 2H), 1.96 (t, 2H), 3.92 (s, 3H), 4.11 (t, 2H), 7.18 (s, 1H), 7.43 (t, 1H), 7.78 (m, 2H), 8.12 (dd, 1H), 8.48 (s, 1H), 8.64 (s, 1H), 9.50 (s, 1H), 10.33 (s, 1H).

Example 5

Preparation of 2-(4-(3-ethynylphenylamino)-7-methoxyquinazolin-6-yloxy)-N-hydroxyacetamide (Compound 7)

Step 5a. 4-(3-Ethynylphenylamino)-7-methoxyquinazolin-6-yl acetate Hydrochloride (Compound 0111)

A mixture of 4-chloro-7-methoxyquinazolin-6-yl acetate (0105) (2.6 g, 10.2 mmol) and 3-ethynylbenzenamine (0107) (2.4 g, 20.5 mmol) in isopropanol (100 ml) was stirred and heated to reflux for 3 hours. The mixture was cooled to room temperature. The precipitate was isolated and dried to give the title compound 0111 as a yellow solid (2.6 g, 68%): LCMS: m/z 334 [M+1]$^+$; $^1$H NMR (DMSO) δ 2.39 (s, 3H), 3.17 (s, 1H), 3.98 (s, 3H), 7.35 (m, 1H), 7.40 (s, 1H), 7.47 (m, 1H), 7.72 (m, 1H), 7.90 (s, 1H), 8.57 (s, 1H), 8.87 (s, 1H), 10.99 (bs, 1H).

Step 5b. 4-(3-Ethynylphenylamino)-7-methoxyquinazolin-6-ol (Compound 0112)

A mixture of compound 0111 (2.0 g, 5.4 mmol) and LiOH H$_2$O (0.75 g, 17.9 mmol) in methanol (100 ml) and H$_2$O (100 ml) was stirred at room temperature for 0.5 hour. The mixture was neutralized by addition of dilution acetic acid. The precipitate was isolated and dried to give the title compound 0112 as a grey solid (1.52 g, 96%): LCMS: m/z 292 [M+1]$^+$; $^1$H NMR (DMSO) δ 3.17 (s, 1H), 3.98 (s, 3H), 7.18 (d, 1H), 7.21 (s, 1H), 7.37 (t, 1H), 7.80 (s, 1H), 7.90 (d, 1H), 8.04 (m, 1H), 8.47 (s, 1H), 9.41 (s, 1H), 9.68 (bs, 1H).

Step 5c. Ethyl 2-(4-(3-ethynylphenylamino)-7-methoxyquinazolin-6-yloxy)acetate (Compound 0113-7)

The title compound 0113-7 was prepared as a yellow solid (450 mg, 69%) from compound 0112 (500 mg, 1.72 mmol) and ethyl 2-bromoacetate (300 mg, 1.8 mmol) using a procedure similar to that described for compound 0110-1 (Example 1): LCMS: m/z 378 [M+1]$^+$; $^1$H NMR (DMSO) δ 1.22 (t, 3H), 3.97 (s, 3H), 4.21 (q, 2H), 4.97 (t, 2H), 7.22 (d, 1H), 7.24 (s, 1H), 7.42 (t, 1H), 7.84 (m, 2H), 7.86 (d, 1H), 7.96 (s, 1H), 8.51 (s, 1H).

Step 5d. 2-(4-(3-Ethynylphenylamino)-7-methoxyquinazolin-6-yloxy)-N-hydroxyacetamide (Compound 7)

The title compound 7 was prepared as a grey solid (100 mg, 23%) from compound 0113-7 (448 mg, 1.2 mmol) using a procedure similar to that described for compound 1 (Example 1): LCMS: m/z 365 [M+1]$^+$; $^1$H NMR (DMSO) δ 4.00 (s, 3H), 4.26 (s, 1H), 4.65 (s, 2H), 7.27 (s, 1H), 7.37 (d, 1H), 7.49 (t, 1H), 7.73 (d, 1H), 7.85 (s, 1H), 8.03 (s, 1H), 8.78 (s, 1H), 9.17 (bs, 1H), 10.60 (s, 1H), 10.85 (s, 1H).

Example 6

Preparation of 4-(4-(3-ethynylphenylamino)-7-methoxyquinazolin-6-yloxy)-N-hydroxybutanamide (Compound 9)

Step 6a. Ethyl 4-(4-(3-ethynylphenylamino)-7-methoxyquinazolin-6-yloxy)butanoate (Compound 0113-9)

The title compound 0113-9 was prepared as a yellow solid (438 mg, 59%) from compound 0112 (500 mg, 1.72 mmol) and ethyl 4-bromobutyrate (349 mg, 1.8 mmol) using a procedure similar to that described for compound 0110-1 (Example 1): LCMS: m/z 406 [M+1]$^+$; $^1$H NMR (CDCl$_3$) δ 1.37 (t, 3H), 2.34 (m, 2H), 2.56 (t, 2H), 3.07 (s, 1H), 4.03 (s, 3H), 4.32 (m, 4H), 7.21 (m, 1H), 7.25 (s, 1H), 7.36 (t, 1H), 7.94 (s, 1H), 7.97 (m, 1H), 8.20 (s, 1H), 8.28 (m, 1H), 8.70 (s, 1H).

Step 6b. 4-(4-(3-Ethynylphenylamino)-7-methoxyquinazolin-6-yloxy)-N-hydroxybutanamide (Compound 9)

The title compound 9 was prepared as a grey solid (60 mg, 31%) from compound 0113-9 (200 mg, 0.49 mmol) using a procedure similar to that described for compound 1 (Example 1): LCMS: m/z 393 [M+1]$^+$; $^1$H NMR (DMSO) δ 2.06 (m, 2H), 2.22 (t, 2H), 3.30 (s, 1H), 3.95 (s, 3H), 4.16 (t, 2H), 7.19

(m, 2H), 7.40 (t, 1H), 7.85 (s, 1H), 7.91 (d, 1H), 8.02 (s, 1H), 8.51 (s, 1H), 8.74 (s, 1H), 9.49 (s, 1H), 10.49 (s, 1H).

Example 7

Preparation of 6-(4-(3-ethynylphenylamino)-7-methoxyquinazolin-6-yloxy)-N-hydroxyhexanamide (Compound 11)

Step 7a. Ethyl 6-(4-(3-ethynylphenylamino)-7-methoxyquinazolin-6-yloxy)hexanoate (Compound 0113-11)

The title compound 0113-11 was prepared as yellow solid (543 mg, 73%) from compound 0112 from step 5b (500 mg, 1.72 mmol) and ethyl 6-bromohexanoate (401 mg, 1.8 mmol) using a procedure similar to that described for compound 0110-1 (Example 1): LCMS: m/z 434 [M+1]$^+$; $^1$H NMR (CDCl$_3$) δ 1.24 (t, 3H), 1.53 (m, 2H), 1.72 (m, 2H), 1.90 (m, 2H), 2.37 (t, 3H), 3.08 (s, 1H), 3.97 (s, 3H), 4.10 (m, 4H), 7.19 (s, 1H), 7.25 (m, 2H), 7.34 (t, 1H), 7.67 (s, 1H), 7.78 (m, 1H), 7.84 (m, 1H), 8.67 (s, 1H).

Step 7b. 6-(4-(3-Ethynylphenylamino)-7-methoxyquinazolin-6-yloxy)-N-hydroxyhexanamide (Compound 11)

The title compound 11 was prepared as a grey solid (110 mg, 41%) from compound 0113-11 (275 mg, 0.63 mmol) using a procedure similar to that described for compound 1 (Example 1): m.p. 193.4~195.8° C. (dec); LCMS: m/z 421 [M+1]$^+$; $^1$H NMR (DMSO) δ 1.44 (m, 2H), 1.60 (m, 2H), 1.84 (m, 2H), 1.99 (t, 2H), 3.93 (s, 3H), 4.13 (t, 2H), 4.19 (s, 1H), 7.19 (m, 2H), 7.40 (t, 1H), 7.81 (s, 1H), 7.88 (d, 1H), 7.98 (s, 1H), 8.49 (s, 1H), 8.68 (s, 1H), 9.47 (s, 1H), 10.39 (s, 1H).

Example 8

Preparation of 7-(4-(3-ethynylphenylamino)-7-methoxyquinazolin-6-yloxy)-N-hydroxyheptanamide (Compound 12)

Step 8a. Ethyl 6-(4-(3-ethynylphenylamino)-7-methoxyquinazolin-6-yloxy) heptanoate (Compound 0113-12)

The title compound 0113-12 was prepared as a yellow solid (305 mg, 84%) from compound 0112 from step 5b (247 mg, 0.85 mmol) and ethyl 7-bromohepanoate (211 mg, 0.89 mmol) using a procedure similar to that described for compound 0110-1 (Example 1): LCMS: 448 [M+1]$^+$; $^1$H NMR (CDCl$_3$): δ1.15 (t, J=7.5 Hz, 3H), 1.33-1.60 (m, 6H), 1.81 (m, 2H), 2.28 (t, J=7.5 Hz, 2H), 3.92 (s, 3H), 4.03 (q, J=7.2 Hz, 2H), 4.12 (t, J=6.6 Hz, 2H), 4.18 (s, 1H), 7.19 (m, 2H), 7.39 (t, J=7.8 Hz, 1H), 7.80 (s, 1H), 7.89 (d, J=8.1 Hz, 1H), 7.97 (s, 1H), 8.48 (s, 1H), 9.44 (s, 1H).

Step 8b. 7-(4-(3-Ethynylphenylamino)-7-methoxyquinazolin-6-yloxy)-N-hydroxyheptanamide (Compound 12)

The title compound 12 was prepared as a grey solid (100 mg, 41%) from compound 0113-12 (250 mg, 0.56 mmol) using a procedure similar to that described for compound 1 (Example 1): m.p. 171.8~177.2° C. (dec); LCMS: 435 [M+1]$^+$; $^1$H NMR (DMSO-d$_6$): δ1.36 (m, 2H), 1.52 (m, 4H), 1.83 (m, 2H), 1.97 (m, 2H), 3.94 (s, 3H), 4.14 (t, J=6.3 Hz, 2H), 4.20 (s, 1H), 7.21 (m, 2H), 7.41 (t, J=8.1 Hz, 1H), 7.83 (s, 1H), 7.90 (d, J=8.1 Hz, 1H), 8.00 (s, 1H), 8.50 (s, 1H), 8.66 (s, 1H), 9.48 (s, 1H), 10.35 (s, 1H).

Example 8

(METHOD 2) Preparation of 7-(4-(3-ethynylphenylamino)-7-methoxyquinazolin-6-yloxy)-N-hydroxyheptanamide (Compound 12)

Step 8a'. Ethyl 3-hydroxy-4-methoxybenzoate (Compound 0402-12)

To a solution of ethyl 3,4-dihydroxybenzoate 0401 (12.52 g, 68.7 mmol) in DMF (50 mL) was added potassium carbonate (9.48 g, 68.7 mmol). After the mixture was stirred for 15 minutes, a solution of iodomethane (9.755 g, 68.7 mmol) in DMF (10 mL) was added dropwise. The reaction mixture was stirred at 20° C. for 24 hours. After reaction the mixture was filtered, and the filtrate was concentrated. The residue was dissolved in dichloromethane and washed with brine. The organic phase was dried over sodium sulfate, filtered and concentrated in vacuo to give crude product. The crude product was purified by column chromatography to give the title compound 0402-12 as a white solid (7.1 g, 53%): LCMS: 197 [M+1]$^+$, $^1$H NMR (DMSO-d$_6$): δ 1.29 (t, J=6.6 Hz, 3H), 3.83 (s, 3H), 4.25 (q, J=6.6 Hz, 2H), 7.00 (d, J=8.4 Hz, 1H), 7.38 (d, J=1.8 Hz, 1H), 7.43 (dd, J=8.4 Hz, 2.1 Hz, 1H), 9.36 (s, 1H).

Step 8b'. Ethyl 3-(7-ethoxy-7-oxoheptyloxy)-4-methoxybenzoate (Compound 0403-12)

A mixture of compound 0402-12 (6.34 g, 32.3 mmol), ethyl 7-bromoheptanoate (7.66 g, 32.3 mmol) and potassium carbonate (13.38 g, 96.9 mmol) in DMF (80 mL) was stirred at 60° C. for 3 hours. After reaction the mixture was filtrated. The filtrate was concentrated in vacuo and the residue was dissolved in dichloromethane and washed with brine twice. The organic phase was dried over sodium sulfate, filtered and concentrated to give the title product 0403-12 as a white solid (9.87 g, 86.7%): LCMS: 353 [M+1]$^+$, $^1$H NMR (DMSO-d$_6$): δ1.17 (t, J=6.9 Hz, 3H), 1.31 (t, J=7.2 Hz, 3H) 1.39 (m, 4H), 1.54 (m, 2H), 1.72 (m, 2H), 2.29 (t, J=7.2 Hz, 2H), 3.83 (s, 3H), 3.98 (t, J=7.2 Hz, 2H), 4.06 (q, J=6.9 Hz, 2H), 4.29 (q, J=7.2 Hz, 2H), 7.06 (d, J=8.4 Hz, 1H), 7.42 (d, J=1.8 Hz, 1H), 7.57 (dd, J=8.4 Hz, 1.8 Hz, 1H).

Step 8c'. Ethyl 5-(7-ethoxy-7-oxoheptyloxy)-4-methoxy-2-nitrobenzoate (Compound 0404-12)

Compound 0403-12 (9.87 g, 28.0 mmol) was dissolved in acetic acid (20 mL) and stirred at 20° C. Fuming nitric acid (17.66 g, 280.0 mmol) was added slowly dropwise. The mixture was stirred at 20° C. for 1 hour. After reaction the mixture was poured into ice-water and extracted with dichloromethane twice. The combined organic phase was washed with brine, aqueous NaHCO$_3$ solution and brine. The combined organic phase was dried over sodium sulfate, filtered and concentrated to give the title product 0404-12 as a yellow solid (10.75 g, 96.4%): LCMS: 398 [M+1]$^+$, $^1$H NMR (DMSO-d$_6$): δ1.17 (t, J=7.2 Hz, 3H), 1.27 (t, J=7.2 Hz, 3H), 1.38 (m, 4H), 1.53 (m, 2H), 1.74 (m, 2H), 2.29 (t, J=7.2 Hz, 2H), 3.91 (s, 3H), 4.03 (q, J=7.2 Hz, 2H), 4.08 (t, J=6.3 Hz, 2H), 4.30 (q, J=7.2 Hz, 2H), 7.29 (s, 1H), 7.63 (s, 1H).

Step 8d'. Ethyl 2-amino-5-(7-ethoxy-7-oxoheptyloxy)-4-methoxybenzoate (Compound 0405-12)

A mixture of 0404-12 (10.75 g 27.0 mmol), ethanol (120 mL), water (40 mL) and hydrogen chloride (4 mL) was stirred to form a clear solution. The iron powder (15.16 g, 27.0 mmol) was added batchwise. The mixture was stirred at reflux for 30 min, and was then cooled to room temperature, adjusted pH to 8 with 10% sodium hydroxide solution, and filtered. The filtrate was concentrated to remove ethanol and extracted with dichloromethane twice. The combined organic phase was washed with brine and dried over sodium sulfate, filtered and concentrated to give the title product 0405-12 as a yellow solid (8.71 g, 87.8%): LCMS: 368 [M+1]$^+$, $^1$H NMR (DMSO-d$_6$): δ 1.17 (t, J=7.2 Hz, 3H), 1.28 (t, J=7.2 Hz, 3H), 1.37 (m, 4H), 1.53 (m, 2H), 1.66 (m, 2H), 2.29 (t, J=7.2 Hz, 2H), 3.74 (s, 3H), 3.78 (t, J=6.9 Hz, 2H), 4.06 (q, J=7.2 Hz, 2H), 4.22 (q, J=7.2 Hz, 2H), 6.35 (s, 1H), 6.44 (s, 2H), 7.15 (s, 1H).

Step 8e'. Ethyl 7-(7-methoxy-4-oxo-3,4-dihydroquinazolin-6-yloxy) heptanoate (Compound 0406-12)

A mixture of compound 0405-12 (8.71 g, 23.7 mmol), ammonium formate (1.48 g, 23.7 mmol) and formamide (40 mL) was stirred at 180° C. for 3 hours. After reaction the mixture was cooled to room temperature. The formamide was removed under reduce pressure, and the residue was dissolved in dichloromethane and washed with brine. The organic phase was dried over sodium sulfate, filtered and concentrated to give the title product 0406-12 as a pale white solid (8.18 g, 99%): LCMS: 349 [M+1]$^+$, $^1$H NMR (DMSO-d$_6$): δ1.17 (t, J=6.9 Hz, 3H), 1.38 (m, 4H), 1.55 (m, 2H), 1.75 (m, 2H), 2.29 (t, J=7.2 Hz, 2H), 3.90 (s, 3H), 4.05 (m, 4H), 7.13 (s, 1H), 7.42 (s, 1H), 7.97 (d, J=3.6 Hz, 1H), 12.07 (s, 1H).

Step 8f'. Ethyl 7-(4-chloro-7-methoxyquinazolin-6-yloxy)heptanoate (Compound 0407-12)

A mixture of product 0406-12 (8.18 g, 23.5 mmol) and phosphoryl trichloride (50 mL) was stirred at reflux for 4 hours. After reaction the excessive phosphoryl trichloride was removed under reduced pressure. The residue was dissolved in dichloromethane and washed with water, aqueous NaHCO$_3$ solution and brine. The organic phase was dried over sodium sulfate, filtered and concentrated to give the title product 0407-12 as a yellow solid (5.93 g, 69.7%): LCMS: 367 [M+1]$^+$, $^1$H NMR (DMSO-d$_6$): δ1.17 (t, J=6.9 Hz, 3H), 1.38 (m, 4H), 1.54 (m, 2H), 1.81 (m, 2H), 2.30 (t, J=7.2 Hz, 2H), 4.02 (s, 3H), 4.06 (q, J=6.9 Hz, 2H), 4.18 (t, J=6.3 Hz, 2H), 7.37 (s, 1H), 7.45 (s, 1H), 8.87 (s, 1H).

Step 8g'. Ethyl 7-(4-(3-ethynylphenylamino)-7-methoxyquinazolin-6-yloxy) heptanoate (Compound 0408-12)

A mixture of product 0407-12 (5.93 g, 16.4 mmol) and 3-ethynylbenzenamine (1.92 g, 16.4 mmol) in isopropanol (80 mL) was stirred at reflux 4 hours. After reaction the mixture was cooled to room temperature and resulting precipitate was isolated, washed with isopropanol and ether, and dried to give the title compound 0408-12 as a yellow solid (4.93 g, 67.1%): LCMS: 448 [M+1]$^+$, $^1$H NMR (DMSO-d$_6$): δ1.16 (t, J=7.2 Hz, 3H), 1.36-1.59 (m, 6H), 1.80 (m, 2H), 2.29 (t, J=7.2 Hz, 2H), 3.93 (s, 3H), 4.04 (q, J=6.9 Hz, 2H), 4.13 (t, J=6.6 Hz, 2H), 4.19 (s, 1H), 7.20 (m, 2H), 7.39 (t, J=7.8 Hz, 1H), 7.81 (s, 1H), 7.89 (d, J=8.4 Hz, 1H), 7.97 (s, 1H), 8.48 (s, 1H), 9.45 (s, 1H).

Step 8h'. 7-(4-(3-ethynylphenylamino)-7-methoxyquinazolin-6-yloxy)-N-hydroxyheptanamide (Compound 12)

The freshly prepared hydroxylamine solution (30 mL, 110 mmol) was placed in 50 mL flask. Compound 0408-12 (4.93 g, 11.0 mmol) was added to this solution and stirred at 25° C. for 24 hours. After reaction the mixture was neutralized with acetic acid, and the resulting precipitate was isolated, washed with water, and dried to give the title compound 12 as a white solid (3.99 g, 83.6%): mp 174.1~177.2° C. LCMS: 435 [M+1]$^+$, $^1$H NMR (DMSO-d$_6$): δ1.36 (m, 2H), 1.52 (m, 4H), 1.83 (m, 2H), 1.98 (m, 2H), 3.94 (s, 3H), 4.14 (t, J=6.6 Hz, 2H), 4.20 (s, 1H), 7.21 (m, 2H), 7.41 (t, J=7.8 Hz, 1H), 7.80 (s, 1H), 7.90 (d, J=7.8 Hz, 1H), 8.00 (s, 1H), 8.50 (s, 1H), 8.66 (s, 1H), 9.48 (s, 1H), 10.35 (s, 1H).

Purification by Crystallization:

To a 30 L 4-necked flask, was added crude product (1.3 kg, KF=11%), followed by THF (26 L). The solution was heated to reflux until a nearly clear solution. The solution was filtered at 45-55° C., and the filtrate was charged into a 30 L reactor, with stirring speed at 350 (r.m.p), IT=40-42° C. The solution was gradually cooled to 30° C. (during 6-8 hours). Solids appeared at 32-33° C., stirred at this temperature for 6-8 hours. Then the solution was cooled to 15-25° C. (During 4-5 hours). The solids were collected by filtration, and rinsed with THF (5 L). The damp solids were dried under vacuum at 35-40° C. for 15 h, to give crystalline compound 12 (0.9 Kg, 2.07 mol. Yield 69.2%).

Note (after vacuum drying, there is always about 10% of THF contained in the compound, pulping in ethyl acetate will remove THF).

Pulping in Ethyl Acetate to Remove THF:

The above solids (0.9 kg) were charged into 30 L 4-necked flack, added ethyl acetate (9 ml), the suspension was stirred at 25-30 C for 1 hour, then was filtered, and rinsed with ethyl acetate (2×2 L). The damp solids were vacuum dried at 60-70 C for 20 h to give crystalline compound 12 (0.86 kg). GC check no THF contained.

Example 9

Preparation of 2-(4-(3-chloro-4-fluorophenylamino) quinazolin-6-yloxy)-N-hydroxyacetamide (Compound 13)

Step 9a. 6-Hydroxyquinazolin-4(3H)-one (compound 0202)

To a solution of 2-amino-5-hydroxybenzoic acid 0201 (30.6 g, 0.2 mol) in formamide was stirred and heated to 190° C. for 0.5 h. The mixture was allowed to cool to room temperature. The precipitate was isolated, washed with ether and dried to obtain title compound 0202 (32 g, brown solid, yield: 99%): LC-MS m/z 163 [M+1]; $^1$H NMR (DMSO) δ7.25 (dd, 1H), 7.40 (d, 1H), 7.46 (d, 1H), 7.88 (s, 1H).

Step 9b. 3,4-Dihydro-4-oxoquinazolin-6-yl acetate (Compound 0203)

A mixture of compound 0202 (30.0 g, 0.185 mol) and pyridine (35 ml) in acetic anhydride (275 ml) was stirred and heated at 100° C. for 2 hours. The reaction was poured into a mixture of ice and water (500 ml). The precipitate was isolated, washed with water and dried to obtain the title compound 0203 (24 g, pale white solid, yield: 61%): LC-MS m/z 205 [M+1]; 1H-NMR (DMSO) δ 2.32 (s, 3H), 7.50 (dd, 1H), 7.80 (d, 1H), 7.98 (s, 1H), 8.02 (s, 1H).

Step 9c. 4-Chloroquinazolin-6-yl acetate (Compound 0204)

A mixture of compound 0203 (20.0 g, 0.1 mol) in $POCl_3$ (150 ml) was stirred and heated to reflux for 2 hours. The reaction was evaporated and the residue was partitioned between ethyl acetate and a saturated aqueous $NaHCO_3$ solution. The organic phase was washed with water, dried over $Na_2SO_4$ and evaporated. The mixture was purified by column chromatography (silica gel, elution: 1:2=ethyl acetate/petroleum) to obtained the title compound 0204 (7.5 g, white solid, yield: 35%): LC-MS m/z 223 [M+1]; $^1$H-NMR ($CDCl_3$) δ2.40 (s, 3H), 7.74 (dd, 1H), 8.00 (d, 1H), 8.09 (d, 1H), 9.05 (s, 1H).

Step 9d. 4-(3-Chloro-4-fluorophenylamino)quinazolin-6-yl acetate (Compound 0207)

A mixture of 0204 (1.0 g, 4.5 mmol) and 3-chloro-4-fluorobenzenamine 0205 (0.7 g, 5.0 mmol) in isopropanol (45 ml) was stirred and heated at 90° C. for 1 hours. The reaction was cooled to room temperature and the precipitate was isolated. The solid was washed in turn with isopropanol and methanol, dried to provide the title compound 0207 (1.3 g, pale yellow solid, yield: 87%): LC-MS m/z 332 [M+1]; 1H-NMR (DMSO) δ2.37 (s, 3H), 7.54 (t, 1H), 7.75 (m, 1H), 7.94 (dd, 1H), 7.99 (s, 1H), 8.02 (m, 1H), 8.64 (s, 1H), 8.95 (s, 1H).

Step 9e. 4-(3-Chloro-4-fluorophenylamino)quinazolin-6-ol (Compound 0209)

A mixture of 0207 (0.8 g, 2.6 mmol) and lithium hydroxide monohydrate (0.13 g, 3.2 mmol) in methanol (10 ml)/water (15 ml) was stirred at room temperature for 1 hour. The pH was adjusted to 4 with acetic acid and filtered. The collected yellow solid was washed by water and dried to obtained title compound 0209 (0.6 g, yellow solid, yield: 88%): LC-MS m/z 290 [M+1]; $^1$H-NMR (DMSO) δ7.42 (s, 1H), 7.45 (m, 1H), 7.70 (d, 1H), 7.76 (s, 1H), 7.86 (m, 1H), 8.24 (q, 1H), 8.48 (s, 1H), 9.61 (s, 1H).

Step 9f. Ethyl 2-(4-(3-chloro-4-fluorophenylamino) quinazolin-6-yloxy)acetate (Compound 0210-13)

A mixture of 0209 (0.2 g, 0.77 mmol), ethyl 3-bromopropanoate (0.14 g, 0.85 mmol) and $K_2CO_3$ (0.8 g, 5.8 mmol) in DMF (15 ml) was stirred and heated to 80° C. for 2 hours. The reaction was filtered and the filtrate was evaporated. The resulting solid was washed with ether to obtain the title compound 0210-13 (0.2 g, yellow solid, yield: 75%): mp 161-163° C.; LC-MS m/z 376 [M+1]; 1H-NMR (DMSO) δ1.20 (t, 3H), 4.20 (q, 2H), 4.96 (s, 2H), 7.45 (t, 1H), 7.55 (dd, 1H), 7.78 (m, 2H), 7.94 (d, 1H), 8.16 (dd, 1H), 8.54 (s, 1H), 9.69 (s, 1H).

Step 9g. 2-(4-(3-Chloro-4-fluorophenylamino) quinazolin-6-yloxy)-N-hydroxyacetamide (Compound 13)

To a stirred solution of hydroxyamine hydrochloride (4.67 g, 67 mmol) in methanol (24 ml) at 0° C. was added a solution of potassium hydroxide (5.61 g, 100 mmol) in methanol (14 ml). After addition, the mixture was stirred for 30 minutes at 0° C., and was allowed to stand at low temperature. The resulting precipitate was isolated, and the solution was prepared to give free hydroxyamine.

Take above solution (1.4 ml, 2.4 mmol) into 5 ml flask. Compound 0210-13 (0.1 g, 0.29 mmol) was added into this solution and stirred at 0° C. for 10 minutes, and then allowed to warm to room temperature. The reaction process was monitored by TLC. The mixture was adjusted pH to 6 with acetic acid and then concentrated under reduce pressure. The residue was purified by preparation HPLC eluted by methanol/water. The band containing the product was collected. The solvent was evaporated to obtain title compound 13 (30 mg, yellow solid, yield: 29%): LC-MS m/z 363 [M+1]; 1H-NMR (DMSO) δ4.64 (s, 2H), 7.46 (t, 1H), 7.58 (d, 1H), 7.79 (d, 2H), 7.7 (s, 1H), 8.11 (s, 1H), 8.52 (s, 1H), 9.02 (s, 1H), 9.67 (s, 1H), 10.96 (s, 1H).

Example 10

Preparation of 4-(4-(3-chloro-4-fluorophenylamino) quinazolin-6-yloxy)-N-Hydroxybutanamide (Compound 15)

The title compound 15 was prepared (20 mg) from compound 0209 from step 9e and ethyl 4-bromobutanoate using a procedure similar to that described for compound 13 (Example 9): mp 128-132° C.; LC-MS m/z 391 [M+1]; $^1$H-NMR (DMSO+D2O) δ2.05 (m, 2H), 2.24 (t, 2H), 4.21 (t, 2H) 7.46 (t, 1H), 7.54 (dd, 1H), 7.65 (m, 1H), 7.76 (d, 1H), 7.82 (m 1H), 7.99 (m, 1H), 8.43 (s, 1H).

Example 11

Preparation of 6-(4-(3-chloro-4-fluorophenylamino) quinazolin-6-yloxy)-N-hydroxy hexanamide (Compound 17)

Step 11a. Ethyl 6-(4-(3-chloro-4-fluorophenylamino) quinazolin-6-yloxy)hexanoate (compound 0210-17)

The title compound 0210-17 (0.2 g) was prepared from compound 0209 4-(3-chloro-4-fluorophenylamino)quinazolin-6-ol and ethyl 6-bromohexanoate using a procedure similar to that described for compound 0210-13 (Example 9): LC-MS m/z 433 [M+1], $^1$H-NMR (DMSO) δ1.13 (t, 3H), 1.45 (m, 2H), 1.60 (m, 2H) 1.76 (m, 2H), 2.30 (t, 2H), 4.05 (q, 2H), 4.11 (t, 2H), 7.41 (d, 1H), 7.45 (dd, 1H), 7.68 (d, 1H), 7.80 (m, 1H), 7.86 (m, 1H), 8.13 (dd, 1H), 8.48 (s, 1H).

Step 11b. 6-(4-(3-Chloro-4-fluorophenylamino) quinazolin-6-yloxy)-N-hydroxyhexanamide (Compound 17)

The title compound 17 (30 mg) was prepared from compound 0210-17 using a procedure similar to that described for compound 13 (Example 9): LC-MS [M+1] 419 $^1$H-NMR (DMSO) δ1.28 (m, 2H), 1.60 (m, 2H) 1.73 (m, 2H), 2.05 (t, 2H), 4.17 (t, 2H), 7.25 (d, 1H), 7.47 (t, 1H), 7.55 (dd, 1H) 7.76 (d, 1H) 7.73 (m, 1H), 8.05 (m, 1H), 8.48 (s, 1H).

Example 12

Preparation of 7-(4-(3-chloro-4-fluorophenylamino) quinazolin-6-yloxy)-N-hydroxyheptanamide (Compound 18)

Step 12a. Ethyl 7-(4-(3-chloro-4-fluorophenylamino) quinazolin-6-yloxy)heptanoate (Compound 0210-18)

The title compound 0210-18 (0.2 g) was prepared from compound 2-6 4-(3-chloro-4-fluorophenylamino)quinazolin-6-ol (0209) of step 9e and ethyl 7-bromoheptanoate using a procedure similar to that described for compound 0210-13 (Example 9): LC-MS m/z 420 [M+1], $^1$H-NMR (DMSO) δ1.13 (t, 3H), 1.36 (m, 2H), 1.46 (m, 2H), 1.54 (m, 2H) 1.78 (m, 2H), 2.27 (t, 2H), 4.05 (q, 2H), 4.11 (t, 2H), 7.41 (d, 1H), 7.47 (dd, 1H), 7.70 (d, 1H), 7.81 (m, 1H), 7.84 (m, 1H), 8.13 (dd, 1H), 8.50 (s, 1H).

Step 12b. 7-(4-(3-Chloro-4-fluorophenylamino) quinazolin-6-yloxy)-N-hydroxyheptanamide (Compound 18)

The title compound 18 (20 mg) was prepared from compound ethyl 7-(4-(3-chloro-4-fluorophenylamino)quinazolin-6-yloxy-heptanoate (0210-18) using a procedure similar to that described for compound 13 (Example 9): LC-MS m/z 433 [M+1], mp 145-149° C., $^1$H-NMR (DMSO) δ1.32 (m, 2H), 1.47 (m, 4H) 1.88 (m, 2H), 1.94 (t, 2H), 4.12 (t, 2H), 7.43 (t, 1H), 7.51 (dd, 1H), 7.71 (d, 1H) 7.80 (m, 1H) 7.86 (d, 1H), 8.15 (dd, 1H), 8.51 (s, 1H).

Example 13

Preparation of 2-(4-(3-ethynylphenylamino)quinazolin-6-yloxy)-N-hydroxyacetamide (Compound 19)

Step 13a. 4-(3-Ethynylphenylamino)quinazolin-6-yl acetate (Compound 0208)

The title compound 0208 (0.8 g, yield: 73%) was prepared from 4-chloroquinazolin-6-yl acetate 0204 and 3-ethynyl-benzenamine 0206 using a procedure similar to that described for compound 0207 (Example 9): LC-MS m/z 304 [M+1], $^1$H-NMR (DMSO) δ2.36 (s, 3H), 4.26 (s, 1H), 7.43 (d, 1H), 7.53 (t, 1H), 7.77 (d, 1H), 7.95 (m, 2H), 8.02 (d, 1H), 8.71 (s, 1H), 8.96 (s, 1H).

Step 13b. 4-(3-Ethynylphenylamino)quinazolin-6-ol (Compound 0211)

The title compound 0211 (0.6 g, yield: 88%) was prepared using a procedure similar to that described for compound 0209 (Example 9): LC-MS m/z 262 [M+1], 1H-NMR (DMSO) δ4.17 (s, 1H), 7.19 (d, 1H), 7.36 (t, 1H), 7.43 (dd, 1H, 7.65 (d, 1H), 0.82 (d, 1H), 95 (d, 1H), 8.10 (s, 1H), 48 (s, 1H).

Step 13c. Ethyl 2-(4-(3-Ethynylphenylamino) quinazolin-6-yloxy)acetate (Compound 0212-19)

The title compound 0212-19 (0.2 g, yield: 75%) was prepared from 4-(3-ethynylphenylamino)quinazolin-6-ol 0211 and ethyl 2-bromoacetate using a procedure similar to that described for compound 0210-13 (Example 9): LC-MS m/z 322 [M+1], mp 181-182° C.) $^1$H-NMR (DMSO) δ1.28 (t, 3H), 4.20 (q, 2H), 4.25 (s, 1H) 4.32 (s, 2H), 7.23 (d, 1H), 7.41 (t, 1H), 7.57 (dd, 1H), 7.74 (d, 1H), 7.91 (d, 1H), 7.95 (m, 1H), 8.10 (s, 1H), 8.48 (s, 1H).

Step 13d. 2-(4-(3-Ethynylphenylamino)quinazolin-6-yloxy)-N-hydroxyacetamide (Compound 19)

The title compound 12 (40 mg) was prepared from ethyl 2-(4-(3-ethynylphenylamino)quinazolin-6-yloxy)acetate 0212-19 using a procedure similar to that described for compound 13 (Example 9): LC-MS m/z 335 [M+1], mp: 189-191° C., $^1$H-NMR (DMSO) δ4.27 (s, 1H), 4.69 (s, 2H), 7.39 (d, 1H), 7.49 (t, 1H), 7.76 (m, 2H), 7.83 (m, 2H), 7.88 (s, 1H), 8.10 (s, 1H), 8.82 (m, 1H).

Example 14

Preparation of 4-(4-(3-ethynylphenylamino)quinazolin-6-yloxy)-N-hydroxybutanamide (Compound 21)

Step 14a. Ethyl 4-(4-(3-ethynylphenylamino) quinazolin-6-yloxy)butanoate (Compound 0212-21)

The title compound 0212-21 (0.2 g, 78%) was prepared from compound 4-(3-ethynylphenylamino)quinazolin-6-ol (0211) and ethyl 4-bromobutanoate using a procedure similar to that described for compound 0210-13 (Example 9): LC-MS m/z 376 [M+1], $^1$H-NMR (DMSO) δ1.12 (t, 3H), 1.79 (m, 2H), 2.32 (t, 2H), 4.04 (q, 2H), 4.16 (t, 2H), 4.21 (s, 1H), 7.02 (dd, 1H), 7.21 (d, 1H), 7.39 (dd, 1H), 7.70 (t, 1H), 7.88 (s, 1H), 8.00 (m, 1H), 8.51 (s, 1H), 8.65 (s, 1H).

Step 14b. 4-(4-(3-Ethynylphenylamino)quinazolin-6-yloxy)-N-hydroxybutanamide (Compound 21)

The title compound 21 (50 mg) was prepared from ethyl 4-(4-(3-ethynylphenylamino)quinazolin-6-yloxy)butanoate (0212-21) using a procedure similar to that described for compound 13 (Example 9): LC-MS m/z 363 [M+1], mp 182-186° C., $^1$H-NMR (DMSO) δ2.02 (m, 2H), 2.20 (t, 2H), 4.16 (t, 2H), 4.20 (s, 1H), 7.24 (d, 1H), 7.43 (t, 1H), 7.52 (dd, 1H), 7.75 (d, 1H), 7.94 (m, 2H), 8.06 (s, 1H), 8.53 (s, 1H).

Example 15

Preparation of 6-(4-(3-ethynylphenylamino)quinazolin-6-yloxy)-N-hydroxyhexanamide (Compound 23)

Step 15a. 6-(4-(3-Ethynylphenylamino)quinazolin-6-yloxy) hexanoate (Compound 0212-23)

The title compound ethyl 6-(4-(3-ethynylphenylamino) quinazolin-6-yloxy) hexanoate (0212-23) (0.3 g, 64%) was prepared from compound 4-(3-ethynylphenylamino) quinazolin-6-ol (0211) and ethyl 6-bromohexanoate using a procedure similar to that described for compound 0210-13 (Example 9): LC-MS m/z 404 [M+1].

Step 15b. 6-(4-(3-Ethynylphenylamino)quinazolin-6-yloxy)-N-hydroxyhexanamide (Compound 23)

The title compound 23 (50 mg) was prepared from ethyl 6-(4-(3-ethynylphenylamino)quinazolin-6-yloxy)hexanoate (0212-23) using a procedure similar to that described for compound 13 (Example 9): LC-MS m/z 391 [M+1], mp 176-182° C., ¹H-NMR (DMSO) δ1.46 (m, 2H), 1.60 (m, 2H), 1.81 (m, 2H), 2.00 (t, 2H), 4.15 (t, 2H), 4.20 (s, 1H), 7.24 (d, 1H), 7.43 (t, 1H), 7.52 (dd, 1H), 7.72 (d, 1H), 7.92 (m, 2H), 8.04 (s, 1H), 8.53 (s, 1H).

Example 16

4-(4-(3-Chloro-4-fluorophenylamino)-7-methoxyquinazolin-6-yloxy)-N-hydroxybutanamide (Compound 4)

Step 16a. Ethyl 4-(4-(3-chloro-4-fluorophenylamino)-7-methoxyquinazolin-6-yloxy)butanoate (Compound 0110-4)

The title compound 0110-4 was prepared as a yellow solid (600 mg, 88.4%) from compound 0109 from step 1f (500 mg, 1.56 mmol) and methyl 5-bromopentanoate (320 mg, 1.64 mmol) using a procedure similar to that described for compound 0110-1 (Example 1): LCMS: 434 [M+1]$^+$; ¹H NMR (CDCl$_3$): δ 1.80~1.97 (m, 4H), 2.48 (t, J=6.6 Hz, 2H), 3.67 (s, 3H), 3.97 (s, 3H), 4.18 (t, J=7.2 Hz, 2H), 7.14 (t, J=8.7 Hz, 1H), 7.24 (s, 1H), 7.29 (s, 1H), 7.66~7.11 (m, 1H), 7.96 (dd, J=6.9 Hz, 2.7 Hz, 1H), 8.03 (s, 1H), 8.66 (s, 1H).

Step 16b. 4-(4-(3-Chloro-4-fluorophenylamino)-7-methoxyquinazolin-6-yloxy)-N hydroxybutanamide (Compound 4)

The title compound 4 was prepared as a white solid (140 mg, 35%) form compound 0110-4 (400 mg, 0.92 mmol) using a procedure similar to that described for compound 1 (Example 1): LCMS: 435 [M+1]$^+$; ¹H NMR (DMSO-d$^6$): δ 1.69~1.84 (m, 4H), 2.07 (t, J=6.6 Hz, 2H), 3.94 (s, 3H), 4.15 (t, J=6.0 Hz, 2H), 7.21 (s, 1H), 7.45 (t, J=9.0 Hz, 1H), 7.78~7.83 (m, 2H), 8.13 (dd, J=6.9 Hz, 2.4 Hz, 1H), 8.03 (s, 1H), 8.50 (s, 1H), 8.72 (s, 1H), 9.54 (s, 1H), 10.41 (s, 1H).

Example 17

5-(4-(3-Ethynylphenylamino)-7-methoxyquinazolin-6-yloxy)-N-hydroxypentanamide (Compound 10)

Step 117a. Methyl 5-(4-(3-ethynylphenylamino)-7-methoxyquinazolin-6-yloxy)pentanoate (Compound 0113-10)

The title compound 0113-10 was prepared as a yellow solid (500 mg, 72%) from compound 0112 (500 mg, 1.7 mmol) and methyl 5-bromopentanoate (211 mg, 0.89 mmol) using a procedure similar to that described for compound 0110-1 (Example 1): LCMS: 406 [M+1]$^+$.

Step 17b. 5-(4-(3-Ethynylphenylamino)-7-methoxyquinazolin-6-yloxy)-N-hydroxypentanamide (Compound 10)

The title compound 10 was prepared as a white solid (200 mg, 40%) from compound 0113-10 (500 mg, 1.23 mmol) using a procedure similar to that described for compound 1 (Example 1): LCMS: 407 [M+1]$^+$; ¹H NMR (DMSO-d$_6$): δ 1.71~1.85 (m, 4H), 2.07 (t, J=7.2 Hz, 2H), 3.93 (s, 3H), 4.16 (t, J=6.3 Hz, 2H), 4.20 (s, 1H), 7.19 (m, 2H), 7.41 (t, J=8.1 Hz, 1H), 7.84 (s, 1H), 7.90 (dd, J=8.4 Hz, 1.2 Hz, 1H), 8.00 (t, J=1.8 Hz, 1H), 8.50 (s, 1H), 8.72 (s, 1H), 9.48 (s, 1H), 10.40 (s, 1H).

Example 18

Preparation of 5-(4-(3-chloro-4-fluorophenylamino)quinazolin-6-yloxy)-N-hydroxypentanamide (Compound 16)

Step 18a. ethyl 5-(4-(3-chloro-4-fluorophenylamino)quinazolin-6-yloxy)pentanoate (compound 0210-16)

The title compound 0210-16 (0.2 g, 68%) was prepared from compound 0209 4-(3-chloro-4-fluorophenylamino)quinazolin-6-ol (0.2 g, 0.69 mmol) and methyl 5-bromopentanoate (0.14 g, 0.69 mmol) using a procedure similar to that described for compound 0210-13 (Example 9): LCMS 376 [M+1]$^+$.

Step 18b. 5-(4-(3-chloro-4-fluorophenylamino)quinazolin-6-yloxy)-N-hydroxypentanamide (Compound 16)

The title compound 16 (24 mg, 67%) was prepared from compound 0210-16 (37 mg, 0.09 mmol) using a procedure similar to that described for compound 13 (Example 9): mp: 85.9° C.; LCMS 405 [M+1]$^+$, ¹H NMR (DMSO-d$_6$) δ 1.74 (m, 4H), 2.04 (t, J=7.5 Hz, 2H), 4.14 (t, J=6 Hz, 2H), 7.44 (t, J=9 Hz, 1H), 7.51 (dd, J=9 Hz, J=2.4 Hz, 1H), 7.73 (d, J=8.7 Hz, 1H), 7.82 (m, 1H), 7.88 (d, J=2.4, 1H) 8.16 (dd, J=6.9 Hz, J=2.7 Hz 1H), 8.52 (s, 1H), 8.69 (s, 1H), 9.67 (s, 1H), 10.38 (s, 1H).

Example 19

Preparation of 7-(4-(3-ethynylphenylamino)quinazolin-6-yloxy)-N-hydroxyheptanamide (Compound 24)

Step 19a. Ethyl 7-(4-(3-ethynylphenylamino)quinazolin-6-yloxy)heptanoate (Compound 0212-24)

The title compound 0212-24 (0.21 g, 58%) was prepared from compound 4-(3-ethynylphenylamino)quinazolin-6-ol (0211) (0.23 g, 0.86 mmol) and ethyl 7-bromoheptanoate (0.20 g, 0.86 mmol) using a procedure similar to that described for compound 0210-13 (Example 9): LCMS 418 [M+1]$^+$.

Step 19b. 7-(4-(3-Ethynylphenylamino)quinazolin-6-yloxy)-N-hydroxyheptanamide (Compound 24)

The title compound 24 (50 mg, 42%) was prepared from compound 0212-24 (123 mg, 0.29 mmol) using a procedure similar to that described for compound 13 (Example 9): LCMS 405 [M+1]$^+$, ¹H NMR (DMSO-d$_6$): δ 1.44 (m, 2H), 1.48 (m, 2H), 1.59 (m, 2H), 1.67 (m, 2H), 2.11 (t, J=7.2 Hz, 2H), 3.50 (s, 1H), 4.17 (t, J=6.3 Hz, 2H), 7.28 (d, J=7.5 Hz, 1H), 7.37 (t, J=6.9 Hz, 1H), 7.48 (d, J=9.0 Hz, 1H), 7.78 (dd, J=21.3 Hz, J=7.8 Hz, 1H), 7.93 (s, 1H), 7.92 (m, 2H), 8.45 (s, 1H).

Example 20

Example 1 Synthesis of 7-(4-(3-Chloro-4-fluorophenylamino)-7-(2-methoxyethoxy)quinazolin-6-yloxy)-N-hydroxyheptanamide (Compound 30)

Step 20a. Ethyl 3-hydroxy-4-(2-methoxyethoxy)benzoate (Compound 0402-30)

To a solution of 0401 (1.82 g, 10.0 mmol) in N,N-dimethylformamide (20 mL) was added potassium carbonate (1.38 g, 10.0 mmol). The mixture was stirred for 15 minutes and then a solution of 2-methoxyethyl 4-methylbenzenesulfonate (2.30 g, 10.0 mmol) in N,N-dimethylformamide (5 mL) was added slowly dropwise. The mixture was stirred 48 hours at room temperature and filtered. The filtrate was concentrated in vacuo and the residue was dissolved in ethyl acetate (30 mL) then the organic layer was washed with brine (20 mL×3) and dried over sodium sulfate, filtered and evaporated to give the title product 0402-30 as a white solid (1.2 g, 50%): LCMS: 241 [M+1]$^+$. $^1$H NMR (DMSO-d$_6$) δ 1.26 (t, J=7.5 Hz, 3H), 3.65 (m, J=1.5 Hz, 2H), 4.11 (m, J=4.5 Hz, 2H), 4.21 (m, J=4.5 Hz, 2H), 7.00 (d, J=9 Hz, 1H), 7.37 (m, J=2 Hz, 2H), 9.40 (s, 1H).

Step 20b. Ethyl 3-(7-ethoxy-7-oxoheptyloxy)-4-(2-methoxyethoxy)benzoate (Compound 0403-30)

Compound 0402-30 (204.0 mg, 0.85 mmol) and ethyl 7-bromoheptanoate (201.0 mg, 0.85 mmol) and potassium carbonate (353.0 mg, 2.50 mmol) in N,N-dimethylformamide (5 mL) was stirred at 60° C. for 3 hours. The mixture was filtrated. The filtrate was concentrated in vacuo and the residue was dissolved in ethyl acetate (30 mL) then the organic layer was washed with brine (20 mL×3) and dried over sodium sulfate, filtered and evaporated to give the title product 0403-30 as a yellow solid (325 mg, 96%): LCMS: 397 [M+1]$^+$.

Step 20c. Ethyl 5-(7-ethoxy-7-oxoheptyloxy)-4-(2-methoxyethoxy)-2-nitrobenzoate (Compound 0404-30)

Compound 0403-30 (325.0 mg, 0.82 mmol) was dissolved in acetic acid (2 mL) and stirred at room temperature. Then fuming nitric acid (0.39 g, 6.0 mmol) was added slowly dropwise. The mixture was stirred at room temperature for 2 hours. Poured into ice-water (50 mL) and extracted with ethyl acetate (20 mL×2). The combined organic layer was washed with aqueous NaHCO$_3$ solution (10 mL×3) and brine (10 mL×3) and dried over sodium sulfate, filtered and evaporated to give the title product 0404-30 as a yellow oil (330 mg, 100%): LCMS: 442 [M+1]$^+$.

Step 20d. Ethyl 2-amino-5-(7-ethoxy-7-oxoheptyloxy)-4-(2-methoxyethoxy)benzoate (Compound 0405-30)

A mixture of 0404-30 (370.0 mg 0.82 mmol), ethanol (4.4 mL), water (3 mL) and hydrogen chloride (0.08 mL) was stirred to form a clear solution. The powder iron (459.0 mg, 8.2 mmol) was added. The mixture was stirred at reflux for 30 minutes and cooled to room temperature, adjust pH to 8 with 10% sodium hydroxide solution in ice-water bath. The mixture was filtered and the filtrate was concentrated to remove ethanol and was then extracted whit ethyl acetate (20 mL×2). The combined organic layer was washed with brine (10 mL×3) and dried over sodium sulfate, filtered and evaporated to give the title product 0405-30 as a yellow oil (315 mg, 93%): LCMS: 412 [M+1]$^+$.

Step 20e. Ethyl 7-(7-(2-methoxyethoxy)-4-oxo-3,4-dihydroquinazolin-6-yloxy)heptanoate (Compound 0406-30)

A mixture of compound 0405-30 (315.0 mg, 0.76 mmol), ammonium formate (48.0 mg, 0.76 mmol) and formamide (2.46 mL) was stirred at 190° C. for 3 hours. The reaction mixture was cooled to room temperature. The formamide was removed under reduce pressure, and the residue was dissolved in ethyl acetate (30 mL). The organic layer was washed with brine (10 mL×5) and dried over sodium sulfate, filtered and evaporated to give the title product 0406-30 as a white solid (235 mg, 98%): LCMS: 393 [M+1]$^+$.

Step 20f. Ethyl 7-(4-chloro-7-(2-methoxyethoxy)quinazolin-6-yloxy)heptanoate (Compound 0407-30)

A mixture of product 0406-30 (235.0 mg, 0.6 mmol) and phosphoryl trichloride (3 mL) was stirred at reflux for 4 hours. When a clear solution was obtained, the excessive phosphoryl trichloride was removed under reduced pressure. The residue was dissolved in ethyl acetate (30 mL) and the organic layer was washed in turn with water (10 mL×2), aqueous NaHCO$_3$ solution (10 mL×2) and brine (20 mL×1), dried over sodium sulfate, filtered and evaporated to give the title product 0407-30 as a yellow solid (233 mg, 94%): LCMS: 411 [M+1]$^+$.

Step 20g. Ethyl 7-(4-(3-chloro-4-fluorophenylamino)-7-(2-methoxyethoxy)-quinazolin-6-yloxy)heptanoate (Compound 0408-30)

A mixture of product 0407-30 (117.0 mg, 0.28 mmol) and 3-chloro-4-fluorobenzenamine (50.0 mg, 0.34 mmol) in isopropanol (3 mL) was stirred at reflux overnight. The mixture was cooled to room temperature and resulting precipitate was isolated, washed with isopropanol and ether. The solid was then dried to give the title compound 0408-30 as a yellow solid (102 mg, 70%): LCMS: 520 [M+1]$^+$.

Step 20h. 7-(4-(3-Chloro-4-fluorophenylamino)-7-(2-methoxyethoxy)quinazolin-6-yloxy)-N-hydroxyheptanamide (Compound 30)

The freshly prepared hydroxylamine solution (3 mL, 2.0 mmol) was placed in 25 mL flask. Compound 408-30 (102.0 mg, 0.2 mmol) was added and stirred at room temperature for 24 hours. The mixture was neutralized with acetic acid/methanol. The mixture was concentrated under reduce pressure. The residue was purified by preparation HPLC to give the title compound 30 as a yellow solid (85 mg, 84%): LCMS: 507 [M+1]$^+$; $^1$H NMR (DMSO-d$_6$) δ 1.33 (m, 2H), 1.50 (m, 4H), 1.79 (s, 2H), 1.94 (t, 2H), 3.29 (s, 3H), 3.72 (s, 2H), 4.11 (s, 2H), 4.25 (s, 2H), 7.19 (s, 1H), 7.42 (t, 1H), 7.79 (s, 1H), 8.10 (d, 1H), 8.47 (s, 1H), 8.65 (s, 1H), 9.52 (s, 1H), 10.33 (s, 1H).

Example 21

Preparation of 7-(4-(3-Ethynylphenylamino)-7-(2-methoxyethoxy)quinazolin-6-yloxy)-N-hydroxyheptanamide (Compound 36)

Step 21a. Ethyl 7-(4-(3-ethynylphenylamino)-7-(2-methoxyethoxy)quinazolin-6-yloxy)heptanoate (Compound 0408-36)

A mixture of product 0407-30 (102.0 mg, 0.25 mmol) and 3-ethynylbenzenamine (35.0 mg, 0.3 mmol) in isopropanol (3 mL) was stirred at reflux overnight. The mixture was cooled to room temperature and resulting precipitate was isolated, washed with isopropanol and ether. The solid was then dried to give the title compound 0408-36 as a yellow solid (88 mg, 72%): LCMS: 491 [M+1]$^+$.

Step 21b. 7-(4-(3-Ethynylphenylamino)-7-(2-methoxyethoxy)quinazolin-6-yloxy)-N-hydroxyheptanamide (compound 36)

The freshly prepared hydroxylamine solution (3 mL, 2 mmol) was placed in 25 mL flask. Compound 0408-36 (88.0 mg, 0.18 mmol) was added to this solution and stirred at room temperature for 24 hours. The mixture was neutralized with acetic acid/methanol and was concentrated under reduce pressure. The residue was purified by preparative HPLC to give the title compound 36 as a white solid (40 mg, 47%): LCMS: 479 [M+1]$^+$; $^1$H NMR (DMSO-d$_6$) δ1.33 (m, 2H), 1.50 (m, 4H), 1.79 (s, 1H), 1.94 (t, 2H), 3.72 (s, 2H), 4.11 (s, 2H), 4.25 (s, 2H), 7.19 (s, 1H), 7.42 (t, 1H), 7.79 (s, 1H), 8.10 (d, 1H), 8.47 (s, 1H), 8.65 (s, 1H), 9.52 (s, 1H), 10.33 (s, 1H).

Example 22

Preparation of N$^1$-(4-(3-chloro-4-fluorophenylamino)-7-methoxyquinazolin-6-yl)-N$^5$-hydroxyglutaramide (Compound 38)

Step 22a. 7-Chloroquinazolin-4(3H)-one (Compound 0302)

A mixture of compound 0301 (17.2 g, 100 mmol) and formamide (20 mL) was stirred at 130° C. for 30 minutes and to 190° C. for 4 hours. The mixture was allowed to cool to room temperature. It was then poured into a mixture of ice and water. The precipitate was isolated, washed with water and dried to give the title compound 0302 (15.8 g, 87.7%). $^1$H NMR (DMSO-d$_6$): δ 7.65 (dd, 1H), 7.72 (d, 1H), 8.12 (d, 1H), 8.36 (s, 1H).

Step 22b. 7-Chloro-6-nitroquinazolin-4(3H)-one (compound 0303)

Compound 0302 (18.0 g, 100 mmol) was added portionwise to a stirred mixture of concentrated sulfuric acid (60 mL) and fuming nitric acid (60 mL) which had been cooled to 0° C., the mixture was stirred at ambient temperature for 1 hour and then heated to 45° C. overnight. The mixture was poured into the mixture of ice and water. The precipitate was isolated, washed with water and dried. Recrystallization from acetic acid to give the title compound 0303 (14.1 g, 62.7%). $^1$H NMR (DMSO-d$_6$): δ 8.00 (s, 1H), 8.27 (s, 1H), 8.65 (s, 1H), 12.70 (s, 1H).

Step 22c. 7-Methoxy-6-nitroquinazolin-4(3H)-one (compound 0304)

A mixture of compound 0303 (4.0 g, 18.0 mmol) and sodium (2.4 g, 45 mmol) in methanol (50 mL) was heated at 100° C. in a sealed pressure vessel for 20 hours. The solution was neutralized with acetic acid and diluted with water to give the title compound 0304 (3.0 g, 77%). $^1$H NMR (DMSO-d$_6$): δ4.10 (s, 3H), 7.40 (s, 1H), 8.24 (s, 1H), 8.50 (s, 1H), 12.67 (s, 1H).

Step 22d. 4-Chloro-7-methoxy-6-nitroquinazoline (compound 0305)

Compound 0304 (3.8 g, 17.2 mmol) was suspended in POCl$_3$ (75 mL), the mixture was heated to reflux for 4 hours. The additional POCl$_3$ was removed in a vacuum. The residue was dissolved in a mixture of dichloromethane (50 mL) and aqueous NaHCO$_3$ (50 mL). The organic layer was dried and the solvent was removed to give the title compound 0305 (3.4 g, 83%). $^1$H NMR (DMSO-d$_6$): δ 4.05 (s, 3H), 7.44 (s, 1H), 8.27 (s, 1H), 8.53 (s, 1H).

Step 22e. N-(3-chloro-4-fluorophenyl)-7-methoxy-6-nitroquinazolin-4-amine Hydrochloride (compound 0307)

A mixture of compound 0305 (3.4 g, 14.2 mmol) and 3-chloro-4-fluoroaniline (0406) (2.2 g, 15.2 mmol) and isopropanol (120 mL) was stirred at reflux for 3 hours. The mixture was cooled to ambient temperature and the precipitate was isolated, washed with methanol and ether and then dried to give the title compound 0307 (4.66 g, 85%). $^1$H NMR (DMSO-d$_6$): δ4.10 (s, 3H), 7.55 (dd, 2H), 7.74 (m, 1H), 8.07 (dd, 1H), 8.90 (s, 1H), 9.55 (s, 1H), 11.6 (s, 1H).

Step 22f. N-(3-chloro-4-fluorophenyl)-7-methoxy-6-nitroquinazolin-4-amine (Compound 0308)

A mixture of compound 0307 (3.5 g, 10.0 mmol) and iron dust (11.2 g, 200.0 mmol) and ethanol (100 mL) and concentrated hydrochloric acid (2 mL), and water (30 mL) was heated to reflux for 1 hour. Removed iron dust by filtration. The filtrate was concentrated to ⅕ volume. The precipitate was isolated and dried to give the title compound 0308 (2.2 g, 69%). $^1$H NMR (DMSO-d$_6$): δ3.97 (s, 3H), 5.38 (s, 2H), 7.10 (s, 1H), 7.36 (s, 1H), 7.39 (t, 1H), 7.80 (m, 1H), 8.08 (dd, 1H), 8.38 (s, 1H), 9.39 (s, 1H).

Step 22g. Methyl 3-(4-(3-chloro-4-fluorophenylamino)-7-methoxyquinazolin-6-ylcarbamoyl)propanoate (Compound 0310-38)

The compound 0308 (500.0 mg, 1.57 mmol) and triethylamine (165.0 mg, 1.65 mmol) was dissolved in dichloromethane (50 mL). The mixture was cooled to 0° C. and the solution of methyl 5-chloro-5-oxopentanoate (270 mg, 1.65 mmol) in dichloromethane (5 mL) was added into above mixture dropwise under 0° C. in 20 minutes. The reaction mixture was allowed to stir at ambient temperature for 1 hour. The mixture was washed with water (50 mL×2) and brine (50 mL). The organic layer was dried over MgSO$_4$, filtered and concentrated to give the title compound 0310-38 (550 mg, 78%), LCMS: 448 [M+1]$^+$.

Step 22h. N$^1$-(4-(3-chloro-4-fluorophenylamino)-7-methoxyquinazolin-6-yl)-N$^5$-hydroxyglutaramide (Compound 38)

To a stirred solution of hydroxylamine hydrochloride (4.67 g, 67 mmol) in methanol (24 mL) at 0° C. was added a solution of potassium hydroxide (5.61 g, 100 mmol) in methanol (14 mL). After addition, the mixture was stirred for 30 minutes at 0° C. and was allowed to stand at low temperature. The resulting precipitate was isolated, and the solution was prepared to give free hydroxylamine.

The above freshly prepared hydroxylamine solution (5.6 mL, 10.0 mmol) was placed in 10 mL flask. Compound 0310-38 (550.0 mg, 1.23 mmol) was added to this solution and stirred at 0° C. for 10 minutes and was allowed to warm to room temperature. The reaction process was monitored by TLC. The mixture was neutralized with acetic acid. The mixture was concentrated under reduce pressure. The residue was purified by preparative HPLC to give the title compound 38 as a grey solid (250 mg, 45%): LCMS: 448 [M+1]$^+$; $^1$H NMR (DMSO-d$_6$): δ1.85 (m, 2H), 2.06 (t, J=7.5 Hz, 2H), 2.48 (t, J=7.2 Hz, 2H), 4.00 (s, 3H), 7.24 (s, 1H), 7.42 (t, J=9.0 Hz, 1H), 7.80 (m, 1H), 8.10 (dd, J=7.2 Hz, 2.7 Hz, 1H), 8.52 (s, 1H), 8.70 (s, 1H), 8.82 (s, 1H), 9.48 (s, 1H). 9.79 (s, 1H), 10.40 (s, 1H).

Example 23

Preparation of N$^1$-(4-(3-chloro-4-fluorophenylamino)-7-methoxyquinazolin-6-yl)-N$^8$-hydroxyoctanediamide (Compound 40)

Step 23a. Methyl 8-(4-(3-chloro-4-fluorophenylamino)-7-methoxyquinazolin-6-ylamino)-8-oxooctanoate (Compound 0310-40)

The title compound 0310-40 was prepared as a yellow solid (350 mg, 78%) from compound 0308 (319 mg, 1.0 mmol) and methyl 8-chloro-8-oxooctanoate (227 mg, 1.1 mmol) using a procedure similar to that described for compound 0310-38 (Example 22): LCMS: 489 [M+1]$^+$.

Step 23b. N$^1$-(4-(3-chloro-4-fluorophenylamino)-7-methoxyquinazolin-6-yl)-N$^8$-hydroxyoctanediamide (Compound 40)

The title compound 40 was prepared as a yellow solid (120 mg, 30%) from compound 0310-38 (400 mg, 0.8 mmol) using a procedure similar to that described for compound 38 (Example 22): LCMS: 490 [M+1]$^+$; $^1$H NMR (DMSO-d$_6$): δ1.29 (m, 4H), 1.48 (m, 2H), 1.59 (m, 2H), 1.93 (t, J=7.2 Hz, 2H), 2.45 (t, J=7.2 Hz, 2H), 4.00 (s, 3H), 4.18 (s, 1H), 7.26 (s, 1H), 7.41 (t, J=9.0 Hz, 1H), 7.74 (m, 1H), 8.08 (d, J=1.2 Hz, 1H), 8.54 (s, 1H), 8.66 (s, 1H), 8.83 (s, 1H), 9.46 (s, 1H), 9.95 (s, 1H), 10.33 (s, 1H).

Example 24

Preparation of N$^1$-(4-(3-ethynylphenylamino)-7-methoxyquinazolin-6-yl)-N$^5$-hydroxyglutaramide (Compound 42)

Step 24a. N-(3-ethynylphenyl)-7-methoxy-6-nitroquinazolin-4-amine Hydrochloride (Compound 0307-42)

The title compound 0307-42 was prepared as a yellow solid (4.7 g, 84.5%) from compound 0305 (350 mg, 0.78 mmol) and 3-ethynylbenzenamine (2.34 g, 20.0 mmol) using a procedure similar to that described for compound 0306-38 (Example 22): LCMS: 321 [M+1]$^+$; $^1$H NMR (DMSO-d$_6$): δ4.11 (s, 3H), 4.24 (s, 1H), 7.42 (d, 1H), 7.50 (t, 1H), 7.61 (s, 1H), 7.79 (d, 1H), 7.93 (m, 1H), 8.93 (s, 1H), 9.57 (s, 1H), 11.56 (bs, 1H).

Step 24b. N$^4$-(3-ethynylphenyl)-7-methoxyquinazoline-4,6-diamine (Compound 0309-42)

The title compound 0309-42 was prepared as a yellow solid (2.0 g, 69%) from compound 0307-42 (3.2 g, 10.0 mmol) using a procedure similar to that described for compound 0308-38 (Example 22): LCMS: 291 [M+1]$^+$; $^1$H NMR (DMSO-d$_6$): δ3.95 (s, 3H), 4.14 (s, 1H), 5.33 (s, 2H), 7.08 (m, 2H), 7.34 (m, 2H), 7.88 (m, 1H), 8.04 (s, 1H), 8.36 (s, 1H), 9.29 (s, 1H).

Step 24c. Methyl 5-(4-(3-ethynylphenylamino)-7-methoxyquinazolin-6-ylamino)-5-oxopentanoate (Compound 0311-42)

The title compound 0311-42 was prepared as a yellow solid (450 mg, 77%) from compound 0309-42 (407 mg, 1.4 mmol) and methyl 5-chloro-5-oxopentanoate (254 mg, 1.54 mmol) using a procedure similar to that described for compound 0310-38 (Example 22): LCMS: 419 [M+1]$^+$.

Step 24d. N$^1$-(4-(3-ethynylphenylamino)-7-methoxyquinazolin-6-yl)-N$^5$-hydroxyglutaramide (Compound 42)

The title compound 42 was prepared as a yellow solid (100 mg, 47%) from compound 0311-42 (211 mg, 0.5 mmol) using a procedure similar to that described for compound 38 (Example 22).

Example 25

Preparation of N$^1$-(4-(3-ethynylphenylamino)-7-methoxyquinazolin-6-yl)-N$^6$-hydroxyadipamide (Compound 43)

Step 25a. Methyl 6-(4-(3-ethynylphenylamino)-7-methoxyquinazolin-6-ylamino)-6-oxohexanoate (Compound 0311-43)

The title compound 0311-43 was prepared as a yellow solid (530 mg, 71%) from compound 0309-42 (500 mg, 1.72 mmol) and methyl 6-chloro-6-oxohexanoate (323 mg, 1.81 mmol) using a procedure similar to that described for compound 0311-42 (Example 24): LCMS: 433 [M+1]$^+$.

Step 25b. N$^1$-(4-(3-ethynylphenylamino)-7-methoxyquinazolin-6-yl)-N$^6$-hydroxyadipamide (Compound 43)

The title compound 43 was prepared as a yellow solid (105 mg, 24%) from compound 0311-43 (432 mg, 1.0 mmol) using a procedure similar to that described for compound 42 (Example 24): m.p.: 191.2~196.7° C.; LCMS: 434 [M+1]$^+$; $^1$H NMR (DMSO-d$_6$): δ 1.58 (m, 4H), 1.98 (t, J=6.3 Hz, 2H), 2.44 (m, 2H), 3.99 (s, 3H), 4.16 (s, 1H), 7.18 (d, J=7.8 Hz, 1H), 7.25 (s, 1H), 7.37 (t, J=8.1 Hz, 1H), 7.84 (d, J=8.4 Hz, 1H), 7.98 (s, 1H), 8.51 (s, 1H), 8.66 (s, 1H), 8.82 (s, 1H), 9.42 (s, 1H), 9.73 (s, 1H), 10.35 (s, 1H).

Example 26

$N^1$-(4-(3-ethynylphenylamino)-7-methoxyquinazolin-6-yl)-$N^8$-hydroxyoctanediamide (Compound 44)

Step 26a. Methyl 8-(4-(3-ethynylphenylamino)-7-methoxyquinazolin-6-ylamino)-8-oxooctanoate (Compound 0311-44)

The title compound 0311-44 was prepared as a yellow solid (150 mg, 78%) from compound 0309-42 (120 mg, 0.4 mmol) and methyl 8-chloro-8-oxooctanoate (91 mg, 0.44 mmol) using a procedure similar to that described for compound 0311-42 (Example 24): LCMS: 461 [M+1]$^+$.

Step 26b. $N^1$-(4-(3-ethynylphenylamino)-7-methoxyquinazolin-6-yl)-$N^8$-hydroxyoctanediamide (Compound 44)

The title compound 44 was prepared as a yellow solid (30 mg, 20%) from compound 0311-44 (150 mg, 0.3 mmol) using a procedure similar to that described for compound 42 (Example 24): LCMS: 462 [M+1]$^+$; $^1$H NMR (DMSO-$d_6$): δ 1.30 (m, 4H), 1.51 (m, 2H), 1.62 (m, 2H), 1.95 (t, J=7.2 Hz, 2H), 2.45 (t, J=7.2 Hz, 2H), 4.00 (s, 3H), 4.18 (s, 1H), 7.19 (d, J=7.2 Hz, 1H), 7.26 (s, 1H), 7.38 (t, J=7.8 Hz, 1H), 7.86 (d, J=7.8 Hz, 1H), 7.99 (s, 1H), 8.52 (s, 1H), 8.83 (s, 1H), 9.44 (s, 1H).

Example 27

Preparation of (E)-3-(4-(2-(4-(3-chloro-4-fluorophenylamino)-7-methoxyquinazolin-6-yloxy)ethoxy)phenyl)-N-hydroxyacrylamide (Compound 66)

Step 27a. (E)-Methyl 3-(4-hydroxyphenyl)acrylate (Compound 0501-66)

A mixture of 4-hydroxycinnamic acid (8.2 g, 50 mmol) and a drop of $H_2SO_4$ in methanol (30 mL) was heated to reflux overnight. Then the solvent was evaporated, the residue was dissolved in ethyl acetate, washed with saturated $NaHCO_3$ solution twice, brine, dried over $MgSO_4$, concentrated to give the title compound 0501-66 as white solid (8.7 g, 98%): LCMS: 179 [M+1]$^+$.

Step 27b. (E)-Methyl 3-(4-(2-(tosyloxy)ethoxy)phenyl)acrylate (Compound 0502-66)

A mixture of compound 0501-66 (5.0 g, 28.0 mmol) and 2-bromoethanol (3.9 g, 62.0 mmol) and potassium carbonate in N,N-dimethylformamide was stirred at 80° C. for 24 hours. The reaction process was monitored by TLC. The mixture was filtrated. The filtrate was concentrated under reduce pressure. The residue was wash with diethyl ether and dried to give (E)-methyl 3-(4-(2-hydroxyethoxy)phenyl)-acrylate as yellow solid (1.6 g, 26.0%): LCMS: 223 [M+1]$^+$.

To a mixture of triethylamine (0.3 g, 3 mol) and dichloromethane (20 mL) was added tosyl chloride (285 mg, 1.5 mmol) batchwise and stirred for 0.5 hour. Compound (E)-methyl 3-(4-(2-hydroxyethoxy)phenyl)acrylate (333 mg, 1.5 mmol) was added into above mixture and heated to reflux for 24 hours. The reaction mixture was added saturated ammonium chloride solution and the organic layer was separated and washed by brine, dried ($MgSO_4$), evaporated to give compound 0502-66 as white solid (200 mg, 36%): LCMS: 377 [M+1]$^+$.

Step 27c. (E)-Methyl 3-(4-(2-(4-(3-chloro-4-fluorophenylamino)-7-methoxyquinazolin-6-yloxy)ethoxy)phenyl)acrylate (Compound 0503-66)

A mixture of compound 0109 (176 mg, 0.55 mmol) and 0502-66 (152 mg, 0.94 mmol) and potassium carbonate in N,N-dimethylformamide was stirred at 80° C. for 24 hours. The reaction process was monitored by TLC. The mixture was filtrated. The filtrate was concentrated under reduce pressure. The residue was wash with diethyl ether and dried to give the title compound 0503-66 as yellow solid (281 mg, 98%): LCMS: 524 [M+1]$^+$.

Step 27d. (E)-3-(4-(2-(4-(3-Chloro-4-fluorophenylamino)-7-methoxyquinazolin-6-yloxy)ethoxy)phenyl)-N-hydroxyacrylamide (Compound 66)

The title compound 66 was prepared as a white solid (65 mg, 19%) from compound 0503-66 (346.0 mg, 0.66 mmol) using a procedure similar to that described for compound 1 (Example 1): LCMS: 525 [M+1]$^+$; $^1$H NMR (DMSO-$d_6$): δ 3.93 (s, 3H), 4.48 (s, 4H), 6.31 (d, J=16.2 Hz, 1H), 7.05 (d, J=8.1 Hz, 2H), 7.21 (s, 1H), 7.44 (t, J=9.0 Hz, 1H), 7.52 (d, J=8.1 Hz, 2H), 7.78 (d, J=10.2 Hz, 1H), 7.88 (m, 1H), 8.12 (dd, J=6.6 Hz, 2.7 Hz, 1H), 8.50 (s, 1H), 8.96 (s, 1H), 8.50 (s, 1H), 9.56 (s, 1H), 10.65 (s, 1H).

Example 28

Preparation of $N^1$-(4-(3-chloro-4-fluorophenylamino)-7-(2-methoxyethoxy)quinazolin-6-yl)-$N^5$-hydroxyglutaramide (Compound 68)

Step 28a. 7-(2-Methoxyethoxy)-6-nitroquinazolin-4 (3H)-one (compound 0304-68)

Sodium (2.07 g, 90 mmol) was added to 2-methoxyethanol (125 mL) at 0° C. until sodium was dissolved. Compound 0303 (6.77 g, 30.0 mmol) was added to the solution.

The mixture was stirred at 90° C. for 24 hours and was then adjusted to pH7 by acetic acid. Water (50 mL) was added to the mixture and resulting yellow precipitate was isolated, washed with water and dried to provide the title compound 0304-68 as a yellow solid (7.003 g, 88%): LCMS: 266 [M+1]$^+$.

Step 28b. 4-Chloro-7-(2-methoxyethoxy)-6-nitroquinazoline (compound 0305-68)

A mixture of product 0304-68 (5.30 g, 20.0 mmol) and phosphoryl trichloride (50 mL) was stirred at reflux for 5 hours. When a clear solution was obtained, the excessive phosphoryl trichloride was removed under reduced pressure. The residue was dissolved in ethyl acetate (100 mL) and the organic layer was washed in turn with water (30 mL×2), aqueous $NaHCO_3$ solution (20 mL×2) and brine (20 mL×1), dried over sodium sulfate, filtered and evaporated to give the title product 0305-68 as a yellow solid (5.31 g, 94%): LCMS: 284 [M+1]$^+$.

Step 28c. N-(3-chloro-4-fluorophenyl)-7-(2-methoxyethoxy)-6-nitroquinazolin-4-amine (compound 0306-68)

A mixture of product 0305-68 (5.31 g, 18.7 mmol) and 3-chloro-4-fluorobenzenamine (5.45 g, 37.4 mmol) in isopropanol (150 mL) was stirred at reflux overnight. The mixture was cooled to room temperature and resulting precipitate was isolated, washed with methanol and ether. The solid was then dried to give the title compound 0306-68 as a yellow solid (5.70 g, 77%): LCMS: 393 [M+1]$^+$.

Step 28d. N$^4$-(3-chloro-4-fluorophenyl)-7-(2-methoxyethoxy) quinazoline-4,6-diamine (compound 0308-68)

A mixture of 0306-68 (5.70 g, 14.5 mmol), ethanol (165 mL), water (43.5 mL) and hydrogen chloride (2.9 mL) was stirred to form a clear solution. The powder iron (16.24 g, 290.0 mmol) was added. The mixture was stirred at reflux for 2 hours. Cooled to room temperature, adjusted pH to 11 with 10% sodium hydroxide solution in ice-water bath and was filtered. The filtrate was concentrated to remove ethanol and extracted whit ethyl acetate (100 mL×2), The combined organic layer was washed with brine (30 mL×3) and dried over sodium sulfate, filtered and evaporated to give the title product 0308-68 as a yellow solid (4.92 g, 93%): LCMS: 363 [M+1]$^+$.

Step 28e. Methyl 5-(4-(3-chloro-4-fluorophenylamino)-7-(2-methoxyethoxy)quinazolin-6-ylamino)-5-oxopentanoate (Compound 0310-68)

The methyl 5-chloro-5-oxopentanoate (0.198 g, 1.2 mmol) was added to a solution of compound 0308-68 (0.22 g, 0.6 mmol) in 30 mL of dichloromethane and triethylamine (0.48 g, 4.8 mmol). The mixture was stirred for 2 hours at 0° C. The reaction mixture was then washed with water and dried over sodium sulfate, filtered and evaporated to give the title product 0310-68 as a brown oil (270 mg, 92%): LCMS: 491 [M+1]$^+$.

Step 28f. N$^1$-(4-(3-chloro-4-fluorophenylamino)-7-(2-methoxyethoxy)quinazolin-6-yl)-N$^5$-hydroxyglutaramide (Compound 68)

To a stirred solution of hydroxylamine hydrochloride (4.67 g, 67 mmol) in methanol (24 mL) at 0° C. was added a solution of potassium hydroxide (5.61 g, 100 mmol) in methanol (14 mL). After addition, the mixture was stirred for 30 minutes at 0° C. and was allowed to stand at low temperature. The resulting precipitate was isolated, and the solution was prepared to give free hydroxylamine.

The above freshly prepared hydroxylamine solution (6 mL, 4.0 mmol) was placed in 25 mL flask. Compound 0310-68 (270 mg, 0.55 mmol) was added to this solution and stirred at room temperature for 4 hours. The mixture was neutralized with acetic acid/methanol. The mixture was concentrated under reduce pressure. The residue was purified by preparative HPLC to give the title compound 68 as a yellow solid (220 mg, 75%): LCMS: 492 [M+1]$^+$; $^1$H NMR (DMSO-d$_6$): 1.83 (m, J=7.5 Hz, 2H), 2.05 (t, J=7.2 Hz, 2H), 2.43 (t, J=6.9 Hz, 2H), 3.31 (s, 3H), 3.76 (t, J=4.5 Hz, 2H), 4.32 (t, J=4.2 Hz, 2H), 7.28 (s, 1H), 7.40 (t, J=9 Hz, 1H), 7.77 (m, 1H), 8.10 (m, J=2.1 Hz, 1H), 8.50 (s, 1H), 8.67 (s, 1H), 8.752 (s, 1H), 9.33 (s, 1H), 9.77 (s, 1H), 10.38 (s, 1H).

Example 29

Preparation of N$^1$-(4-(3-chloro-4-fluorophenylamino)-7-(2-methoxyethoxy)quinazolin-6-yl)-N$^6$-hydroxyadipamide (Compound 69)

Step 29a. Methyl 6-(4-(3-chloro-4-fluorophenylamino)-7-(2-methoxyethoxy) quinazolin-6-ylamino)-6-oxohexanoate (Compound 0310-69)

The methyl 6-chloro-6-oxohexanoate (0.36 g, 1.76 mmol) was added to a solution of compound 0308-68 (0.15 g, 0.4 mmol), 25 mL of dichloromethane and triethylamine (0.162 g, 1.6 mmol). The reaction mixture was stirred for 2 hours at 0° C. The reaction was washed with water and dried over sodium sulfate, filtered and evaporated to give the title product 0310-69 as a brown oil (185 mg, 92%): LCMS: 505 [M+1]$^+$.

Step 29b. N$^1$-(4-(3-chloro-4-fluorophenylamino)-7-(2-methoxyethoxy)quinazolin-6-yl)-N$^6$-hydroxyadipamide (compound 69)

The freshly prepared hydroxylamine solution (6 mL, 4 mmol) was placed in 25 mL flask. Compound 0310-69 (185 mg, 0.38 mmol) was added to this solution and stirred at room temperature for 4 hours. The mixture was neutralized with acetic acid/methanol. The mixture was concentrated under reduce pressure. The residue was purified by preparative HPLC to give the title compound 69 as a white solid (150 mg, 74%): LCMS: 506 [M+1]$^+$; $^1$H NMR (DMSO-d$_6$): 1.58 (m, 4H), 1.98 (t, J=5.7 Hz, 2H), 2.46 (t, 2H), 3.30 (s, 3H), 3.78 (t, J=4.2 Hz, 2H), 4.32 (t, J=5.1 Hz, 2H), 7.28 (s, 1H), 7.39 (t, J=9 Hz, 1H), 7.79 (m, 1H), 8.11 (m, J=2.7 Hz, 1H), 8.50 (s, 1H), 8.64 (s, 1H), 8.75 (s, 1H), 9.25 (s, 1H), 9.76 (s, 1H), 10.33 (s, 1H).

Example 30

Preparation of N$^1$-(4-(3-chloro-4-fluorophenylamino)-7-(2-methoxyethoxy)quinazolin-6-yl)-N$^8$-hydroxyoctanediamide (Compound 70)

Step 30a. Methyl 8-(4-(3-chloro-4-fluorophenylamino)-7-(2-methoxyethoxy)quinazolin-6-ylamino)-8-oxooctanoate (Compound 0310-70)

Methyl 8-chloro-8-oxooctanoate (0.496 g, 2.4 mmol) was added to a solution of compound 0308-68 (0.219 g, 0.6 mmol), 30 mL of dichloromethane and triethylamine (0.48 g, 2.4 mmol). The mixture was stirred for 2 hours at 0° C. The reaction was washed with water and dried over sodium sulfate, filtered and evaporated to give the title product 0310-70 as a brown oil (281 mg, 88%): LCMS: 533 [M+1]$^+$. $^1$H NMR (DMSO-d$_6$), 1.35 (m, 4H), 1.58 (m, 2H), 1.61 (m, 2H), 2.29 (t, J=7.2 Hz, 2H), 2.41 (t, J=7.2 Hz, 2H), 3.35 (s, 3H), 3.77 (t, J=4.5 Hz, 2H), 4.32 (t, J=4.5 Hz, 2H), 7.28 (s, 1H), 7.40 (t, J=9.3 Hz, 1H), 7.78 (m, 1H), 8.11 (m, 1H), 8.50 (s, 1H), 8.74 (s, 1H), 9.24 (s, 1H), 9.76 (s, 1H).

Step 30b. N$^1$-(4-(3-chloro-4-fluorophenylamino)-7-(2-methoxyethoxy)quinazolin-6-yl)-N$^8$-hydroxyoctanediamide (compound 70)

The freshly prepared hydroxylamine solution (6 mL, 4.0 mmol) was placed in 25 mL flask. Compound 0310-70 (281 mg, 0.53 mmol) was added to this solution and stirred at room temperature for 4 hours. The mixture was neutralized with acetic acid/methanol. The mixture was concentrated under reduce pressure. The residue was purified by preparative HPLC to give the title compound 70 as a yellow solid (126 mg, 40%): LCMS: 506 [M+1]$^+$; $^1$H NMR (DMSO-d$_6$), 1.35 (m, 4H), 1.58 (m, J=6.9 Hz, 2H), 1.61 (m, J=7.2 Hz, 2H), 1.93 (t, J=7.2 Hz, 2H), 2.42 (t, J=7.5 Hz, 2H), 3.35 (s, 3H), 3.77 (t, J=4.5 Hz, 2H), 4.32 (t, J=4.5 Hz, 2H), 7.28 (s, 1H), 7.40 (t, J=9.3 Hz, 1H), 7.78 (m, 1H), 8.11 (m, J=2.4 Hz, 1H), 8.50 (s, 1H), 8.62 (d, J=1.5 Hz, 1H), 8.75 (s, 1H), 9.25 (s, 1H), 9.76 (s, 1H), 10.31 (s, 1H).

Example 31

Preparation of 7-(4-(3-ethynyl-4-fluorophenylamino)-7-methoxyquinazolin-6-yloxy)-N-hydroxyheptanamide (Compound 75)

Step 31a. 2-Bromo-1-fluoro-4-nitrobenzene (compound 0602)

To a solution of 1-bromo-2-fluorobenzene (35.0 g, 200 mmol) in 200 mL of concentrated sulfuric acid was added 20 mL of 68% nitric acid. The temperature of the mixture was maintained below 20° C. After the addition was completed, the mixture was stirred at 10° C. overnight, then diluted with ice water. The resulting solid was collected by filtration. The solid was recrystallized from petroleum ether to give the title compound 0602 as a yellow solid (38 g, 89%): m.p. 55.8-56.7° C., $^1$H NMR (DMSO-d$_6$): δ 7.66 (t, J=9 Hz, 1H), 8.32 (m, 1H), 8.58 (dd, J=3 Hz, 6 Hz, 1H).

Step 31b. ((2-Fluoro-5-nitrophenyl)ethynyl)trimethylsilane (Compound 0603)

A mixture of compound 0602 (11.0 g, 50 mmol), ethynyltrimethylsilane (7.5 g, 75 mmol), triphenylphosphine (0.5 g) and palladium (II) acetate (0.25 g) in 125 mL of deaerated triethylamine was heated at 100° C. overnight under argon. The reaction was cooled and was filtrated, and the filtrate was concentrated to a dark brown oil which was distilled under reduce pressure to give title compound 0603 as a light brown solid (4.7 g, 40%). $^1$H NMR (CDCl$_3$): δ 0.3 (s, 9H, SiCH), 7.22 (t, J=9.0 Hz, 1H), 8.2-8.5 (m, 2H).

Step 31c. 4-Fluoro-3-((trimethylsilyl)ethynyl)benzenamine (Compound 0604)

In 25 mL of methanol was mixed with compound 0603 (3.5 g, 14.8 mmol) and iron filings (4.14 g, 74.0 mmol). To this mixture was added concentrated hydrochloric acid and water to adjust pH 4-5. The mixture was heated to reflux for 3 hours, cooled, and filtrated through silica gel. The filtrate was concentrated to yield a yellow solid residue which was then extracted with ether. The combined organic phase was dried over magnesium sulfate and concentrated to give the title compound 0604 as a brown solid (2.69 g, 88%): LCMS 208 [M+1]$^+$.

Step 31d. 3-Ethynyl-4-fluorobenzenamine (Compound 0605)

Compound 0604 obtained above was treated with 100 mg potassium hydroxide in 20 mL of methanol at room temperature overnight. The solution was concentrated, dilute with water, brought to neutrality, and then extracted with ether. The combined organic phase was dried over magnesium sulfate, concentrated to yield the title compound 0605 as a brown oil (1.49 g, 85%): LCMS 136 [M+1]$^+$. The product was used in the next step without further purification.

Step 31e. 4-(3-Ethynyl-4-fluorophenylamino)-7-methoxyquinazolin-6-yl acetate (Compound 0606)

A mixture of 4-chloro-7-methoxyquinazolin-6-yl acetate (compound 0105) (252 mg, 1.0 mmol) and 3-ethynyl-4-fluorobenzenamine (605) (200 mg, 1.5 mmol) in isopropanol (10 mL) was stirred and heated to reflux for 3 hours. The mixture was cooled to room temperature and resulting precipitate was isolated. The solid was then dried to give the title compound 0606 (260 mg, 74.0%) as a light yellow solid: LCMS: 352 [M+1]$^+$.

Step 31f. 4-(3-Ethynyl-4-fluorophenylamino)-7-methoxyquinazolin-6-ol (Compound 0607)

A mixture of compound 0606 (260 mg, 0.74 mmol), LiOH H$_2$O (250 mg, 5.8 mmol) in methanol (25 ml) and H$_2$O (25 ml) was stirred at room temperature for 0.5 hour. The mixture was neutralized by addition of dilution acetic acid. The precipitate was isolated and dried to give the title compound 0607 (234 mg, 100%) as a grey solid: LCMS: 310 [M+1]$^+$.

Step 31g. Ethyl 7-(4-(3-ethynyl-4-fluorophenylamino)-7-methoxyquinazolin-6-yloxy)heptanoate (Compound 0608-75)

The title compound 0608-75 was prepared as a yellow solid (300 mg, 87.0%) from compound 607 (230 mg, 0.74 mmol) and ethyl 7-bromoheptanoate (176 mg, 0.74 mmol) using a procedure similar to that described for compound 0110-1 (Example 1): LCMS: 466 [M+1]$^+$.

Step 31h. 7-(4-(3-Ethynyl-4-fluorophenylamino)-7-methoxyquinazolin-6-yloxy)-N-hydroxyheptanamide (compound 75)

The title compound 75 was prepared as a white solid (176 mg, 70%) from compound 0608 (250 mg, 0.54 mmol) using a procedure similar to that described for compound 1 (Example 1): mp 150.4~164.5° C. (dec); LCMS: 453 [M+1]$^+$, $^1$H NMR (DMSO-d$_6$): δ 1.33 (m, 2H), 1.48 (m, 4H), 1.80 (m, 2H), 1.94 (t, J=7.2 Hz, 2H), 3.91 (s, 3H), 4.10 (t, J=6.0 Hz, 2H), 4.51 (s, 1H), 7.17 (s, 1H), 7.31 (t, J=7.5 Hz, 1H), 7.77 (s, 1H), 7.85 (m, 1H), 7.98 (m, 1H), 8.45 (s, 1H), 8.65 (s, 1H), 9.47 (s, 1H), 10.33 (s, 1H).

Example 32

Preparation of (R)—N-hydroxy-6-(7-methoxy-4-(1-phenylethylamino)quinazolin-6-yloxy)-hexanamide (Compound 77)

Step 32a. (R)-7-Methoxy-4-(1-phenylethylamino) quinazolin-6-ol (Compound 0701-77)

A mixture of compound 0105 (2.0 g, 8.0 mmol), (R)-1-phenylethanamine (2.91 g, 24.0 mmol) and isopropanol (50 mL) was stirred at 60° C. overnight. Isopropanol was removed and the residue was purified by column chromatography to give the title compound 0701-77 (1.32 g, 56%). LCMS: 296 [M+1]$^+$.

Step 32b. (R)-Ethyl 6-(7-methoxy-4-(1-phenylethylamino)quinazolin-6-yloxy)hexanoate (Compound 0702-77)

A mixture of compound 0701-77 (500.0 mg, 1.69 mmol), K$_2$CO$_3$ (700.0 mg, 5.07 mmol), ethyl 6-bromohexanoate (378.0 mg, 1.69 mmol) and DMF (20 mL) was heated at 60° C. for 3 h. The DMF was moved under reduced pressure, the residue was suspended in water, and the resulting solid was collected and dried to give the title compound 0702-77 (320 mg, 43%). LCMS: 438 [M+1]$^+$.

Step 32c. (R)—N-Hydroxy-6-(7-methoxy-4-(1-phenylethylamino)quinazolin-6-yloxy)-hexanamide (compound 77)

A mixture of compound 0702-77 (320.0 mg, 0.73 mmol) and 1.77 mol/L NH$_2$OH/MeOH (4.0 mL, 6.77 mmol) was stirred at room temperature for 0.5 h. The reaction mixture was neutralized with AcOH and concentrated. The residue was suspended in water and the resulting solid was isolated and dried to give crude product. This crude product was purified by pre-HPLC to give the title compound 77 (36 mg, 12%). LCMS: 425 [M+1]$^+$; $^1$H NMR (DMSO-d$_6$): δ 1.46 (m, 2H), 1.59 (m, 5H), 1.82 (m, 2H), 2.01 (t, J=8.7 Hz, 2H), 3.90 (s, 3H), 4.10 (t, J=6.3 Hz, 2H), 5.63 (m, 1H), 7.09 (s, 1H), 7.21 (m, 1H), 7.32 (m, 2H), 7.42 (d, J=7.2 Hz, 2H), 7.75 (s, 1H), 8.06 (d, J=8.4 Hz, 1H), 8.27 (s, 1H), 8.67 (s, 1H), 10.36 (s, 1H).

Example 33

Preparation of (R)—N-hydroxy-6-(4-(1-phenylethylamino)-quinazolin-6-yloxy)hexanamide (Compound 78)

Step 33a. (R)-4-(1-Phenylethylamino)quinazolin-6-ol (Compound 0701-78)

A mixture of compound 0204 (1.0 g, 4.5 mmol) and (R)-1-(3-chloro-4-fluoro-phenyl)ethanamine (0.87 g, 5.0 mmol) in isopropanol (45 mL) was stirred at 90° C. for 1 hour. The mixture was cooled to room temperature and the resulting precipitate was isolated. The solid was washed in turn with isopropanol and methanol, dried to provide the title compound (R)-4-(1-phenylethylamino)quinazolin-6-yl acetate as a yellow solid (0.62 g, 61%): LCMS 308 [M+1]$^+$.

A mixture of the above product (0.7 g, 2.3 mmol) and lithium hydroxide monohydrate (0.29 g, 6.81 mmol) in methanol (10 mL)/water (15 mL) was stirred at room temperature for 1 hour. The pH was adjusted to 4 with acetic acid and filtered. The collected yellow solid was washed by water and dried to obtained title compound 0701-78 as a yellow solid (0.42 g, 62%), LCMS 266 [M+1]$^+$.

Step 33b. (R)-Ethyl 6-(4-(1-phenylethylamino)quinazolin-6-yloxy)hexanoate (Compound 0702-78)

A mixture of compound 0701-78 (0.31 g, 1.2 mmol), ethyl 6-bromohexanoate (0.27 g, 1.2 mmol) and K$_2$CO$_3$ (0.8 g, 5.8 mmol) in DMF (15 mL) was stirred and heated to 80° C. for 2 hours. The mixture was filtered and the filtrate was evaporated. The resulting solid was washed with ether to obtain the title compound 0702-78 as a pale yellow solid (0.2 g, 42.5%), LCMS 408 [M+1]$^+$.

Step 33c. (R)—N-Hydroxy-6-(4-(1-phenylethylamino)quinazolin-6-yloxy)hexanamide (Compound 78)

The title compound 78 was prepared as a pale yellow solid (42 mg, 26%) from compound 0702-78 (168 mg, 0.41 mmol) using a procedure similar to that described for compound 77 (Example 32): LCMS 395 [M+1]$^+$, $^1$H NMR (DMSO-d$_6$): δ 1.47 (m, 2H), 1.52 (m, 2H) 1.65 (d, J=7.2 Hz, 3H) 1.71 (m, 2H), 2.05 (t, J=3.9 Hz, 2H), 4.04 (t, J=6.3 Hz, 2H), 5.56 (q, J=6.3 Hz, 1H) 7.13 (t, J=7.2 Hz, 1H), 7.26 (t, J=7.8 Hz, 2H), 7.32 (dd, J=2.7, J=9.0 Hz, 1H) 7.39 (d, J=7.2 Hz, 2H), 7.56 (d, J=7.2 Hz, 1H), 7.65 (m, 1H), 8.26 (s, 1H).

Example 34

Preparation of (R)—N-hydroxy-7-(7-methoxy-4-(1-phenylethylamino)quinazolin-6-yloxy)heptanamide (Compound 79)

Step 34a. (R)-Ethyl 7-(7-methoxy-4-(1-phenylethylamino)quinazolin-6-yloxy)heptanoate (Compound 0702-79)

A mixture of compound 0701-79 (500 mg, 1.69 mmol), K$_2$CO$_3$ (700 mg, 5.07 mmol), ethyl 7-bromoheptanoate (401 mg, 1.69 mmol) and DMF (20 mL) was heated at 60° C. for 3 h. The DMF was removed under reduced pressure and the residue was suspended in water. The resulting solid was collected and dried to give the title compound 0702-79 (340 mg, 44%). LCMS: 452 [M+1]$^+$.

Step 34b. (R)—N-Hydroxy-7-(7-methoxy-4-(1-phenylethylamino)quinazolin-6-yloxy)heptanamide (Compound 79)

The title compound 79 was prepared (41 mg, 12%) from compound 0702-79 (340 mg, 0.75 mmol) using a procedure similar to that described for compound 77 (Example 32): LCMS: 439 [M+1]$^+$; $^1$H NMR (DMSO-d$_6$): δ 1.34 (m, 2H), 1.52 (m, 4H), 1.58 (d, J=7.5 Hz, 2H), 1.80 (m, 2H), 1.99 (t, J=8.7 Hz, 2H), 3.89 (s, 3H), 4.10 (t, J=6.3 Hz, 2H), 5.62 (m, 1H), 7.08 (s, 1H), 7.20 (m, 1H), 7.31 (m, 2H), 7.41 (d, J=7.2 Hz, 2H), 7.74 (s, 1H), 8.05 (d, J=8.1 Hz, 1H), 8.26 (s, 1H), 8.63 (s, 1H), 10.32 (s, 1H).

Example 35

Preparation of (S)—N-hydroxy-7-(7-methoxy-4-(1-phenylethylamino)quinazolin-6-yloxy)heptanamide (Compound 80)

Step 35a. (S)-7-Methoxy-4-(1-phenylethylamino)quinazolin-6-ol (Compound 0701-80)

The title compound 0701-80 was prepared as a yellow solid (556 mg, 62.8%) from compound 0105 (750 mg, 3.0 mmol) and (S)-1-phenylethanamine (1089 mg, 9.0 mmol) using a procedure similar to that described for compound 0701-77 (Example 32): LCMS: 296 [M+1]$^+$.

Step 35b. (S)-Ethyl 7-(7-methoxy-4-(1-phenylethylamino)quinazolin-6-yloxy)heptanoate (Compound 0702-80)

The title compound 0702-80 was prepared as a yellow solid (160 mg, 70.95%) from compound 701-80 (148 mg, 0.5 mmol) and ethyl 7-bromoheptanoate (120 mg, 0.5 mmol)

using a procedure similar to that described for compound 0702-77 (Example 32): LCMS: 452 [M+1]$^+$.

Step 35c. (S)—N-hydroxy-7-(7-methoxy-4-(1-phenylethylamino)quinazolin-6-yloxy)heptanamide (Compound 80)

The title compound 80 was prepared as a white solid (95 mg, 61.9%) from compound 0702-80 (160 mg, 0.35 mmol) and fresh NH$_2$OH/CH$_3$OH (3 mL, 5.31 mmol) using a procedure similar to that described for compound 77 (Example 32): m.p. 106.7~111.3° C., LCMS: 439 [M+1]$^+$, $^1$H NMR (DMSO-d$_6$): δ 1.42 (m, 6H), 1.57 (d, J=6.6 Hz, 3H), 1.79 (m, 2H), 1.95 (t, J=7.2 Hz, 2H), 3.88 (s, 3H), 4.08 (t, J=6.9 Hz, 2H), 5.62 (m, J=6.6 Hz, 1H), 7.06 (s, 1H), 7.21 (t, J=7.5 Hz, 1H), 7.30 (t, J=7.5 Hz, 2H), 7.41 (d, J=7.5 Hz, 2H), 7.75 (s, 1H), 8.15 (d, J=9.6 Hz, 1H), 8.29 (s, 1H), 8.60 (s, 1H), 10.30 (s, 1H).

Example 36

Preparation of (R)-7-(4-(1-(4-fluorophenyl)ethylamino)-7-methoxyquinazolin-6-yloxy)-N-hydroxyheptanamide (Compound 81)

Step 36a. (R)-4-(1-(4-Fluorophenyl)ethylamino)-7-methoxyquinazolin-6-ol (Compound 0701-81)

The title compound 0701-81 was prepared as a yellow solid (495 mg, 52.71%) from compound 0105 (750 mg, 3.0 mmol) and (R)-1-(4-fluorophenyl)ethanamine (1251 mg, 9.0 mmol) using a procedure similar to that described for compound 0701-77 (Example 32): LCMS: 314 [M+1]$^+$.

Step 36b. (R)-Ethyl 7-(4-(1-(4-fluorophenyl)ethylamino)-7-methoxyquinazolin-6-yloxy)heptanoate (Compound 0702-81)

The title compound 0702-81 was prepared as a yellow solid (190 mg, 81.0%) from compound 0701-81 (156 mg, 0.5 mmol) and ethyl 7-bromoheptanoate (120 mg, 0.5 mmol) using a procedure similar to that described for compound 0702-77 (Example 32): LCMS: 470 [M+1]$^+$.

Step 36c. (R)-7-(4-(1-(4-Fluorophenyl)ethylamino)-7-methoxyquinazolin-6-yloxy)-N-hydroxyheptanamide (Compound 81)

The title compound 81 was prepared as a white solid (100 mg, 54.12%) from compound 0702-81 (190 mg, 0.40 mmol) and fresh NH$_2$OH/CH$_3$OH (3 mL, 5.31 mmol) using a procedure similar to that described for compound 77 (Example 32): m.p. 118.2-144.3° C., LCMS: 457 [M+1]$^+$, $^1$H NMR (DMSO-d$_6$): δ 1.33 (m, 2H), 1.47 (m, 4H), 1.56 (d, J=7.2 Hz, 3H), 1.78 (m, 2H), 1.95 (t, J=7.2 Hz, 2H), 3.87 (s, 1H), 4.07 (t, J=6.0 Hz, 2H), 5.60 (m, 1H), 7.06 (s, 1H), 7.11 (t, J=9.0 Hz, 2H), 7.44 (m, 2H), 7.71 (s, 1H), 8.04 (d, J=7.5 Hz, 1H), 8.25 (s, 1H), 8.65 (s, 1H), 10.33 (s, 1H).

Example 37

Preparation of (R)-7-(4-(1-(4-chlorophenyl)ethylamino)-7-methoxyquinazolin-6-yloxy)-N-hydroxyheptanamide (Compound 82)

Step 37a. (R)-4-(1-(4-Chlorophenyl)ethylamino)-7-methoxyquinazolin-6-ol (Compound 0701-82)

The title compound 0701-82 was prepared as a yellow solid (0.65 g, 49%) from compound 0105 (1.0 g, 4 mmol) and (R)-1-(4-chlorophenyl)ethanamine (1.87 g, 12 mmol) using a procedure similar to that described for compound 0701-77 (Example 32): LCMS: 300 [M+1]$^+$.

Step 37b. (R)-Ethyl 7-(4-(1-(4-chlorophenyl)ethylamino)-7-methoxyquinazolin-6-yloxy)heptanoate (Compound 0702-82)

The title compound 0702-82 was prepared as a yellow solid (460 mg, 56%) from compound 0701-82 (550 mg, 1.7 mmol) and ethyl 7-bromoheptanoate (404 mg, 1.7 mmol) using a procedure similar to that described for compound 0702-77 (Example 32): LCMS: 486 [M+1]$^+$.

Step 37c. (R)-7-(4-(1-(4-Chlorophenyl)ethylamino)-7-methoxyquinazolin-6-yloxy)-N-hydroxyheptanamide (Compound 82)

The title compound 82 was prepared as a white solid (145 mg, 29%) from compound 0702-81 510 mg, 1.05 mmol) and fresh 0.77 mol/L NH$_2$OH/MeOH (4.7 mL, 8.4 mmol) using a procedure similar to that described for compound 77 (Example 32): LCMS: 473 [M+1]$^+$; $^1$H NMR (DMSO-d$_6$): δ 1.34 (m, 2H), 1.47 (m, 4H), 1.57 (d, J=6.9 Hz, 3H), 1.80 (m, 2H), 1.97 (t, J=7.2 Hz, 2H), 3.89 (s, 3H), 4.10 (t, J=6.6 Hz, 2H), 5.57 (m, 1H), 7.08 (s, 1H), 7.38 (d, J=8.4 Hz, 2H), 7.43 (d, J=8.4 Hz, 2H), 7.73 (s, 1H), 8.04 (d, J=7.8 Hz, 1H), 8.23 (s, 1H), 8.64 (s, 1H), 10.33 (s, 1H).

Example 38

Preparation of (R)—N-hydroxy-7-(7-methoxy-4-(1-(4-methoxyphenyl)ethylamino)quinazolin-6-yloxy)-heptanamide (Compound 83)

Step 38a. (R)-7-Methoxy-4-(1-(4-methoxyphenyl)ethylamino)quinazolin-6-ol (Compound 0701-83)

A mixture of compound 0105 (1.0 g, 4.0 mmol), (R)-1-(4-methoxyphenyl)ethanamine (1.81 g, 12.0 mmol) and isopropanol (25 mL) was stirred at 60° C. overnight. Isopropanol was removed and the residue was purified by column chromatogram to give the title compound 0701-83 (0.81 g, 62%). LCMS: 326 [M+1]$^+$.

Step 38b. (R)-Ethyl 7-(7-methoxy-4-(1-(4-methoxyphenyl)ethylamino)quinazolin-6-yloxy)heptanoate (Compound 0702-83)

A mixture of compound 0701-83 (630 mg, 1.94 mmol), K$_2$CO$_3$ (804 mg, 5.8 mmol), ethyl 7-bromoheptanoate (459 mg, 1.94 mmol) and DMF (20 mL) was heated to 60° C. for 3 h. The DMF was moved away under reduced pressure, the residue was suspended in water, and the solid was collected and dried to give the title compound 0703-83 (440 mg, 47%). LCMS: 482 [M+1]$^+$.

Step 38c. (R)—N-Hydroxy-7-(7-methoxy-4-(1-(4-methoxyphenyl)ethylamino)-quinazolin-6-yloxy)-heptanamide (Compound 83)

A mixture of compound 0702-83 (530 mg, 1.1 mmol) and 1.77 mol/L NH$_2$OH/MeOH (5 mL, 8.8 mmol) was stirred at room temperature for 0.5 h. The reaction mixture was neutralized with AcOH and then the mixture was concentrated and the residue was suspended in water, the precipitate was isolated and dried to give crude product. This product was purified by pre-HPLC to give the title compound 83 (151 mg, 29%). LCMS: 469 [M+1]$^+$; $^1$H NMR (DMSO-d$_6$): δ 1.32 (m, 2H), 1.45 (m, 4H), 1.54 (d, J=6.9 Hz, 3H), 1.78 (m, 2H), 1.95 (t, J=7.2 Hz, 2H), 3.69 (s, 3H), 3.87 (s, 3H), 4.07 (t, J=6.3 Hz, 2H), 5.56 (m, 1H), 6.87 (d, J=8.7 Hz, 2H), 7.05 (s, 1H), 7.31 (d, J=8.7 Hz, 2H), 7.70 (s, 1H), 7.96 (d, J=8.1 Hz, 1H), 8.26 (s, 1H), 8.62 (s, 1H), 10.31 (s, 1H).

Example 39

Preparation of 7-(4-(Benzylamino)-7-methoxyquinazolin-6-yloxy)-N-hydroxyheptanamide (Compound 85)

Step 39a. 4-(Benzylamino)-7-methoxyquinazolin-6-ol (0701-85)

Benzylamine (1.28 g, 12.0 mmol) was added into a mixture of compound 0105 (1.0 g, 4.0 mmol) and 2-propanol (50 ml). The reaction mixture was then stirred at reflux for 3 hours. The mixture was cooled to room temperature and the resulting precipitate was isolated. The solid was then dried to give the title compound 0701-85 as a yellow solid (854 mg, 76%): LCMS: 282 [M+1]$^+$.

Step 39b. Ethyl 7-(4-(benzylamino)-7-methoxyquinazolin-6-yloxy)heptanoate (Compound 0702-85)

The title compound 0702-85 was prepared as a yellow solid liquid (270 mg, 62%) from compound 0701-85 (281 mg, 1.0 mmol) and ethyl 7-bromoheptanoate (236 mg, 1 mmol) using a procedure similar to that described for compound 0702-77 (Example 32): LCMS: 438 [M+1]$^+$.

Step 39c. 7-(4-(Benzylamino)-7-methoxyquinazolin-6-yloxy)-N-hydroxyheptanamide (compound 85)

The title compound 85 was prepared as a yellow solid (64 mg, 24%) from compound 0702-85 (270 mg, 0.62 mmol) using a procedure similar to that described for compound 77 (Example 32): LCMS: 425 [M+1]$^+$; $^1$H NMR (DMSO-d$_6$): δ 1.32 (m, 2H), 1.42 (m, 2H), 1.51 (m, 2H), 1.76 (m, 2H), 1.94 (t, J=7.2 Hz, 2H), 3.88 (s, 3H), 4.03 (t, J=6.3 Hz, 2H), 4.76 (d, J=5.4 Hz, 2H), 7.08 (s, 1H), 7.21 (t, J=6.0 Hz, 2H), 7.30 (t, J=6.0 Hz, 2H), 7.33 (t, J=6.6 Hz, 1H), 7.63 (s, 1H), 8.29 (s, 1H), 8.42 (t, J=6.0 Hz, 1H), 8.64 (s, 1H), 10.32 (s, 1H).

Example 40

Preparation of 7-(4-(4-fluorobenzylamino)-7-methoxyquinazolin-6-yloxy)-N-hydroxyheptanamide (Compound 86)

Step 40a. 4-(4-Fluorobenzylamino)-7-methoxyquinazolin-6-ol (Compound 0701-86)

The title compound 0701-86 was prepared as a yellow solid (489 mg, 54.5%) from compound 0105 (750 mg, 3.0 mmol) and (4-fluorophenyl)methanamine (1125 mg, 9.0 mmol) using a procedure similar to that described for compound 0701-77 (Example 32): LCMS: 300 [M+1]$^+$.

Step 40b. Ethyl 7-(4-(4-fluorobenzylamino)-7-methoxyquinazolin-6-yloxy)heptanoate (Compound 0702-86)

The title compound 0702-86 was prepared as a yellow liquid (408 mg, 89.67%) from compound 0701-86 (300 mg, 1.0 mmol), ethyl 7-bromoheptanoate (237 mg, 1.0 mmol) using a procedure similar to that described for compound 0702-77 (Example 32): LCMS: 456 [M+1]$^+$.

Step 40c. 7-(4-(4-fluorobenzylamino)-7-methoxyquinazolin-6-yloxy)-N-hydroxyheptanamide (Compound 86)

The title compound 86 was prepared as a white solid (300 mg, 69.97%) from compound 0702-86 (442 mg, 0.97 mmol) and fresh NH$_2$OH/CH$_3$OH (4 mL, 7.08 mmol) using a procedure similar to that described for compound 77 (Example 32): LCMS: 443 [M+1]$^+$, $^1$H NMR (DMSO-d$_6$): δ 1.31~1.54 (m, 6H), 1.77 (m, 2H), 1.94 (t, J=7.5 Hz, 2H), 3.88 (s, 3H), 4.03 (t, J=6.3 Hz, 2H), 4.74 (d, J=5.4 Hz, 2H), 7.11 (m, 3H), 7.38 (m, 2H), 7.68 (s, 1H), 8.30 (s, 1H), 8.40 (m, 1H), 8.60 (s, 1H), 10.30 (s, 1H).

Example 41

Preparation of 7-(4-(3,4-difluorobenzylamino)-7-methoxyquinazolin-6-yloxy)-N-hydroxyheptanamide (Compound 87)

Step 41a. 4-(3,4-Difluorobenzylamino)-7-methoxyquinazolin-6-ol (Compound 0701-87)

The title compound 0701-87 was prepared as a light yellow solid (500 mg, 52.6%) from compound 105 (750 mg, 3.0 mmol) and (3,4-difluorophenyl)methanamine (1072 mg, 7.5 mmol) using a procedure similar to that described for compound 0701-77 (Example 32): LCMS: 318 [M+1]$^+$.

Step 41b. Ethyl 7-(4-(3,4-difluorobenzylamino)-7-methoxy-4a,5-dihydroquinazolin-6-yloxy)heptanoate (Compound 0702-87)

The title compound 0702-87 was prepared as a light yellow solid (205 mg, 86.7%) from compound 0701-87 (160 mg, 0.5 mmol), ethyl 7-bromoheptanoate (237 mg, 1.0 mmol) using a procedure similar to that described for compound 0702-77 (Example 32): LCMS: 474 [M+1]$^+$.

Step 41c. 7-(4-(3,4-difluorobenzylamino)-7-methoxyquinazolin-6-yloxy)-N-hydroxyheptanamide (Compound 87)

The title compound 87 was prepared as a white solid (75 mg, 44.5%) from compound 0702-87 (173 mg, 0.366 mmol) and fresh NH$_2$OH/CH$_3$OH (2 mL, 3.4 mmol) using a procedure similar to that described for compound 77 (Example 32): LCMS: 461 [M+1]$^+$, $^1$H NMR (DMSO-d$_6$): δ 1.30 (m, 2H), 1.50 (m, 4H), 1.77 (m, 2H), 1.94 (t, J=7.2 Hz, 2H), 3.88 (s, 1H), 4.03 (t, J=6.6 Hz, 2H), 4.72 (d, J=6.0 Hz, 2H), 7.08 (s, 1H), 7.19 (s, 1H), 7.35 (m, 2H), 7.61 (s, 1H), 8.30 (s, 1H), 8.46 (t, J=6.0 Hz, 1H), 8.64 (s, 1H), 10.32 (s, 1H).

Example 42

Preparation of 7-(4-(3-chloro-4-fluorobenzylamino)-7-methoxyquinazolin-6-yloxy)-N-hydroxyheptanamide (Compound 88)

Step 42a. 4-(3-Chloro-4-fluorobenzylamino)-7-methoxyquinazolin-6-ol (Compound 0701-88)

The title compound 0701-88 was prepared as a light yellow solid (500 mg, 50.1%) from compound 0105 (750 mg, 3.0 mmol) and (3-chloro-4-fluorophenyl)methanamine (1435 mg, 9 mmol) using a procedure similar to that described for compound 0701-77 (Example 32): LCMS: 334 [M+1]$^+$.

Step 42b. Ethyl 7-(4-(3-chloro-4-fluorobenzylamino)-7-methoxyquinazolin-6-yloxy)heptanoate (Compound 0702-88)

The title compound 0702-88 was prepared as a yellow solid (306 mg, 92.02%) from compound 0701-88 (227 mg, 0.68 mmol), ethyl 7-bromoheptanoate (161 mg, 0.68 mmol) using a procedure similar to that described for compound 0702-77 (Example 32): LCMS: 490 [M+1]$^+$.

Step 42c. 7-(4-(3-Chloro-4-fluorobenzylamino)-7-methoxyquinazolin-6-yloxy)-hydroxyheptanamide (Compound 88)

The title compound 88 was prepared as a white solid (210 mg, 70.02%) from compound 0702-88 (306 mg, 0.63 mmol) and fresh NH$_2$OH/CH$_3$OH (3 mL, 5.31 mmol) using a procedure similar to that described for compound 77 (Example 32): m.p. 143.1° C. (decomp), LCMS: 477 [M+1]$^+$, $^1$H NMR (DMSO-d$_6$): δ 1.31 (m, 2H), 1.48 (m, 4H), 1.77 (m, 2H), 1.94 (t, J=7.2 Hz, 2H), 3.89 (s, 3H), 4.04 (t, J=6.6 Hz, 2H), 4.74 (d, J=5.4 Hz, 2H), 7.09 (s, 1H), 7.35 (d, J=7.8 Hz, 2H), 7.54 (d, J=8.4 Hz, 1H), 7.63 (s, 1H), 8.35 (s, 1H), 8.58 (m, 1H), 8.65 (s, 1H), 10.33 (s, 1H), 11.92 (s, 1H).

Example 43

Preparation of 7-(4-(3-bromobenzylamino)-7-methoxyquinazolin-6-yloxy)-N-hydroxyheptanamide (Compound 89)

Step 43a. 4-(3-Bromobenzylamino)-7-methoxyquinazolin-6-ol (Compound 0701-89)

The title compound 0701-89 was prepared as a yellow solid (543 mg, 50.2%) from compound 0105 (750 mg, 3.0 mmol) and (3-bromophenyl)methanamine (1674 mg, 9 mmol) using a procedure similar to that described for compound 0701-77 (Example 32): LCMS: 360 [M+1]$^+$.

Step 43b. Ethyl 7-(4-(3-bromobenzylamino)-7-methoxyquinazolin-6-yloxy)heptanoate (Compound 0702-89)

The title compound 0702-89 was prepared as a yellow solid (230 mg, 89.15%) from compound 0701-89 (180 mg, 0.5 mmol), ethyl 7-bromoheptanoate (120 mg, 0.5 mmol) using a procedure similar to that described for compound 0702-77 (Example 32): LCMS: 516 [M+1]$^+$.

Step 43c. 7-(4-(3-bromobenzylamino)-7-methoxyquinazolin-6-yloxy)-N-hydroxyheptanamide (Compound 89)

The title compound 89 was prepared as a white solid (105 mg, 53.96%) from compound 0702-89 (200 mg, 0.39 mmol) and fresh NH$_2$OH/CH$_3$OH (3 mL, 5.3 μmol) using a procedure similar to that described for compound 77 (Example 32): LCMS: 503 [M+1]$^+$, $^1$H NMR (DMSO-d$_6$): δ 1.31~1.56 (m, 6H), 1.75 (m, 2H), 1.94 (t, J=7.2 Hz, 2H), 3.88 (s, 3H), 4.06 (t, J=6.6 Hz, 2H), 4.75 (d, J=5.7 Hz, 2H), 7.08 (s, 1H), 7.27 (t, J=7.5 Hz, 1H), 3.7.33 (m, 2H), 7.42 (s, 1H), 7.61 (s, 1H), 7.93 (s, 1H), 8.30 (s, 1H), 8.41 (t, J=6.0 Hz, 1H), 8.60 (s, 1H), 10.29 (s, 1H).

Example 44

Preparation of 4-(2-(4-(3-chloro-4-fluorophenylamino)-7-methoxyquinazolin-6-yloxy)ethoxy)-N-hydroxybenzamide (Compound 92)

Step 44a. Methyl 4-(2-bromoethoxy)benzoate (Compound 0502-92)

A mixture of compound 4-hydroxybenzoic acid methyl ester (457.0 mg, 3.0 mmol), K$_2$CO$_3$ (828 mg, 6 mmol) and 1,2-dibromoethane (10 mL) was heated at 130° C. for 8 h. The 1,2-dibromoethane was removed under reduced pressure and the residue was suspended in water. The resulting precipitate was isolated and dried to give the title compound 0502-92 as a white solid (440 mg, 57%). LCMS: 259 [M+1]$^+$.

Step 44b. Methyl 4-(2-(4-(3-chloro-4-fluorophenylamino)-7-methoxyquinazolin-6-yloxy)ethoxy)benzoate (Compound 0503-92)

A mixture of compound 109 (384 mg, 1.2 mmol), K$_2$CO$_3$ (276 mg, 2 mmol), compound 0502-92 (311 mg, 1.2 mmol) and DMF (10 mL) was heated at 40° C. overnight. The DMF was removed under reduced pressure and the residue was suspended in water. The precipitate was collected and dried to give the title compound 0503-92 as a white solid (430 mg, 72%). LCMS: 259 [M+1]$^+$.

Step 44c. 4-(2-(4-(3-Chloro-4-fluorophenylamino)-7-methoxyquinazolin-6-yloxy)ethoxy)-N-hydroxybenzamide (Compound 92)

A mixture of compound 0502-92 (249 mg, 0.5 mmol) and 1.77 mol/L NH$_2$OH/MeOH (5 mL, 8.85 mmol) was stirred at room temperature for 0.5 h. The reaction mixture was neutralized with AcOH and the mixture was concentrated and the residue was suspended in water. The resulting precipitate was isolated and dried to give crude product. This crude product was purified by pre-HPLC to give the title compound 92 as a white solid (80 mg, 32%). LCMS: 439 [M+1]$^+$; $^1$H NMR (DMSO-d$_6$): δ 2.07 (s, 2H), 3.93 (s, 3H), 4.50 (s, 4H), 7.08 (d, J=8.4 Hz, 2H), 7.22 (s, 2H), 7.44 (t, J=9.0 Hz, 1H), 7.76 (m, 3H), 7.89 (s, 1H), 8.12 (m, 1H), 8.51 (s, 1H), 8.87 (s, 1H), 9.54 (s, 1H), 11.05 (s, 1H).

Example 45

Preparation of 7-(4-(3-ethynylphenylamino)-7-methoxyquinazolin-6-yloxy)-N-methoxyheptanamide (Compound 95)

A mixture of compound 0802 (544 mg, 1.25 mmol) and Inodomethane (0804) (177 mg, 1.25 mmol) and potassium carbonate (1.0 g, 7.25 mmol) in N,N-dimethylformamide (15 mL) was stirred at room temperature for 12 hours. The solvent was removed under reduce pressure and the residue was dissolved in ethyl acetate (50 mL). The organic layer was washed with saturation aqueous $NaHCO_3$ (20 mL) and brine (20 mL). The organic layer was dried over $MgSO_4$ and concentrated to give the title compound 95 as pale yellow solid (500 mg, 89%). m.p. 195~197.0° C.; LCMS: 449 [M+1]$^+$; $^1$H NMR (DMSO-$d_6$): δ 1.35 (m, 2H), 1.50 (m, 4H), 1.80 (m, 2H), 1.94 (t, J=7.2 Hz, 2H), 3.54 (s, 3H), 3.92 (s, 3H), 4.12 (t, J=6.3 Hz, 2H), 4.19 (s, 1H), 7.19 (m, 2H), 7.40 (t, J=7.8 Hz, 1H), 7.80 (s, 1H), 7.87 (d, J=9.6 Hz, 1H), 7.97 (s, 1H), 8.48 (s, 1H), 9.45 (s, 1H), 10.92 (s, 1H).

Example 46

Preparation of N-acetoxy-7-(4-(3-chloro-4-fluorophenylamino)-7-methoxyquinazolin-6-yloxy)heptanamide (Compound 96)

A mixture of compound 0801 (50 mg, 0.108 mmol) and $Ac_2O$ (204 mg, 2.0 mmol) and AcOH (2 mL) was stirred at room temperature for 1 h. The reaction mixture was neutralized with $NaHCO_3$ saturation solution. The precipitate was isolated and dried to give product 96 (42 mg, 77%). LCMS: 505 [M+1]$^+$; $^1$H NMR (DMSO-$d_6$): δ 1.40 (m, 2H), 1.50 (m, 2H), 1.55 (m, 2H), 1.80 (m, 2H), 2.09 (s, 3H), 2.12 (m, 2H), 3.94 (s, 3H), 4.13 (t, J=6.9 Hz, 2H), 7.20 (s, 1H), 7.43 (t, J=9.0 Hz, 1H), 7.78 (m, 1H), 7.84 (s, 1H), 8.12 (m, 1H), 8.49 (s, 1H), 9.67 (s, 1H).

Example 47

Preparation of N-acetoxy-7-(4-(3-ethynylphenylamino)-7-methoxyquinazolin-6-yloxy)heptanamide (Compound 97)

The title compound 97 was prepared as a solid (45 mg, 86.0%) from compound 0802 (48 mg, 0.11 mmol) and $Ac_2O$ (204 mg, 2 mmol) using a procedure similar to that described for compound 96 (Example 46): LCMS: 476.5 [M+1]$^+$; $^1$H NMR (DMSO-$d_6$): δ 1.40 (m, 2H), 1.46 (m, 2H), 1.58 (m, 2H), 1.80 (m, 2H), 2.12 (s, 3H), 2.13 (m, 2H), 3.94 (s, 3H), 4.14 (t, J=6.6 Hz, 2H), 4.19 (s, 1H), 7.20 (d, J=6.3 Hz, 2H), 7.40 (t, J=7.8 Hz, 1H), 7.83 (s, 1H), 7.89 (d, J=7.8 Hz, 1H), 7.99 (s, 1H), 8.49 (s, 1H), 9.50 (s, 1H), 11.55 (s, 1H).

Example 48

Preparation of N-(cyclohexanecarbonyloxy)-7-(4-(3-ethynylphenylamino)-7-methoxyquinazolin-6-yloxy)heptanamide (Compound 98)

Compound 0802 (218 mg, 0.5 mmol) and triethylamine (75 mg, 0.75 mmol) were dissolved in acetone (20 mL) and N,N-dimethylformamide (2 mL). The reaction mixture was cooled to 0° C. and a solution of cyclohexanecarbonyl chloride (73 mg, 0.5 mmol) in acetone (5 mL) was added into the above solution dropwise. The reaction mixture was allowed to raise to ambient temperature and stirred for 1 hour. The mixture was concentrated under reduce pressure and the residue was purified by column chromatography to give the title compound 98 as a yellow solid (50 mg, 18%): LCMS: 545 [M+1]$^+$; $^1$H NMR (DMSO-$d_6$): δ 1.21~1.63 (m, 15H), 1.81 (m, 4H), 2.11 (t, J=7.2 Hz, 2H), 3.92 (s, 3H), 4.12 (t, J=7.2 Hz, 2H), 4.17 (s, 1H), 7.19 (m, 2H), 7.39 (t, J=7.8 Hz, 1H), 7.81 (s, 1H), 7.88 (d, J=8.4 Hz, 1H), 7.97 (s, 1H), 8.47 (s, 1H), 9.45 (s, 1H), 11.50 (s, 1H).

Example 49

Preparation of 7-(4-(3-ethynylphenylamino)-7-methoxyquinazolin-6-yloxy)-N-(isobutyryloxy)heptanamide (Compound 99)

The title compound 99 was prepared as a yellow solid (100 mg, 44.0%) from compound 0802 (195 mg, 0.45 mmol) and isobutyryl chloride (48 mg, 0.45 mmol) using a procedure similar to that described for compound 98 (Example 48): LCMS: 505 [M+1]$^+$; $^1$H NMR (DMSO-$d_6$): δ 1.10 (d, J=7.2 Hz, 6H), 1.39 (m, 2H), 1.47 (m, 2H), 1.56 (m, 2H), 1.81 (m, 2H), 2.11 (t, J=7.5 Hz, 2H), 2.68 (m, J=7.2 Hz, 2H), 3.92 (s, 3H), 4.12 (t, J=6.6 Hz, 2H), 4.17 (s, 1H), 7.19 (m, 2H), 7.38 (t, J=7.8 Hz, 1H), 7.82 (s, 1H), 7.88 (d, J=8.7 Hz, 1H), 7.97 (s, 1H), 8.47 (s, 1H), 9.50 (s, 1H), 11.55 (s, 1H).

Example 50

Preparation of 7-(4-(3-ethynylphenylamino)-7-methoxyquinazolin-6-yloxy)-N-(propionyloxy)heptanamide (Compound 100)

The title compound 100 was prepared as a yellow solid (100 mg, 41.0%) from compound 0802 (218 mg, 0.5 mmol) and propionyl chloride (47 mg, 0.5 mmol) using a procedure similar to that described for compound 98 (Example 48): LCMS: 491 [M+1]$^+$; $^1$H NMR (DMSO-$d_6$): δ 1.05 (t, J=7.5 Hz, 3H), 1.39 (m, 2H), 1.48 (m, 2H), 1.56 (m, 2H), 1.81 (m, 2H), 2.12 (t, J=6.6 Hz, 2H), 2.41 (q, J=7.5 Hz, 2H), 3.92 (s, 3H), 4.12 (t, J=6.6 Hz, 2H), 4.18 (s, 1H), 7.19 (m, 2H), 7.38 (t, J=7.8 Hz, 1H), 7.80 (s, 1H), 7.88 (d, J=8.1 Hz, 1H), 7.97 (s, 1H), 8.47 (s, 1H), 9.45 (s, 1H), 11.53 (s, 1H).

Example 51

Preparation of N-(benzoyloxy)-7-(4-(3-ethynylphenylamino)-7-methoxyquinazolin-6-yloxy)heptanamide (Compound 101)

The title compound 101 was prepared as a yellow solid (150 mg, 56.0%) from compound 0802 (218 mg, 0.5 mmol) and benzoyl chloride (72 mg, 0.5 mmol) using a procedure similar to that described for compound 98 (Example 48): LCMS: 539 [M+1]$^+$; $^1$H NMR (DMSO-$d_6$): δ 1.51 (m, 4H), 1.61 (m, 2H), 1.84 (m, 2H), 2.21 (t, J=7.5 Hz, 2H), 3.93 (s, 3H), 4.14 (t, J=6.9 Hz, 2H), 4.19 (s, 1H), 7.19 (m, 2H), 7.38 (t, J=7.8 Hz, 1H), 7.55 (m, 2H), 7.72 (t, J=7.8 Hz, 1H), 7.82 (s, 1H), 7.89 (d, J=8.7 Hz, 1H), 7.99 (m, 3H), 8.48 (s, 1H), 9.48 (s, 1H), 11.88 (s, 1H).

Biological Assays:

As stated hereinbefore the derivatives defined in the present invention possess anti-proliferation activity. These properties may be assessed, for example, using one or more of the procedures set out below:

(a) An In Vitro Assay which Determines the Ability of a Test Compound to Inhibit EGFR Kinase.

The ability of compounds to inhibit receptor kinase (EGFR) activity was assayed using HTScan™ EGF Receptor Kinase Assay Kits (Cell Signaling Technologies, Danvers, Mass.). EGFR tyrosine kinase was obtained as GST-kinase fusion protein which was produced using a baculovirus expression system with a construct expressing human EGFR (His672-Ala1210) (GenBank Accession No. NM_005228) with an amino-terminal GST tag. The protein was purified by one-step affinity chromatography using glutathione-agarose. An anti-phosphotyrosine monoclonal antibody, P-Tyr-100, was used to detect phosphorylation of biotinylated substrate peptides (EGFR), Biotin-PTP1B (Tyr66). Enzymatic activity was tested in 60 mM HEPES, 5 mM $MgCl_2$ 5 mM $MnCl_2$ 200 µM ATP, 1.25 mM DTT, 3 µM $Na_3VO_4$, 1.5 mM peptide, and 50 ng EGF Receptor Kinase. Bound antibody was detected using the DELFIA system (PerkinElmer, Wellesley, Mass.) consisting of DELFIA® Europium-labeled Anti-mouse IgG (PerkinElmer, #AD0124), DELFIA® Enhancement Solution (PerkinElmer, #1244-105), and a DELFIA® Streptavidin coated, 96-well Plate (PerkinElmer, AAAND-0005). Fluorescence was measured on a WALLAC Victor 2 plate reader and reported as relative fluorescence units (RFU). Data were plotted using GraphPad Prism (v4.0a) and IC50's calculated using a sigmoidal dose response curve fitting algorithm.

Test compounds were dissolved in dimethylsulphoxide (DMSO) to give a 20 mM working stock concentration. Each assay was setup as follows: Added 100 µl of 10 mM ATP to 1.25 ml 6 mM substrate peptide. Diluted the mixture with $dH_2O$ to 2.5 ml to make 2×ATP/substrate cocktail ([ATP]=400 mM, [substrate]=3 mM). Immediately transfer enzyme from −80° C. to ice. Allowed enzyme to thaw on ice. Microcentrifuged briefly at 4° C. to bring liquid to the bottom of the vial. Returned immediately to ice. Added 10 µl of DTT (1.25 mM) to 2.5 ml of 4×HTScan™ Tyrosine Kinase Buffer (240 mM HEPES pH 7.5, 20 mM $MgCl_2$, 20 mM MnCl, 12 mM $NaVO_3$) to make DTT/Kinase buffer. Transfer 1.25 ml of DTT/Kinase buffer to enzyme tube to make 4× reaction cocktail ([enzyme]=4 ng/µL in 4× reaction cocktail). Incubated 12.5 µl of the 4× reaction cocktail with 12.5 µl/well of prediluted compound of interest (usually around 10 µM) for 5 minutes at room temperature. Added 25 µl of 2×ATP/substrate cocktail to 25 µg/well preincubated reaction cocktail/compound. Incubated reaction plate at room temperature for 30 minutes. Added 50 µl/well Stop Buffer (50 mM EDTA, pH 8) to stop the reaction. Transferred 25 µl of each reaction and 75 µl $dH_2O$/well to a 96-well streptavidin-coated plate and incubated at room temperature for 60 minutes. Washed three times with 200 µl/well PBS/T (PBS, 0.05% Tween-20). Diluted primary antibody, Phospho-Tyrosine mAb (P-Tyr-100), 1:1000 in PBS/T with 1% bovine serum albumin (BSA). Added 100 µl/well primary antibody. Incubated at room temperature for 60 minutes. Washed three times with 200 µl/well PBS/T. Diluted Europium labeled anti-mouse IgG 1:500 in PBS/T with 1% BSA. Added 100 µl/well diluted antibody. Incubated at room temperature for 30 minutes. Washed five times with 200 µl/well PBS/T. Added 100 µl/well DELFIA® Enhancement Solution. Incubated at room temperature for 5 minutes. Detected 615 nm fluorescence emission with appropriate Time-Resolved Plate Reader.

(b) An In Vitro Assay which Determines the Ability of a Test Compound to Inhibit the EGF-Stimulated EGFR Phosphorylation.

Allowed A431 cell growth in a T75 flask using standard tissue culture procedures until cells reach near confluency ($\sim 1.5 \times 10^7$ cells; D-MEM, 10% FBS). Under sterile conditions dispensed 100 µl of the cell suspension per well in 96-well microplates (x cells plated per well). Incubated cells and monitor cell density until confluency is achieved with well-to-well consistency; approximately three days. Removed complete media from plate wells by aspiration or manual displacement. Replaced media with 50 µl of pre-warmed serum free media per well and incubated 4 to 16 hours. Made two fold serial dilutions of inhibitor using pre-warmed D-MEM so that the final concentration of inhibitor range from 10 µM to 90 pM. Removed media from A431 cell plate. Added 100 µl of serial diluted inhibitor into cells and incubate 1 to 2 hours. Removed inhibitor from plate wells by aspiration or manual displacement. Added either serum free media for resting cells (mock) or serum free media with 100 ng/ml EGF. Used 100 µl of resting/activation media per well. Allowed incubation at 37° C. for 7.5 minutes. Removed activation or stimulation media manually or by aspiration. Immediately fixed cells with 4% formaldehyde in 1×PBS. Allowed incubation on bench top for 20 minutes at RT with no shaking. Washed five times with 1×PBS containing 0.1% Triton X-100 for 5 minutes per Wash. Removed Fixing Solution. Using a multi-channel pipettor, added 200 µl of Triton Washing Solution (1×PBS+0.1% Triton X-100). Allowed wash to shake on a rotator for 5 minutes at room temperature. Repeated washing steps 4 more times after removing wash manually. Using a multi-channel pipettor, blocked cells/wells by adding 100 µl of LI-COR Odyssey Blocking Buffer to each well. Allowed blocking for 90 minutes at RT with moderate shaking on a rotator. Added the two primary antibodies into a tube containing Odyssey Blocking Buffer. Mixed the primary antibody solution well before addition to wells (Phospho-EGFR Tyr1045, (Rabbit; 1:100 dilution; Cell Signaling Technology, 2237; Total EGFR, Mouse; 1:500 dilution; Biosource International, AHR5062). Removed blocking buffer from the blocking step and added 40 µl of the desired primary antibody or antibodies in Odyssey Blocking Buffer to cover the bottom of each well. Added 100 µl of Odyssey Blocking Buffer only to control wells. Incubated with primary antibody overnight with gentle shaking at RT. Washed the plate five times with 1×PBS+0.1% Tween-20 for 5 minutes at RT with gentle shaking, using a generous amount of buffer. Using a multi-channel pipettor added 200 µl of Tween Washing Solution. Allowed wash to shake on a rotator for 5 minutes at RT. Repeated washing steps 4 more times. Diluted the fluorescently labeled secondary antibody in Odyssey Blocking Buffer (Goat anti-mouse IRDyeTM 680 (1:200 dilution; LI-COR Cat. #926-32220) Goat anti-rabbit IRDyeTM 800CW (1:800 dilution; LI-COR Cat. #926-32211). Mixed the antibody solutions well and added 40 µl of the secondary antibody solution to each well. Incubated for 60 minutes with gentle shaking at RT. Protected plate from light during incubation. Washed the plate five times with 1×PBS+0.1% Tween-20 for 5 minutes at RT with gentle shaking, using a generous amount of buffer. Using a multi-channel pipettor added 200 µl of Tween Washing Solution. Allowed wash to shake on a rotator for 5 minutes at RT. Repeated washing steps 4 more times. After final wash, removed wash solution completely from wells. Turned the plate upside down and tap or blot gently on paper towels to remove traces of wash buffer. Scanned the plate with detection in both the 700 and 800 channels using the Odyssey Infrared Imaging System (700 nm detection for IRDye™ 680 antibody and 800 nm detection for IRDye™ 800CW antibody). Determined the ratio of total to phosphorylated protein (700/800) using Odyssey software and plot the results in Graphpad Prism (V4.0a). Data were plotted using GraphPad Prism (v4.0a) and IC50's calculated using a sigmoidal dose response curve fitting algorithm.

(c) An In Vitro Assay which Determines the Ability of a Test Compound to Inhibit HDAC Enzymatic Activity.

HDAC inhibitors were screened using an HDAC fluorimetric assay kit (AK-500, Biomol, Plymouth Meeting, Pa.). Test compounds were dissolved in dimethylsulphoxide (DMSO) to give a 20 mM working stock concentration. Fluorescence was measured on a WALLAC Victor 2 plate reader and reported as relative fluorescence units (RFU). Data were plotted using GraphPad Prism (v4.0a) and IC50's calculated using a sigmoidal dose response curve fitting algorithm. Each assay was setup as follows: Defrosted all kit components and kept on ice until use. Diluted HeLa nuclear extract 1:29 in Assay Buffer (50 mM Tris/Cl, pH 8.0, 137 mM NaCl, 2.7 mM KCl, 1 mM MgCl2). Prepared dilutions of Trichostatin A (TSA, positive control) and tested compounds in assay buffer (5× of final concentration). Diluted Fluor de Lys™ Substrate in assay buffer to 100 uM (50 fold=2× final). Diluted Fluor de Lys™ developer concentrate 20-fold (e.g. 50 µl plus 950 µl Assay Buffer) in cold assay buffer. Second, diluted the 0.2 mM Trichostatin A 100-fold in the 1× Developer (e.g. 10 µl in 1 ml; final Trichostatin A concentration in the 1× Developer=2 µM; final concentration after addition to HDAC/Substrate reaction=1 µM). Added Assay buffer, diluted trichostatin A or test inhibitor to appropriate wells of the microtiter plate. Added diluted HeLa extract or other HDAC sample to all wells except for negative controls. Allowed diluted Fluor de Lys™ Substrate and the samples in the microtiter plate to equilibrate to assay temperature (e.g. 25 or 37° C. Initiated HDAC reactions by adding diluted substrate (25 µl) to each well and mixing thoroughly. Allowed HDAC reactions to proceed for 1 hour and then stopped them by addition of Fluor de Lys™ Developer (50 µl). Incubated plate at room temperature (25° C.) for 10-15 min. Read samples in a microtiter-plate reading fluorimeter capable of excitation at a wavelength in the range 350-380 nm and detection of emitted light in the range 440-460 nm.

The following TABLE B lists compounds representative of the invention and their activity in HDAC and EGFR assays. In these assays, the following grading was used: I≧10 µM, 10 µM>II>1 µM, 1 µM>III>0.1 µM, and IV≦0.1 µM for $IC_{50}$.

TABLE B

| Compound No. | HDAC | EGFR |
| --- | --- | --- |
| 1 | I | IV |
| 2 | I | IV |
| 3 | I | IV |
| 4 | III | IV |
| 5 | IV | IV |
| 6 | IV | IV |
| 7 | I | IV |
| 8 | I | IV |
| 9 | III | IV |
| 10 | III | IV |
| 11 | IV | IV |
| 12 | IV | IV |
| 13 | I | IV |
| 14 | II | IV |
| 15 | IV | III |
| 16 | III | IV |
| 17 | IV | IV |
| 18 | IV | IV |
| 19 | I | IV |
| 21 | II | III |
| 22 | IV | IV |
| 23 | IV | III |
| 24 | IV | III |
| 30 | IV | IV |
| 36 | IV | IV |
| 38 | II | IV |
| 40 | IV | IV |
| 42 | III | IV |
| 43 | III | IV |
| 44 | IV | IV |
| 45 | I | III |
| 50 | III | III |
| 63 | III | II |
| 66 | III | IV |
| 68 | II | IV |
| 69 | III | IV |
| 70 | IV | IV |
| 75 | IV | IV |
| 76 | IV | IV |
| 77 | IV | IV |
| 78 | IV | III |
| 79 | IV | IV |
| 80 | IV | II |
| 81 | III | III |
| 82 | III | III |
| 83 | IV | I |
| 84 | IV | III |
| 85 | IV | IV |
| 86 | IV | III |
| 87 | IV | III |
| 88 | IV | IV |
| 89 | IV | III |
| 90 | IV | N/A |
| 91 | II | IV |
| 92 | III | IV |
| 93 | II | IV |
| 94 | I | IV |

A representative number of compounds were assayed against several different cell lines using the cell proliferation assay:

Cell Proliferation Assay:

Cancer cell lines were plated at 5,000 to 10,000 per well in 96-well flatted bottomed plates with various concentration of compounds. The cells were incubated with compounds for 72 hours in the presence of 0.5% of fetal bovine serum. Growth inhibition was accessed by adenosine triphosphate (ATP) content assay using Perkin Elmer ATPlite kit. ATPlite is an ATP monitoring system based on firefly luciferase. Briefly, 25 µl of mammalian cell lysis solution was added to 50 µl of phenol red-free culture medium per well to lyse the cells and stabilize the ATP. 25 µl of substrate solution was then added to the well and subsequently the luminescence was measured.

The results are presented below in TABLE C. In these assays, the following grading was used: I≧10 µM, 10 µM>II>1 µM, 1 µM>III>0.1 µM, and IV≦0.1 µM for $IC_{50}$.

FIG. 1 shows that compounds of the invention, such as compounds 6 and 12 are more active than erlotinib and SAHA in EFGR enzyme assay and HDAC enzyme assay. In the EFGR enzyme assay, compounds of the invention are more potent than erlotinib by approximately 15-20 fold. In the HDAC enzyme assay, compounds of the invention are more potent than SAHA by approximately 5-10 fold.

Figure 2:
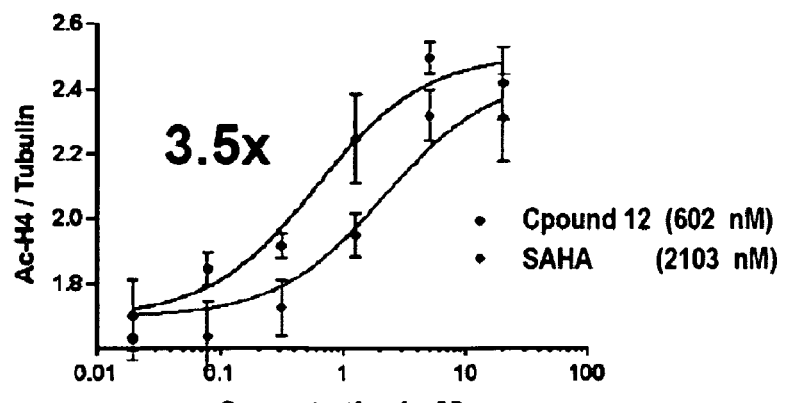
FIG. 2 illustrates inhibition of HDAC and EGFR in MDA-MB-468 breast cancer cell line: (a) Ac-H4 Accumulation, (b) Ac-H3 Accumulation, (c) EGFR inhibition.
Figure 2:
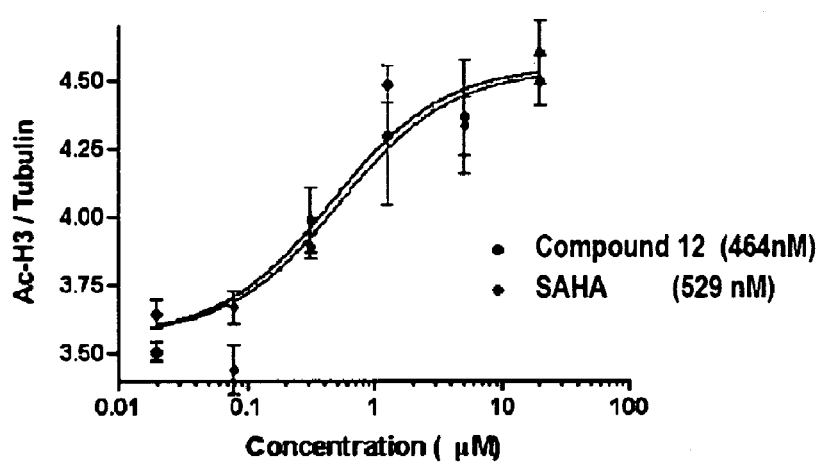
Figure 2:
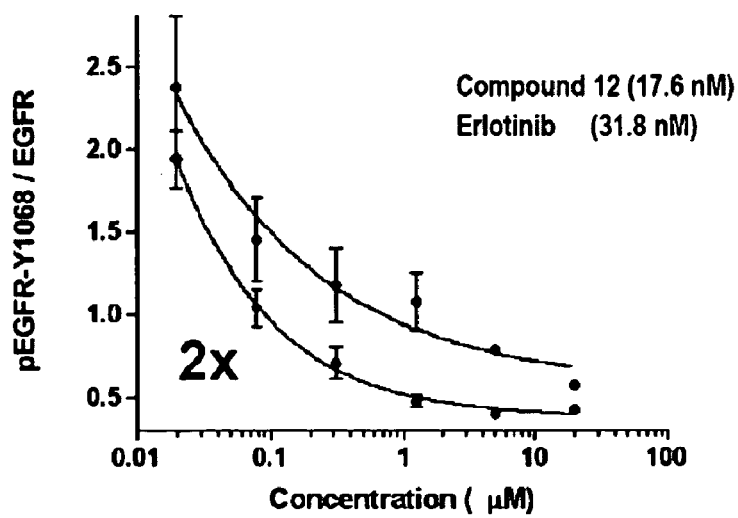

FIG. 2 illustrates the improvement in inhibition of histone acetylation and EGFR phosphorylation by compound 12 as compared with SAHA and Erlotinib respectively. Inhibition on both kinase (EGFR) and non-kinase (HDAC) cancer targets by a compound 12.

Table D illustrates the potency of compounds of the invention. For example, compound 12 is more active than Erlotinib and SAHA in various cancer cell lines (IC50 in µM). Cell lines from five major types of cancer (lung, breast, prostate, colon, and pancreas) responded better to compound 12 than a combination of erlotinib and SAHA. Surprisingly, the compounds of the invention are active against cell lines that are resistant to Tarceva® and Iressa®. In these assays, the following grading was used: D≧5 µM, 5 µM>C≧0.5 µM, 0.5 µM>B≧0.05 µM, and A≦0.05 µM for $IC_{50}$.

TABLE D

| Tumor Line | Tumor Type | SAHA | Erlotinib | Erlotinib/SAHA Combined | Compound 12 |
|---|---|---|---|---|---|
| MDA-MB-231 | Breast adenocarcinoma | B | D | B | A |
| HCT116 | Colon cancer | C | D | C | A |
| MCF-7 | Breast adenocarcinoma | C | D | C | A |
| MDA-MB-468 | Breast adenocarcinoma | C | C | C | A |
| SKBr3 | Breast carcinoma | C | D | C | B |
| PC-3 | Prostate adenocarcinoma | C | D | C | C |
| Caki-1 | Renal carcinoma | B | B | B | A |
| A431 | Epidermoid carcinoma | C | C | C | B |
| 22RV1 | Prostate carcinoma | B | B | B | B |

TABLE C

| Cell Line | \multicolumn{10}{c}{Compound No.} | | | | | | | | | |
|---|---|---|---|---|---|---|---|---|---|---|
| | 6 | 12 | 18 | 40 | 44 | 66 | 70 | 77 | 79 | 85 |
| Breast_MCF7 | | IV | | | | | | | | |
| Breast_MDAMB468 | | IV | | | | | | | | |
| Breast_SkBr3 | | III | | | | | | | | |
| Colon_HCT116 | | III | III | | | | | | | III |
| Epidermoid_A431 | | III | | | | | | | | |
| Lung_H1703 | III | III | | | II | | | | | |
| Lung_H1975 | III | III | | | II | | | | | |
| Lung_H2122 | III | III | | | II | | | | | |
| Lung_H292 | | IV | | | | | | | | |
| Lung_H358 | III | III | | | II | | | | | |
| Lung_H460 | III | III | | | II | | | | | |
| Lung_HCC827 | IV | III | | | III | | | | | |
| Pancreas_BxPC3 | III | IV | III | II | II | II | II | II | II | III |
| Pancreas_Capan1 | II | III | | | II | | | | | |
| Pancreas_CFPAC | | III | III | II | | I | II | II | II | II |
| Pancreas_HPAC | | II | II | | | II | I | I | I | II |
| Pancreas_MiaPaCa2 | | III | III | II | | II | II | III | II | II |
| Pancreas_PANC1 | | III | III | II | | II | II | I | II | II |
| Prostate_22RV1 | | III | | | | | | | | |
| Prostate_PC3 | III | III | | | | | | | | |

Figure 3:
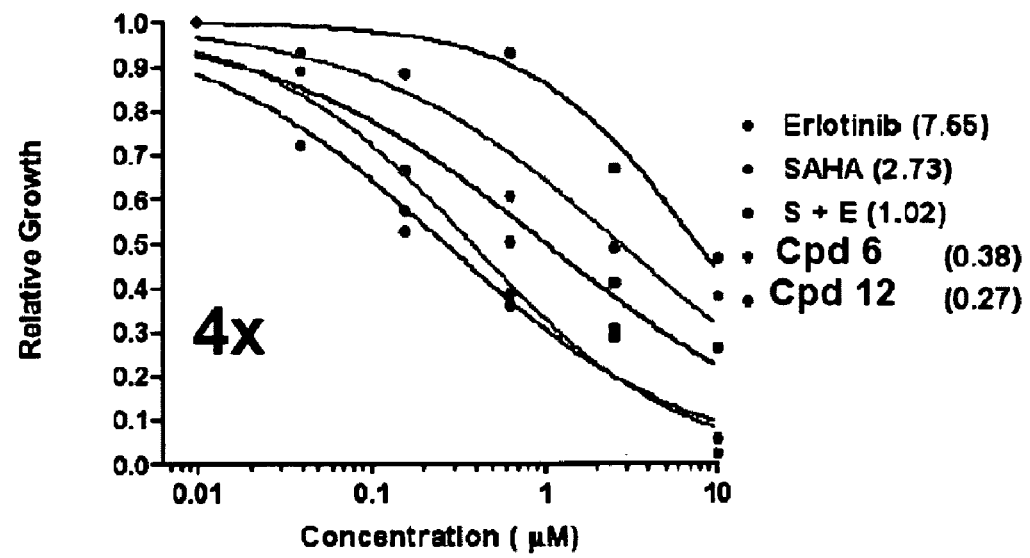
FIG. 3 shows comparative data of anti-proliferative activity against several different cancer cell lines: (a) pancreatic cancer (BxPC3), (b) NSCLC (H1703), (c) breast cancer (MDA-MB-468), (d) prostate cancer (PC3).
Figure 3:
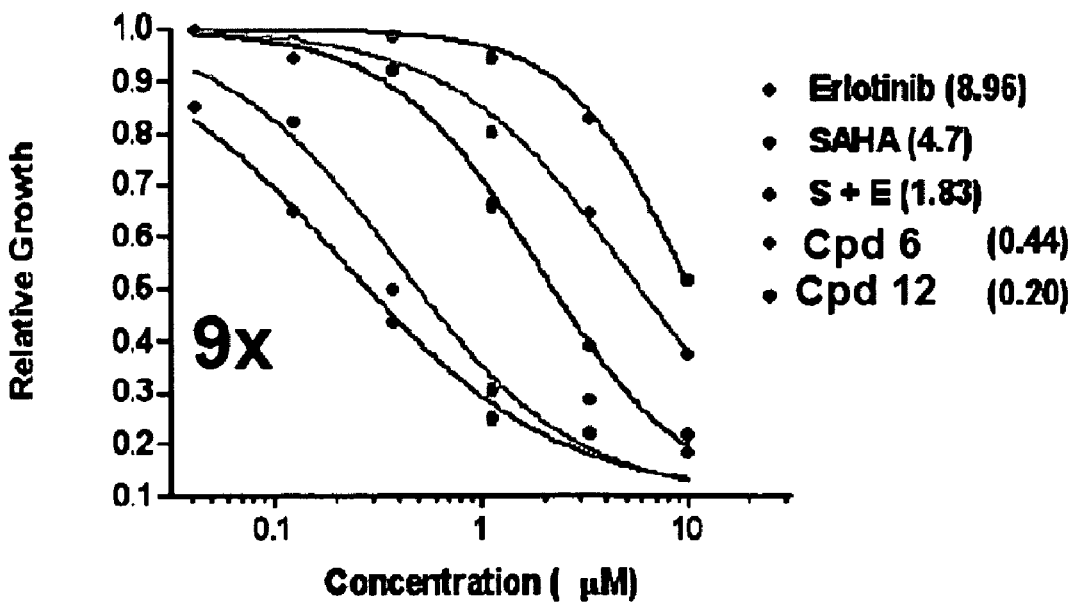
Figure 3:
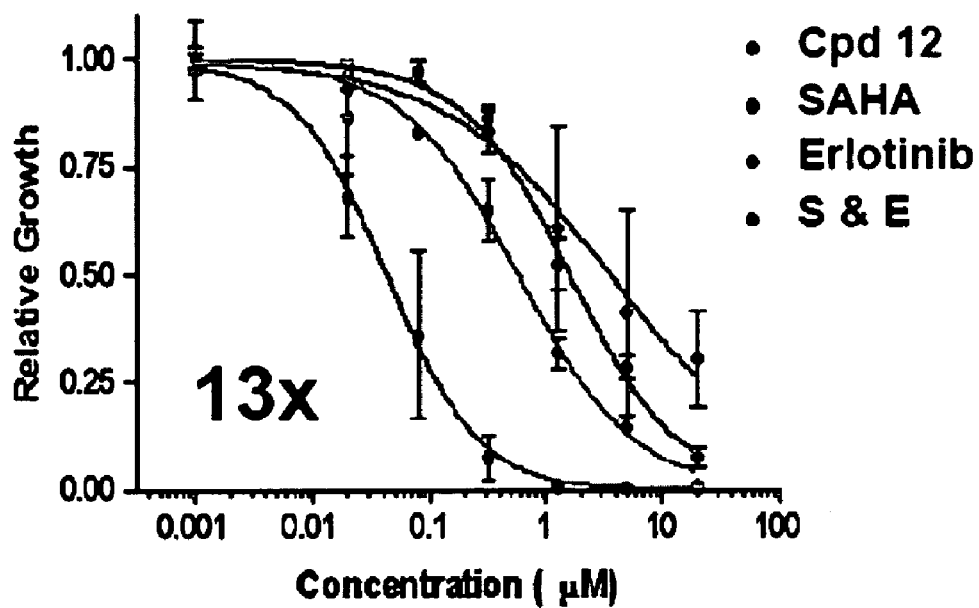
Figure 3:
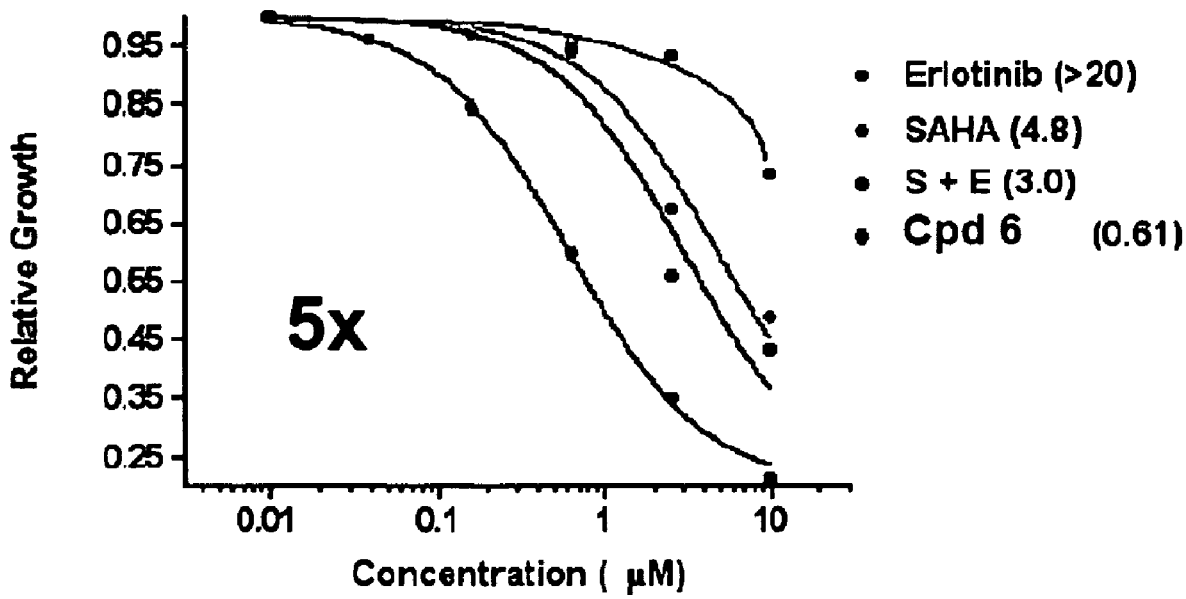

FIG. 3 shows examples of greater anti-proliferative activity against several different cancer cell lines. FIG. 3 further shows that compounds of the invention are more potent than SAHA alone, Erlotinib alone, and SAHA and Erlotinib combined.

Figure 4:
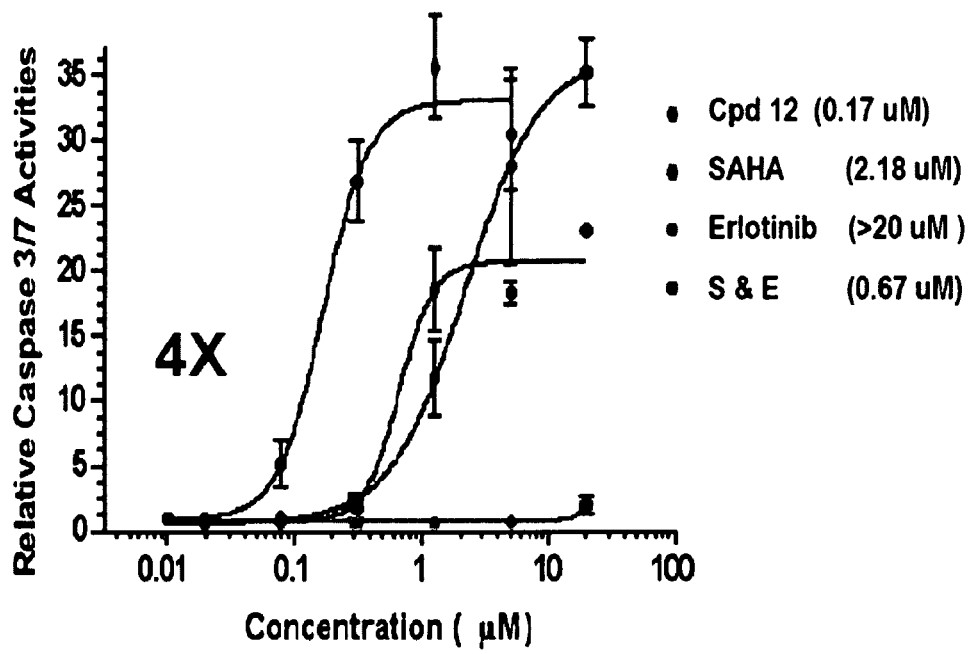
FIG. 4 illustrates the potency of compound 12 induction of apoptosis in cancer cells: (a) HCT-116 (colon, 24 hours), (b) SKBr3 (breast, 24 hours).
Figure 4:
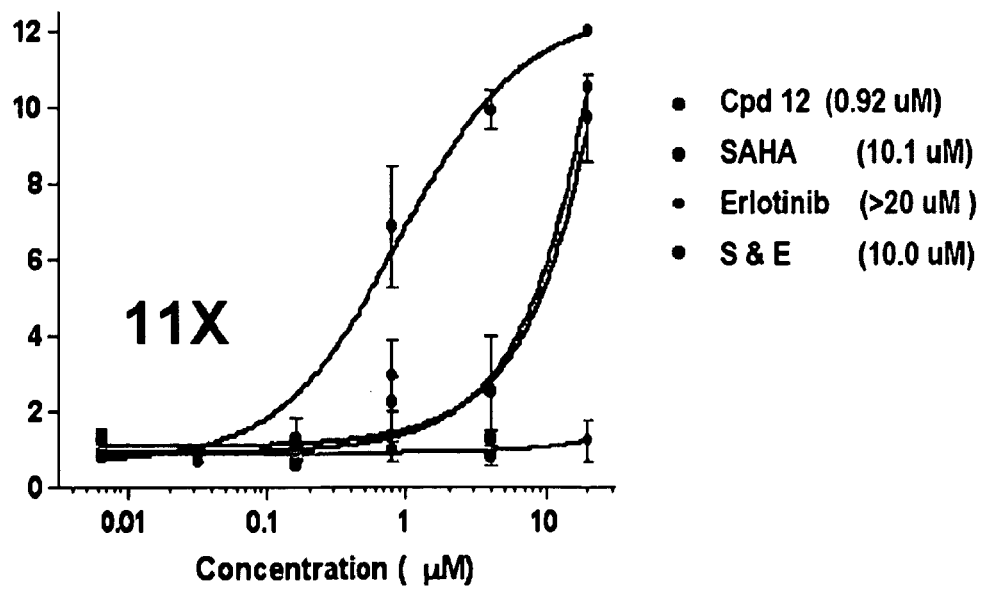
Figure 5:
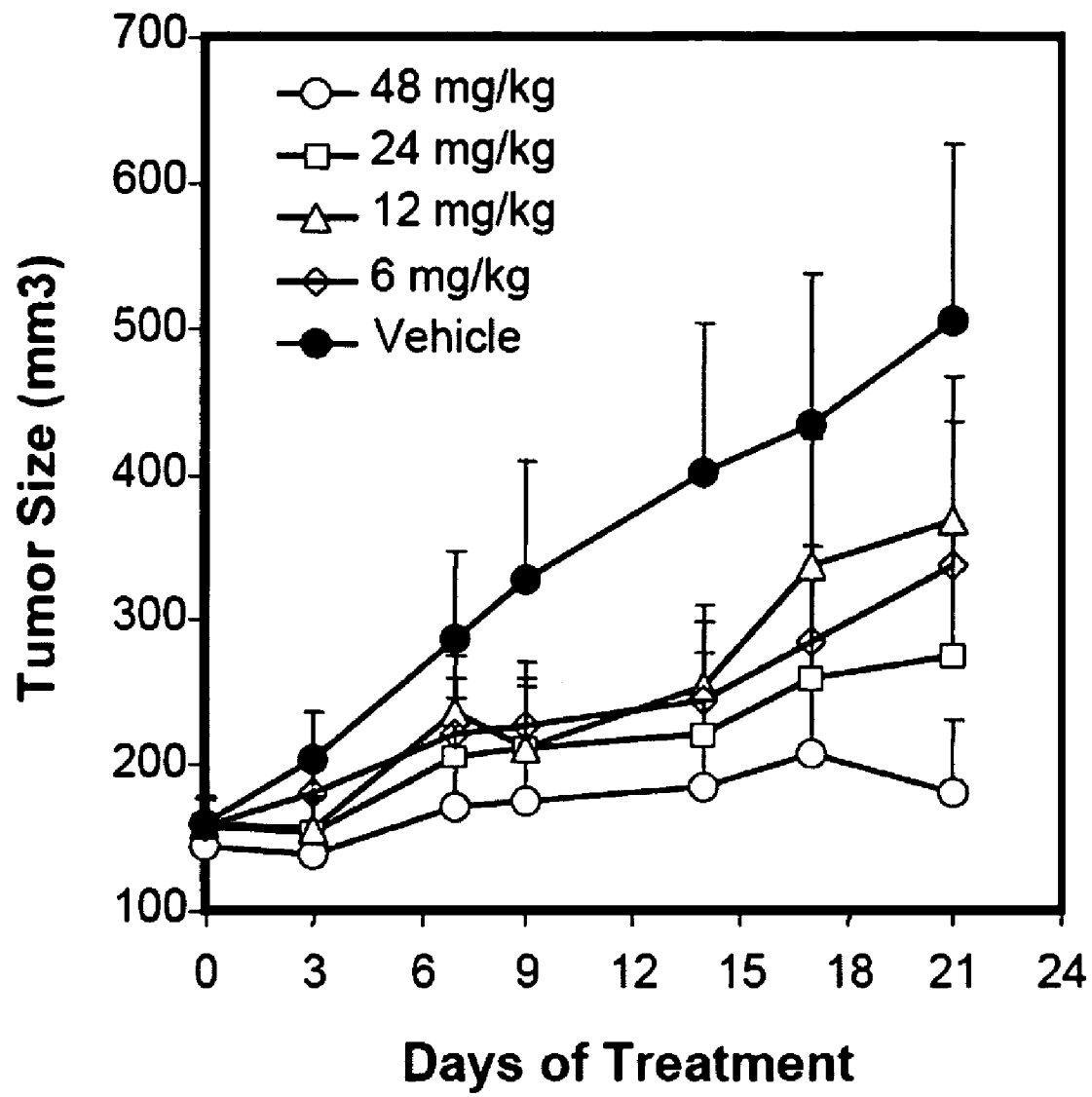
FIG. 5 shows the efficacy of compound 12 in A431 Epidermoid Tumor Xenograft Model (IP Dosing).
Figure 6:
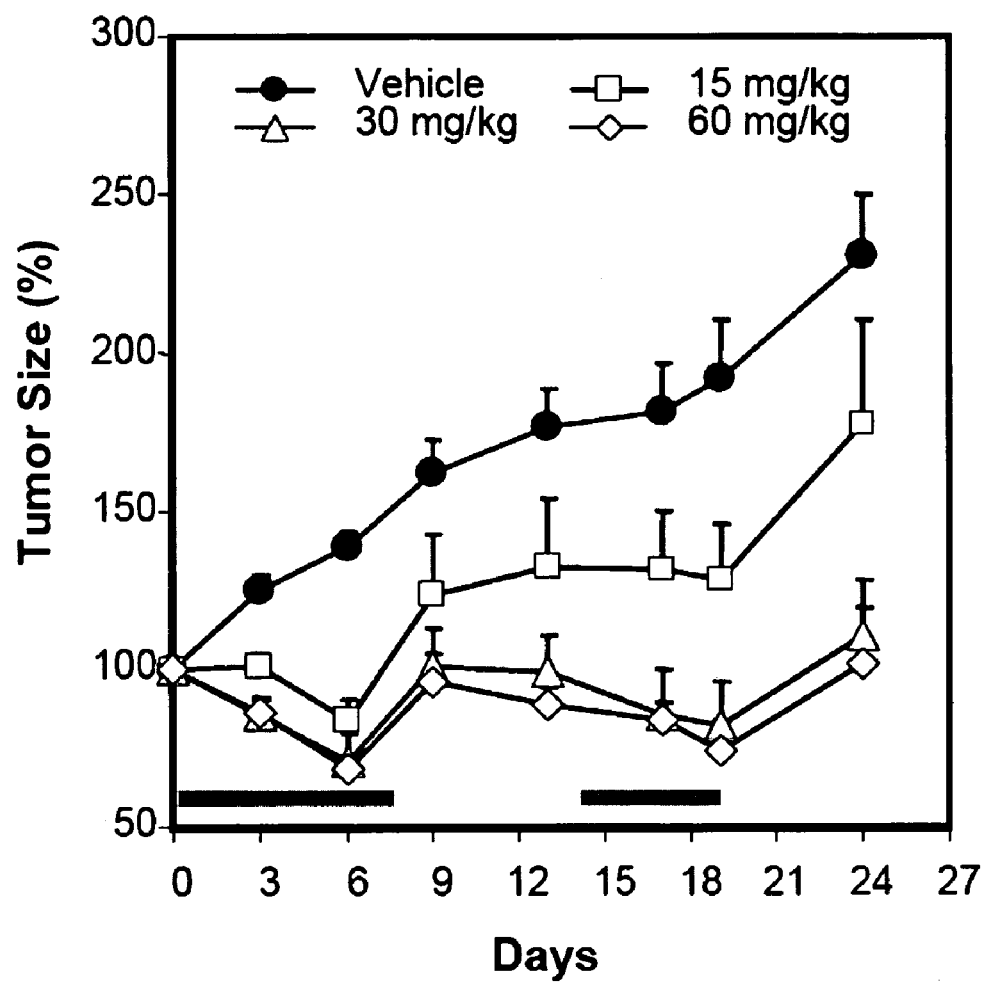
FIG. 6 shows the efficacy of compound 12 in H358 NSCLC Xenograft Model (2-Min IV infusion).
Figure 7:
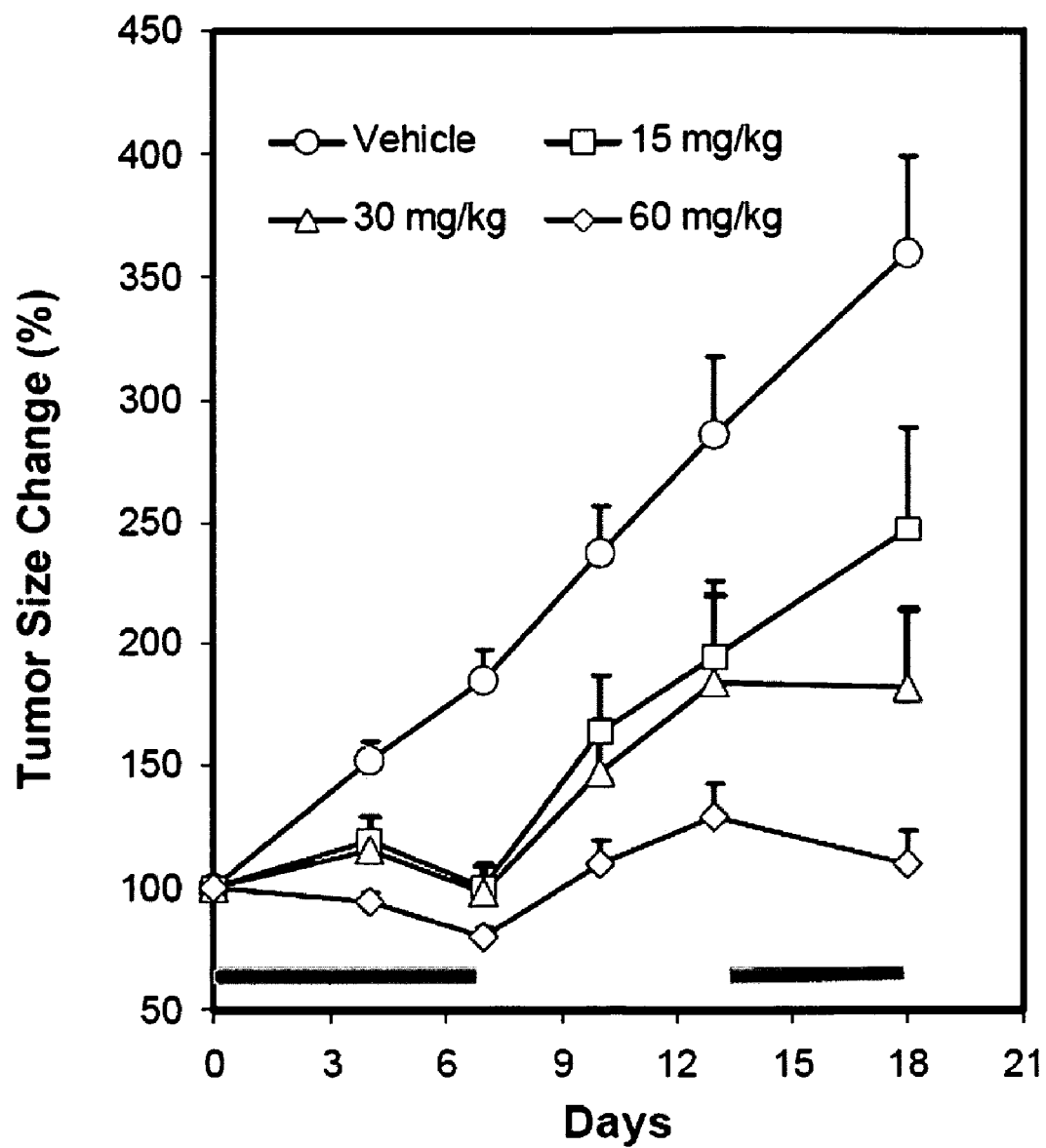
FIG. 7 shows the efficacy of compound 12 in H292 NSCLC Xenograft Model (2-Min IV infusion).
Figure 8:
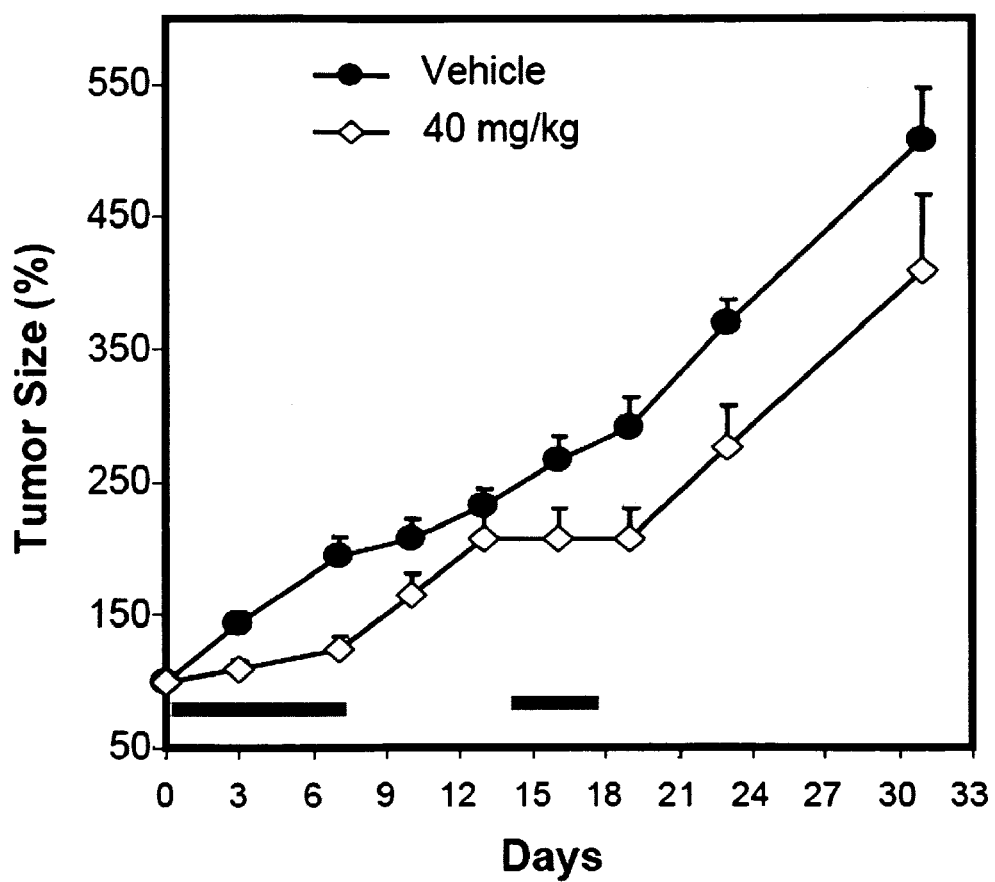
FIG. 8 shows the efficacy of compound 12 in BxPC3 Pancreatic Cancer Xenograft Model (2-Min IV infusion).
Figure 9:
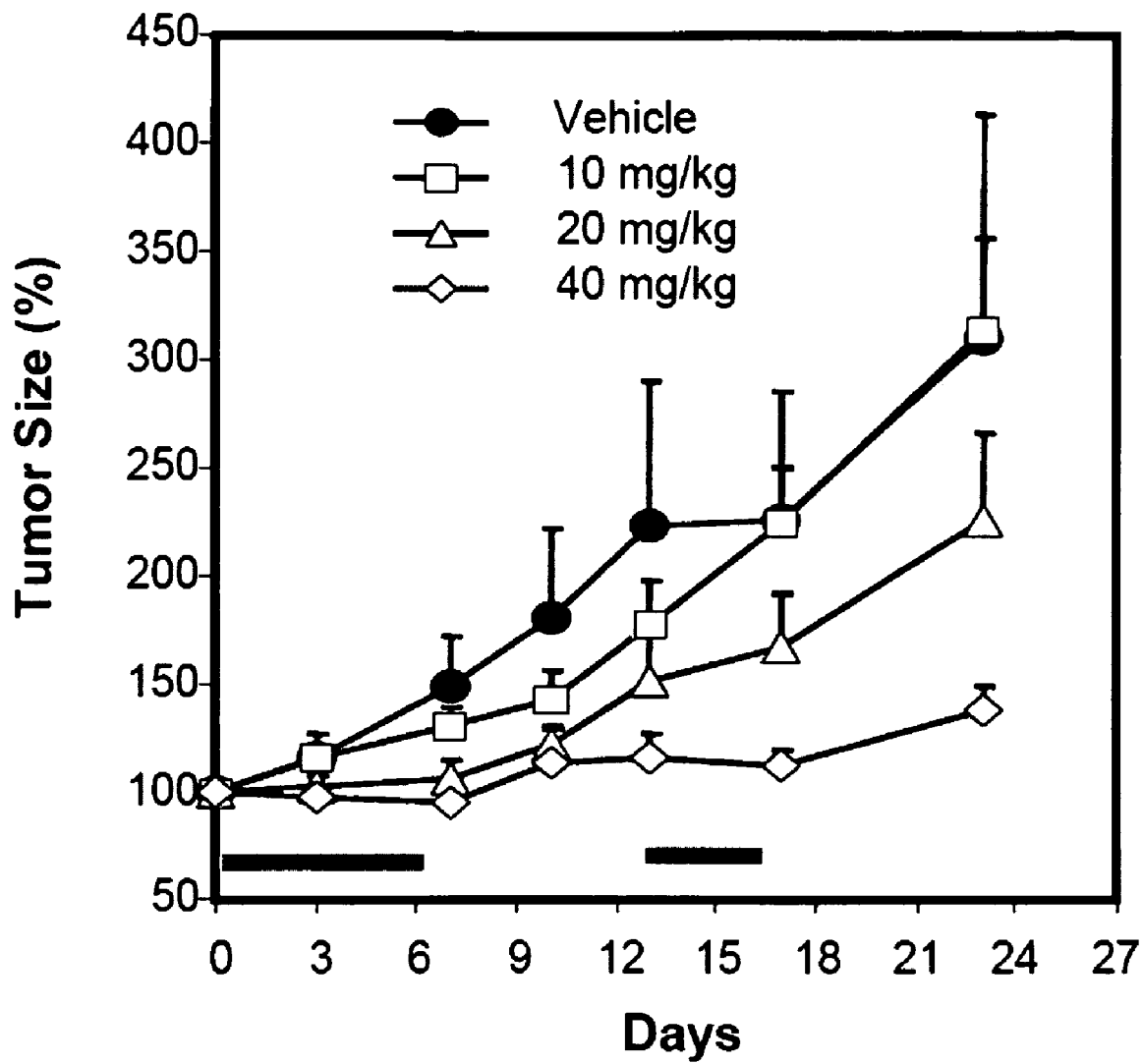
FIG. 9 shows the efficacy of compound 12 in PC3 Prostate Cancer Xenograft Model (2-Min IV infusion).
Figure 10:
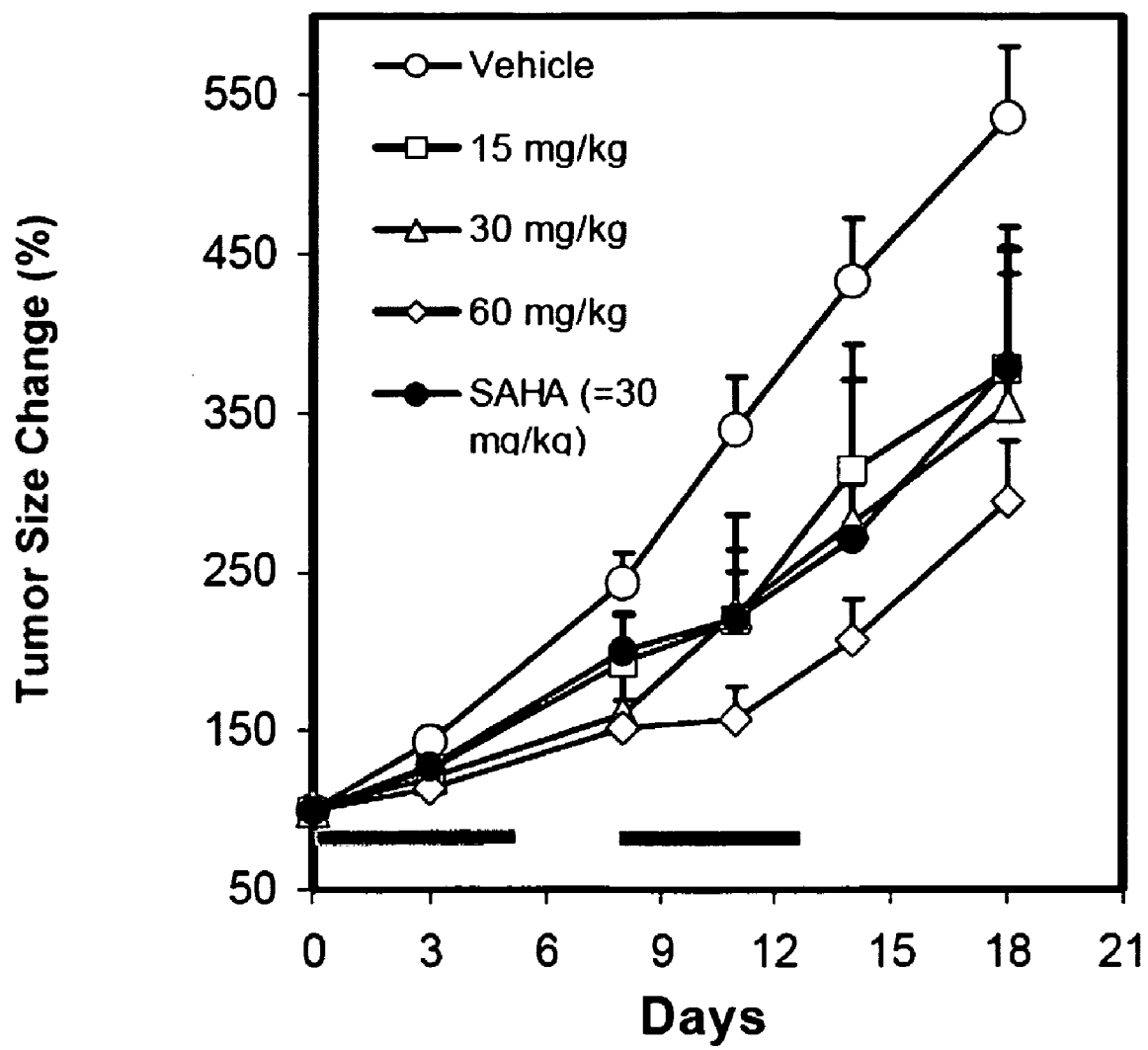
FIG. 10 shows the efficacy of compound 12 in HCT116 Colon Cancer Xenograft Model (2-Min IV infusion).

FIG. 4 displays the potency of compound 12 in induction of apoptosis in colon and breast cancer cells. Compound 12 induced approximately 4-11 times more cell apoptosis as measured by increased Caspase 3&7 activity. Erlotinib was inactive at a concentration <20 µM. The high potency displayed by compound 12 over Erlotinib suggests that compounds of the invention can be used to treat tumor cells that are resistant to Erlotinib.

FIGS. 5-10 illustrate the efficacy of compound 12 in various tumor xenograft models. Table E below summarizes the in vivo experiments that were carried out to give results represented in FIGS. 5-10.

TABLE E

| Model | Cancer type | Dosage groups | Method of administration | Dosing regimen (on-off-on) | Pre-treatment tumor size |
|---|---|---|---|---|---|
| A431 | Epidermoid | vehicle<br>6 mg/kg<br>12 mg/kg<br>24 mg/kg<br>48 mg/kg | IP | Once daily for 21 days | 156 ± 57 mm$^3$ |
| H358 | NSCLC | vehicle<br>15 mg/kg<br>30 mg/kg<br>60 mg/kg | IV - 2 min infusion | 7-7-5 | 84 ± 23 mm$^3$ |
| H292 | NSCLC | vehicle<br>15 mg/kg<br>30 mg/kg<br>60 mg/kg | IV - 2 min infusion | 7-7-5 | 116 ± 23 mm$^3$ |
| BxPC3 | Pancreatic | vehicle<br>10 mg/kg<br>20 mg/kg<br>40 mg/kg | IV - 2 min infusion | 7-7-2 | 201 ± 53 mm$^3$ |
| PC3 | Prostate | vehicle<br>10 mg/kg<br>20 mg/kg<br>40 mg/kg | IV - 2 min infusion | 7-7-5 | 195 ± 50 mm$^3$ |
| HCT116 | Colon | vehicle<br>15 mg/kg<br>30 mg/kg<br>60 mg/kg<br>SAHA 20 mg/kg | IV - 2 min infusion | 5-2-5 | 91 ± 23 mm$^3$ |
| HCC827 (apoptosis/anti-proliferation) | NSCLC | vehicle<br>30 mg/kg | IV - 2 min infusion | Once daily for 3 days | 149 ± 36 mm$^3$ |
| BxPC3 (apoptosis/anti-proliferation) | Pancreatic | 60 mg/kg | IV - 2 min infusion | Single IV infusion | NA |

A representative protocol for the in vivo experiment is as followed:

1-10×10$^6$ human cancer cells were implanted subcutaneously to the athymic (nu/nu) mice. When the tumors reached about 100 mm$^3$ in volume, the mice were treated with the compound by tail vein infusion. Routinely 5 groups (8-12 mice per group) are needed for a typical efficacy study, including one negative control, one positive control, and three testing groups for 3 dose levels of the same compound. Usually a 7-7-5 (on-off-on) regimen was used for one typical study. The tumor size was measured with an electronic caliper and body weight measured with a scale twice weekly. The tumors were removed from euthanized mice at the end of the study. One half of each tumor was frozen in dry ice and stored at −80° C. for PK or Western blot analysis. The other half was fixed with formalin. The fixed tissues were processed, embedded in paraffin and sectioned for immunohistochemistry staining.

Protocol for Radioisotope Assay for HER2

10 nM HER2 and 0.1 mg/ml polyEY were placed in the reaction buffer and 2 mM MnCl$_2$, 1 µM ATP and 1% DMSO final were added. The reaction mixture was incubated for 2 hours at room temperature. The conversion rate of ATP was 22%.

HER2 (Accession number: GenBank X03363) is characterized as follows: N-terminal GST-tagged, recombinant, human HER2 amino acids 679-1255, expressed by baculovirus in Sf9 insect cells. Purity >90% by SDS PAGE and Coomassie blue staining. MW=91.6 kDa. Specific Activity of 40 U/mg, where one unit of activity is defined as 1 nmol phosphate incorporated into 30 ug/ml Poly (Glu:Tyr) 4:1 substrate per minute at 30° C. with a final ATP concentration of 100 µM. Enzyme is in 25 mM Tris-HCl, pH 8.0, 100 mM NaCl, 0.05% Tween-20, 50% glycerol, 10 mM reduced glutathione, and 3 mM DTT.

REFERENCES

1. Meyer, M. et al., EMBO J. 18, 363-374 (1999)
2. Rahimi, N. et al., J. Biol Chem 275, 16986-16992 (2000)

Compounds of the invention are found to be active against various kinases. For example, Table F shows inhibition of compound 12 in a panel of kinase assays. Furthermore, Compound 12 is much more active than Erlotinib in Her-2 assay.

TABLE F

| Assays | Concentrations (µM) | Inhibition (%) |
|---|---|---|
| Abl Kinase | 5 | 57 |
| FGFR2 Kinase | 5 | 73 |
| FLT-3 Kinase | 5 | 85 |
| VEGFR2 Kinase | 5 | 64 |
| Lck Kinase | 5 | 56 |
| Lyn Kinase | 5 | 95 |
| Ret Kinase | 5 | 93 |

Her-2
Compound 12 IC50 = 188 nM
Erlotinib IC50 = 1473 nM

Example 52

Preparation of CAPTISOL® Formulation of Compound 12

A. Preparation of 25, 30, 40, 50 and 60 mg/ml Solutions of Compound 12 in 30% CAPTISOL®.

(i) With Tartaric Acid

A 30% CAPTISOL® formulation was prepared by adding 2.7 ml water to a vial containing 0.9 g CAPTISOL®. The mixture was then mixed on a vortexer to give 3 ml of a clear solution.

In order to prepare a formulation of 25 mg/ml solution of compound 12, 1 ml of the 30% CAPTISOL® solution was added to a vial containing 25 mg of compound 12 and 8.6 mg tartaric acid and the resulting mixture was mixed on a vortexer or sonicated at 30° C. for 15 to 20 minutes to give a clear yellowish solution. The resulting solution is stable at room temperature.

In order to prepare a formulation of 30 mg/ml solution of compound 12, 1 ml of the 30% CAPTISOL® solution was added to a vial containing 30 mg of compound 12 and 10.4 mg tartaric acid (1.0 eq) at room temperature.

In order to prepare a formulation of 40 mg/ml solution of compound 12, 1 ml of the 30% CAPTISOL® solution was added to a vial containing 40 mg of compound 12 and 17.9 mg tartaric acid (1.3 eq) at 36° C.

In order to prepare a formulation of 50 mg/ml compound 12 in CAPTISOL®, 1 ml of 30% CAPTISOL® was added to 50 mg compound 12, 22.5 mg tartaric acid (1.3 eq) at 37° C.

In order to prepare a formulation of 60 mg/ml compound 12 in CAPTISOL®, the 30% CAPTISOL® was added to a vial containing 60 mg compound 12 and 26.9 mg tartaric acid (1.3 eq) at 36° C. The solution was diluted in 1× water and 2×D5W. The diluted solution is stable at room temperature for >12 h.

(ii) With Citric Acid

In order to prepare a formulation of 25 mg/ml solution of compound 12, 1 ml of the 30% CAPTISOL® solution was added to a vial containing 25 mg of compound 12 and 11.1 mg citric acid (1.0 eq) and the resulting mixture was mixed on a vortexer or sonicated at room temperature for 15 to 20 minutes to give a clear yellowish solution.

(iii) With Hydrochloric Acid

In order to prepare a formulation of 25 mg/ml solution of compound 12, 1 ml of the 30% CAPTISOL® solution was added to a vial containing 25 mg of compound 12 and 57.5 μl hydrochloric acid (1.0 eq) and the resulting mixture was mixed on a vortexer or sonicated at room temperature for 15 to 20 minutes to give a clear yellowish solution.

(iiii) With Sodium Salt

In order to prepare a formulation of 7.5 mg/ml solution of compound 12, 1 ml of the 30% CAPTISOL® solution was added to a vial containing 7.5 mg of compound 12 sodium salt and the resulting mixture was mixed on a vortexer or sonicated at room temperature for 15 to 20 minutes to give a clear yellowish solution.

B. Filtration of the Solution.

The formulations of compound 12 from A (i) was filtered through a 0.2-μm presterilized filter with >98% recovery.

C. Preparation of a Lyophilisate.

The formulations of compound 12 (25 mg/ml) from A (i) and A (iii) were lyophilized to form lyophilisate as a yellow powder.

The lyophilisate resulted from A (i) formulation was chemically stable at following temperatures, −20° C., room temperature, and 40° C. for at least 2 weeks. It can be stored at 4° C. for greater than 2 weeks without decomposition. The lyophilisate resulted from A (iii) was stable at −20° C. for at least two weeks.

D. Dilution Study.

The formulations of compound 12 from A (i) were diluted with D5W (10-, 20-, and 50-fold) and were chemically stable and remained in solution without precipitation (>48 hours).

The formulations of compound 12 from A (ii), A (iii) and A (iiii) were diluted with D5W (10-fold) and remained in solution without precipitation (>12 hours).

Example 53

Characteristics of Sodium, Hydrochloride, Citric Acid and Tartaric Acid Salts or Complexes of Compound 12 Formulated in Captisol®

Sodium, hydrochloride, citrate and tartrate salts of a test compound of Formula I were prepared in 30% CAPTISOL® solutions and were studied for the following:

Table G shows the physiochemical as well as pharmacokinetic (PK) and pharmacodynamic (PD) properties of sodium, hydrochloride, citric acid and tartaric acid salts of Compound 12.

TABLE G

|  | Sodium | HCl | Citric Acid | Tartaric Acid |
| --- | --- | --- | --- | --- |
| Solubility | 7.5 mg/ml | 25 mg/ml | 25 mg/ml | 60 mg/ml |
| pH | 10-11 | 2-3 | 4-5 | 3-4 |
| IV Tissue | High | High | Low | High |
| Dilution with D5W | >10x | >10x | >10x | >50x |
| Chemical stability in diluted solution | >12 h | >12 h | >12 h | >12 h |
| 2-week chemical stability in lyophilisate | ND | −20° C. | ND | −20° C., RT, 40° C. |
| Deliverable highest daily dose in humans | 220-250 mg | >750 mg | >750 mg | >1800 mg |

Example 54

Figure 11A:
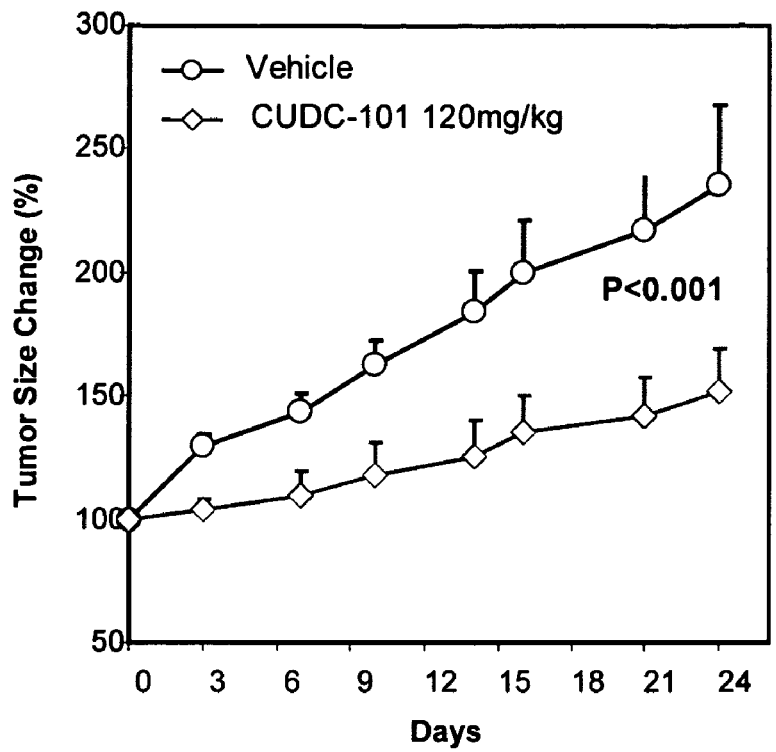
FIG. 11A shows the percent of change in tumor size in animals treated with compound 12 or vehicle in A549 NSCLC Xenograft model.
Figure 11B:
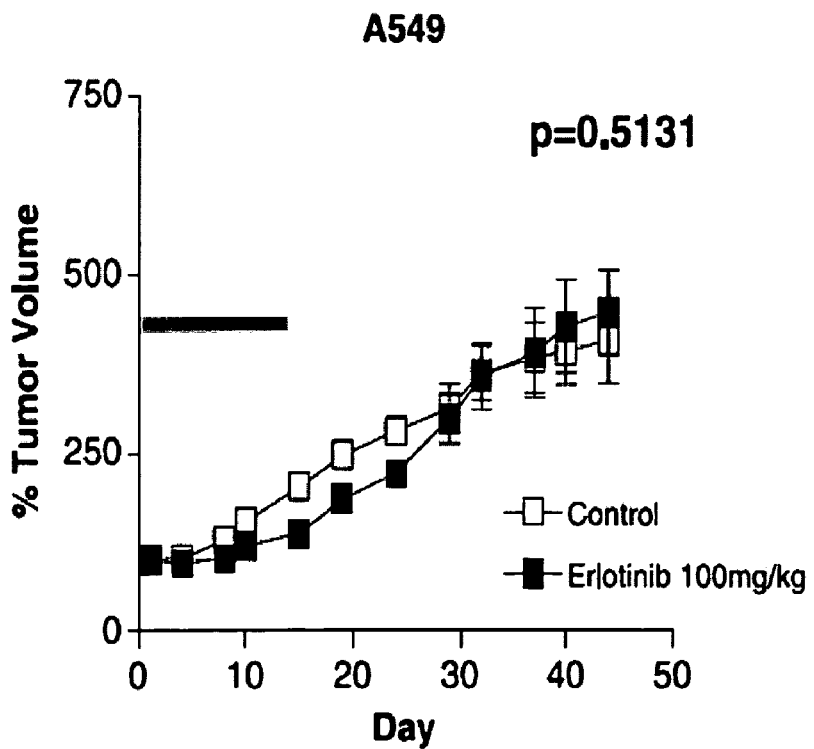
FIG. 11B shows the percent of change in tumor size in animals treated with Erlotinib and control in A549 NSCLC Xenograft model.

Comparison of Anti-Tumor Activity of Composition of Compound 12 in 30% CAPTISOL® and Erlotinib, a Prototype EGFRi in A549 NSCLC Xenograft Model Administration of compound 12 in 30% CAPTISOL® attenuated tumor growth in the NSCLC xenograft model. As shown in FIG. 11A, after 24 hours, animals treated with compound 12 showed a 150% increase in tumor size whereas animals treated with vehicle showed about a 240% change in tumor size. As shown in FIG. 11B, treatment of animals with Erolotinib did not significantly affect tumor size as compared to control.

Example 55

Figure 12A:
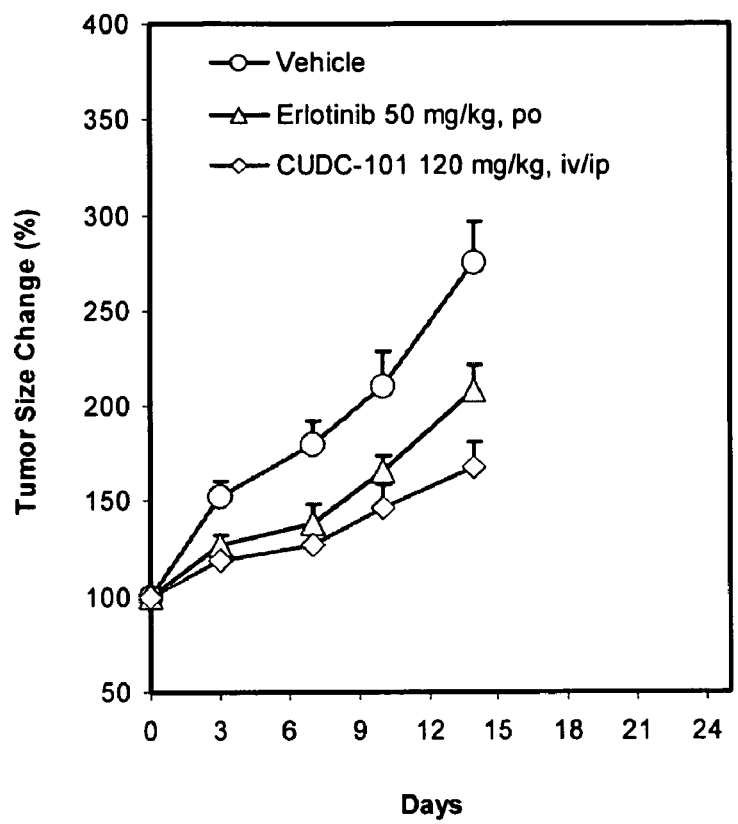
FIG. 12A shows the percent of change in tumor size in animals treated with compound 12, Erlotinib or vehicle in HPAC pancreatic cancer cells.
Figure 12B:
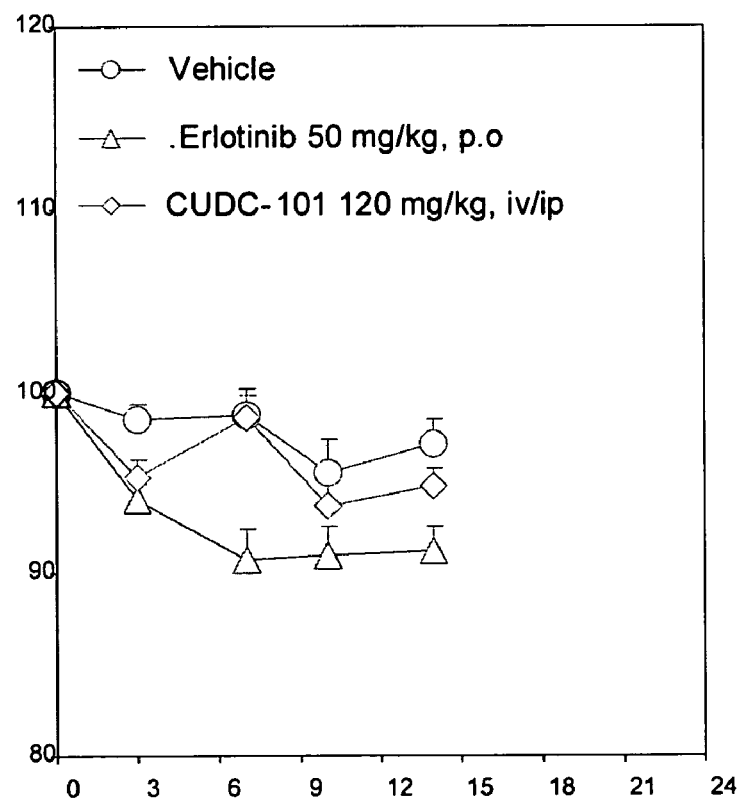
FIG. 12B shows the percent of change in body weight in animals treated with compound 12, Erlotinib or vehicle in HPAC pancreatic cancer cells.

Effect of Composition of Compound 12 in 30% CAPTISOL® in HPAC Pancreatic Cancer Cells 120 mg/kg of compound 12 in 30% CAPTISOL®, 50 mg/kg erlotinib or vehicle were administered to animals daily and change in tumor size over time (days) was measured. As shown in FIG. 12A, administration of 120 mg/kg compound 12 in 30% CAPTISOL® (iv/ip) resulted in greater attenuation of tumor growth than either erlotinib (po) or vehicle.

Pharmacokinetic Studies in Mice, Rats, and Dogs

The experimental methods used for Examples 56-64 are described below. Animals: Mice (CD-1, male, 25-30 g), rats (Spraque Dawle, 260-300 g) and dogs (Beagles, male, 9-11 kg) were used for the PK studies. Animals were provided pelleted food and water ad libitum and kept in a room conditioned at 23±1° C., humidity of 50-70%, and a 12-hour light/12-hour dark cycle.

Drug Preparation and Administration. Compound 12 was dissolved in 30% CAPTISOL® with equal molar concentration of tartaric acid or HCl or citric acid, or NaOH. Compound was administered via an intravenous (iv) infusion. Conditions for iv infusion for each animal are shown below:

Mouse: 20 mg/kg and 60 mg/kg for 2 min i.v. infusioin
Rat: 20 mg/kg for 5 min i.v. infusion
Beagle: 25 mg/kg for 30 min i.v. infusion Blood and tissue Sample Collection. Blood was collected into tubes containing sodium heparin anticoagulant at various time points. The plasma was separated via centrifugation and stored in −40° C. before analysis.

Plasma Sample Extraction. Plasma samples were prepared by protein precipitation. An internal standard was added into plasma samples. A 50 µl of plasma was combined with 150 µl of acetonitrile, vortexed, and centrifuged for 10 min at 10000 rpm. The supernatant was then injected onto LC/MS/MS.

Samples were compared to standards made in plasma. These standards were prepared by serial dilution. An internal standard was added into the plasma with standard.

Tissue Sample Extraction. Lung and colon samples (20-200 mg) were used for extraction. Tissues were homogenized in 0.8 ml water. An internal standard was added into the tissue homogenates. The homogenates were extracted with 1-ml ethyl acetate for three times. After evaporation, the residual was reconstituted in 0.1 ml acetonitrile for LC/MS/MS assay.

LC/MS/MS Analytical Methods.

LC Conditions are shown below.

| | |
|---|---|
| LC Instrument: | Agilent HPLC 1100 Series |
| Autosampler: | Agilent G1367A Autosampler |
| Analytical Column: | YMC Pro C18 S3 (3µ, 2.0 * 50 mm, 120 Å) |
| Guard Column: | YMC Pro C18 S3 Guard Column (3µ, 2.0 * 10 mm, 120 Å) |
| Column Temp: | in ambient |
| Mobile Phase: | A: acetonitrile:water:formic acid (5:95:0.1, v/v/v) |
| | B: acetonitrile:water:formic acid (95:5:0.1, v/v/v) |
| LC Gradient Program | 0~1 min: mobile phase A: 100% |
| | 1~2.5 min: mobile phase A: 100% to 20% |
| | 2.5~3 min: mobile phase A: 20% |
| | 3~4 min: mobile phase A: 20% to 100% |
| Flow Rate: | 200 µl/min |
| Autosampler Temp: | in ambient |
| Injection Volumn: | 5 µl |

Mass Spectrometer conditions are shown below:

| | |
|---|---|
| Instrument: | PE Sciex API 3000 |
| Interface: | Turbo Ion Spray (TIS) |
| Polarity: | Positive Ion |
| Scan: | Multiple Reaction Monitoring (MRM) |

Single or Multiple Dosing Toxicity Study in Mice and Rats

The experimental methods used for the toxicity studies below are described as follows:

Experiment Design:
1. Single Dosing MTD in Mice
   a. CD-1 mice, male, 24-26 gram
   b. Dosing at 0, 50, 100, 200, 400 mg/kg, iv infusion 2 min
   c. 8 mice per group
2. Single Dosing MTD in Rats
   a. Sprague Dawley, male and female, 240-260 gram
   b. Dosing at 0, 25, 50, 100, 200 mg/kg, iv infusion 5 min
   c. 6 rats per group (3 male and 3 female)
3. 7-Day-Multiple Dosing MTD in Mice
   a. CD-1 mice, male, 24-26 gram
   b. Dosing at 0, 50, 100, 200 mg/kg/d ip
   c. 6 mice per group
   d. Blood and organs will be collected 2 hr after last dosing on Day 7 for hematology
4. 7-Day Multiple Dosing MTD in Rats
   a. Sprague Dawley, male and female, 220-250 gram
   b. Dose, 25, 50, 100, 200 mg/kg/d) iv infusion 5 min
   c. 6 per group (3 male and 3 female)
   d. Blood and organs will be collected 2 hr after last dosing on Day 7 for hematology Compound Preparation.

The compound was dissolved in 30% CAPTISOL® with equal molar concentration of tartaric acid. The stock solution: 25 mg/ml Tartaric form in 30% CAPTISOL®, 1 ml/vial store at −40° C. For example, 1000 mg compound, 345 mg tartaric acid (0.345 mg tartaric acid per mg compound) and 40 ml 30% CAPTISOL® or 1000 mg compound, 2.3 ml 1N HCl (2.3 ul 1N HCl per mg compound), 12 gram CAPTISOL®, Add water to 40 ml. Stock solution is diluted with 30% CAPTISOL® before use.

Example 56

Figure 13:
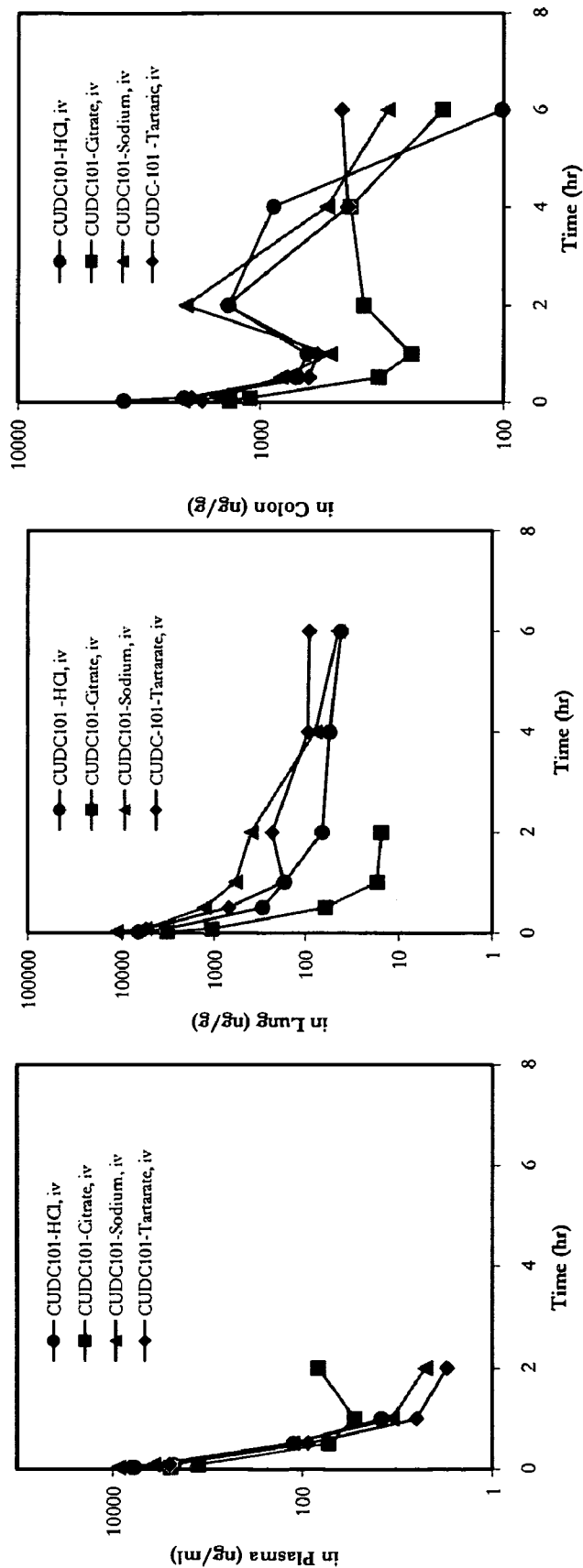
FIG. 13 shows the concentration of compound 12 in plasma, lung and colon after administration of hydrochloride, citrate, sodium and tartrate salts of compound 12.

Pharmacokinetics of Test Salts in Plasma, Lung and Colon after Intravenous Administration 20 mg/kg of hydrochloride, citrate, sodium and tartrate salts of compound 12 in 30% CAPTISOL® was administered intravenously to mice in order to determine the concentration (ng/ml) over time (hours) of compound 12 after intravenous (iv) administration in plasma, lung and colon. The results of these studies are shown in FIG. 13. As shown there, the concentration of the tartrate salt of compound 12 in plasma decreased from about 10,000 ng/ml in 2 hours. In lung, the concentration of the tartrate salt of compound 12 decreased from about 10,000 ng/ml in 6 hours. In colon, the concentration of the tartrate salt went decreased from over 1000 ng/ml in 6 hours.

Example 57

Pharmacokinetic Study of Compound 12 Formulation in Mice 20 mg/kg and 60 mg/kg of a hydrochloride salt of compound 12 in 30% CAPTISOL® was administered intravenously (iv) and intraperitoneally (ip) to mice and the half life (t1/2), maximal observed concentration (Cmax) and area under the curve (AUC) were determined. As shown in Table H below, the concentration of compound 12 is dose proportional when administered intravenously but not intraperitoneally. The half-life of compound 12 in tissue is greater than that in plasma.

TABLE H

|  | Plasma | | Lung | | Colon | |
| --- | --- | --- | --- | --- | --- | --- |
|  | 20 mgkg | 60 mg/kg | 20 mgkg | 60 mg/kg | 20 mgkg | 60 mg/kg |
| IV Dose | | | | | | |
| T ½ (hr) | 0.2 | 0.3 | 3.9 | 1.9 | 1.7 | 2.2 |
| Cmax (uM) | 27.7 | 61.7 | 15.2 | 96.9 | 8.5 | 29.4 |
| AUC (h * ng/ml) | 715 | 3124 | 1571 | 8313 | 5529 | 13473 |
| IP Dose | | | | | | |
| T ½ (hr) | 0.26 | 0.51 | 2.2 | 3.5 | NA | NA |
| Cmax (uM) | 8.5 | 14.4 | 7.8 | 11.6 | NA | NA |
| AUC (h * ng/ml) | 3751 | 5721 | 4433 | 8309 | NA | NA |

Example 58

Figure 14:
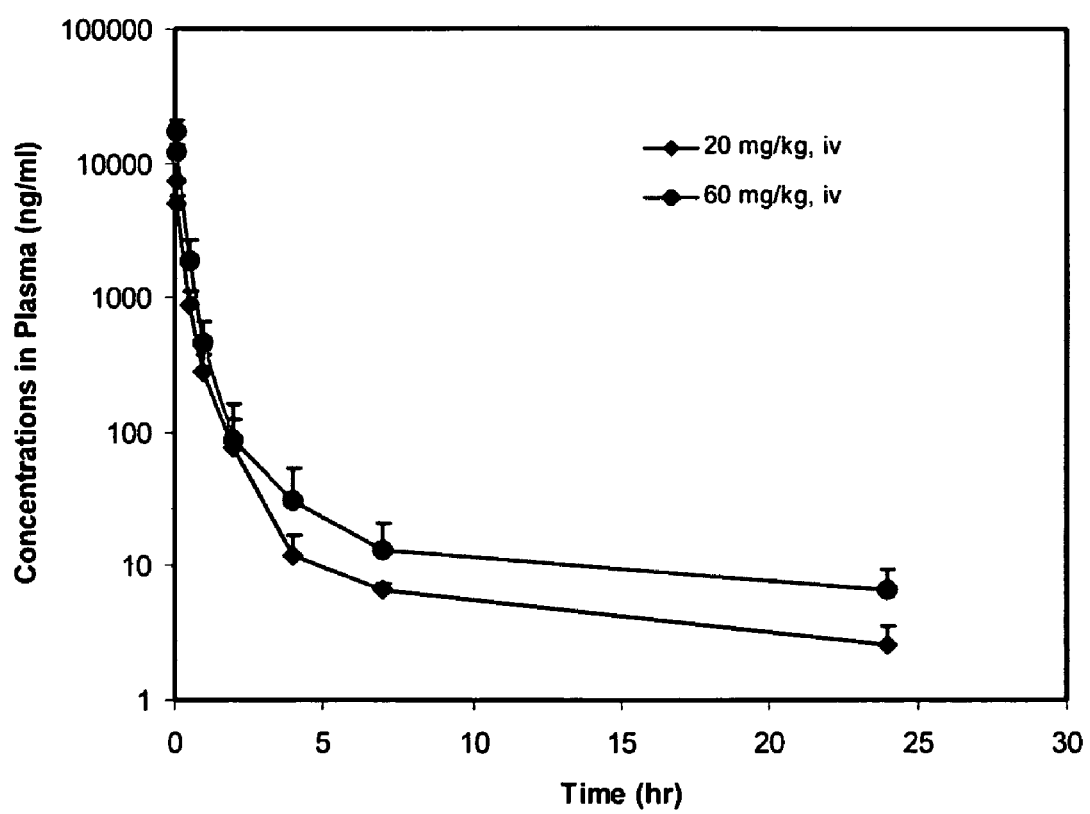
FIG. 14 shows the concentration of compound 12 in the plasma of mice administered compound 12 in 30% CAPTISOL®.

Pharmacokinetic Study of Compound 12 Formulation in Rats 20 mg/kg and 60 mg/kg of a hydrochloride salt of compound 12 in 30% CAPTISOL® was administered (iv) to rats and the concentration (ng/ml) of the compound was measured in plasma over thirty hours. As shown in FIG. 14, the concentration of compound 12 in the plasma of the rat was proportional to the dose of compound 12 administered.

Example 59

Single Dose IV Toxicity Study in Mice with the Compound 12 Formulation

Figure 15:
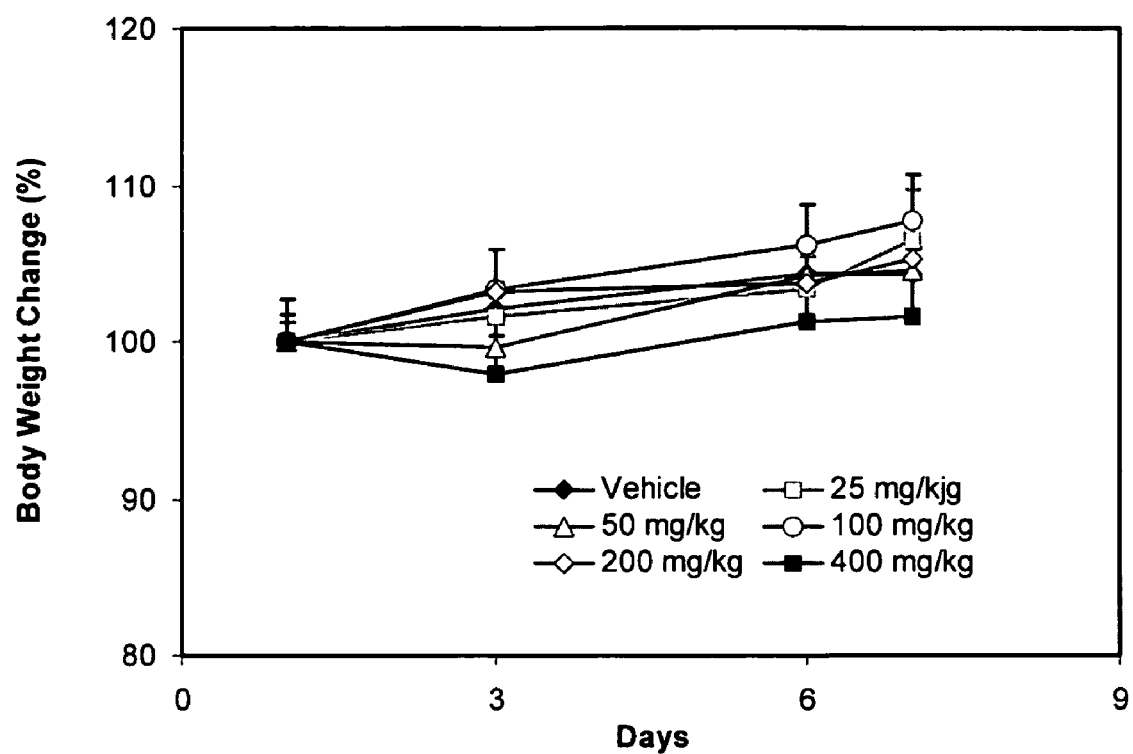
FIG. 15 shows the percent change in mouse body weight after administration of an IV dose of compound 12 (25, 50, 100, 200 and 400 mg/kg) in 30% CAPTISOL®.

A single dose of compound 12 (25, 50, 100, 200 or 400 mg/kg) in 30% CAPTISOL® was administered (iv) to mice and change in body weight was measured over nine day to assess toxicity of the various doses of compound 12. As shown in FIG. 15, administration of up to 200 mg/kg of compound 12 did not result in a significant change in body weight.

Example 60

Seven Day Repeat IP Toxicity Study in Mice Using Compound 12 Formulation

Figure 16:
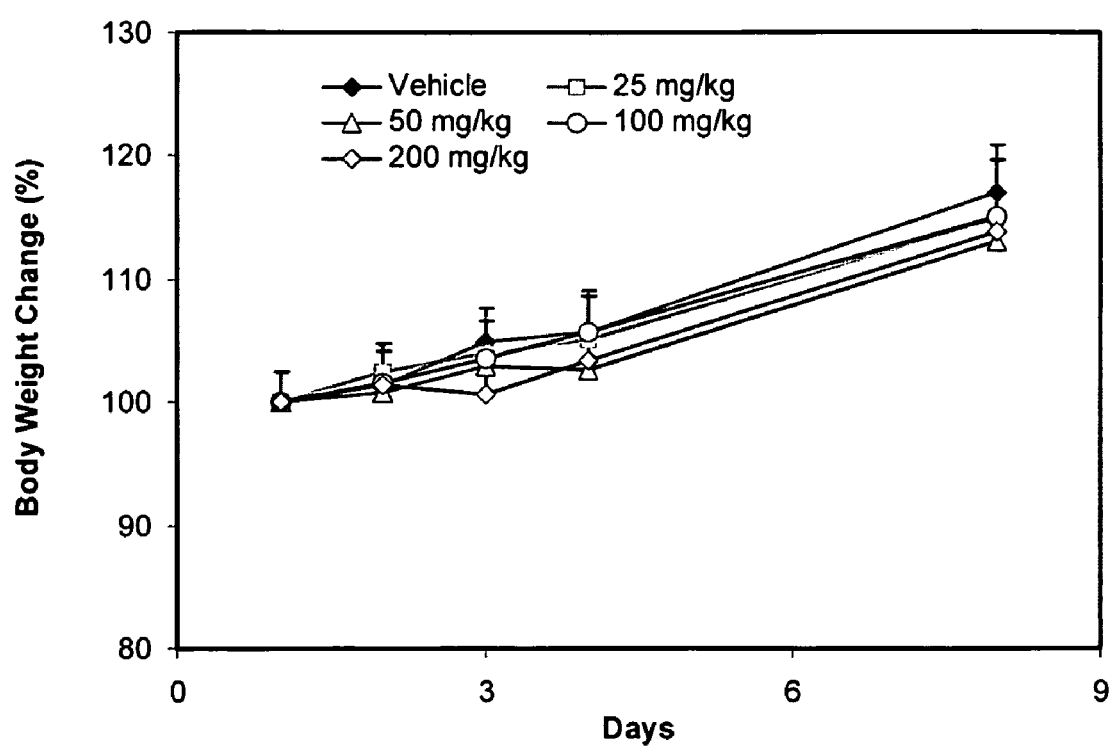
FIG. 16 shows the percent change in mouse body weight after 7 days repeat IP dosing of compound 12 (25, 50, 100, 200 and 400 mg/kg) in 30% CAPTISOL®.

Repeated dosing of compound 12 over seven days (25, 50, 100, 200 or 400 mg/kg) in 30% CAPTISOL® was administered (ip) to mice and change in body weight was measured over seven days. As shown in FIG. 16, repeated administration of up to 100 mg/kg of compound 12 did not result in a significant change in body weight.

Example 61

Single Dose IV Toxicity Study in Rats Using Compound 12 Formulation

Figure 17:
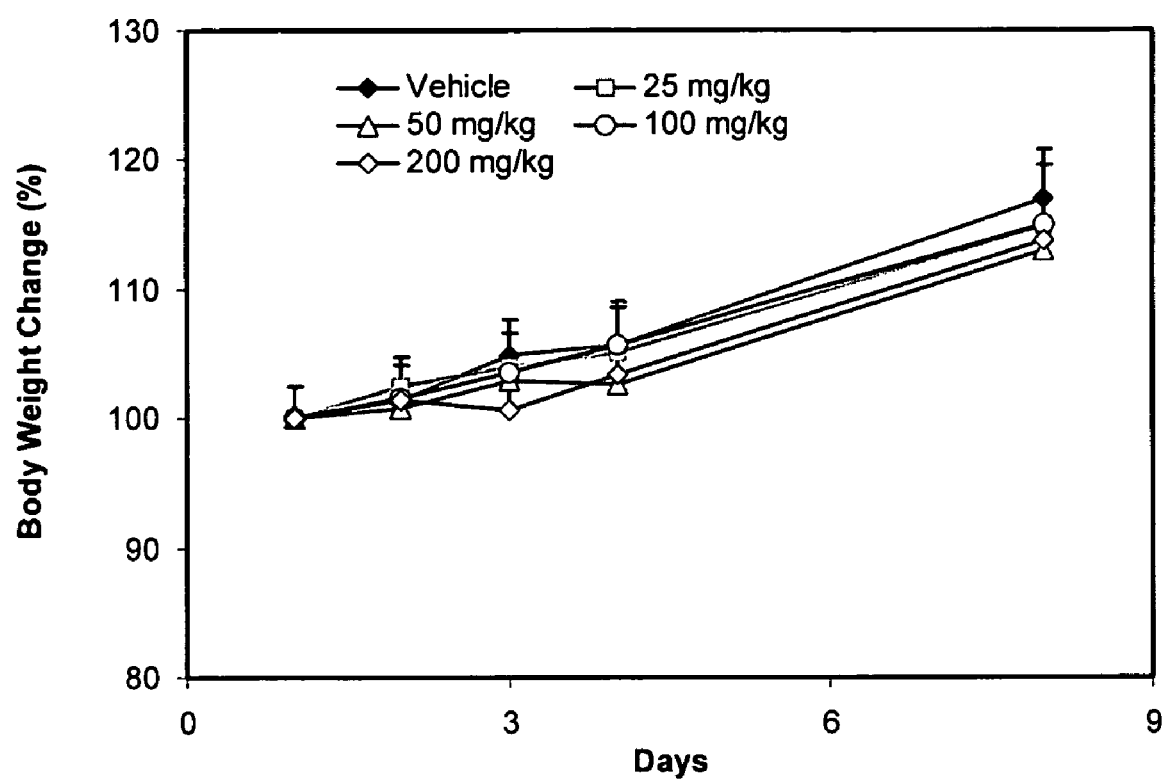
FIG. 17 shows the percent change in rat body weight after administration of an IV dose of compound 12 (25, 50, 100 and 200 mg/kg) in 30% CAPTISOL®.

A single dose of compound 12 (25, 50, 100 or 200 mg/kg) in 30% CAPTISOL® was administered (iv) to rats and change in body weight was measured over eight days to assess toxicity of the different doses of compound 12. As shown in FIG. 17, administration of up to 200 mg/kg did not result in a significant change in body weight.

Example 62

Seven Day Repeat Dose IV Toxicity in Rats Using Compound 12 Formulation

Figure 18:
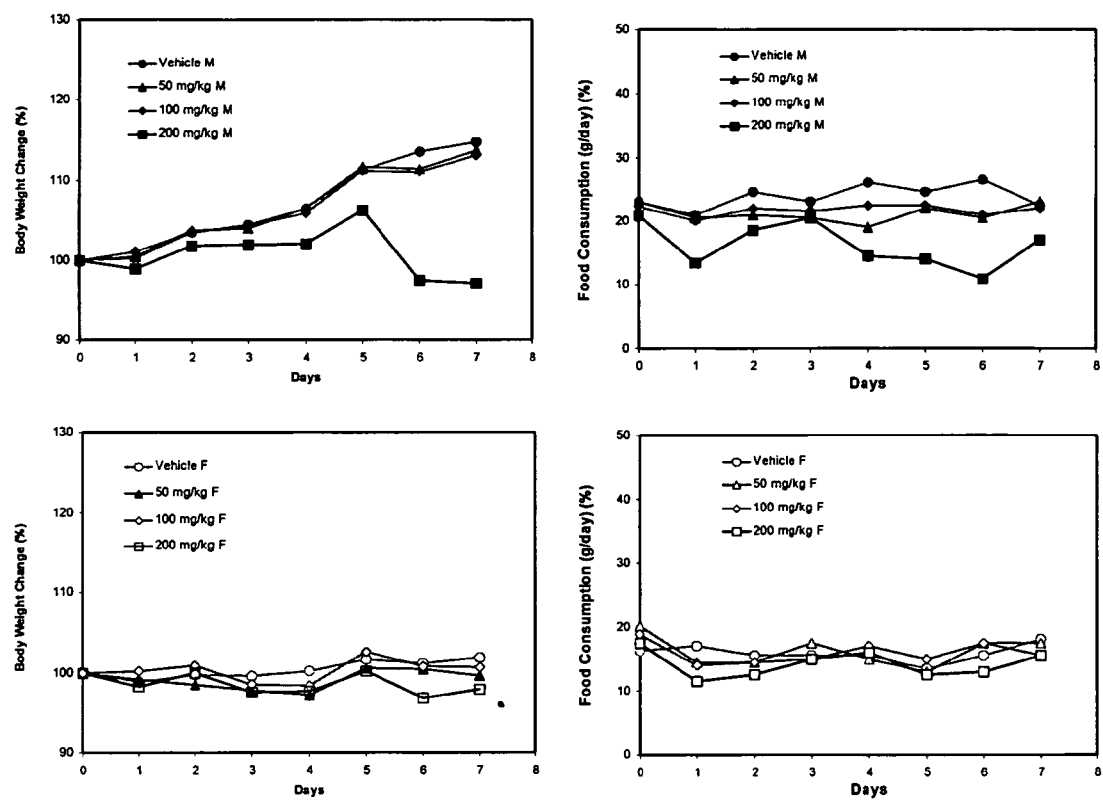
FIG. 18 shows the percent change in rat body weight and food consumption after 7 days repeat IP dosing of compound 12 (50, 100 and 200 mg/kg) in 30% CAPTISOL®.

Repeated dosing of compound 12 over seven days (25, 50, 100 or 200 mg/kg) in 30% CAPTISOL® was administered (iv) to rats and change in body weight and food consumption was measured over seven days. As shown in FIG. 18, administration of up to 100 mg/kg did not result in a significant change in body weight or food consumption.

Example 63

Figure 19:
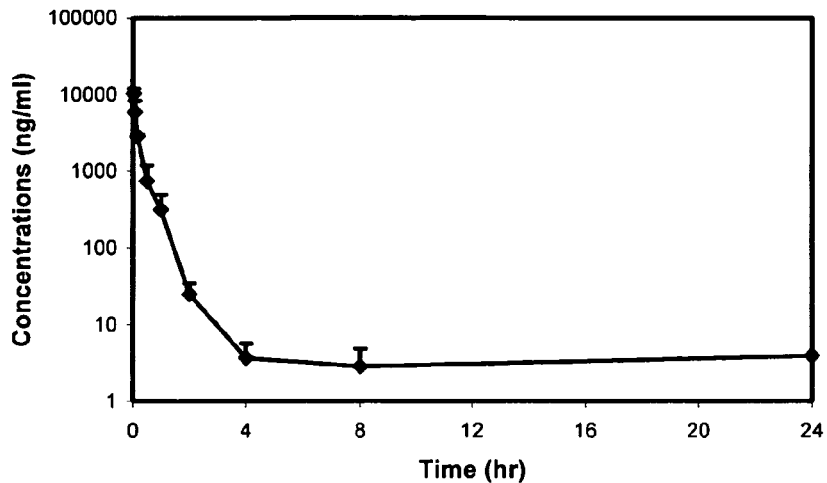
FIG. 19 shows the concentration of compound 12 in the plasma of dogs administered the tartrate salt of compound 12 in CAPTISOL®.

Pharmacokinetic Study of Compound 12 in Dogs 25 mg/kg of a tartrate salt of compound 12 in 30% CAPTISOL® was administered to dogs to study plasma pharmacokinetics. The results of this study are shown in FIG. 19. As shown there the concentration of compound 12 in plasma decreased from about 10,000 ng/ml to less than 10 mg/ml in 4 hours.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A tartaric acid salt or complex of a compound represented by formula (II):

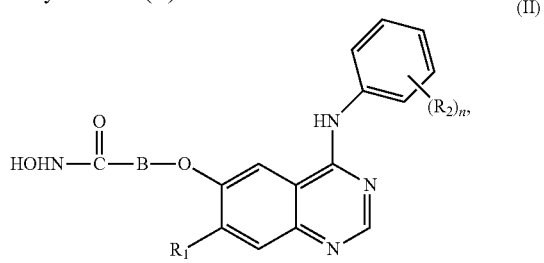

wherein B is a $C_3$ to $C_9$ alkylene;
$R_1$ is selected from hydrogen, $C_1$ to $C_4$ alkoxy or substituted $C_1$ to $C_4$ alkoxy;
each $R_2$ is independently selected from halogen, $C_1$ to $C_4$ alkyl, $C_2$ to $C_4$ alkenyl, and $C_2$ to $C_4$ alkynyl; and
n is 1, 2 or 3.

2. The salt or complex of claim 1 wherein B is a straight chain $C_5$ to $C_7$ alkylene.

3. The salt or complex of claim 2 wherein B is a straight chain $C_6$ alkylene.

4. The salt or complex of claim 1 wherein n is 1.

5. The salt or complex of claim 4 wherein $R_2$ is ethynyl.

6. The salt or complex of claim 5 wherein $R_1$ is methoxy.

7. The salt or complex of claim 1 wherein the tartaric acid is the L-tartaric acid.

8. The salt or complex of claim 1 wherein the tartaric acid is the D-tartaric acid.

9. The salt or complex of claim 1 wherein the tartaric acid is D,L-tartaric acid.

10. The salt or complex of claim 1 wherein the tartaric acid is meso-tartaric acid.

11. A tartaric acid salt or complex of claim 1 wherein the compound is represented by formula (III):

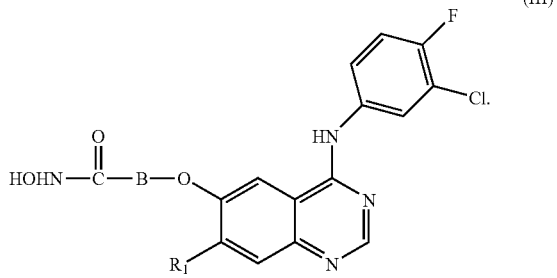

12. The salt or complex of claim 11 wherein B is a straight chain $C_5$ to $C_7$ alkylene.

13. The salt or complex of claim 12 wherein $R_1$ is hydrogen and B is a straight chain $C_6$ alkylene.

14. The salt or complex of claim 11 wherein the tartaric acid is the L-tartaric acid.

15. The salt or complex of claim 11 wherein the tartaric acid is the D-tartaric acid.

16. The salt or complex of claim 11 wherein the tartaric acid is D,L-tartaric acid.

17. The salt or complex of claim 11 wherein the tartaric acid is meso-tartaric acid.

18. The tartaric acid salt or complex of claim 1 wherein the compound is represented by formula (IV):

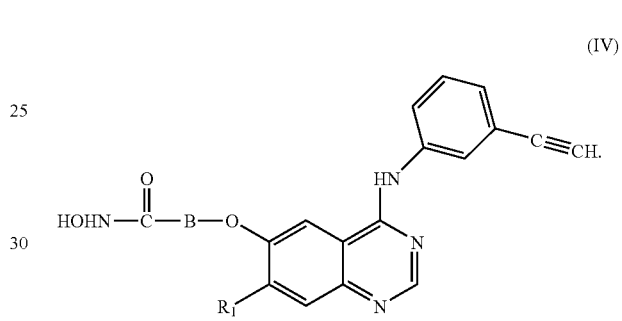

19. The salt or complex of claim 18 wherein B is a straight chain $C_5$ to $C_7$ alkylene.

20. The salt or complex of claim 19 wherein $R_1$ is methoxy and B is a straight chain $C_6$ alkylene.

21. The salt or complex of claim 18 wherein the tartaric acid is the L-tartaric acid.

22. The salt or complex of claim 18 wherein the tartaric acid is the D-tartaric acid.

23. The salt or complex of claim 18 wherein the tartaric acid is D,L-tartaric acid.

24. The salt or complex of claim 18 wherein the tartaric acid is meso-tartaric acid.

25. A pharmaceutical composition comprising as an active ingredient the salt or complex of claim 1 and a pharmaceutical acceptable carrier.

* * * * *